(12) United States Patent
Claiborne et al.

(10) Patent No.: US 9,718,788 B2
(45) Date of Patent: Aug. 1, 2017

(54) HETEROARYL COMPOUNDS USEFUL AS INHIBITORS OF E1 ACTIVATING ENZYMES

(71) Applicant: MILLENNIUM PHARMACEUTICALS, INC., Cambridge, MA (US)

(72) Inventors: Christopher F. Claiborne, Cambridge, MA (US); Stephen Critchley, Braintree, MA (US); Steven P. Langston, North Andover, MA (US); Hirotake Mizutani, Arlington, MA (US); Edward J. Olhava, Newton, MA (US); Stephane Peluso, Natick, MA (US); Irache Visiers, Arlington, MA (US); Stepan Vyskocil, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/249,851

(22) Filed: Aug. 29, 2016

(65) Prior Publication Data
US 2017/0050935 A1    Feb. 23, 2017

Related U.S. Application Data

(60) Division of application No. 14/827,556, filed on Aug. 17, 2015, now Pat. No. 9,458,108, which is a division of application No. 14/480,513, filed on Sep. 8, 2014, now Pat. No. 9,150,525, which is a division of application No. 13/911,415, filed on Jun. 6, 2013, now Pat. No. 8,901,136, which is a division of application No. 13/216,352, filed on Aug. 24, 2011, now Pat. No. 8,481,550, which is a continuation of application No. 11/890,338, filed on Aug. 6, 2007, now Pat. No. 8,008,307.

(Continued)

(51) Int. Cl.

| | | |
|---|---|---|
| C07D 213/82 | (2006.01) |
| C07D 239/48 | (2006.01) |
| C07D 487/04 | (2006.01) |
| C07D 239/42 | (2006.01) |
| C07D 213/56 | (2006.01) |
| C07D 213/69 | (2006.01) |
| C07D 401/04 | (2006.01) |
| C07D 403/04 | (2006.01) |
| C07D 471/04 | (2006.01) |
| C07D 471/08 | (2006.01) |
| C07D 473/34 | (2006.01) |
| C07D 473/30 | (2006.01) |
| A61K 31/53 | (2006.01) |
| C07D 251/18 | (2006.01) |
| C07D 251/48 | (2006.01) |
| C07D 213/74 | (2006.01) |
| C07D 401/06 | (2006.01) |
| C07D 213/81 | (2006.01) |
| C07D 239/36 | (2006.01) |

(52) U.S. Cl.
CPC ............ *C07D 239/42* (2013.01); *A61K 31/53* (2013.01); *C07D 213/56* (2013.01); *C07D 213/69* (2013.01); *C07D 213/74* (2013.01); *C07D 213/81* (2013.01); *C07D 213/82* (2013.01); *C07D 239/36* (2013.01); *C07D 239/48* (2013.01); *C07D 251/18* (2013.01); *C07D 251/48* (2013.01); *C07D 401/04* (2013.01); *C07D 401/06* (2013.01); *C07D 403/04* (2013.01); *C07D 471/04* (2013.01); *C07D 471/08* (2013.01); *C07D 473/30* (2013.01); *C07D 473/34* (2013.01); *C07D 487/04* (2013.01)

(58) Field of Classification Search
CPC .. C07D 213/56; C07D 213/74; C07D 213/82; C07D 239/36; C07D 239/48; C07D 487/04; A61K 31/4402; A61K 31/4406; A61K 31/505; A61K 31/4162
USPC ........ 544/280, 317, 319, 326; 546/316, 323; 514/256, 265.1, 269, 354, 355
See application file for complete search history.

(56) References Cited

U.S. PATENT DOCUMENTS

| | | |
|---|---|---|
| 5,194,446 A | 3/1993 | Lo et al. |
| 7,078,525 B2 | 7/2006 | Guzi et al. |

(Continued)

FOREIGN PATENT DOCUMENTS

| | | |
|---|---|---|
| JP | 200508581 | 1/2005 |
| WO | WO 97/05132 A1 | 2/1997 |

(Continued)

OTHER PUBLICATIONS

Brownell et al., "Substrate-Assisted Inhibition of Ubiquitin-Like Protein-Activating Enzymes: The NEDD8 E1 Inhibitor MLN4924 Forms A NEDD8-AMP Mimetic In Situ," Mol. Cell. 37:102-111, (2010).

(Continued)

*Primary Examiner* — Deepak Rao
(74) *Attorney, Agent, or Firm* — Sterne, Kessler, Goldstein & Fox P.L.L.C.

(57) ABSTRACT

This invention relates to compounds that inhibit E1 activating enzymes, pharmaceutical compositions comprising the compounds, and methods of using the compounds. The compounds are useful for treating disorders, particularly cell proliferation disorders, including cancers, inflammatory and neurodegenerative disorders; and inflammation associated with infection and cachexia.

1 Claim, No Drawings

Related U.S. Application Data

(60) Provisional application No. 60/836,158, filed on Aug. 8, 2006.

(56) References Cited

U.S. PATENT DOCUMENTS

| | | | |
|---|---|---|---|
| 7,196,092 B2 | 3/2007 | Guzi et al. | |
| 7,563,798 B2 | 7/2009 | Guzi et al. | |
| 7,642,266 B2 | 1/2010 | Guzi et al. | |
| 7,903,055 B2 | 3/2011 | Nishikawa et al. | |
| 8,008,307 B2 * | 8/2011 | Claiborne | C07D 213/69 514/256 |
| 8,207,177 B2 | 6/2012 | Langston et al. | |
| 8,242,692 B2 | 8/2012 | Kim et al. | |
| 8,481,550 B2 * | 7/2013 | Claiborne | C07D 213/69 514/256 |
| 8,901,136 B2 * | 12/2014 | Critchley | C07D 213/69 514/263.2 |
| 9,150,525 B2 * | 10/2015 | Claiborne | C07D 213/69 |
| 9,458,108 B2 * | 10/2016 | Claiborne | C07D 213/69 |
| 2004/0102451 A1 | 5/2004 | Guzi et al. | |
| 2007/0082901 A1 | 4/2007 | Guzi et al. | |
| 2007/0191293 A1 | 8/2007 | Langston et al. | |
| 2008/0051404 A1 | 2/2008 | Claiborne et al. | |
| 2011/0021544 A1 | 1/2011 | Armitage et al. | |
| 2012/0077814 A1 | 3/2012 | Wang et al. | |
| 2012/0258927 A1 | 10/2012 | Langston et al. | |
| 2013/0150388 A1 | 6/2013 | McCarron et al. | |
| 2013/0217682 A1 | 8/2013 | Afroze et al. | |

FOREIGN PATENT DOCUMENTS

| | | | |
|---|---|---|---|
| WO | WO 03/073989 | A2 | 9/2003 |
| WO | WO 2004/022559 | A1 | 3/2004 |
| WO | WO 2004/026229 | A2 | 4/2004 |
| WO | WO 2004/043955 | A1 | 5/2004 |
| WO | WO 2004/087707 | A1 | 10/2004 |
| WO | WO 2005/007621 | A2 | 1/2005 |
| WO | WO 2005/037845 | A1 | 4/2005 |
| WO | WO 2006/002284 | A1 | 1/2006 |
| WO | WO 2006/084281 | * | 8/2006 |
| WO | WO 2007/044401 | A2 | 4/2007 |
| WO | WO 2007/092213 | A2 | 8/2007 |
| WO | WO 2009/082691 | A1 | 7/2009 |
| WO | WO 2010/086040 | A1 | 8/2010 |
| WO | WO 2010/088518 | A2 | 8/2010 |
| WO | WO 2010/132110 | A2 | 11/2010 |
| WO | WO 2015/002994 | A2 | 1/2015 |

OTHER PUBLICATIONS

Extended European Search Report for European patent Application No. 12825411.7 mailed Mar. 25, 2015 (5 pages).
International Search Report and Written Opinion PCT/US07/017463 dated Nov. 23, 2007 corresponding to U.S. Appl. No. 11/890,338.
International Search Report PCT/US15/38712 mailed Sep. 29, 2015.
Non-Final Office Action dated Dec. 9, 2010 in U.S. Appl. No. 11/890,338.
Non-Final Office Action dated Nov. 21, 2012 in U.S. Appl. No. 13/216,352.
Non-Final Office Action dated Dec. 31, 2013 in U.S. Appl. No. 13/911,415.
Non-Final Office Action dated May 23, 2013, in U.S. Appl. No. 13/592,389.
Notice of Allowability dated Apr. 26, 2011, in U.S. Appl. No. 11/890,336.
Notice of Allowability dated Mar. 7, 2013, in U.S. Appl. No. 13/216,352.
Notice Allowability dated Apr. 10, 2014 in U.S. Appl. No. 13/592,389.
Notice of Allowability dated Jun. 5, 2014 in U.S. Appl. No. 13/911,415.
Notice of Allowability dated Apr. 3, 2015, in U.S. Appl. No. 13/767,314.
Notice of Allowability dated May 14, 2015, in U.S. Appl. No. 14/480,513.
Notice of Allowability dated Jul. 13, 2015, U.S. Appl. No. 13/767,314.
Notice of Allowability dated Nov. 16, 2015, in U.S. Appl. No. 13/767,314.
PCT Notification of Transmittal of the International Search Report and the Written Opinion of the International Searching Authority, or the Declaration for International Application No. PCT/US2013/026113 mailed Apr. 11, 2013.
Restriction Requirement dated Aug. 31, 2010, in U.S. Appl. No. 11/890,338.
Restriction Requirement dated Jun. 21, 2012, in U.S. Appl. No. 13/216,352.
Restriction Requirement dated Dec. 19, 2014, in U.S. Appl. No. 13/767,314.
Supplementary European Search Report dated Jul. 17, 2015 of European Application No. EP 13 74 8707.
Gura, T., "Systems for identifying New Drugs Are Often Faulty," *Science 278(5340)*: 1041-1042, AAAS, United States (1997).
Johnson, J.I., et al., "Relationships between drug activity in NCI preclinical in vitro and in vivo models and early clinical trials," *British Journal of Cancer 84(10)*: 1424-1431, Nature Publishing Group, England (2001).
Pearce, H.L., et al., "Failure modes in anticancer drug discovery and development," in *Cancer Drug Design and Discovery*, Neidle, S., ed., Chapter 18, pp. 424-435, Elsevier, Inc., United States (2008).
Simone, J.V., "Oncology: Introduction," in *Cecil Textbook of Medicine*, Bennett, J.C. and Plum, F., eds., 20th Edition, vol. 1, pp. 1004-1010, W.B. Saunders Company, United States (1996).
Xu, G.W., et al., "The ubiquitin-activating enzyme EI as a therapeutic target for the treatment of leukemia and multiple myeloma," *Blood 115(11)* : 2251-2259, American Society of Hematology, United States (2010).
Gosseling, G., et al., "A short and novel synthesis of carbocyclic nucleosides and 4'-epi-carbocyclic nucleosides from 2-cyclopenten-1-ones," *Tetrahedron 62(5)*:906-914, Elsevier, Ltd., The Netherlands (2006).

* cited by examiner

HETEROARYL COMPOUNDS USEFUL AS INHIBITORS OF E1 ACTIVATING ENZYMES

PRIORITY CLAIM

This is a division of application Ser. No. 14/827,556, filed Aug. 17, 2015, which is a division of application Ser. No. 14/480,513, filed Sep. 8, 2014 (now U.S. Pat. No. 9,150,525), which is a division of application Ser. No. 13/911,415, filed Jun. 6, 2013 (now U.S. Pat. No. 8,901,136), which is a division of application Ser. No. 13/216,352, filed Aug. 24, 2011 (now U.S. Pat. No. 8,481,550), which is a continuation of application Ser. No. 11/890,338, filed Aug. 6, 2007 (now U.S. Pat. No. 8,008,307), which claims the benefit of U.S. Provisional Application No. 60/836,158, filed Aug. 8, 2006, all of which are incorporated herein by reference.

FIELD OF THE INVENTION

This invention relates to compounds, compositions and methods for the treatment of various disorders, particularly disorders of cell proliferation, including cancers, and inflammatory disorders. In particular, the invention provides compounds which inhibit the activity of E1 type activating enzymes.

BACKGROUND OF THE INVENTION

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

The biological consequence of ubl modification depends on the target in question. Ubiquitin is the best characterized of the ubls and a consequence of modification by ubiquitination is the degradation of poly-ubiquitinated proteins by the 26S proteasome. Ubiquitin is conjugated to its target proteins through an enzymatic cascade involving its specific E1 activating enzyme, Uba1 (ubiquitin activating enzyme, UAE), a conjugating enzyme from the family of E2s, and a ubiquitin ligase from either the RING or HECT classes of E3s. See, Huang et al., *Oncogene*, 23:1958-71 (2004). Target specificity is controlled by the particular combination of E2 and E3 protein, with >40 E2s and >100 E3s being known at present. In addition to ubiquitin, there are at least 10 ubiquitin-like proteins, each believed to be activated by a specific E1 activating enzyme and processed through similar but distinct downstream conjugation pathways. Other ubls for which E1 activating enzymes have been identified include Nedd8 (APPBP1-Uba3), ISG15 (UBE1L) and the SUMO family (Aos1-Uba2).

The ubl Nedd8 is activated by the heterodimer Nedd8-activating enzyme (APPBP1-Uba3) (NAE) and is transferred to a single E2 (Ubc12), ultimately resulting in ligation to cullin proteins. The function of neddylation is the activation of cullin-based ubiquitin ligases involved in the ubiquitination and hence turnover of many cell cycle and cell signaling proteins, including p27 and I-κB. See Pan et al., *Oncogene*. 23:1985-97 (2004). The ubl SUMO is activated by the heterodimer sumo activating enzyme (Aos1-Uba2) (SAE) and is transferred to a single E2 (Ubc9), followed by coordination with multiple E3 ligases, ultimately resulting in sumoylation of target proteins. Sumo modification can affect the cellular localization of target proteins and proteins modified by SUMO family members are involved in nuclear transport, signal transduction and the stress response. See Seeler and Dejean, *Nat Rev Mol Cell Biol*. 4:690-9, (2003). The function of sumoylation includes activation of cell signaling pathways (e.g., cytokine, WNT, growth factor, and steroid hormone signaling) involved in transcription regulation; as well as pathways involved in control of genomic integrity (e.g., DNA replication, response to DNA damage, recombination and repair). See Muller et al, *Oncogene*. 23:1998-2006, (2004). There are other ubls (e.g., ISG15, FAT10, Apg12p) for which the biological functions are still under investigation.

A particular pathway of importance which is regulated via E1 activating enzyme activities is the ubiquitin-proteasome pathway (UPP). As discussed above, the enzymes UAE and NAE regulate the UPP at two different steps in the ubiquitination cascade. UAE activates ubiquitin in the first step of the cascade, while NAE, via activation of Nedd8, is responsible for the activation of the cullin based ligases, which in turn are required for the final transfer of ubiquitin to certain target proteins A functional UPP pathway is required for normal cell maintenance. The UPP plays a central role in the turnover of many key regulatory proteins involved in transcription, cell cycle progression and apoptosis, all of which are important in disease states, including tumor cells. See, e.g., King et al., *Science* 274: 1652-1659 (1996); Vorhees et al., *Clin. Cancer Res.*, 9: 6316-6325 (2003); and Adams et al., *Nat. Rev. Cancer*, 4: 349-360 (2004). Proliferating cells are particularly sensitive to inhibition of the UPP. See, Drexler, *Proc. Natl. Acad. Sci., USA* 94: 855-860 (1977). The role of the UPP pathway in oncogenesis has led to the investigation of proteasome inhibition as a potential anticancer therapy. For example, modulation of the UPP pathway by inhibition of the 26S proteasome by VELCADE® (bortezomib) has proven to be an effective treatment in certain cancers and is approved for the treatment of multiple myeloma and mantle cell lymphoma patients who have received at least one prior therapy. Examples of proteins whose levels are controlled by cullin-based ubiquitin ligases which are downstream of NAE and UAE activity include the CDK inhibitor p27$^{Kip1}$ and the inhibitor of NFκB, IκB. See, Podust et al., *Proc. Natl. Acad. Sci.*, 97: 4579-4584 (2000), and Read et al., *Mol. Cell Biol.*, 20: 2326-2333 (2000). Inhibition of the degradation of p27 is expected to block the progression of cells through the G1 and S phases of the cell cycle. Interfering with the degradation of IκB should prevent the nuclear localization of NF-κB, transcription of various NF-κB-dependent genes associated with the malignant phenotype, and resistance to standard cytotoxic therapies. Additionally, NF-κB plays a key role in the expression of a number of pro-inflammatory mediators, implicating a role for such inhibitors in inflammatory diseases. Furthermore, inhibition of UPP has been implicated as a useful target for additional therapeutics, such as inflammatory disorders, including, e.g., rheumatoid arthritis, asthma, multiple sclerosis, psoriasis and reperfusion injury; neurodegenerative disorders, including e.g., Parkinson's disease, Alzheimer's disease, triplet repeat disorders; neuropathic pain; ischemic disorders, e.g., stroke, infarction, kidney disorders; and cachexia. See, e.g., Elliott and Ross, *Am. J. Clin. Pathol.,* 116:637-46 (2001); Elliott et al., *J. Mol. Med.,* 81:235-45 (2003); Tarlac and Storey, *J. Neurosci. Res.* 74: 406-416 (2003); Mori et al., *Neuropath. Appl. Neurobiol.,* 31: 53-61 (2005); Manning, *Curr. Pain Headache Rep.,* 8: 192-8 (2004); Dawson and Dawson, *Science,* 302: 819-822 (2003); Kukan, *J. Physiol. Pharmacol.,* 55: 3-15 (2004); Wojcik and DiNapoli, *Stroke,* 35:1506-18 (2004); Lazarus et al., *Am J Physiol.,* 27:E332-41 (1999).

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE, NAE, and SAE, as regulators of diverse cellular functions, are potentially important therapeutic targets for the identification of novel approaches to treatment of diseases and disorders.

DESCRIPTION OF THE INVENTION

This invention provides compounds that are effective inhibitors of E1 activating enzymes, particularly NAE. The compounds are useful for inhibiting E1 activity in vitro and in vivo, and are useful for the treatment of disorders of cell proliferation, particularly cancers, and other disorders associated with E1 activity. Compounds of the invention are of the general formula (I):

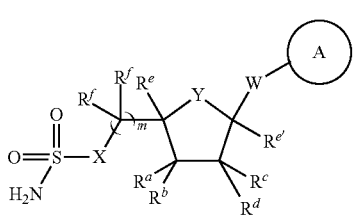

(I)

or a pharmaceutically acceptable salt thereof, wherein:
Ring A is a 6-membered nitrogen-containing heteroaryl ring, optionally fused to a 5- or 6-membered aryl, heteroaryl, cycloaliphatic or heterocyclic ring, wherein either or both rings is optionally substituted and one ring nitrogen atom is optionally oxidized;
W is —$CH_2$—, —CHF—, —$CF_2$—, —CH($R^1$)—, —CF($R^1$)—, —NH—, —N($R^1$)—, —O—, —S—, or —NHC(O)—;
$R^1$ is $C_{1-4}$ aliphatic or $C_{1-4}$ fluoroaliphatic; or $R^1$ is a $C_{2-4}$ alkylene chain that is attached to a ring position on Ring A to form a 5-, 6-, or 7-membered fused ring, wherein the alkylene chain optionally is substituted with $C_{1-4}$ aliphatic, $C_{1-4}$ fluoroaliphatic, =O, —CN, or —C(O)N($R^4$)$_2$;
X is —$CH_2$—, —CHF—, —$CF_2$—, —NH—, or —O—;
Y is —O—, —S—, or —C($R^m$)($R^n$)—;
$R^a$ is selected from the group consisting of hydrogen, fluoro, —CN, —$N_3$, —$OR^5$, —N($R^4$)$_2$, —$NR^4CO_2R^6$, —$NR^4C(O)R^5$, —C(O)N($R^4$)$_2$, —C(O)$R^5$, —OC(O)N($R^4$)$_2$, —OC(O)$R^5$, —$OCO_2R^6$, or a $C_{1-4}$ aliphatic or $C_{1-4}$ fluoroaliphatic optionally substituted with one or two substituents independently selected from the group consisting of —$OR^{5x}$, —N($R^{4x}$)($R^{4y}$), —$CO_2R^{5x}$, or —C(O)N($R^{4x}$)($R^{4y}$); or $R^a$ and $R^c$ together form a bond;
$R^b$ is selected from the group consisting of hydrogen, fluoro, $C_{1-4}$ aliphatic, and $C_{1-4}$ fluoroaliphatic;
$R^c$ is selected from the group consisting of hydrogen, fluoro, —CN, —$N_3$, —$OR^5$, —N($R^4$)$_2$, —$NR^4CO_2R^6$, —$NR^4C(O)R^5$, —C(O)N($R^4$)$_2$, —C(O)$R^5$, —OC(O)N($R^4$)$_2$, —OC(O) $R^5$, —$OCO_2R^6$, or a $C_{1-4}$ aliphatic or $C_{1-4}$ fluoroaliphatic optionally substituted with one or two substituents independently selected from the group consisting of —$OR^{5x}$, —N($R^{4x}$)($R^{4y}$), —$CO_2R^{5x}$, or —C(O)N($R^{4x}$)($R^{4y}$); or $R^a$ and $R^c$ together form a bond;
$R^d$ is selected from the group consisting of hydrogen, fluoro, $C_{1-4}$ aliphatic, and $C_{1-4}$ fluoroaliphatic;
$R^e$ is hydrogen, or $C_{1-4}$ aliphatic; or $R^e$, taken together with one $R^f$ and the intervening carbon atoms, forms a 3- to 6-membered spirocyclic ring; or $R^e$, taken together with $R^m$ and the intervening carbon atoms, forms a fused cyclopropane ring, which is optionally substituted with one or two substituents independently selected from fluoro or $C_{1-4}$ aliphatic;
$R^{e'}$ is hydrogen or $C_{1-4}$ aliphatic; or $R^{e'}$, taken together with $R^m$ and the intervening carbon atoms, forms a fused cyclopropane ring, which is optionally substituted with one or two substituents independently selected from fluoro or $C_{1-4}$ aliphatic;
each $R^f$ is independently hydrogen, fluoro, $C_{1-4}$ aliphatic, or $C_{1-4}$ fluoroaliphatic; or two $R^f$ taken together form =O; or two $R^f$, taken together with the carbon atom to which they are attached, form a 3- to 6-membered carbocyclic ring; or one $R^f$, taken together with $R^e$ and the intervening carbon atoms, forms a 3- to 6-membered spirocyclic ring;
$R^m$ is hydrogen, fluoro, —N($R^4$)$_2$, or an optionally substituted $C_{1-4}$ aliphatic group; or $R^m$ and $R^n$ together form =O or =C($R^5$)$_2$; or $R^m$ and $R^e$, taken together with the intervening carbon atoms, form a fused cyclopropane ring, which is optionally substituted with one or two substituents independently selected from fluoro or $C_{1-4}$ aliphatic; or $R^m$ and $R^{e'}$, taken together with the intervening carbon atoms, form a fused cyclopropane ring, which is optionally substituted with one or two substituents independently selected from fluoro or $C_{1-4}$ aliphatic;
$R^n$ is hydrogen, fluoro, or an optionally substituted $C_{1-4}$ aliphatic group; or $R^m$ and $R^n$ together form =O or =C($R^5$)$_2$;
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted;

$R^{4y}$ is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S; and each $R^5$ independently is hydrogen or an optionally substituted aliphatic, aryl, heteroaryl, or heterocyclyl group;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

each $R^6$ independently is an optionally substituted aliphatic, aryl, or heteroaryl group; and m is 1, 2, or 3.

Compounds of the invention include those described generally above, and are further defined and illustrated by the detailed description and examples herein.

As used herein, the term "E1," "E1 enzyme," or "E1 activating enzyme" refers to any one of a family of related ATP-dependent activating enzymes involved in activating or promoting ubiquitin or ubiquitin-like (collectively "ubl") conjugation to target molecules. E1 activating enzymes function through an adenylation/thioester intermediate formation to transfer the appropriate ubl to the respective E2 conjugating enzyme through a transthiolation reaction. The resulting activated ubl-E2 promotes ultimate conjugation of the ubl to a target protein. A variety of cellular proteins that play a role in cell signaling, cell cycle, and protein turnover are substrates for ubl conjugation which is regulated through E1 activating enzymes (e.g., NAE, UAE, SAE). Unless otherwise indicated by context, the term "E1 enzyme" is meant to refer to any E1 activating enzyme protein, including, without limitation, nedd8 activating enzyme (NAE (APPBP1/Uba3)), ubiquitin activating enzyme (UAE (Uba1)), sumo activating enzyme (SAE (Aos1/Uba2)), or ISG15 activating enzyme (Ube1L). Preferably, the term "E1 enzyme" refers to human NAE, SAE or UAE, and more preferably refers to NAE.

The term "E1 enzyme inhibitor" or "inhibitor of E1 enzyme" is used to signify a compound having a structure as defined herein, which is capable of interacting with an E1 enzyme and inhibiting its enzymatic activity. Inhibiting E1 enzymatic activity means reducing the ability of an E1 enzyme to activate ubiquitin like (ubl) conjugation to a substrate peptide or protein (e.g., ubiquitination, neddylation, sumoylation). In various embodiments, such reduction of E1 enzyme activity is at least about 50%, at least about 75%, at least about 90%, at least about 95%, or at least about 99%. In various embodiments, the concentration of E1 enzyme inhibitor required to reduce an E1 enzymatic activity is less than about 1 µM, less than about 500 nM, less than about 100 nM, less than about 50 nM, or less than about 10 nM.

In some embodiments, such inhibition is selective, i.e., the E1 enzyme inhibitor reduces the ability of one or more E1 enzymes (e.g., NAE, UAE, or SAE) to promote ubl conjugation to substrate peptide or protein at a concentration that is lower, preferably at least 2-fold, 5-fold, 10-fold, 50-fold, or 100-fold lower, than the concentration of the inhibitor that is required to produce another, unrelated biological effect. In some such embodiments, the E1 enzyme inhibitor reduces the activity of one E1 enzyme at a concentration that is lower than the concentration of the inhibitor that is required to reduce enzymatic activity of a different E1 enzyme. In other embodiments, the E1 enzyme inhibitor also reduces the enzymatic activity of another E1 enzyme, preferably one that is implicated in regulation of pathways involved in cancer (e.g., NAE and UAE).

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "aliphatic", as used herein, means straight-chain, branched or cyclic $C_1$-$C_{12}$ hydrocarbons which are completely saturated or which contain one or more units of unsaturation, but which are not aromatic. For example, suitable aliphatic groups include substituted or unsubstituted linear, branched or cyclic alkyl, alkenyl, alkynyl groups and hybrids thereof, such as cycloalkyl, (cycloalkyl)alkyl, (cycloalkenyl)alkyl or (cycloalkyl)alkenyl. In various embodiments, the aliphatic group has one to ten, one to eight, one to six, one to four, or one, two, or three carbons.

The terms "alkyl", "alkenyl", and "alkynyl", used alone or as part of a larger moiety, refer to a straight and branched chain aliphatic group having from one to twelve carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl. The term "alkoxy" refers to an —O-alkyl radical.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on a cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic"

includes aliphatic rings that are fused to one or more aryl, heteroaryl, or heterocyclyl rings, where the radical or point of attachment is on the aliphatic ring. Nonlimiting examples include indanyl, 5,6,7,8-tetrahydroquinoxalinyl, decahydronaphthyl, or tetrahydronaphthyl, where the radical or point of attachment is on the aliphatic ring.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro. Nonlimiting examples of fluoroaliphatics include —$CH_2F$, —$CHF_2$, —$CF_3$, —$CH_2CF_3$, —$CF_2CH_3$, and —$CF_2CF_3$.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on an aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

In some embodiments, two adjacent substituents on a heteroaryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14 π electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as —NH—, —$CH_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain which is optionally substituted.

The term "alkylene" refers to a bivalent alkyl group. An "alkylene chain" is a polymethylene group, i.e., —$(CH_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)CO$_2$—, —C(O)N(R$^+$)—, —C(O)—, —C(O)—C(O)—, —CO$_2$—, —OC(O)—, —OC(O)O—, —OC(O)N(R$^+$)—, —C(NR)=N, —C(OR*)=N—, —N(R$^+$)—N(R$^+$)—, or —N(R$^+$)S(O)$_2$—. Each R$^+$, independently, is hydrogen or an optionally substituted aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S. Each R* independently is hydrogen or an optionally substituted aliphatic, aryl, heteroaryl, or heterocyclyl group.

Examples of $C_{3-6}$ alkylene chains that have been "interrupted" with —O— include —$CH_2OCH_2$—, —$CH_2O(CH_2)_2$—, —$CH_2O(CH_2)_3$—, —$CH_2O(CH_2)_4$—, —$(CH_2)_2OCH_2$—, —$(CH_2)_2O(CH_2)_2$—, —$(CH_2)_2O(CH_2)_3$—, —$(CH_2)_3O(CH_2)$—, —$(CH_2)_3O(CH_2)_2$—, and —$(CH_2)_4O(CH_2)$—. Other examples of alkylene chains that are "interrupted" with functional groups include —$CH_2GCH_2$—, —$CH_2G(CH_2)_2$—, —$CH_2G(CH_2)_3$—, —$CH_2G(CH_2)_4$—, —$(CH_2)_2GCH_2$—, —$(CH_2)_2G(CH_2)_2$—, —$(CH_2)_2G(CH_2)_3$—, —$(CH_2)_3G(CH_2)$—, —$(CH_2)_3G(CH_2)_2$—, and —$(CH_2)_4G(CH_2)$—, wherein G is one of the "interrupting" functional groups listed above.

For purposes of clarity, all bivalent groups described herein, including, e.g., the alkylene chain linkers described above and the variables D, E, F, G, Q, U, W, Y, $V^1$, $T^1$, $T^2$, $T^3$, and $T^4$ are intended to be read from left to right, with a corresponding left-to-right reading of the formula or structure in which the variable appears. When the bivalent group is contained within a ring, a left-to-right reading of the variable corresponds to a clockwise reading of the ring structure in which the variable appears.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably from about −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)$_2$, —CCR*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R$^o$, —OC(O)N(R$^+$)$_2$, —O—C(O)R*, —CO$_2$R*, —C(O)—C(O)R*, —C(O)R*, —C(O)N(R$^+$)$_2$, —C(O)N(R$^+$)OR*, —C(O)N(R$^+$)C(=NR$^+$)—N(R$^+$)$_2$, —C(=NR$^+$)—N(R$^+$)$_2$, —C(=NR$^+$)—N(R$^+$)—OR*, —C(=NR$^+$)—OR*, —C(R$^o$)=N—OR*, —N(R$^+$)—N(R$^+$)$_2$, —N(R$^+$)OR*, —N(R$^+$)C(=NR$^+$)—N(R$^+$)$_2$, —N(R$^+$)C(=NR$^+$)—N(R$^+$)—C(O)R*, —N(R$^+$)C(=NR$^+$)—R$^o$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, wherein R$^o$ is an optionally substituted aliphatic or aryl group, and R$^+$ and R* are as defined above, or two adjacent substituents, taken together with their intervening atoms, form a 5- to 6-membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R$^+$)$_2$, =NOR*, =N—NHC(O)R*, =N—NHCO$_2$R$^o$, =N—NHSO$_2$R$^o$, or =N—R*, where = represents a double bond, and each R* and R$^o$ is as defined above. One of ordinary skill in the art will recognize that substituents that are attached by way of a double bond requires replacement of two hydrogen radicals on the substitutable carbon atom. For the purposes of clarity, the term "substituted aliphatic" refers to an aliphatic group having at least one non-aliphatic substituent.

Suitable substituents on a substitutable nitrogen atom of a heteroaryl or heterocyclic ring include —$R^*$, —$N(R^*)_2$, —$C(O)R^*$, —$CO_2R^o$, —$C(O)$—$C(O)R^*$—$C(O)CH_2C(O)R^*$, —$SO_2R^o$, —$SO_2N(R^*)_2$, —$C(=S)N(R^*)_2$, —$C(=NH)$—$N(R^*)_2$, and —$NR^*SO_2R^o$; wherein each $R^*$ and $R^o$ is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

It also will be apparent to one skilled in the art that certain compounds of this invention may exist in tautomeric forms, all such tautomeric forms of the compounds being within the scope of the invention. Unless stereochemical configuration is expressly defined, structures depicted herein are meant to include all stereochemical forms of the structure; i.e., the R and S configurations for each asymmetric center. Therefore, unless otherwise indicated, single stereochemical isomers as well as enantiomeric and diastereomeric mixtures of the present compounds are within the scope of the invention. By way of example, the compounds of formula (I) wherein $R^a$ is hydroxy can have R or S configuration at the carbon atom bearing $R^a$. Both the R and the S stereochemical isomers, as well as all mixtures thereof, are included within the scope of the invention.

Where stereochemical configuration at a given asymmetric center is defined by structure, unless stated otherwise, the depicted configuration indicates stereochemistry relative to other asymmetric centers in the molecule. Where stereochemical configuration is defined by chemical name, the designations (rel), (R*), and (S*) indicate relative stereochemistry, while the designations (+), (−), (R), (S), and (abs) indicate absolute stereochemistry.

In the compounds of formula (I), where relative stereochemistry is defined, the diastereomeric purity of the compound preferably is at least 80%, more preferably at least 90%, still more preferably at least 95%, and most preferably at least 99%. As used herein, the term "diastereomeric purity" refers to the amount of a compound having the depicted relative stereochemistry, expressed as a percentage of the total amount of all diastereomers present.

In some embodiments, stereochemical configurations depicted at asterisked positions indicate absolute as well as relative stereochemistry. Preferably, the enantiomeric purity of the compound is at least 80%, more preferably at least 90%, still more preferably at least 95%, and most preferably at least 99%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC, using a chiral column packing material. Enantiomers may also be distinguishable by NMR if first derivatized with an optically enriched derivatizing agent, e.g., Mosher's acid.

In the compounds of formula (I), X is —$CH_2$—, —CHF—, —$CF_2$—, —NH—, or —O—. In some embodiments, X is —$CH_2$—, —NH—, or —O—. In certain embodiments, X is —NH— or —O—. In certain particular embodiments, X is —O—.

In the compounds of formula (I), Y is —O—, —S—, or —$C(R^m)(R^n)$—, where $R^m$ and $R^n$ are as described above. In some embodiments, $R^m$ is hydrogen, fluoro, —$NH_2$, —NH ($C_{1-4}$ aliphatic), —$N(C_{1-4}$ aliphatic$)_2$, or $C_{1-4}$ aliphatic. In some other embodiments, $R^m$ and $R^n$ together form =O. In other embodiments, $R^m$ and $R^e$, taken together with the intervening carbon atoms, form a fused cyclopropane ring, which is optionally substituted with one or two substituents independently selected from fluoro or $C_{1-4}$ aliphatic; or $R^m$ and $R^{e'}$, taken together with the intervening carbon atoms, form a fused cyclopropane ring, which is optionally substituted with one or two substituents independently selected from fluoro or $C_{1-4}$ aliphatic. In certain embodiments, Y is —O— or —$CH_2$—. In certain particular embodiments, Y is —$CH_2$—.

In the compounds of formula (I), W is —$CH_2$—, —CHF—, —$CF_2$—, —$CH(R^1)$—, —$CF(R^1)$—, —NH—, —$N(R^1)$—, —O—, —S—, or —NHC(O)—, where $R^1$ is $C_{1-4}$ aliphatic or $C_{1-4}$ fluoroaliphatic, or $R^1$ is a $C_{2-4}$ alkylene chain that is attached to a ring position on Ring A to form a 5-, 6-, or 7-membered fused ring, wherein the alkylene chain optionally is substituted with $C_{1-4}$ aliphatic, $C_{1-4}$ fluoroaliphatic, =O, —CN, or —$C(O)N(R^4)_2$. In some embodiments, W is —$CH(R^1)$— or —$N(R^1)$—, and $R^1$ is a $C_{2-3}$ alkylene chain that is attached to a ring position on Ring A to form a 5- or 6-membered fused ring, wherein the alkylene chain optionally is substituted with $C_{1-4}$ aliphatic, $C_{1-4}$ fluoroaliphatic, =O, —CN, or —$C(O)N(R^4)_2$. In some other embodiments, W is —$CH_2$—, —CHF—, —$CF_2$—, —NH—, —O—, —S—, or —NHC(O)—. In certain embodiments, W is —O—, —NH—, or —NHC(O)—. In certain particular embodiments, W is —NH—.

In the compounds of formula (I), $R^a$ is selected from the group consisting of hydrogen, fluoro, —CN, —$N_3$, —$OR^5$, —$N(R^4)_2$, —$NR^4CO_2R^6$, —$NR^4C(O)R^5$, —$C(O)N(R^4)_2$, —$C(O)R^5$, —$OC(O)N(R^4)_2$, —$OC(O)R^5$, —$OCO_2R^6$, or a $C_{1-4}$ aliphatic or $C_{1-4}$ fluoroaliphatic optionally substituted with one or two substituents independently selected from the group consisting of —$OR^{5x}$, —$N(R^{4x})(R^{4y})$, —$CO_2R^{5x}$, or —$C(O)N(R^{4x})(R^{4y})$; or $R^a$ and $R^c$ together form a bond. In some embodiments $R^a$ is selected from the group consisting of hydrogen, fluoro, —CN, $N_3$, $C_{1-4}$ aliphatic, $C_{1-4}$ fluoroaliphatic, —$OR^{5x}$, —$NH(R^4)$, —$N(H)CO_2R^5$, —$N(H)C(O)R^5$, —$C(O)NHR^4$, —$C(O)R^5$, —$OC(O)NHR^4$, —$OC(O)R^5$, and —$OC(O)OR^5$. In some embodiments, $R^a$ selected from the group consisting of hydrogen, —OH, —$OCH_3$, $C_{1-4}$ aliphatic, $C_{1-4}$ fluoroaliphatic, and fluoro. In certain embodiments, $R^a$ is selected from the group consisting of hydrogen, —OH, —$OCH_3$, —$CH_3$, and fluoro. In certain particular embodiments, $R^a$ is —OH.

In the compounds of formula (I), $R^c$ is selected from the group consisting of hydrogen, fluoro, —CN, —$N_3$, —$OR^5$, —$N(R^4)_2$, —$NR^4CO_2R^6$, —$NR^4C(O)R^5$, —$C(O)N(R^4)_2$, —$C(O)R^5$, —$OC(O)N(R^4)_2$, —$OC(O)R^5$, —$OCO_2R^6$, or a $C_{1-4}$ aliphatic or $C_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$); or R$^a$ and R$^c$ together form a bond. In some embodiments, R$^c$ is hydrogen, fluoro, —CN, N$_3$, C$_{1-4}$ aliphatic, C$_{1-4}$ fluoroaliphatic, —OR$^{5x}$, —NH(R$^4$), —N(H) CO$_2$R$^5$, —N(H)C(O)R$^5$, —C(O)NHR$^4$, —C(O)R$^5$, —OC (O)NHR$^4$, —OC(O)R$^5$, and —OC(O)OR$^5$. In certain embodiments, R$^c$ is hydrogen, —OH, —OCH$_3$, or fluoro. In certain particular embodiments, R$^c$ is hydrogen or —OH.

In the compounds of formula (I), R$^b$ and R$^d$ are each independently selected from the group consisting of hydrogen, fluoro, C$_{1-4}$ aliphatic, and C$_{1-4}$ fluoroaliphatic. In some embodiments, one of R$^b$ and R$^d$ is C$_{1-4}$ aliphatic and the other is hydrogen. In some embodiments, R$^b$ and R$^d$ are each hydrogen.

In one embodiment, R$^a$ and R$^c$ are each —OH, and R$^b$ and R$^d$ are each hydrogen. In another embodiment, R$^a$ is —OH, and each of R$^b$, R$^c$, and R$^d$ is hydrogen. In another embodiment, R$^a$ is —OH, R$^c$ is fluoro or —OCH$_3$, and R$^b$ and R$^d$ are each hydrogen. In another embodiment, R$^a$ is —OH, R$^b$ is —CH$_3$, R$^c$ is hydrogen or —OH, and R$^d$ is hydrogen. In another embodiment, R$^a$ and R$^c$ together form a bond, and R$^b$ and R$^d$ are each hydrogen.

In the compounds of formula (I), each R$^f$ independently is hydrogen, fluoro, C$_{1-4}$ aliphatic, or C$_{1-4}$ fluoroaliphatic; or two R$^f$, taken together with the carbon atom to which they are attached, form a 3- to 6-membered cycloaliphatic ring; or one R$^f$, taken together with R$^e$ and the intervening carbon atoms, forms a 3- to 6-membered spirocyclic ring; or two R$^f$ together form =O. In some embodiments, R$^f$ is not fluoro if X is —O— or —NH—. In some embodiments, each R$^f$ independently is hydrogen or C$_{1-4}$ aliphatic. In some such embodiments, each R$^f$ independently is hydrogen or —CH$_3$. In certain embodiments, one R$^f$ is hydrogen or —CH$_3$, and the other R$^f$ is hydrogen. In certain particular embodiments, each R$^f$ is hydrogen.

In the compounds of formula (I), R$^e$ is hydrogen or C$_{1-4}$ aliphatic; or R$^e$, taken together with one R$^f$ and the intervening carbon atoms, forms a 3- to 6-membered spirocyclic ring; or R$^e$, taken together with R$^m$ and the intervening carbon atoms, forms a fused cyclopropane ring, which is optionally substituted with one or two substituents independently selected from fluoro or C$_{1-4'}$ aliphatic. In some embodiments, R$^e$ is hydrogen or C$_{1-4}$ aliphatic. In some such embodiments, R$^e$ is hydrogen or —CH$_3$. In certain embodiments, R$^e$ is hydrogen.

In the compounds of formula (I), R$^{e'}$ is hydrogen or C$_{1-4}$ aliphatic; or R$^{e'}$, taken together with R$^m$ and the intervening carbon atoms, forms a fused cyclopropane ring, which is optionally substituted with one or two substituents independently selected from fluoro or C$_{1-4}$ aliphatic. In some embodiments, R$^{e'}$ is hydrogen or C$_{1-4}$ aliphatic. In some such embodiments, R$^{e'}$ is hydrogen or —CH$_3$. In certain embodiments, R$^{e'}$ is hydrogen.

In the compounds of formula (I), the variable m is 1, 2, or 3. In some embodiments, m is 1.

In the compounds of formula (I), Ring A is a 6-membered nitrogen-containing heteroaryl ring, optionally fused to a 5- or 6-membered aryl, heteroaryl, cycloaliphatic or heterocyclic ring, wherein either or both rings are optionally substituted and one ring nitrogen atom is optionally oxidized. In some embodiments, Ring A is an optionally substituted pyridine, pyrimidine, or 1,3,5-triazine ring. In other embodiments, Ring A is a pyridine or pyrimidine ring that is fused to a 5- or 6-membered aryl, heteroaryl, cycloaliphatic or heterocyclic ring, wherein either or both rings are optionally substituted. In some such embodiments, Ring A is fused to an optionally substituted benzene, imidazole, pyrrole, or oxazole ring.

In some embodiments, the invention relates to a compound of formula (I) or a pharmaceutically acceptable salt thereof, characterized by one or more of the following features:

(a) X is —O—;
(b) Y is —CH$_2$—;
(c) W is —NH—;
(d) R$^a$ is —OH;
(e) R$^b$ and R$^d$ are each independently hydrogen or C$_{1-4}$ aliphatic;
(f) R$^c$ is hydrogen, fluoro, or —OR$^5$;
(g) R$^e$ and R$^{e'}$ are each hydrogen;
(h) each R$^f$ is hydrogen; and
(i) m is 1.

In some embodiments, the invention relates to a subgenus of the compounds of formula (I), characterized by formula (I-A) or (I-B):

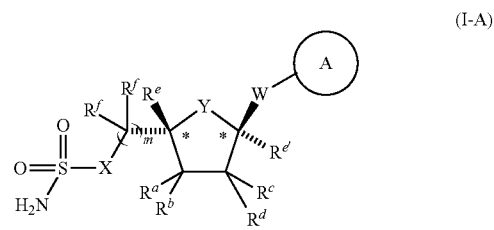

(I-A)

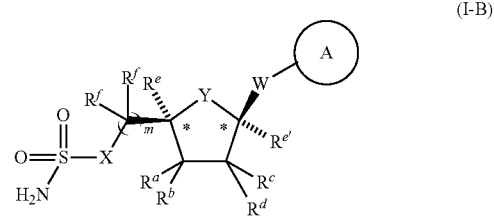

(I-B)

or a pharmaceutically acceptable salt thereof, wherein Ring A and the variables W, X, Y, R$^a$, R$^b$, R$^c$, R$^d$, R$^e$, R$^{e'}$, R$^f$, and m have the values and preferred values described above for formula (I).

In some embodiments, the invention relates to a subgenus of the compounds of formula (I), characterized by formula (II), (II-A), or (II-B):

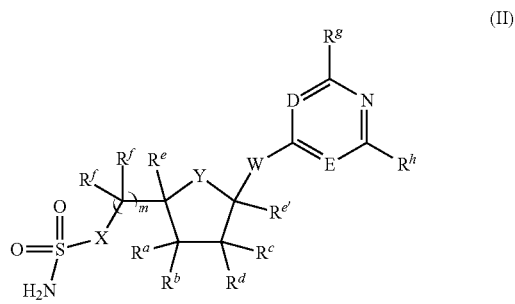

(II)

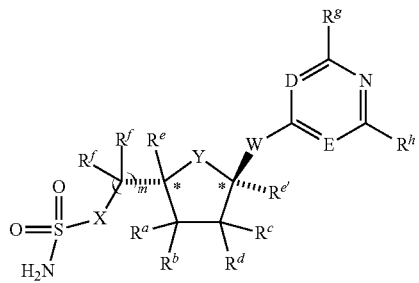

(II-A)

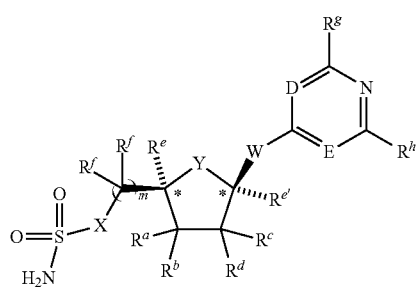

(II-B)

or a pharmaceutically acceptable salt thereof, wherein:

D is —N═ or —C($R^h$)═;

E is —N═ or —C($R^h$)═;

$R^g$ is hydrogen, halo, cyano, —C($R^5$)═C($R^5$)$_2$, —C≡C—$R^5$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N($R^4$)C(═N$R^4$)—N($R^4$)$_2$, —N($R^4$)C(═N$R^4$)—$R^6$, —N$R^4$CO$_2R^6$, —N($R^4$)SO$_2R^6$, —N($R^4$)SO$_2$N($R^4$)$_2$, —O—C(O)$R^5$, —OCO$_2R^5$, —OC(O)N($R^4$)$_2$, —C(O)$R^5$, —CO$_2R^5$, —C(O)N($R^4$)$_2$, —C(O)N($R^4$)—O$R^5$, —C(O)N($R^4$)C(═N$R^4$)—N($R^4$)$_2$, —N($R^4$)C(═N$R^4$)—N($R^4$)—C(O)$R^5$, —C(═N$R^4$)—N($R^4$)$_2$, —C(═N$R^4$)—O$R^5$, —N($R^4$)—N($R^4$)$_2$, —N($R^4$)—O$R^5$, —C(═N$R^4$)—N($R^4$)—O$R^5$, —C($R^6$)═N—O$R^5$, or an optionally substituted aliphatic, aryl, heteroaryl, or heterocyclyl;

each $R^h$ independently is hydrogen, halo, —CN—, —O$R^5$, —N($R^4$)$_2$, —S$R^6$, or an optionally substituted $C_{1-4}$ aliphatic group; and the variables W, X, Y, $R^a$, $R^b$, $R^c$, $R^d$, $R^e$, $R^{e'}$, $R^f$ and m have the values and preferred values described above for formula (I).

In some embodiments, each $R^h$ in formulae (II), (II-A), and (II-B) independently is hydrogen, halo, —CN, —OH, —O—($C_{1-4}$ aliphatic), —NH$_2$, —NH—($C_{1-4}$ aliphatic), —N($C_{1-4}$ aliphatic)$_2$, —SH, —S—($C_{1-4}$ aliphatic), or an optionally substituted $C_{1-4}$ aliphatic group. In certain embodiments, each $R^h$ independently is hydrogen, fluoro, —CH$_3$, —CF$_3$, or —OH. In certain particular embodiments, $R^h$ is hydrogen.

In some embodiments, Ring A is selected from the group consisting of:

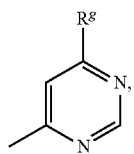

A-i

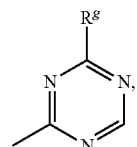

A-ii

A-iii

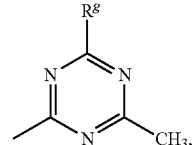

A-iv

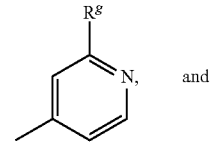

A-v

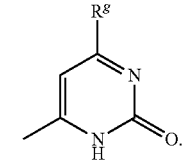

A-vi

In some embodiments, $R^g$ is hydrogen, $C_{1-6}$ aliphatic, $C_{1-6}$ fluoroaliphatic, halo, —$R^{1g}$, —$R^{2g}$, -$T^1$-$R^{1g}$, -$T^1$-$R^{2g}$, —$V^1$-$T^1$-$R^{1g}$, —$V^1$-$T^1$-$R^{2g}$, —$V^1$—$R^{1g}$, or -$T^1$-$V^1$—$R^{1g}$, where the variables $R^{1g}$, $R^{2g}$, $V^1$, and $T^1$ have the values described below.

$T^1$ is a $C_{1-6}$ alkylene chain substituted with 0-2 independently selected $R^{3a}$ or $R^{3b}$, wherein the alkylene chain optionally is interrupted by —C($R^5$)═C($R^5$)—, —C≡C, —O—, —S—, —S(O)—, —S(O)$_2$—, —SO$_2$N($R^4$)—, —N($R^4$)—, —N($R^4$)C(O), —N$R^4$C(O)N($R^4$)—, —N($R^4$)C(═N$R^4$)—N($R^4$)—, —N($R^4$)—C(═N$R^4$)—, —N($R^4$)CO$_2$—, —N($R^4$)SO$_2$—, —N($R^4$)SO$_2$N($R^4$)—, —OC(O)—, —OC(O)N($R^4$)—, —C(O)—, —CO$_2$—, —C(O)N($R^4$)—, —C(═N$R^4$)—N($R^4$)—, —C(N$R^4$)═N($R^4$)—, —C(═N$R^4$)—O—, or —C($R^6$)═N—O—, and wherein $T^1$ or a portion thereof optionally forms part of a 3-7 membered ring. In some embodiments, $T^1$ is a $C_{1-4}$ alkylene chain optionally substituted with one or two groups independently selected from fluoro, $C_{1-4}$ aliphatic, and $C_{1-4}$ fluoroaliphatic.

Each $R^{3a}$ independently is selected from the group consisting of —F, —OH, —O($C_{1-4}$ alkyl), —CN, —N($R^4$)$_2$, —C(O)($C_{1-4}$ alkyl), —CO$_2$H, —CO$_2$($C_{1-4}$ alkyl), —C(O)NH$_2$, and —C(O)NH($C_{1-4}$ alkyl).

Each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered cycloaliphatic ring.

Each $R^7$ independently is an optionally substituted aryl or heteroaryl ring.

$V^1$ is —C($R^5$)═C($R^5$)—, —C≡C—, —O—, —S—, —S(O)—, —S(O)$_2$—, —SO$_2$N($R^4$)—, —N($R^4$)—,

—N(R⁴)C(O)—, —NR⁴C(O)N(R⁴)—, —N(R⁴)C(=NR⁴)—N(R⁴)—, —N(R⁴)C(=NR⁴)—, —N(R⁴)CO₂—, —N(R⁴)SO₂—, —N(R⁴)SO₂N(R⁴)—, —OC(O)—, —OC(O)N(R⁴)—, —C(O)—, —CO₂—, —C(O)N(R⁴)—, —C(O)N(R⁴)—O—, —C(O)N(R⁴)C(=NR⁴)—N(R⁴)—, —N(R⁴)C(=NR⁴)—N(R⁴)—C(O)—, —C(=NR⁴)—N(R⁴)—, —C(NR⁴)=N(R⁴)—, —C(=NR⁴)—O—, or —C(R⁶)=N—O—. In some embodiments, V¹ is —N(R⁴)C(O)—, —N(R⁴)C(O)N(R⁴)—, —N(R⁴)SO₂—, —N(R⁴)SO₂N(R⁴)—, or —N(R⁴)CO₂—. In certain such embodiments, V¹ is —N(R⁴)C(O)— or —N(R⁴)C(O)N(R⁴)—. In other embodiments, V¹ is —C(R⁵)=C(R⁵), —C≡C—, —O—, —S—, or —N(R⁴)—.

Each $R^{1g}$ independently is an optionally substituted aryl, heteroaryl, heterocyclyl, or cycloaliphatic ring.

Each $R^{2g}$ independently is —NO₂, —CN, —C(R⁵)=C(R⁵)₂, —C≡C—R⁵, —OR⁵, —SR⁶, —S(O)R⁶, —SO₂R⁶, —SO₂N(R⁴)₂, —N(R⁴)₂, —NR⁴C(O)R⁵, —NR⁴C(O)N(R⁴)₂, —N(R⁴)C(=NR⁴)—N(R⁴)₂, —N(R⁴)C(=NR⁴)—R⁶, —NR⁴CO₂R⁶, —N(R⁴)SO₂R⁶, —N(R⁴)SO₂N(R⁴)², —O—C(O)R⁵, —OCO₂R⁶, —OC(O)N(R⁴)₂, —C(O)R⁵, —CO₂R⁵, —C(O)N(R⁴)₂, —C(O)N(R⁴)—OR⁵, —C(O)N(R⁴)C(=NR⁴)—N(R⁴)₂, —N(R⁴)C(=NR⁴)—N(R⁴)—C(O)R⁵, —C(=NR⁴)—N(R⁴)₂, —C(=NR⁴)—OR⁵, —N(R⁴)—N(R⁴)₂, —N(R⁴)—OR⁵, —C(=NR⁴)—N(R⁴)—OR⁵, or —C(R⁶)=N—OR⁵.

The invention also relates to a subgenus of the compounds of formula (II), characterized by formula (III):

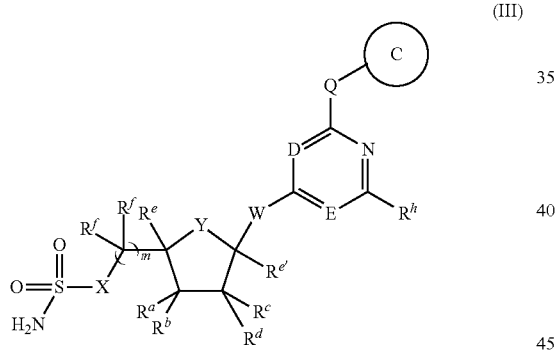

(III)

or a pharmaceutically acceptable salt thereof, wherein:
Q is -T¹- or —V¹-T¹-;
V¹ is —N(R⁸)—, —O—, or —S—;
R⁸ is hydrogen or $C_{1-4}$ aliphatic;
T¹ is a $C_{1-4}$ alkylene chain optionally substituted with one or two groups independently selected from fluoro, $C_{1-4}$ aliphatic, and $C_{1-4}$ fluoroaliphatic;
Ring C is a 3- to 8-membered heterocyclyl or cycloaliphatic ring, or a 5- or 6-membered aryl or heteroaryl ring; and
the variables D, E, W, X, Y, $R^a$, $R^b$, $R^c$, $R^d$, $R^e$, $R^{e'}$, $R^f$, $R^h$, and m have the values and preferred values described above for formulae (I) and (II).

The invention also relates to a subgenus of the compounds of formula (III) characterized by formula (III-A), (III-B), (III-C), or (III-D):

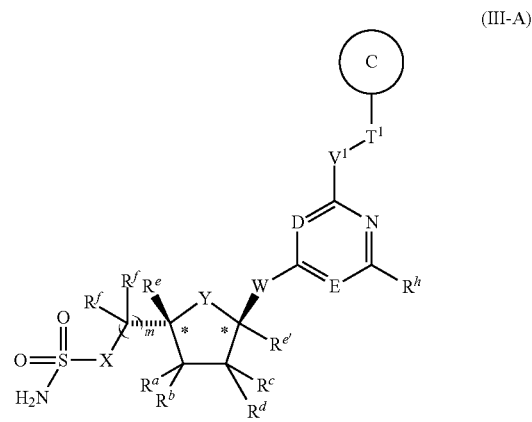

(III-A)

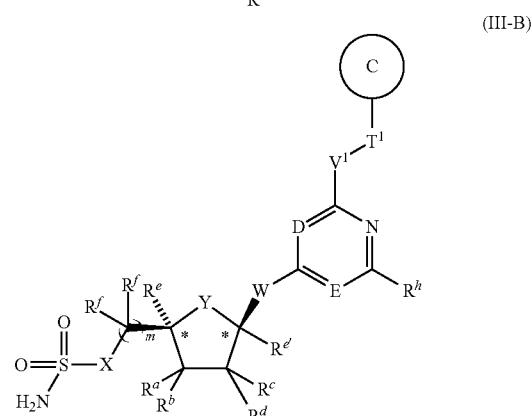

(III-B)

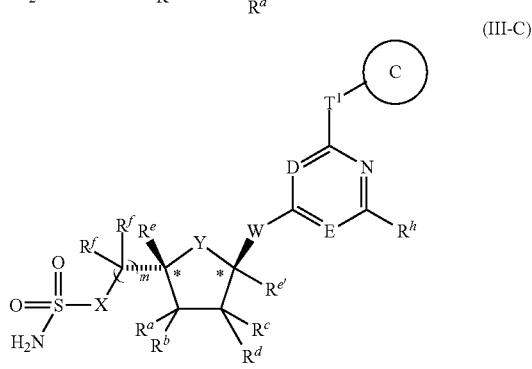

(III-C)

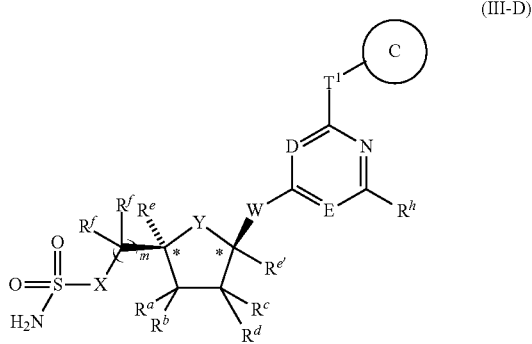

(III-D)

or a pharmaceutically acceptable salt thereof, wherein all variables are as described for formula (III).

In some embodiments, Ring C is substituted with 0-2 $R^o$ and 0-2 $R^{8o}$, where:
each $R^o$ independently is halo, —NO₂, —CN, —C(R⁵)=C(R⁵)₂, —OR⁵, —SR⁶, —S(O)R⁶, —SO₂R⁶, —SO₂N(R⁴)₂, —N(R⁴)₂, —NR⁴C(O)R⁵, —NR⁴C(O)

N(R⁴)₂, —N(R⁴)C(=NR⁴)—N(R⁴)₂, —N(R⁴)C
(=NR⁴)—R⁶, —NR⁴CO₂R⁶, —N(R⁴)SO₂R⁶,
—N(R⁴)SO₂N(R⁴)₂, —O—C(O)R⁵, —OCO₂R⁶,
—OC(O)N(R⁴)₂, —C(O)R⁵, —CO₂R⁵,
—C(O)N(R⁴)₂, —C(O)N(R⁴)—OR⁵, —C(O)N(R⁴)C
(=NR⁴)—N(R⁴)₂, —N(R⁴)C(=NR⁴)—N(R⁴)—C(O)
R⁵, —C(=NR⁴)—N(R⁴)₂, —C(=NR⁴)—OR⁵,
—C(=NR⁴)—N(R⁴)—OR⁵, —C(R⁶)=N—OR⁵, or
an optionally substituted aliphatic, or an optionally
substituted aryl, heterocyclyl, or heteroaryl group; or
two R° on the same saturated ring carbon atom, taken
together with the carbon atom, form an optionally
substituted 3- to 8-membered spirocyclic cycloaliphatic
or heterocyclyl ring; or two adjacent R°, taken together
with the intervening ring atoms, form an optionally
substituted fused 4- to 8-membered aromatic or non-
aromatic ring having 0-3 ring heteroatoms selected
from the group consisting of O, N, and S;

each R⁸° independently is selected from the group con-
sisting of C₁₋₄ aliphatic, C₁₋₄ fluoroaliphatic, halo,
—OR⁵ˣ, —N(R⁴ˣ)(R⁴ʸ), or a C₁₋₄ aliphatic or C₁₋₄
fluoroaliphatic optionally substituted with —OR⁵ˣ,
—N(R⁴ˣ)(R⁴ʸ), —CO₂R⁵ˣ, or —C(O)N(R⁴ˣ)(R⁴ʸ); and
the variables R⁴ˣ, R⁴ʸ, and R⁵ˣ have the values described
above for formula (I).

In some such embodiments, Ring C is a C₃₋₆ cycloali-
phatic, phenyl, pyrrolyl, imidazolyl, oxazolyl, thiazolyl,
isoxazolyl, isothiazolyl, pyrazolyl, triazolyl, tetrazolyl,
oxadiazolyl, thiadiazolyl, pyrrolinyl, imidazolinyl, pyrazoli-
nyl, pyrrolidinyl, imidazolidinyl, pyrazolidinyl, piperidinyl,
morpholinyl, piperazinyl, pyridyl, pyridazinyl, pyrimidinyl,
pyrazinyl, or tetrahydropyrimidinyl ring, any of which is
substituted with 0-2 R° and 0-2 R⁸°. In certain embodiments,
Ring C is a C₃₋₆ cycloaliphatic, phenyl, oxazolyl, or isox-
azolyl ring, any of which is substituted with 0-2 R⁸° and
optionally is fused to an optionally substituted benzene,
dioxolane, or dioxane ring.

The invention also relates to a subgenus of the compounds
of formula (II), characterized by formula (IV), (IV-A), or
(IV-B):

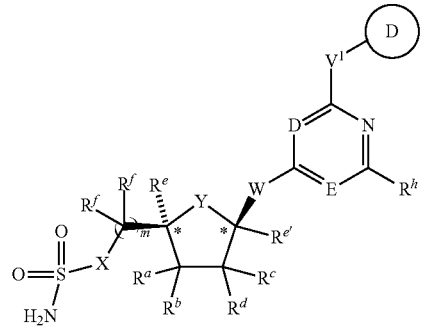

(IV)

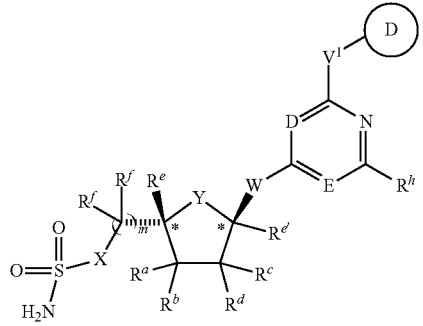

(IV-A)

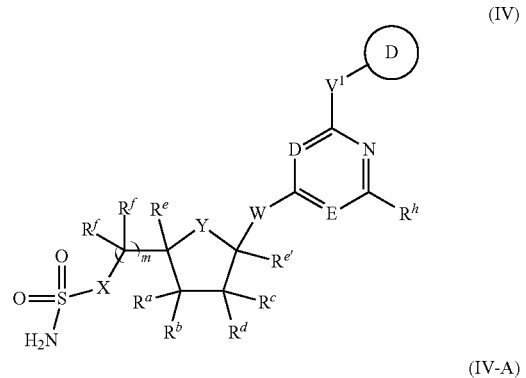

(IV-B)

or a pharmaceutically acceptable salt thereof, wherein:
V¹ is —N(R⁸)—, —O—, or —S—;
R⁸ is hydrogen or C₁₋₄ aliphatic;
Ring D is an optionally substituted mono- or bicyclic ring
system; and
the variables D, E, W, X, Y, Rᵃ, Rᵇ, Rᶜ, Rᵈ, Rᵉ, Rᵉ', Rᶠ, Rʰ,
and m have the values and preferred values described
above for formula (II).

In some embodiments, Ring D an optionally substituted
furanyl, thienyl, pyrrolyl, oxazolyl, thiazolyl, imidazolyl,
pyrazolyl, isoxazolyl, isothiazolyl, oxadiazolyl, triazolyl,
thiadiazolyl, phenyl, naphthyl, pyranyl, pyridyl, pyridazinyl,
pyrimidinyl, pyrazinyl, triazinyl, indolizinyl, indolyl, isoin-
dolyl, indazolyl, benzimidazolyl, benzthiazolyl, benzothie-
nyl, benzofuranyl, purinyl, quinolyl, isoquinolyl, cinnolinyl,
phthalazinyl, quinazolinyl, quinoxalinyl, naphthyridinyl,
pteridinyl, tetrahydrofuranyl, tetrahydrothienyl, pyrrolidi-
nyl, pyrrolidonyl, piperidinyl, pyrrolinyl, tetrahydroquinoli-
nyl, tetrahydroisoquinolinyl, decahydroquinolinyl, oxazo-
lidinyl, piperazinyl, dioxanyl, dioxolanyl, diazepinyl,
oxazepinyl, thiazepinyl, morpholinyl, quinuclidinyl, tetra-
hydroquinolinyl, tetrahydroisoquinolinyl, indanyl, phenan-
thridinyl, tetrahydronaphthyl, indolinyl, benzodioxanyl,
benzodioxolyl, chromanyl, cyclopropyl, cyclobutyl, cyclo-
pentyl, cyclopentenyl, cyclohexyl, cyclohexenyl, cyclohep-
tyl, cycloheptenyl, cyclooctyl, cyclooctenyl, cyclooctadi-
enyl, bicycloheptanyl or bicyclooctanyl. In some
embodiments, Ring D is an optionally substituted cyclopen-
tyl or cyclohexyl. In some embodiments, Ring D is an
optionally substituted indanyl, tetrahydronaphthyl, or chro-
manyl.

Ring D may be unsubstituted or may be substituted on
either or both of its component rings, and the substituents
may be the same or different. In particular, each substitutable
saturated ring carbon atom in Ring D is unsubstituted or
substituted with =O, =S, =C(R⁵)₂, =N—N(R⁴)₂,
=N—OR⁵, =N—NHC(O)R⁵, =N—NHCO₂R⁶,
=N—NHSO₂R⁶, =N—R⁵ or —Rᵖ. Each substitutable
unsaturated ring carbon atom in Ring D is unsubstituted or
substituted with —Rᵖ. Each substitutable ring nitrogen atom
in Ring D is unsubstituted or substituted with —R⁹ᵖ. The
variables Rᵖ and R⁹ᵖ have the values described below.

Each Rᵖ independently is halo, —NO₂, —CN, —C(R⁵)
=C(R⁵)₂, —C≡C—R⁵, —OR⁵, —SR⁶, —S(O)R⁶,
—SO₂R⁶, —SO₂N(R⁴)₂, —N(R⁴)₂, —NR⁴C(O)R⁵,
—NR⁴C(O)N(R⁴)₂, —N(R⁴)C(=NR⁴)—N(R⁴)₂, —N(R')C
(=NR⁴)—R⁶, —NR⁴CO₂R⁶, —N(R⁴)SO₂R⁶, —N(R⁴)
SO₂N(R⁴)₂, —O—C(O)R⁵, —OCO₂R⁶, —OC(O)N(R⁴)₂,
—C(O)R⁵, —CO₂R⁵, —C(O)N(R⁴)₂, —C(O)N(R⁴)—OR,
—C(O)N(R⁴)C(=NR⁴)—N(R⁴)₂, —N(R⁴)C(=NR⁴)—N
(R⁴)—C(O)R⁵, —C(=NR⁴)—N(R⁴)₂, —C(=NR⁴)—OR⁵, —C(=NR⁴)—N(R⁴)—OR⁵, —C(R⁶)=N—OR⁵, or an optionally substituted aliphatic, or an optionally substituted aryl, heterocyclyl, or heteroaryl group; or two R^p on the same saturated carbon atom, taken together with the carbon atom to which they are attached, form an optionally substituted 3- to 6-membered spirocyclic cycloaliphatic ring.

Each R^{9p} independently is —C(O)R⁵, —C(O)N(R⁴)₂, —CO₂R⁶, —SO₂R⁶, —SO₂N(R⁴)₂, or a C_{1-4} aliphatic optionally substituted with R³ or R⁷.

In some embodiments, each R^p independently is selected from the group consisting of halo, C_{1-6} aliphatic, C_{1-6} fluoroaliphatic, —R^{1p}, —R^{2p}, -T²-R^{1p}, and -T²-R^{2p}; or two R^p on the same saturated carbon atom, taken together with the carbon atom to which they are attached, form an optionally substituted 3- to 6-membered spirocyclic cycloaliphatic ring. The variables R^{1p}, R^{2p}, and T² have the values described below.

T² is a C_{1-6} alkylene chain optionally substituted with R^{3a} or R^{3b}.

Each R^{1p} independently is an optionally substituted aryl, heteroaryl, or heterocyclyl group.

Each R^{2p} independently is —NO₂, —CN, —C(R⁵)=C(R⁵)₂, —C≡C—R⁵, —OR⁵, —SR⁶, —S(O)R⁶, —SO₂R⁶, —SO₂N(R⁴)₂, —N(R⁴)₂, —NR⁴C(O)R⁵, —NR⁴C(O)N(R⁴)₂, —N(R⁴)C(=NR⁴)—N(R⁴)₂, —N(R⁴)C(=NR⁴)—R⁶, —NR⁴CO₂R⁶, —N(R⁴)SO₂R⁶, —N(R⁴)SO₂N(R⁴)₂, —O—C(O)R⁵, —OCO₂R⁶, —OC(O)N(R⁴)₂, —C(O)R⁵, —CO₂R⁵, —C(O)N(R⁴)₂, —C(O)N(R⁴)—OR⁵, —C(O)N(R⁴)C(=NR⁴)—N(R⁴)₂, —N(R⁴)C(=NR⁴)—N(R⁴)—C(O)R⁵, —C(=NR⁴)—N(R⁴)₂, —C(=NR⁴)—OR⁵, —C(=NR⁴)—N(R⁴)—OR⁵, or —C(R⁶)=N—OR⁵.

In some embodiments, Ring D is selected from the group consisting of:

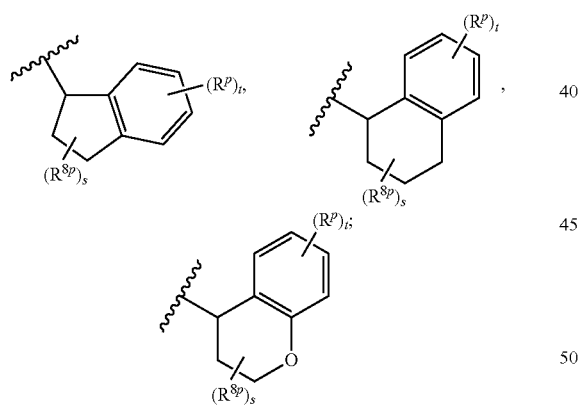

each R_p independently is selected from the group consisting of fluoro, —OR^{5x}, —N(R^{4x})(R^{4y}), —CO₂R^{5x}, or —C(O)N(R^{4x})(R^{4y}), or a C_{1-4} aliphatic or C_{1-4} fluoroaliphatic optionally substituted with —OR^{5x}, —N(R^{4x})(R^{4y}), —CO₂R^{5x}, or —C(O)N(R^{4x})(R^{4y});

each R^{8p} independently is selected from the group consisting of fluoro, —OR^{5x}, —N(R^{4x})(R^{4y}), —CO₂R^{5x}, or —C(O)N(R^{4x})(R^{4y}), or a C_{1-4} aliphatic or C_{1-4} fluoroaliphatic optionally substituted with —OR^{5x}, —N(R^{4x})(R^{4y}), —CO₂R^{5x}, or —C(O)N(R^{4x})(R^{4y}); or two R^{8p} on the same carbon atom together form =O or =C(R^{5x})₂; provided that R^{8p} is other than —OR^{5x} or —N(R^{4x})(R^{4y}) when located at a position adjacent to a ring oxygen atom;

s is 0, 1, 2, 3, or 4;

t is 0, 1, or 2; and the variables R^{4x}, R^{4y}, R^{5x} have the values described above for formula (I).

In some embodiments, s is 0, 1, or 2. In some embodiments, s is 0, 1, 2, or 3. In certain embodiments, Ring D is selected from the group consisting of:

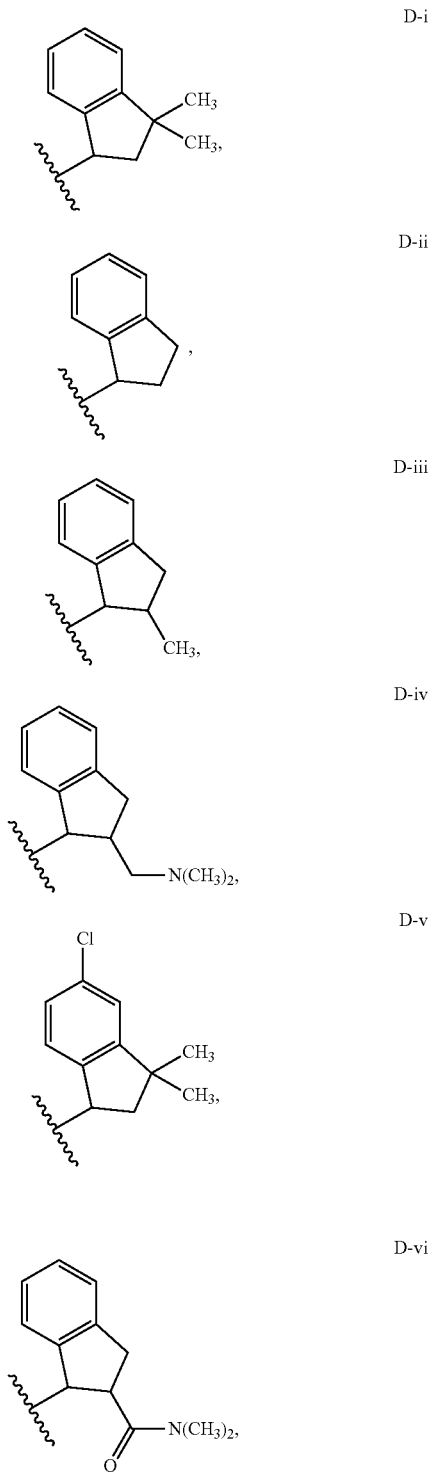

-continued
D-vii 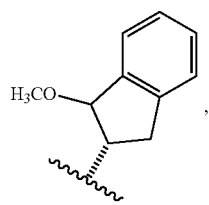
D-viii 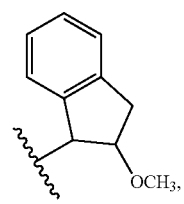
D-ix 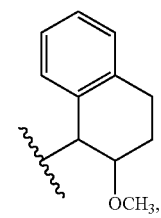
D-x 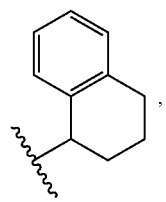
D-xi 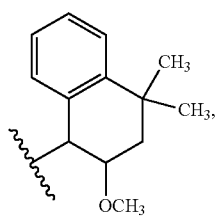
D-xii 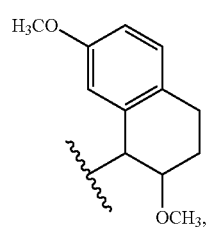
D-xiii 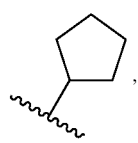
-continued
D-xiv 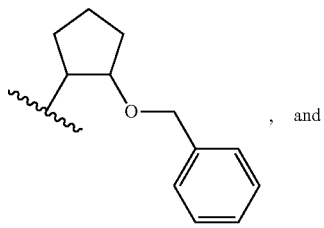, and
D-xv 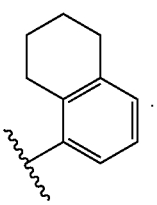.
In certain particular embodiments, Ring D is selected from the group consisting of:
D-xvi 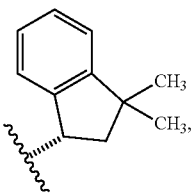
D-xvii 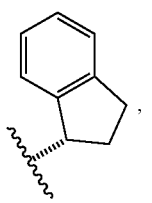
D-xviii 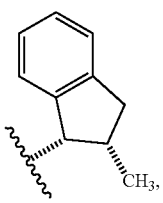
D-xix 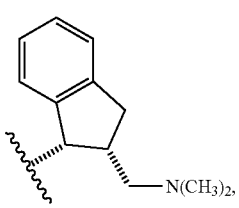

-continued
D-xx 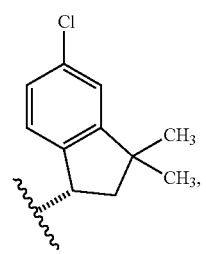
D-xxi 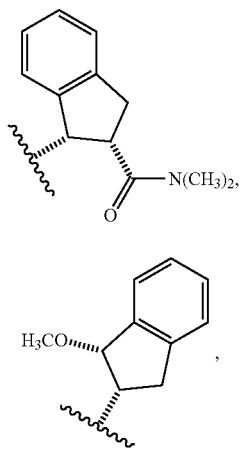
D-xxii 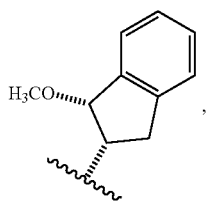
D-xxiii 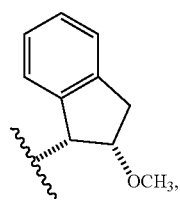
D-xxiv 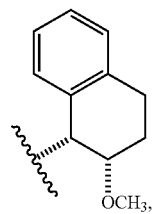
D-xxv 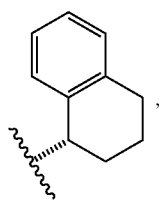
D-xxvi 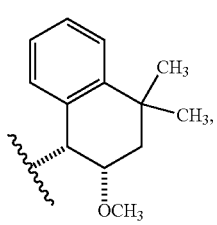
D-xxvii 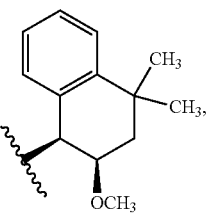
D-xxviii 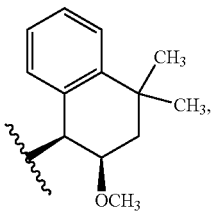
D-xxix 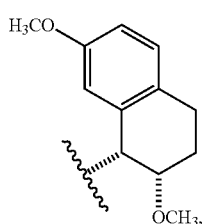
D-xxx 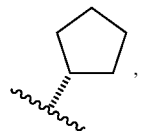
D-xxxi 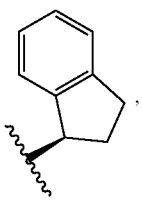
D-xxxii 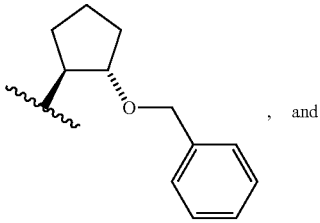, and
D-xxxiii 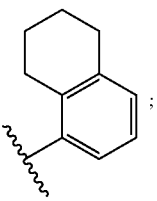;
wherein stereochemical designations indicate absolute configurations.
The invention also relates to a subgenus of the compounds of formula (II), wherein:
$R^g$ is $—N(R^8)(R^9)$;
$R^8$ is hydrogen or $C_{1-4}$ aliphatic;

$R^9$ is hydrogen, $C_{1-4}$ aliphatic, $-T^3-R^{9a}$ or $-T^4-R^{9b}$;

$T^3$ is a $C_{1-6}$ alkylene chain substituted with 0-2 independently selected $R^{3a}$ or $R^{3b}$;

$T^4$ is a $C_{2-6}$ alkylene chain substituted with 0-2 independently selected $R^{3a}$ or $R^{3b}$;

$R^{9a}$ is $-C(R^5)-C(R^5)_2$, $-C\equiv C-R^5$, $-S(O)R^6$, $-SO_2R^6$, $-SO_2-N(R^4)_2$, $-C(R^5)-N-OR^5$, $-CO_2R^5$, $-C(O)-C(O)R^5$, $-C(O)R^5$, $-C(O)N(R^4)_2$, $-C(=NR^4)-N(R^4)_2$, or $-C(=NR^4)-OR^5$; and $R^{9b}$ is halo, $-NO_2$, $-CN$, $-OR^5$, $-SR^6$, $-N(R^4)_2$, $-N(R^4)C(O)R^5$, $-N(R^4)C(O)N(R^4)_2$, $-N(R^4)CO_2R^5$, $-O-CO_2-R^5$, $-OC(O)N(R^4)_2$, $-OC(O)R^5$, $-N(R^4)-N(R^4)_2$, $-N(R^4)S(O)_2R^6$, or $-N(R^4)SO_2-N(R^4)_2$.

In some such embodiments, $R^9$ is hydrogen or a $C_{1-6}$ aliphatic or $C_{1-6}$ fluoroaliphatic optionally substituted with one or two substituents independently selected from the group consisting of $-OR^{5x}$, $-N(R^{4x})(R^{4y})$, $-CO_2R^{5x}$, $-C(O)N(R^{4x})(R^{4y})$.

Another embodiment of the invention relates to a subgenus of the compounds of formula (I) characterized by formula (V), (V-A), or (V-B):

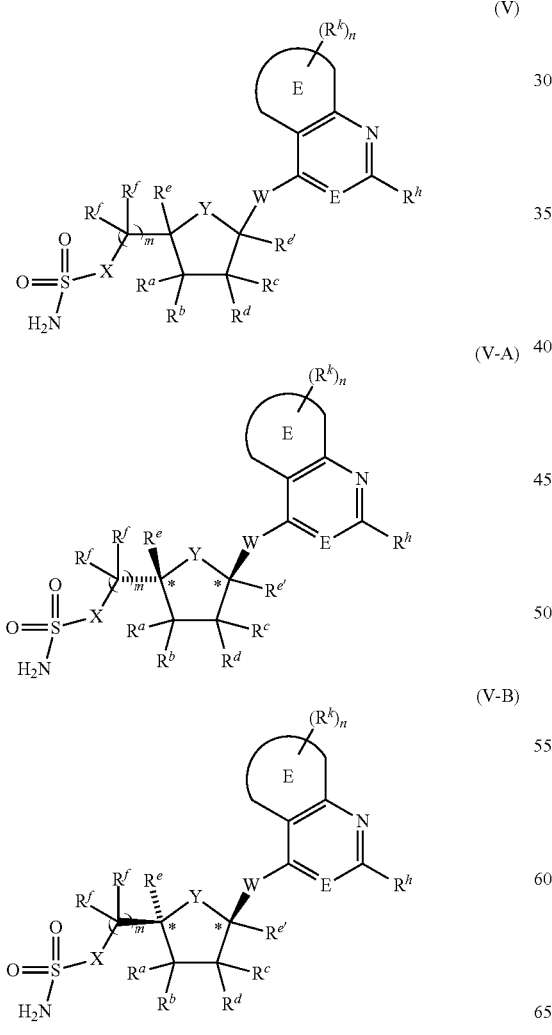

or a pharmaceutically acceptable salt thereof, wherein:

Ring E is a 5- or 6-membered aryl, heteroaryl, cycloaliphatic or heterocyclic ring;

E is $-N=$ or $-C(R^h)-$;

each $R^h$ independently is hydrogen, halo, $-CN-$, $-OR^5$, $-N(R^4)_2$, $-SR^6$, or an optionally substituted $C_{1-4}$ aliphatic group;

each $R^k$ independently is hydrogen, halo, $-NO_2$, $-CN$, $-OR^5$, $-SR^6$, $-S(O)R^6$, $-SO_2R^6$, $-SO_2N(R^4)_2$, $-N(R^4)_2$, $-NR^4C(O)R^5$, $-NR^4C(O)N(R^4)_2$, $-N(R^4)C(=NR^4)-N(R^4)_2$, $-N(R^4)C(=NR^4)-R^6$, $-NR^4CO_2R^6$, $-N(R^4)SO_2R^6$, $-N(R^4)SO_2N(R^4)_2$, $-O-C(O)R^5$, $-OCO_2R^6$, $-OC(O)N(R^4)_2$, $-C(O)R^5$, $-CO_2R^5$, $-C(O)N(R^4)_2$, $-C(O)N(R^4)-OR$, $-C(O)N(R^4)C(=NR^4)-N(R^4)_2$, $-N(R^4)C(=NR^4)-N(R^4)-C(O)R^5$, $-C(=NR^4)-N(R^4)_2$, $-C(=NR^4)-OR^5$, $-N(R^4)-N(R^4)_2$, $-N(R^4)-OR^5$, $-C(=NR^4)-N(R^4)-OR^5$, $-C(R^6)=N-OR^5$, or an optionally substituted aliphatic, aryl, heteroaryl, or heterocyclyl;

n is 0, 1, 2, or 3; and the variables W, X, Y, $R^a$, $R^b$, $R^c$, $R^d$, $R^e$, $R^{e'}$, $R^f$, and m have the values and preferred values described above for formula (I).

In some embodiments, $R^k$ is an optionally substituted $C_{1-6}$ aliphatic, or an optionally substituted 5- or 6-membered aryl, heteroaryl, or heteroaryl ring.

In some embodiments, the invention relates to a subgenus of the compounds of formula (V) characterized by formula (VI), (VI-A), or (VI-B):

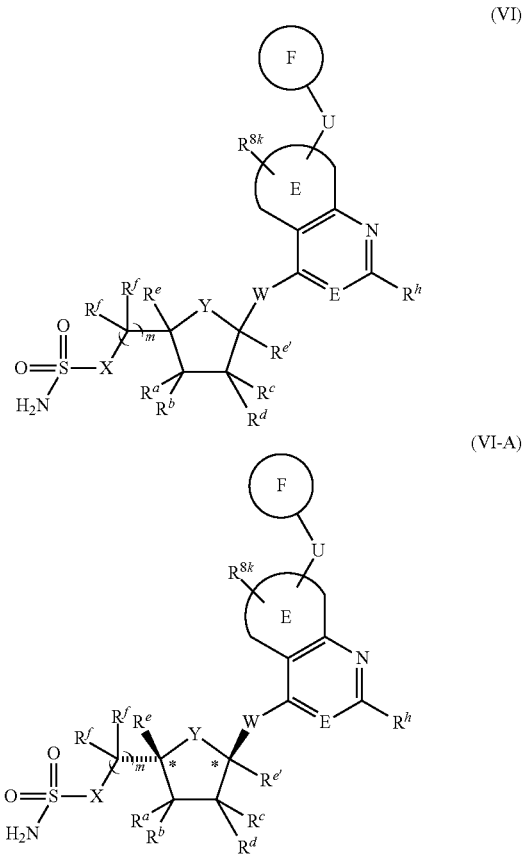

-continued

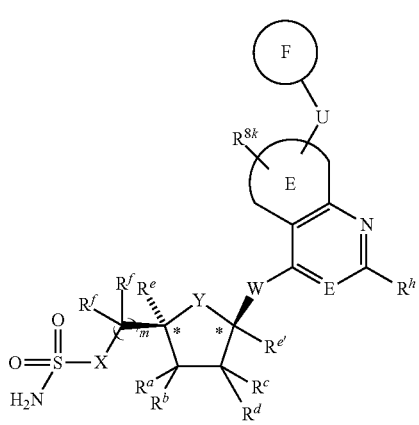

(VI-B)

or a pharmaceutically acceptable salt thereof, wherein:
U is a covalent bond, $C_{1-3}$ alkylene, —O—, —S—, —S(O)—, or —S(O)$_2$—;
$R^{8k}$ is halo, $C_{1-4}$ aliphatic, or $C_{1-4}$ fluoroaliphatic;
Ring F is an optionally substituted mono-, bi-, or tricyclic ring system; and
Ring E, and the variables E, W, X, Y, $R^a$, $R^b$, $R^c$, $R^d$, $R^e$, $R^{e'}$, $R^f$, $R^h$, and m have the values and preferred values described above for formula (V).

In some embodiments, Ring F is selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, purinyl, quinolyl, isoquinolyl, cinnolinyl, phthalazinyl, quinazolinyl, quinoxalinyl, naphthyridinyl, pteridinyl, carbazolyl, fluorenyl, dibenzofuranyl tetrahydrofuranyl, tetrahydrothienyl, pyrrolidinyl, pyrrolidonyl, piperidinyl, pyrrolinyl, dihydrobenzofuranyl, dihydrobenzothienyl tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, tetrahydroquinolinyl, tetrahydroisoquinolinyl, indanyl, phenanthridinyl, tetrahydronaphthyl, indolinyl, benzodioxanyl, benzodioxolyl, chromanyl, cyclopropyl, cyclobutyl, cyclopentyl, cyclopentenyl, cyclohexyl, cyclohexenyl, cycloheptyl, cycloheptenyl, cyclooctyl, cyclooctenyl, cyclooctadienyl, bicycloheptanyl and bicyclooctanyl, any of which optionally is substituted on any substitutable ring carbon atom and any substitutable ring nitrogen atom.

In some embodiments, Ring F is selected from the group consisting of thienyl, oxazolyl, thiazolyl, imidazolyl, pyrazolyl, isoxazolyl, isothiazolyl, phenyl, naphthyl, indolyl, isoindolyl, benzimidazolyl, benzthiazolyl, benzothienyl, benzofuranyl, quinolyl, isoquinolyl, naphthyridinyl, carbazolyl, fluorenyl, dibenzofuranyl, dihydrobenzofuranyl, dihydrobenzothienyl, tetrahydroquinolinyl, tetrahydroisoquinolinyl, tetrahydronaphthyl, indolinyl, benzodioxanyl, benzodioxolyl, cyclopentyl, cyclohexyl, any of which optionally is substituted on any substitutable ring carbon atom and any substitutable ring nitrogen atom. In particular embodiments, Ring F is an optionally substituted phenyl, naphthyl, tetrahydronaphthyl, or dihydrobenzofuranyl.

In some embodiments, each substitutable ring nitrogen atom in Ring F is unsubstituted or is substituted with $R^{9f}$, and the substitutable ring carbon atoms are substituted with 0-4 $R^{8f}$, wherein:

each $R^{8f}$ independently is selected from the group consisting of $C_{1-4}$ aliphatic, $C_{1-4}$ fluoroaliphatic, halo, —OR$^{5x}$, —N(R$^{4x}$)(R$^{4y}$), an optionally substituted 5- or 6-membered aromatic ring, or a $C_{1-4}$ aliphatic or $C_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$);
$R^{9f}$ independently is —C(O)R$^5$, —C(O)N(R$^4$)$_2$, —CO$_2$R$^6$, —SO$_2$R$^6$, —SO$_2$N(R$^4$)$_2$, or a $C_{1-4}$ aliphatic optionally substituted with R$^3$ or R$^7$; and the variables R$^3$, R$^{4x}$, R$^{4y}$, R$^{5x}$, and R$^7$ have the values described above for formula (I).

The invention also relates to a subgenus of the compounds of formula (V) characterized by formula (VII), (VI-A), or (VII-B):

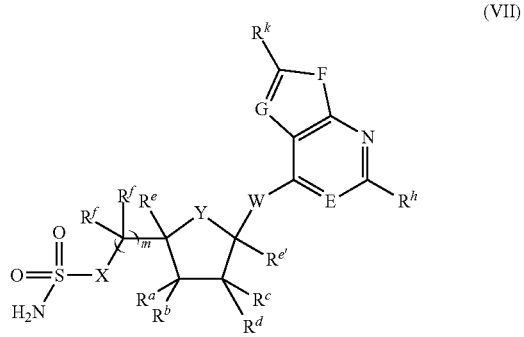

(VII)

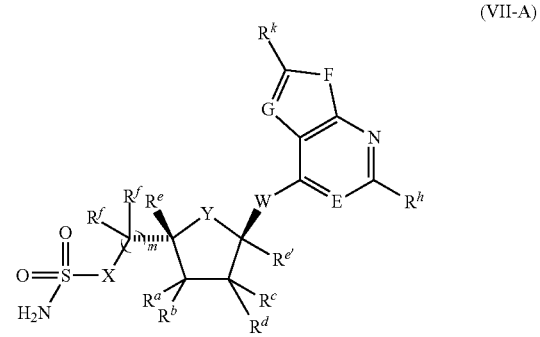

(VII-A)

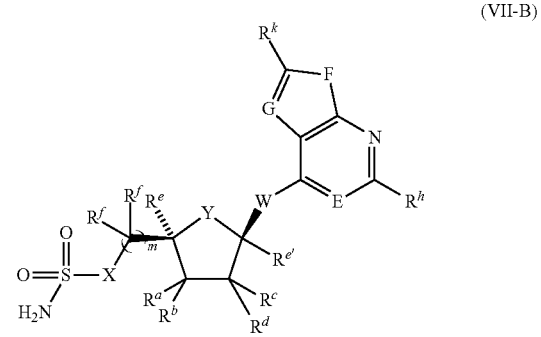

(VII-B)

or a pharmaceutically acceptable salt thereof, wherein:
E is —N═ or —C(R$^h$)═;
F is —N(R$^{9k}$)—, —O—, or —S—;
G is —N═ or —C(R$^k$)═;
$R^{9k}$ is hydrogen, —C(O)R$^5$, —C(O)N(R$^4$)$_2$, —CO$_2$R$^6$, —SO$_2$R$^6$, —SO$_2$N(R$^4$)$_2$, or a $C_{1-4}$ aliphatic optionally substituted with R$^3$ or R$^7$;
each $R^h$ independently is hydrogen, halo, —CN—, —OR$^5$, —N(R$^4$)$_2$, —SR$^6$, or an optionally substituted $C_{1-4}$ aliphatic group;
each $R^k$ independently is hydrogen, halo, —NO$_2$, —CN, —OR$^5$, —SR$^6$, —S(O)R$^6$, —SO$_2$R$^6$, —SO$_2$N(R$^4$)$_2$, —N(R⁴)₂, —NR⁴C(O)R⁵, —NR⁴C(O)N(R⁴)₂, —N(R⁴)C(=NR⁴)—N(R⁴)₂, —N(R⁴)C(=NR⁴)—R⁶, —NR⁴CO₂R⁶, —N(R⁴)SO₂R⁶, —N(R⁴)SO₂N(R⁴)₂, —O—C(O)R⁵, —OCO₂R⁶, —OC(O)N(R⁴)₂, —C(O)R⁵, —CO₂R⁵, —C(O)N(R⁴)₂, —C(O)N(R⁴)—OR⁵, —C(O)N(R⁴)C(=NR)—N(R⁴)₂, —N(R⁴)C(=NR⁴)—N(R⁴)—C(O)R⁵, —C(=NR⁴)—N(R⁴)₂, —C(=NR⁴)—OR⁵, —N(R⁴)—N(R⁴)₂, —N(R⁴)—OR⁵, —C(=NR⁴)—N(R⁴)—OR⁵, —C(R⁶)=N—OR⁵, or an optionally substituted aliphatic, aryl, heteroaryl, or heterocyclyl; and the variables W, X, Y, $R^a$, $R^b$, $R^c$, $R^d$, $R^e$, $R^{e'}$, $R^f$, $R^3$, $R^4$, $R^5$, $R^6$, $R^7$, and m have the values and preferred values described above for formula (I).

In certain embodiments, the invention relates to a subgenus of the compounds of formula (VII), characterized by formula (VII-C) or (VII-D):

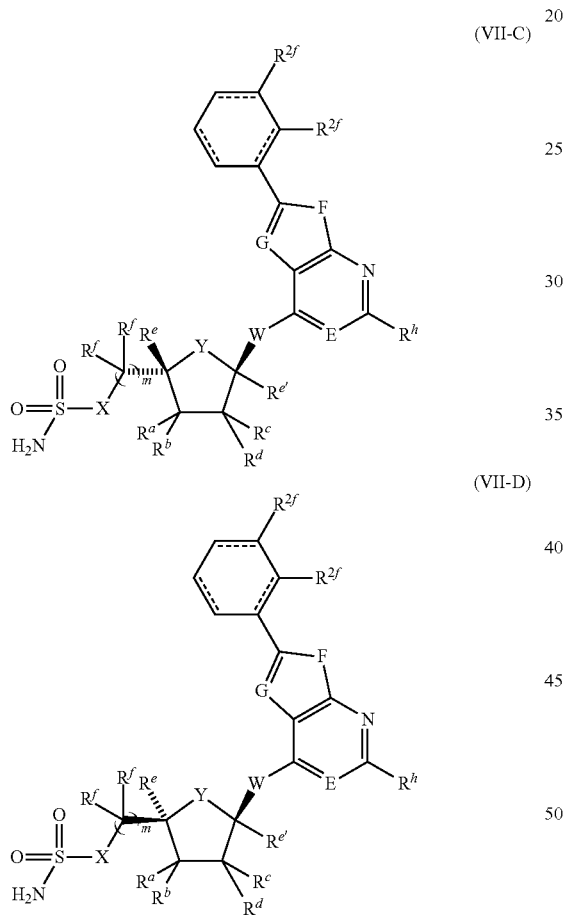

or a pharmaceutically acceptable salt thereof, wherein:
dashed lines indicate single or double bonds;
each $R^{2f}$ independently is hydrogen, halo, —OR⁵ˣ, —N(R⁴ˣ)(R⁴ʸ), or a $C_{1-4}$ aliphatic or $C_{1-4}$ fluoroaliphatic optionally substituted with —OR⁵ˣ, —N(R⁴ˣ)(R⁴ʸ), —CO₂R⁵ˣ, or —C(O)N(R⁴ˣ)(R⁴ʸ); or both $R^{2f}$, taken together with the intervening ring carbon atoms, form an optionally substituted fused 5- or 6-membered cycloaliphatic, aryl, heteroaryl, or heterocyclic ring.

The invention also relates to a subgenus of the compounds of formula (V) characterized by formula (VIII), (VIII-A), or (VIII-B):

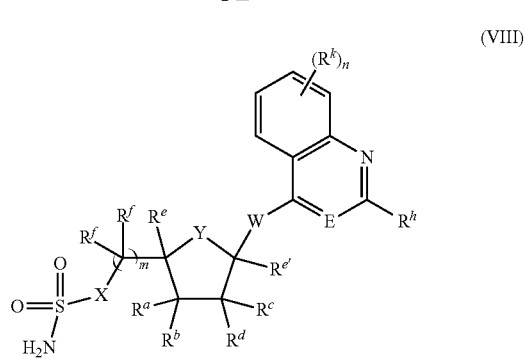

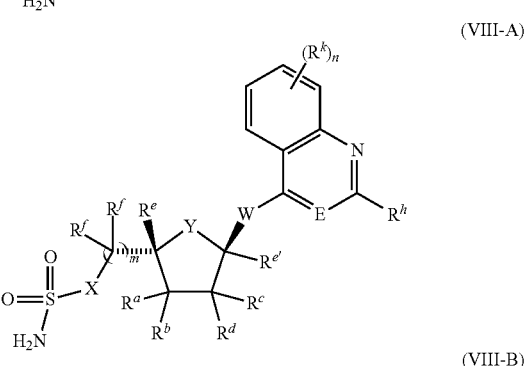

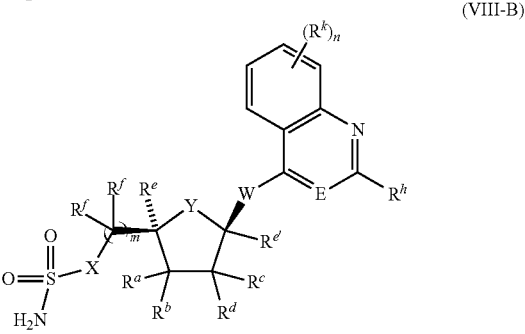

or a pharmaceutically acceptable salt thereof, wherein:
the variables E, W, X, Y, $R^a$, $R^b$, $R^c$, $R^d$, $R^e$, $R^{e'}$, $R^f$, $R^h$, $R^k$, and m have the values and preferred values described above for formulae (VII), (VII-A), and (VII-B).

In some embodiments, $R^k$ in formula (VI), (VII-A), (VII-B), (VIII), (VIII-A), or (VIII-B) has the formula —U-Ring F, wherein the variable U and Ring F have the values and preferred values described above for formula (VI). In some such embodiments, the variable U is a covalent bond.

In a particular embodiment, the invention relates to a subgenus of the compounds of formula (I), characterized by formula (IX-A) or (IX-B):

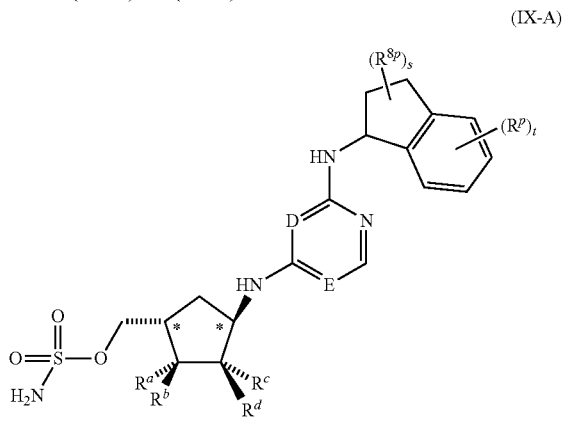

-continued (IX-B)

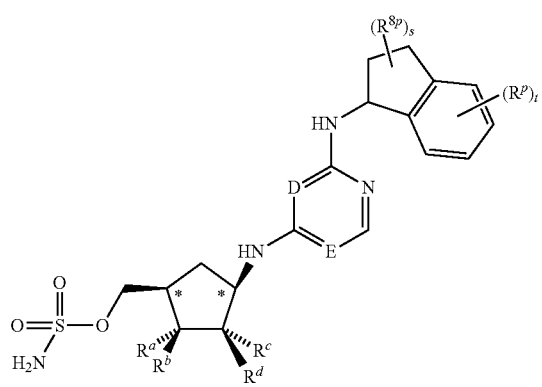

or a pharmaceutically acceptable salt thereof, wherein:
the variables D, E, $R^a$, $R^b$, $R^c$, $R^d$, $R^p$, $R^{8p}$, s, and t have the values and preferred values described above for formulae (I)-(IV).

In some embodiments, the stereochemical configurations depicted at asterisked positions in any preceding formula indicate relative stereochemistry. In other embodiments, stereochemical configurations depicted at asterisked positions indicate absolute stereochemistry. In certain particular embodiments, the invention relates to compounds of formula (I-A), (II-A), (III-A), (IV-A) (V-A), (VI-A), (VII-A), (VIII-A), or (IX-A), wherein the stereochemical configurations depicted at asterisked positions indicate absolute stereochemistry.

Subgenus definitions for Ring A and variables W, X, Y, $R^a$, $R^b$, $R^c$, $R^d$, $R^e$, $R^{e'}$ and $R^f$ described for formula (I) also apply to formulae (II)-(IX). Compounds embodying any combination of the preferred values for the variables described herein are within the scope of the present invention.

Representative examples of compounds of formula (I) are shown in Table 1.

TABLE 1

E1 Activating Enzyme Inhibitors

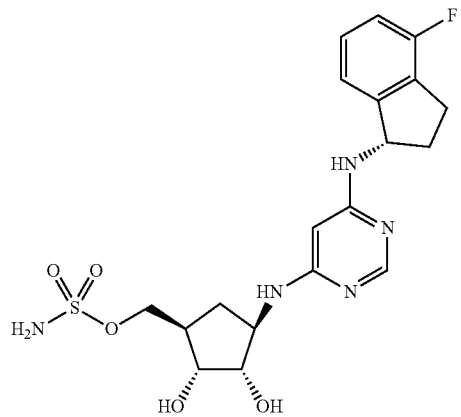 [SMILES: NS(=O)(=O)OC[C@H]1C[C@@H](Nc2cc(N[C@H]3CCc4c(F)cccc43)ncn2)[C@H](O)[C@@H]1O]

I-1

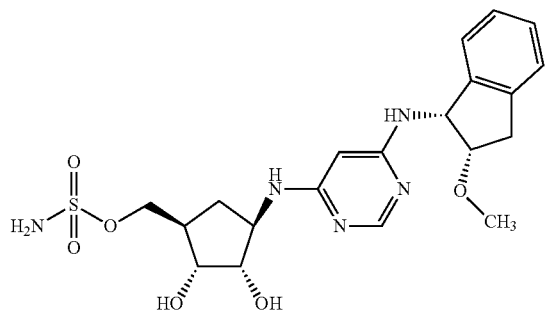 [SMILES: CO[C@H]1Cc2ccccc2[C@H]1Nc1cc(N[C@@H]2C[C@H](COS(N)(=O)=O)[C@@H](O)[C@H]2O)ncn1]

I-2

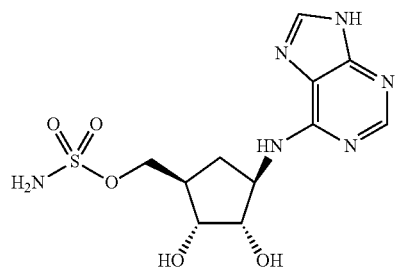 [SMILES: NS(=O)(=O)OC[C@H]1C[C@@H](Nc2ncnc3[nH]cnc23)[C@H](O)[C@@H]1O]

I-3

TABLE 1-continued
E1 Activating Enzyme Inhibitors
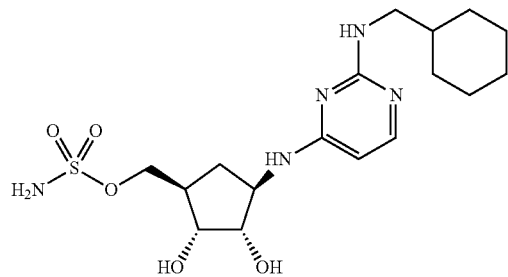 [SMILES: NS(=O)(=O)OC[C@H]1C[C@@H](Nc2ccnc(NCC3CCCCC3)n2)[C@H](O)[C@@H]1O]
I-4
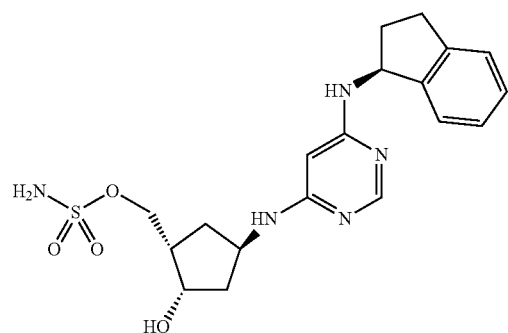 [SMILES: NS(=O)(=O)OC[C@@H]1C[C@@H](Nc2cc(N[C@H]3CCc4ccccc43)ncn2)C[C@@H]1O]
I-5
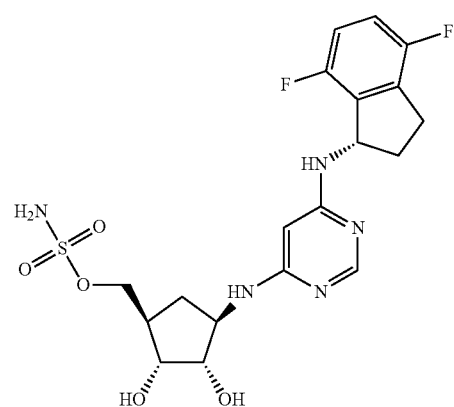 [SMILES: NS(=O)(=O)OC[C@H]1C[C@@H](Nc2cc(N[C@H]3CCc4c(F)ccc(F)c43)ncn2)[C@H](O)[C@@H]1O]
I-6
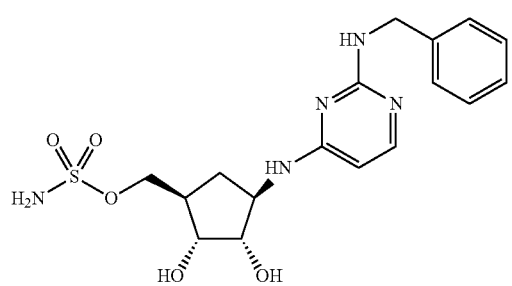 [SMILES: NS(=O)(=O)OC[C@H]1C[C@@H](Nc2ccnc(NCc3ccccc3)n2)[C@H](O)[C@@H]1O]
I-7

TABLE 1-continued
E1 Activating Enzyme Inhibitors
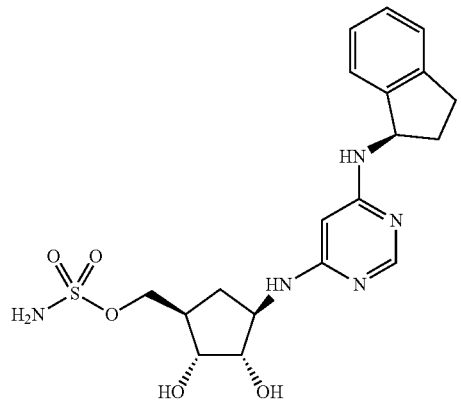 [SMILES: NS(=O)(=O)OC[C@H]1C[C@@H](Nc2cc(N[C@@H]3CCc4ccccc43)ncn2)[C@H](O)[C@@H]1O]
I-8
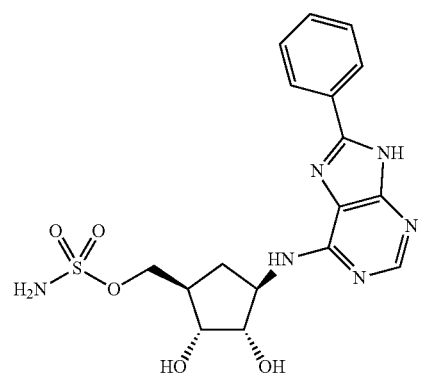 [SMILES: NS(=O)(=O)OC[C@H]1C[C@@H](Nc2ncnc3[nH]c(-c4ccccc4)nc23)[C@H](O)[C@@H]1O]
I-9
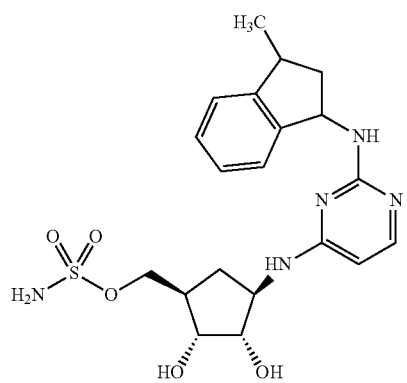 [SMILES: CC1CC(Nc2nccc(N[C@@H]3C[C@H](COS(N)(=O)=O)[C@@H](O)[C@H]3O)n2)c2ccccc21]
I-10
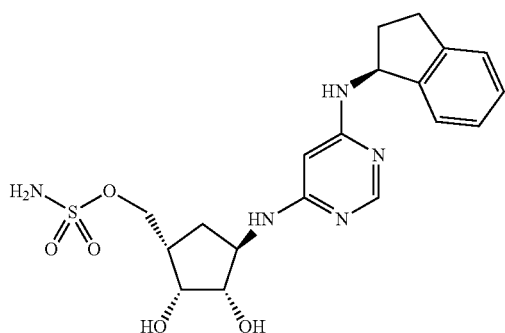 [SMILES: NS(=O)(=O)OC[C@@H]1C[C@@H](Nc2cc(N[C@H]3CCc4ccccc43)ncn2)[C@H](O)[C@@H]1O]
I-11

TABLE 1-continued
E1 Activating Enzyme Inhibitors
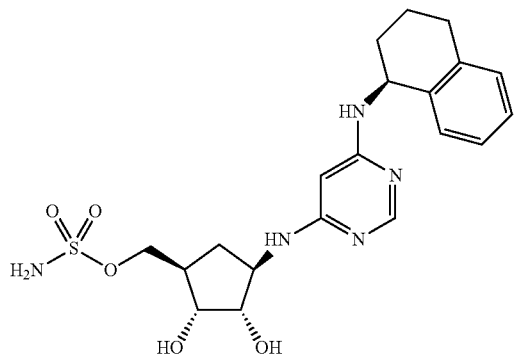 [SMILES: NS(=O)(=O)OC[C@H]1C[C@@H](Nc2cc(N[C@H]3CCCc4ccccc43)ncn2)[C@H](O)[C@@H]1O]
I-12
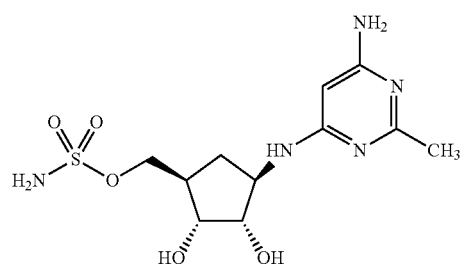 [SMILES: Cc1nc(N)cc(N[C@@H]2C[C@H](COS(N)(=O)=O)[C@@H](O)[C@H]2O)n1]
I-13
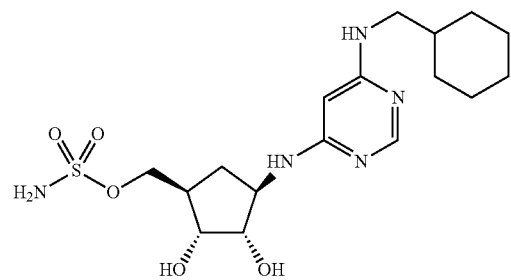 [SMILES: NS(=O)(=O)OC[C@H]1C[C@@H](Nc2cc(NCC3CCCCC3)ncn2)[C@H](O)[C@@H]1O]
I-14
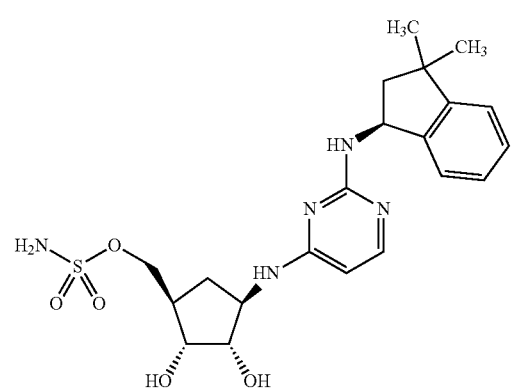 [SMILES: CC1(C)C[C@H](Nc2nccc(N[C@@H]3C[C@H](COS(N)(=O)=O)[C@@H](O)[C@H]3O)n2)c2ccccc21]
I-15
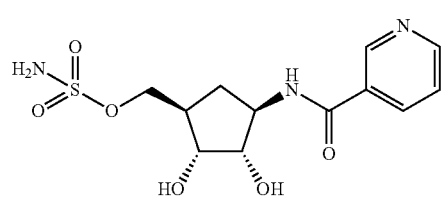 [SMILES: NS(=O)(=O)OC[C@H]1C[C@@H](NC(=O)c2cccnc2)[C@H](O)[C@@H]1O]
I-16

TABLE 1-continued
E1 Activating Enzyme Inhibitors
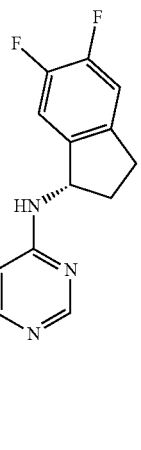
I-17
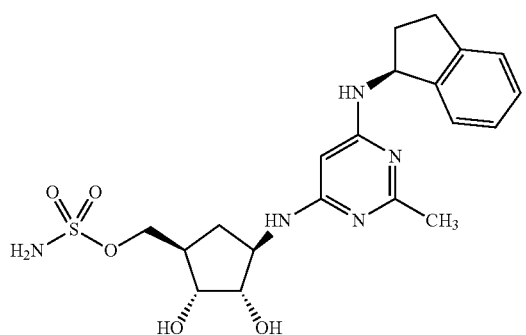 [SMILES: Cc1nc(N[C@H]2CCc3ccccc32)cc(N[C@@H]2C[C@H](COS(N)(=O)=O)[C@@H](O)[C@H]2O)n1]
I-18
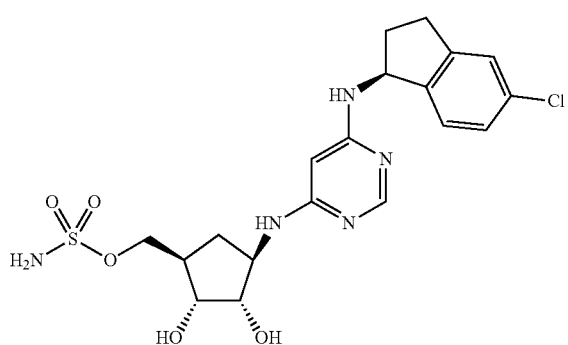 [SMILES: NS(=O)(=O)OC[C@H]1C[C@@H](Nc2cc(N[C@H]3CCc4cc(Cl)ccc43)ncn2)[C@H](O)[C@@H]1O]
I-19
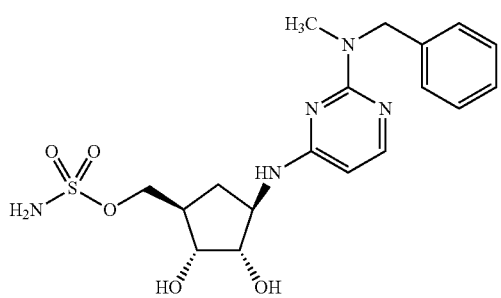 [SMILES: CN(Cc1ccccc1)c1nccc(N[C@@H]2C[C@H](COS(N)(=O)=O)[C@@H](O)[C@H]2O)n1]
I-20

TABLE 1-continued
E1 Activating Enzyme Inhibitors
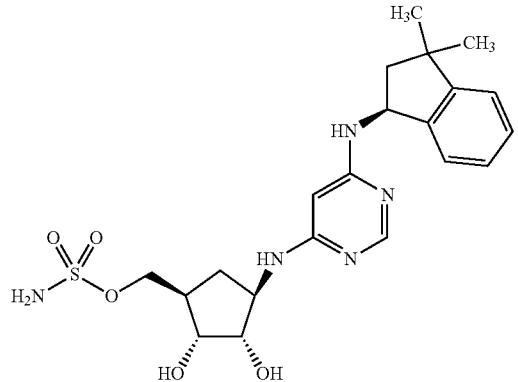 [SMILES: CC1(C)C[C@H](Nc2cc(N[C@@H]3C[C@H](COS(N)(=O)=O)[C@@H](O)[C@H]3O)ncn2)c2ccccc21]
I-21
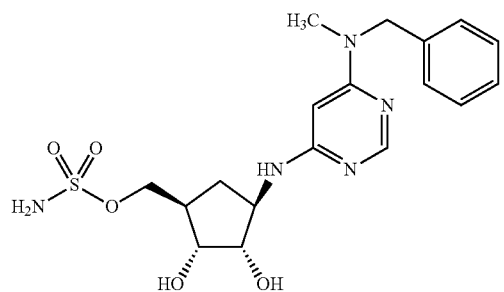 [SMILES: CN(Cc1ccccc1)c1cc(N[C@@H]2C[C@H](COS(N)(=O)=O)[C@@H](O)[C@H]2O)ncn1]
I-22
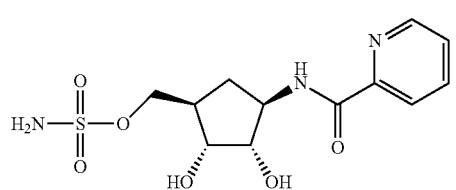 [SMILES: NS(=O)(=O)OC[C@H]1C[C@@H](NC(=O)c2ccccn2)[C@H](O)[C@@H]1O]
I-23
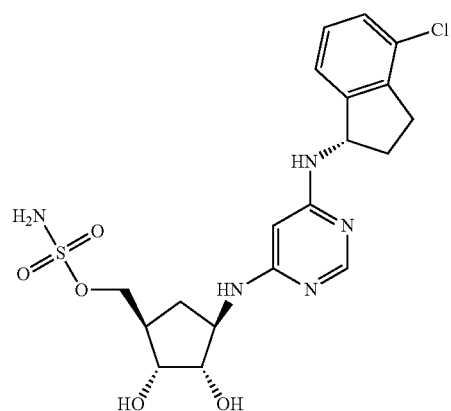 [SMILES: NS(=O)(=O)OC[C@H]1C[C@@H](Nc2cc(N[C@H]3CCc4c(Cl)cccc43)ncn2)[C@H](O)[C@@H]1O]
I-24

TABLE 1-continued
E1 Activating Enzyme Inhibitors
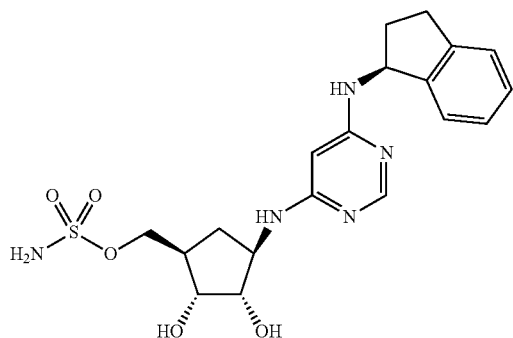 [SMILES: NS(=O)(=O)OC[C@H]1C[C@@H](Nc2cc(N[C@H]3CCc4ccccc43)ncn2)[C@H](O)[C@@H]1O]
I-25
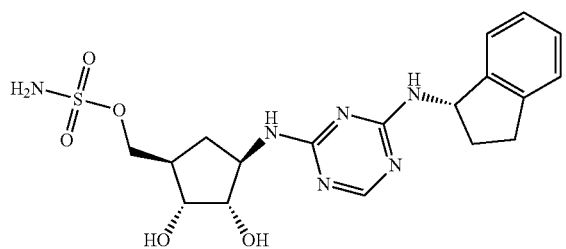 [SMILES: NS(=O)(=O)OC[C@H]1C[C@@H](Nc2ncnc(N[C@H]3CCc4ccccc43)n2)[C@H](O)[C@@H]1O]
I-26
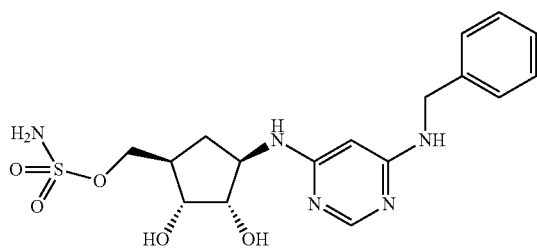 [SMILES: NS(=O)(=O)OC[C@H]1C[C@@H](Nc2cc(NCc3ccccc3)ncn2)[C@H](O)[C@@H]1O]
I-27
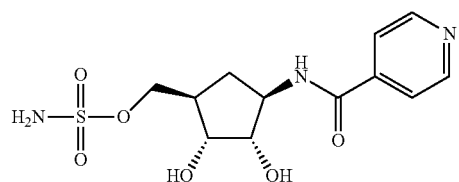 [SMILES: NS(=O)(=O)OC[C@H]1C[C@@H](NC(=O)c2ccncc2)[C@H](O)[C@@H]1O]
I-28
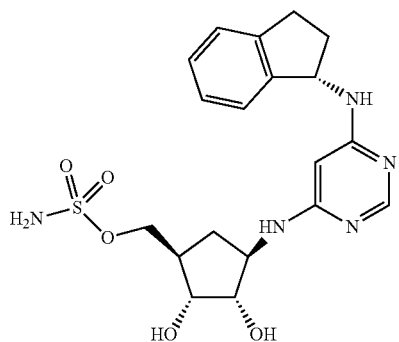 [SMILES: NS(=O)(=O)OC[C@H]1C[C@@H](Nc2cc(N[C@H]3CCc4ccccc43)ncn2)[C@H](O)[C@@H]1O]
I-29

TABLE 1-continued
E1 Activating Enzyme Inhibitors
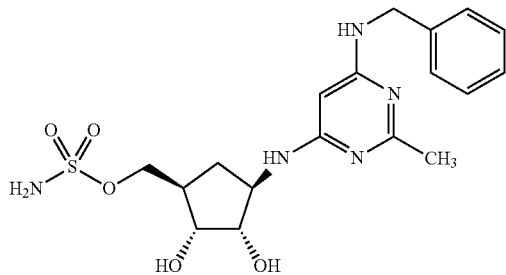 [SMILES: Cc1nc(NCc2ccccc2)cc(N[C@@H]2C[C@H](COS(N)(=O)=O)[C@@H](O)[C@H]2O)n1]
I-30
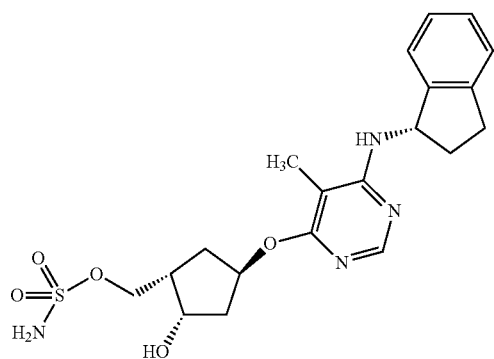 [SMILES: Cc1c(N[C@H]2CCc3ccccc32)ncnc1O[C@@H]1C[C@@H](COS(N)(=O)=O)[C@@H](O)C1]
I-31
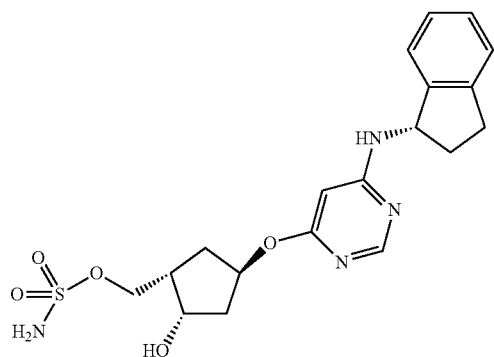 [SMILES: NS(=O)(=O)OC[C@@H]1C[C@@H](Oc2cc(N[C@H]3CCc4ccccc43)ncn2)C[C@@H]1O]
I-32
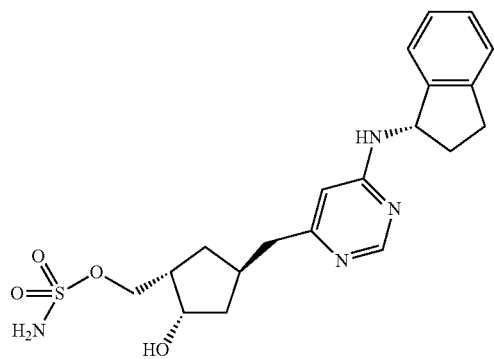 [SMILES: NS(=O)(=O)OC[C@@H]1C[C@@H](Cc2cc(N[C@H]3CCc4ccccc43)ncn2)C[C@@H]1O]
I-33

TABLE 1-continued
E1 Activating Enzyme Inhibitors
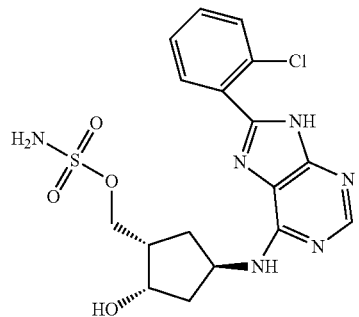 [SMILES: NS(=O)(=O)OC[C@@H]1C[C@@H](Nc2ncnc3[nH]c(-c4ccccc4Cl)nc23)C[C@@H]1O]
I-34
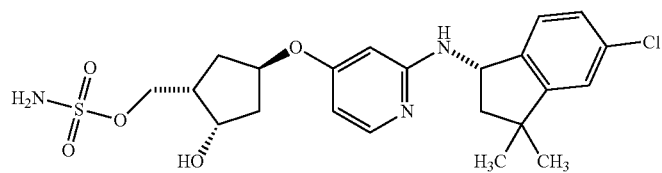
I-35
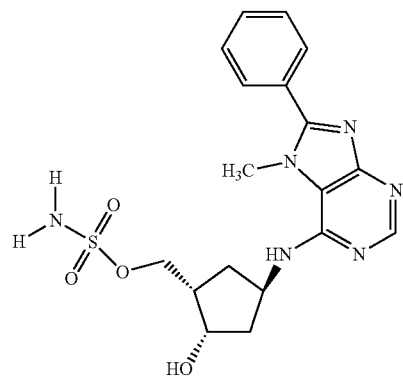 [SMILES: Cn1c(-c2ccccc2)nc2ncnc(N[C@@H]3C[C@@H](COS(N)(=O)=O)[C@@H](O)C3)c21]
I-36
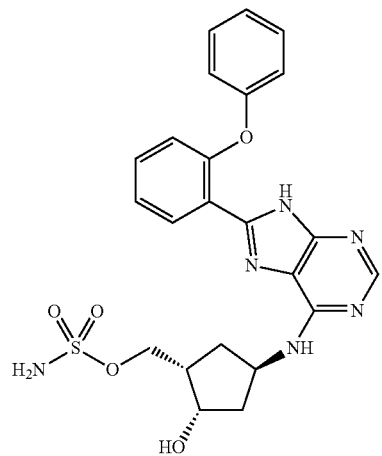 [SMILES: NS(=O)(=O)OC[C@@H]1C[C@@H](Nc2ncnc3[nH]c(-c4ccccc4Oc4ccccc4)nc23)C[C@@H]1O]
I-37

TABLE 1-continued
E1 Activating Enzyme Inhibitors
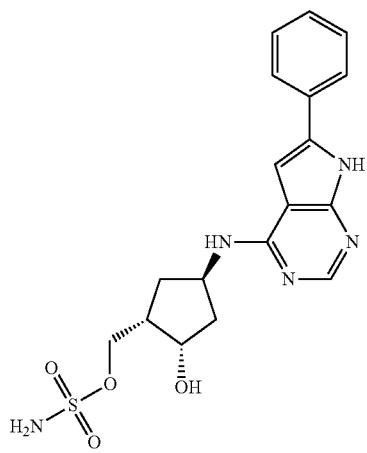 [SMILES: NS(=O)(=O)OC[C@@H]1C[C@@H](Nc2ncnc3[nH]c(-c4ccccc4)cc23)C[C@@H]1O]
I-38
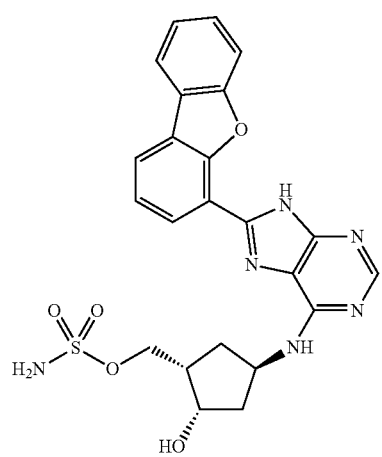 [SMILES: NS(=O)(=O)OC[C@@H]1C[C@@H](Nc2ncnc3[nH]c(-c4cccc5c4oc4ccccc45)nc23)C[C@@H]1O]
I-39
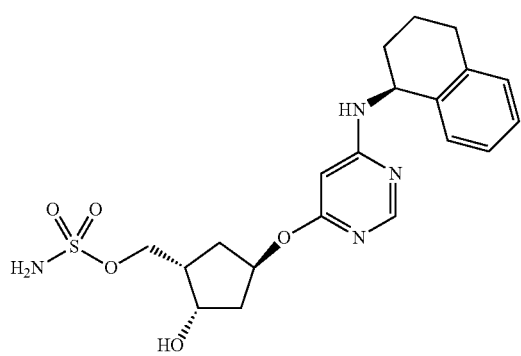 [SMILES: NS(=O)(=O)OC[C@@H]1C[C@@H](Oc2cc(N[C@H]3CCCc4ccccc43)ncn2)C[C@@H]1O]
I-40
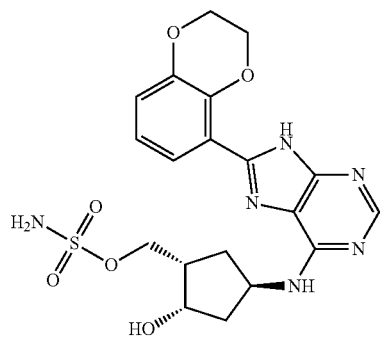 [SMILES: NS(=O)(=O)OC[C@@H]1C[C@@H](Nc2ncnc3[nH]c(-c4cccc5c4OCCO5)nc23)C[C@@H]1O]
I-41

TABLE 1-continued
E1 Activating Enzyme Inhibitors
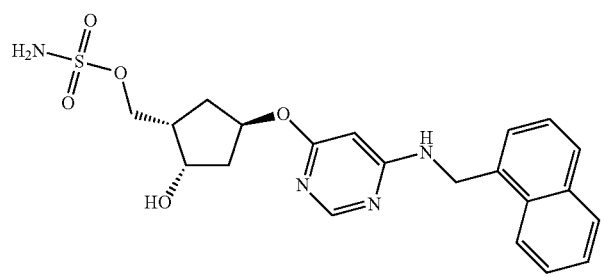
I-42
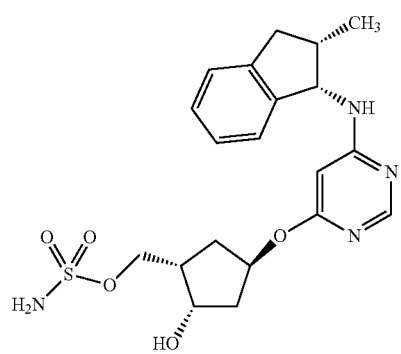 [SMILES: C[C@H]1Cc2ccccc2[C@H]1Nc1cc(O[C@@H]2C[C@@H](COS(N)(=O)=O)[C@@H](O)C2)ncn1]
I-43
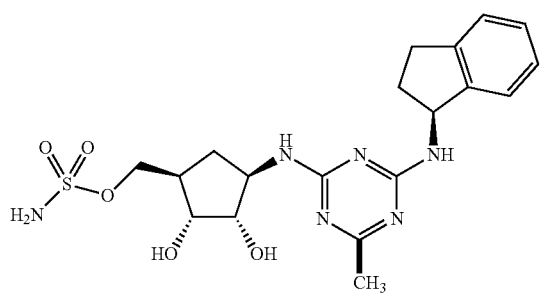
I-45
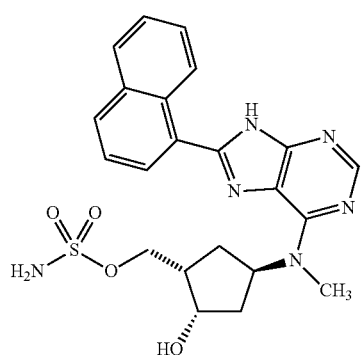 [SMILES: CN(c1ncnc2[nH]c(-c3cccc4ccccc34)nc12)[C@@H]1C[C@@H](COS(N)(=O)=O)[C@@H](O)C1]
I-46
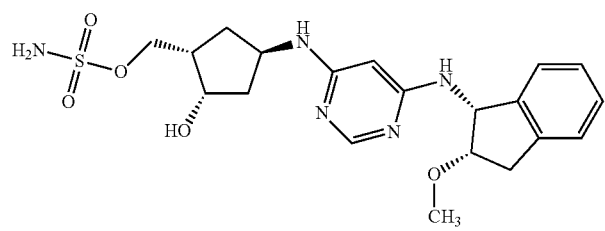
I-47

TABLE 1-continued
E1 Activating Enzyme Inhibitors
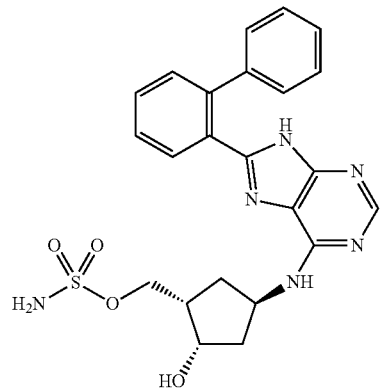 [SMILES: NS(=O)(=O)OC[C@@H]1C[C@@H](Nc2ncnc3[nH]c(-c4ccccc4-c4ccccc4)nc23)C[C@@H]1O]
I-48
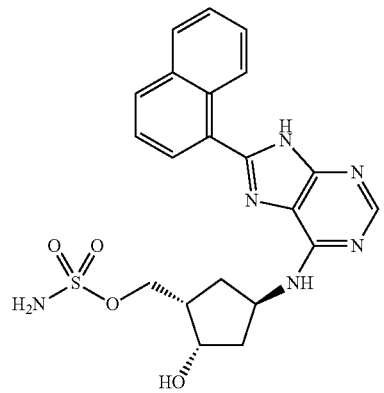 [SMILES: NS(=O)(=O)OC[C@@H]1C[C@@H](Nc2ncnc3[nH]c(-c4cccc5ccccc45)nc23)C[C@@H]1O]
I-49
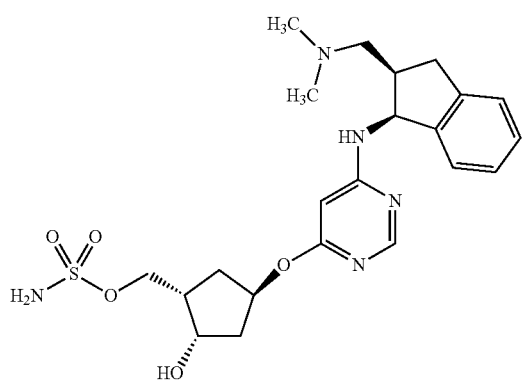 [SMILES: CN(C)C[C@H]1Cc2ccccc2[C@H]1Nc1cc(O[C@@H]2C[C@@H](COS(N)(=O)=O)[C@@H](O)C2)ncn1]
I-53
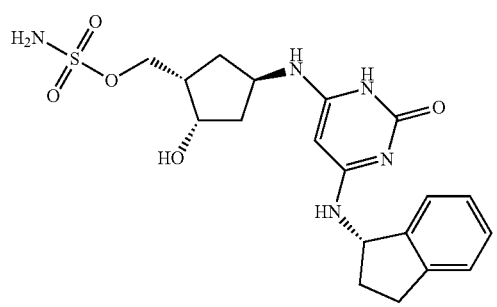 [SMILES: NS(=O)(=O)OC[C@@H]1C[C@@H](Nc2cc(N[C@H]3CCc4ccccc43)nc(=O)[nH]2)C[C@@H]1O]
I-54

TABLE 1-continued
E1 Activating Enzyme Inhibitors
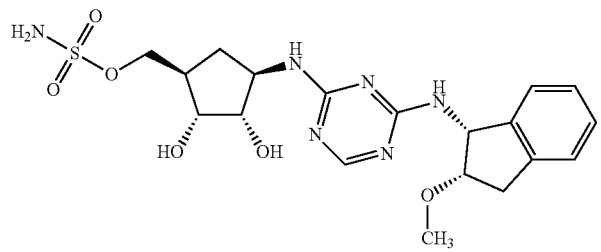 [SMILES: CO[C@H]1Cc2ccccc2[C@H]1Nc1ncnc(N[C@@H]2C[C@H](COS(N)(=O)=O)[C@@H](O)[C@H]2O)n1] I-55
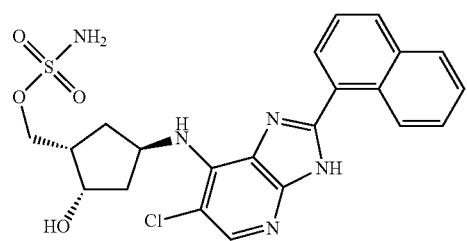 [SMILES: NS(=O)(=O)OC[C@@H]1C[C@@H](Nc2c(Cl)cnc3[nH]c(-c4cccc5ccccc45)nc23)C[C@@H]1O] I-56
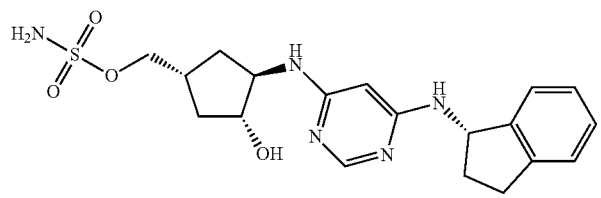 [SMILES: NS(=O)(=O)OC[C@H]1C[C@@H](O)[C@H](Nc2cc(N[C@H]3CCc4ccccc43)ncn2)C1] I-58
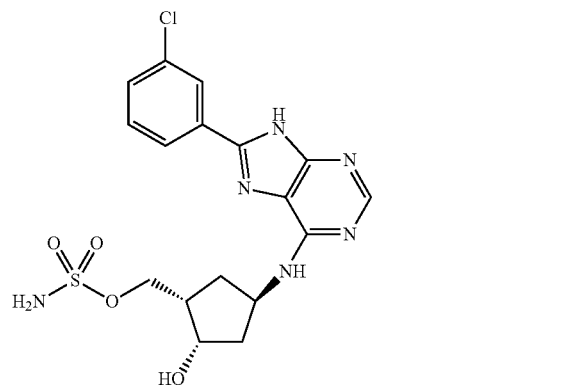 [SMILES: NS(=O)(=O)OC[C@@H]1C[C@@H](Nc2ncnc3[nH]c(-c4cccc(Cl)c4)nc23)C[C@@H]1O] I-60
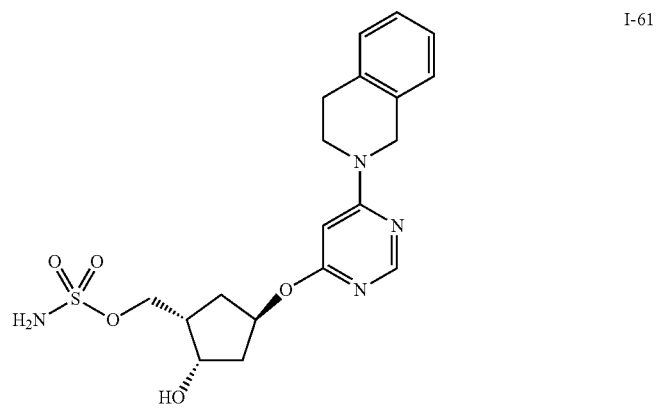 I-61

TABLE 1-continued
E1 Activating Enzyme Inhibitors
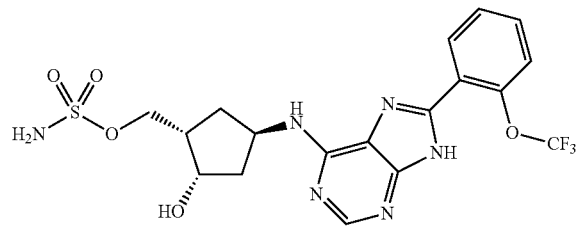 [SMILES: NS(=O)(=O)OC[C@@H]1C[C@@H](Nc2ncnc3[nH]c(-c4ccccc4OC(F)(F)F)nc23)C[C@@H]1O]
I-62
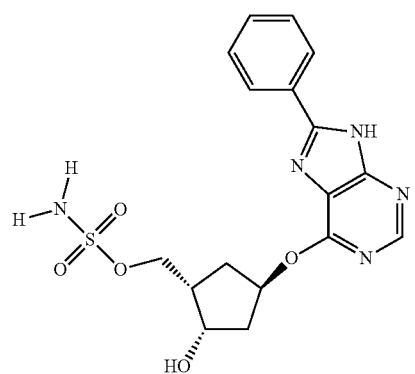 [SMILES: NS(=O)(=O)OC[C@@H]1C[C@@H](Oc2ncnc3[nH]c(-c4ccccc4)nc23)C[C@@H]1O]
I-63
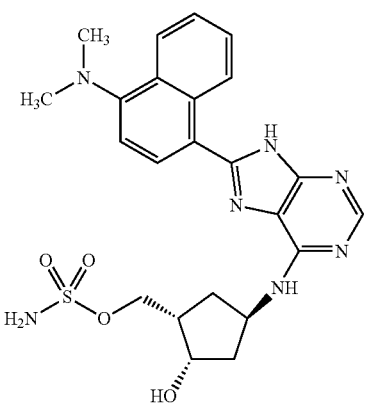 [SMILES: CN(C)c1ccc(-c2nc3c(N[C@@H]4C[C@@H](COS(N)(=O)=O)[C@@H](O)C4)ncnc3[nH]2)c2ccccc12]
I-64
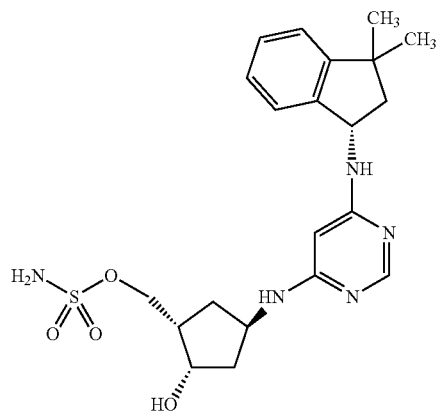 [SMILES: CC1(C)C[C@H](Nc2cc(N[C@@H]3C[C@@H](COS(N)(=O)=O)[C@@H](O)C3)ncn2)c2ccccc21]
I-65

TABLE 1-continued
E1 Activating Enzyme Inhibitors
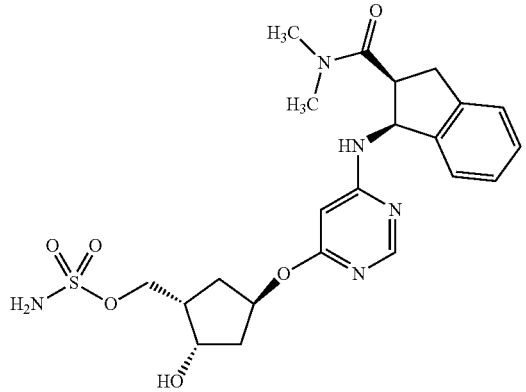 [SMILES: CN(C)C(=O)[C@H]1Cc2ccccc2[C@H]1Nc1cc(O[C@@H]2C[C@@H](COS(N)(=O)=O)[C@@H](O)C2)ncn1]
I-66
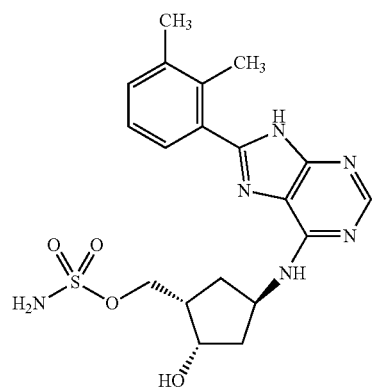 [SMILES: Cc1cccc(-c2nc3c(N[C@@H]4C[C@@H](COS(N)(=O)=O)[C@@H](O)C4)ncnc3[nH]2)c1C]
I-67
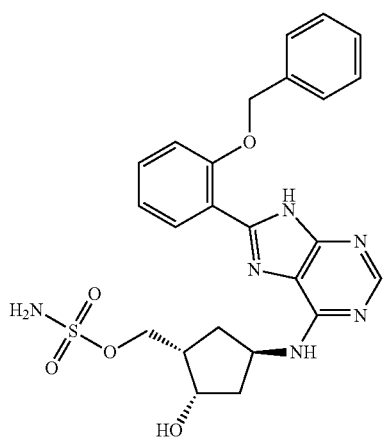 [SMILES: NS(=O)(=O)OC[C@@H]1C[C@@H](Nc2ncnc3[nH]c(-c4ccccc4OCc4ccccc4)nc23)C[C@@H]1O]
I-68
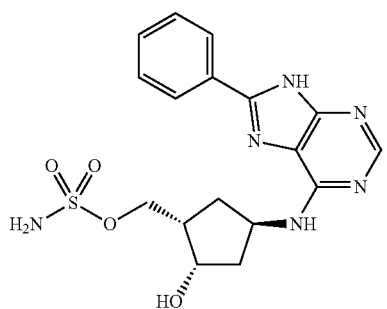 [SMILES: NS(=O)(=O)OC[C@@H]1C[C@@H](Nc2ncnc3[nH]c(-c4ccccc4)nc23)C[C@@H]1O]
I-69

TABLE 1-continued
E1 Activating Enzyme Inhibitors
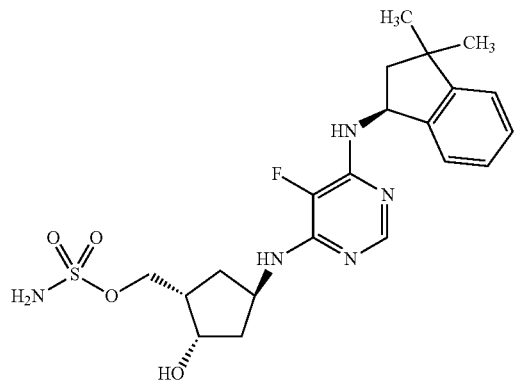 [SMILES: CC1(C)C[C@H](Nc2ncnc(N[C@@H]3C[C@@H](COS(N)(=O)=O)[C@@H](O)C3)c2F)c2ccccc21]
I-71
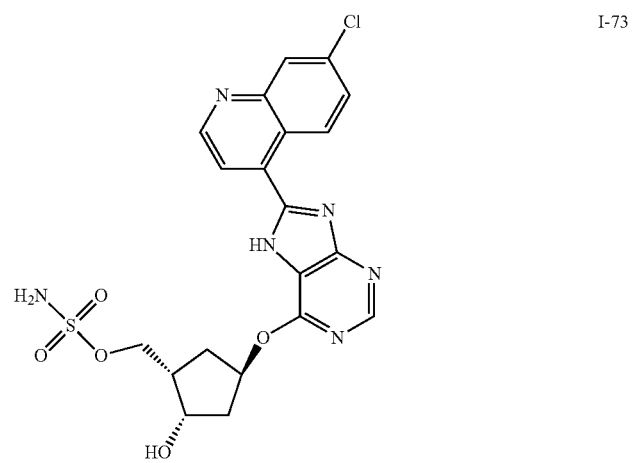
I-73
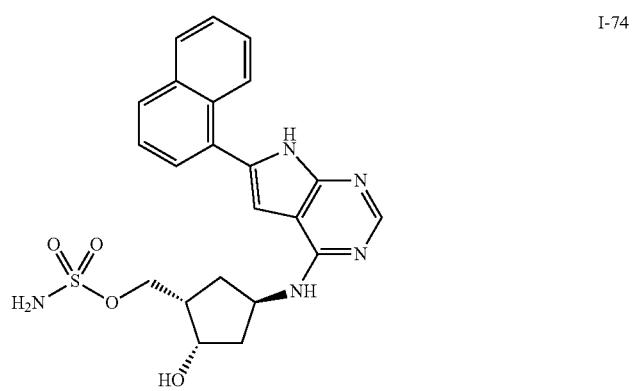
I-74
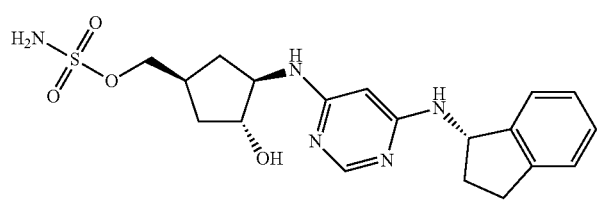 [SMILES: NS(=O)(=O)OC[C@@H]1C[C@@H](O)[C@H](Nc2cc(N[C@H]3CCc4ccccc43)ncn2)C1]
I-76

TABLE 1-continued
E1 Activating Enzyme Inhibitors
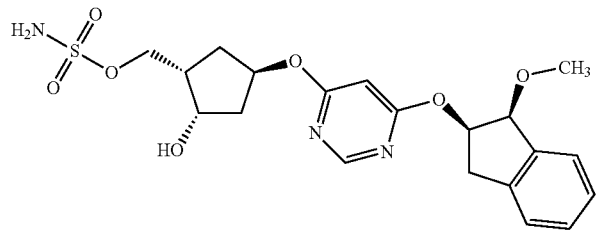 [SMILES: CO[C@H]1c2ccccc2C[C@H]1Oc1cc(O[C@@H]2C[C@@H](COS(N)(=O)=O)[C@@H](O)C2)ncn1]
I-77
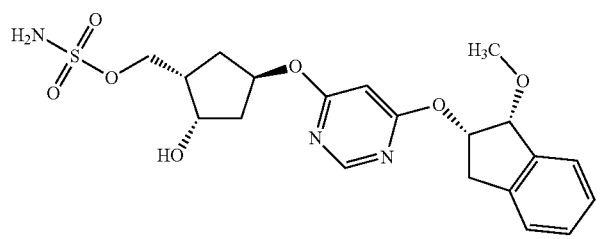 [SMILES: CO[C@@H]1c2ccccc2C[C@@H]1Oc1cc(O[C@@H]2C[C@@H](COS(N)(=O)=O)[C@@H](O)C2)ncn1]
I-79
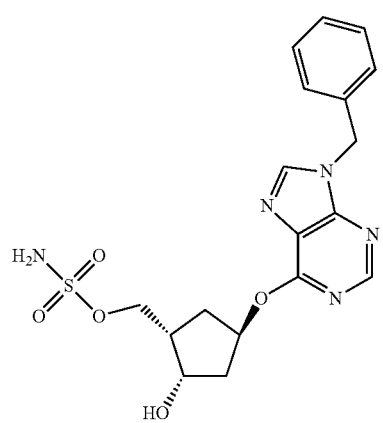 [SMILES: NS(=O)(=O)OC[C@@H]1C[C@@H](Oc2ncnc3c2ncn3Cc2ccccc2)C[C@@H]1O]
I-80
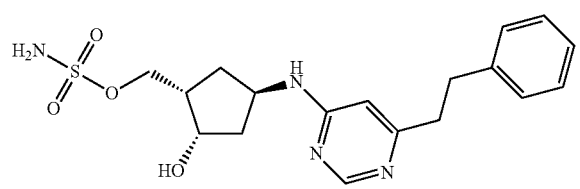 [SMILES: NS(=O)(=O)OC[C@@H]1C[C@@H](Nc2cc(CCc3ccccc3)ncn2)C[C@@H]1O]
I-81
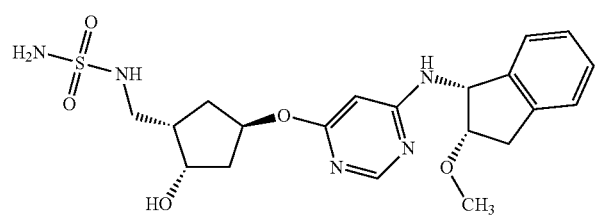 [SMILES: CO[C@H]1Cc2ccccc2[C@H]1Nc1cc(O[C@@H]2C[C@@H](CNS(N)(=O)=O)[C@@H](O)C2)ncn1]
I-82

TABLE 1-continued
E1 Activating Enzyme Inhibitors
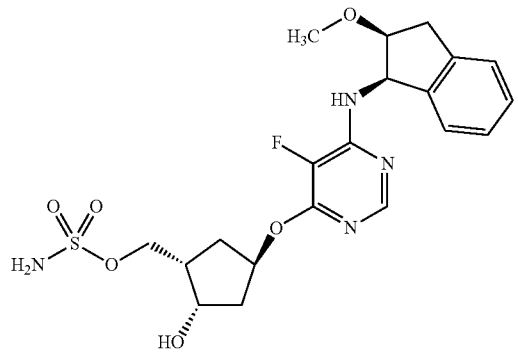 [SMILES: CO[C@H]1Cc2ccccc2[C@H]1Nc1ncnc(O[C@@H]2C[C@@H](COS(N)(=O)=O)[C@@H](O)C2)c1F]
I-83
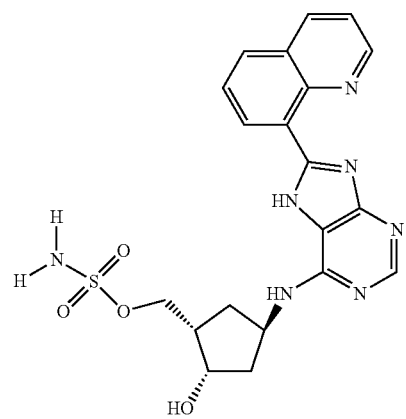 [SMILES: NS(=O)(=O)OC[C@@H]1C[C@@H](Nc2ncnc3nc(-c4cccc5cccnc45)[nH]c23)C[C@@H]1O]
I-84
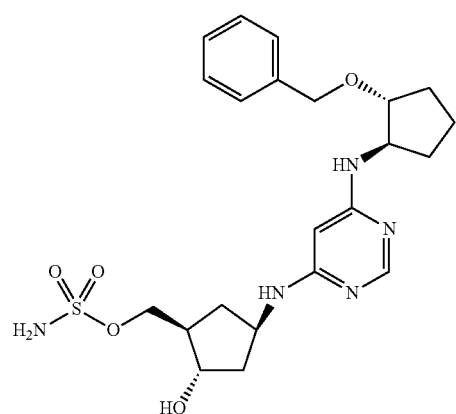 [SMILES: NS(=O)(=O)OC[C@H]1C[C@@H](Nc2cc(N[C@@H]3CCC[C@H]3OCc3ccccc3)ncn2)C[C@@H]1O]
I-85
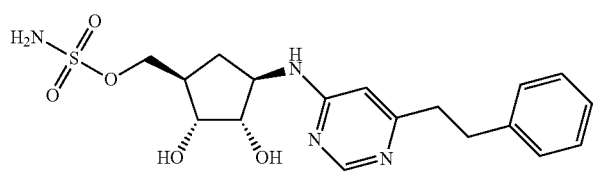 [SMILES: NS(=O)(=O)OC[C@H]1C[C@@H](Nc2cc(CCc3ccccc3)ncn2)[C@H](O)[C@@H]1O]
I-86

TABLE 1-continued
E1 Activating Enzyme Inhibitors
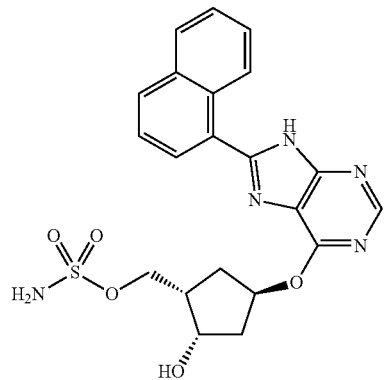 [SMILES: NS(=O)(=O)OC[C@@H]1C[C@@H](Oc2ncnc3[nH]c(-c4cccc5ccccc45)nc23)C[C@@H]1O]
I-87
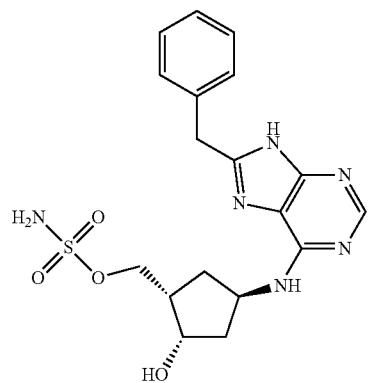 [SMILES: NS(=O)(=O)OC[C@@H]1C[C@@H](Nc2ncnc3[nH]c(Cc4ccccc4)nc23)C[C@@H]1O]
I-88
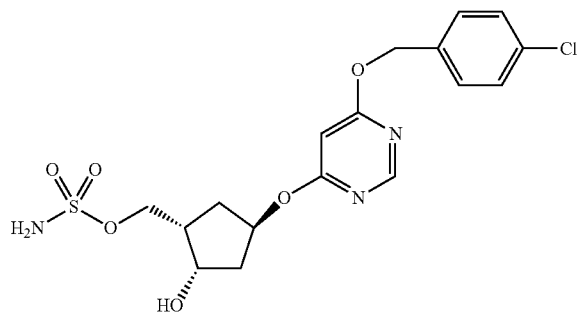 [SMILES: NS(=O)(=O)OC[C@@H]1C[C@@H](Oc2cc(OCc3ccc(Cl)cc3)ncn2)C[C@@H]1O]
I-89
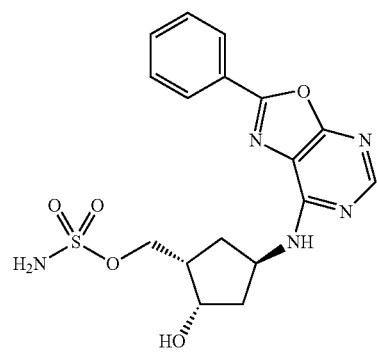 [SMILES: NS(=O)(=O)OC[C@@H]1C[C@@H](Nc2ncnc3oc(-c4ccccc4)nc23)C[C@@H]1O]
I-90

TABLE 1-continued
E1 Activating Enzyme Inhibitors
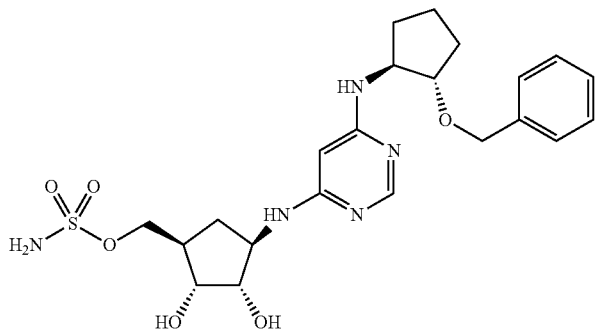 [SMILES: NS(=O)(=O)OC[C@H]1C[C@@H](Nc2cc(N[C@H]3CCC[C@@H]3OCc3ccccc3)ncn2)[C@H](O)[C@@H]1O]
I-92
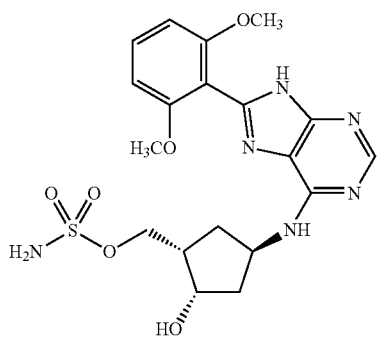 [SMILES: COc1cccc(OC)c1-c1nc2c(N[C@@H]3C[C@@H](COS(N)(=O)=O)[C@@H](O)C3)ncnc2[nH]1]
I-93
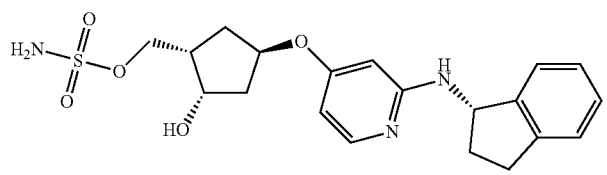 [SMILES: NS(=O)(=O)OC[C@@H]1C[C@@H](Oc2ccnc(N[C@H]3CCc4ccccc43)c2)C[C@@H]1O]
I-94
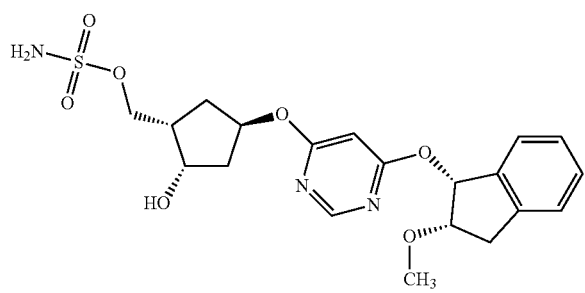 [SMILES: CO[C@H]1Cc2ccccc2[C@H]1Oc1cc(O[C@@H]2C[C@@H](COS(N)(=O)=O)[C@@H](O)C2)ncn1]
I-96
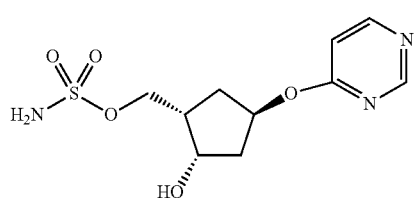 [SMILES: NS(=O)(=O)OC[C@@H]1C[C@@H](Oc2ccncn2)C[C@@H]1O]
I-97

TABLE 1-continued
E1 Activating Enzyme Inhibitors
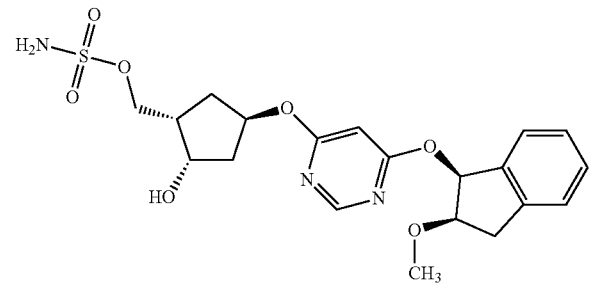 [SMILES: CO[C@@H]1Cc2ccccc2[C@@H]1Oc1cc(O[C@@H]2C[C@@H](COS(N)(=O)=O)[C@@H](O)C2)ncn1]
I-98
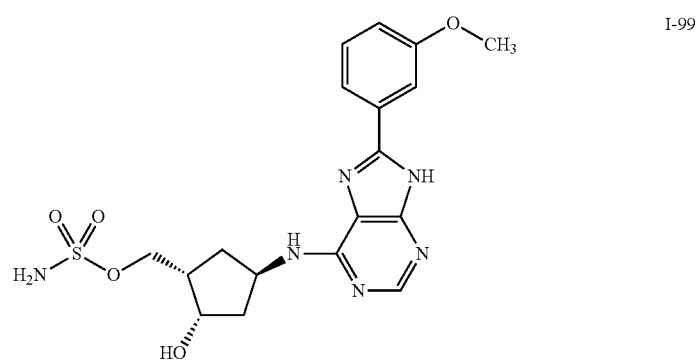
I-99
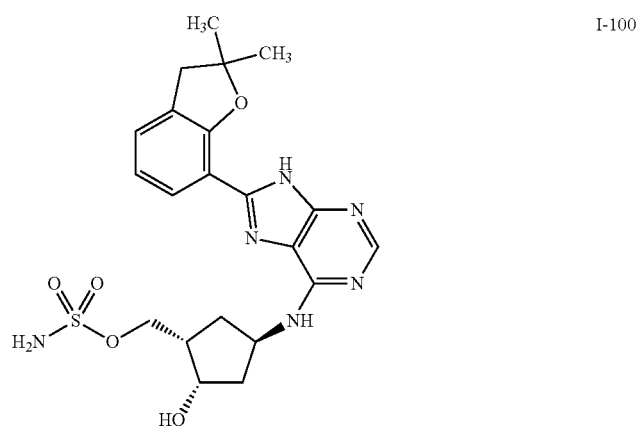
I-100
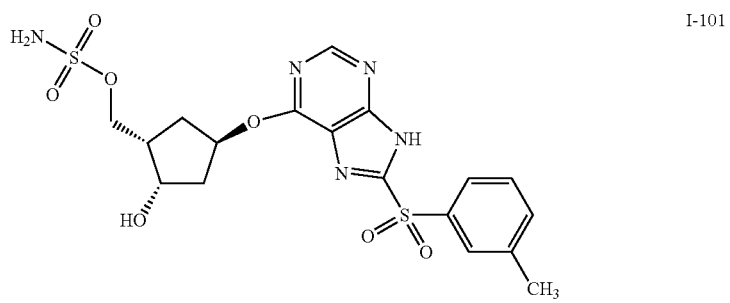
I-101

TABLE 1-continued
E1 Activating Enzyme Inhibitors
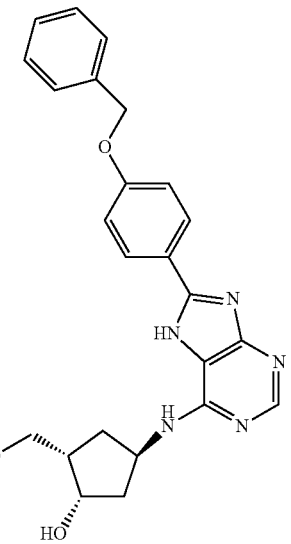
I-102
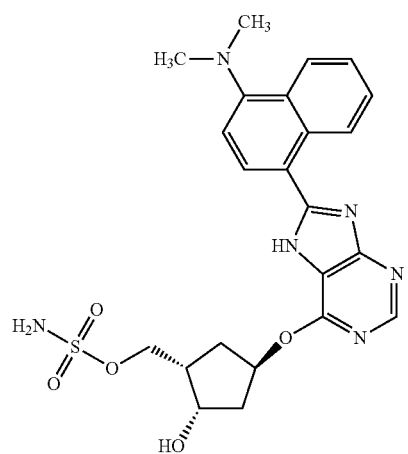 [SMILES: CN(C)c1ccc(-c2nc3ncnc(O[C@@H]4C[C@@H](COS(N)(=O)=O)[C@@H](O)C4)c3[nH]2)c2ccccc12]
I-103
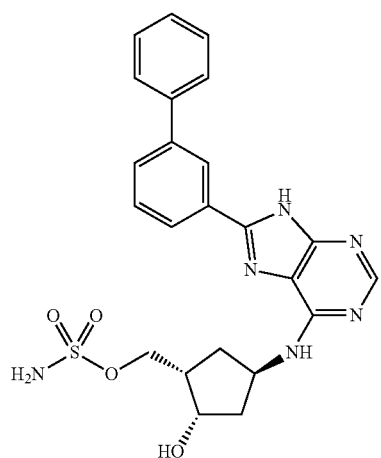 [SMILES: NS(=O)(=O)OC[C@@H]1C[C@@H](Nc2ncnc3[nH]c(-c4cccc(-c5ccccc5)c4)nc23)C[C@@H]1O]
I-105

TABLE 1-continued
E1 Activating Enzyme Inhibitors
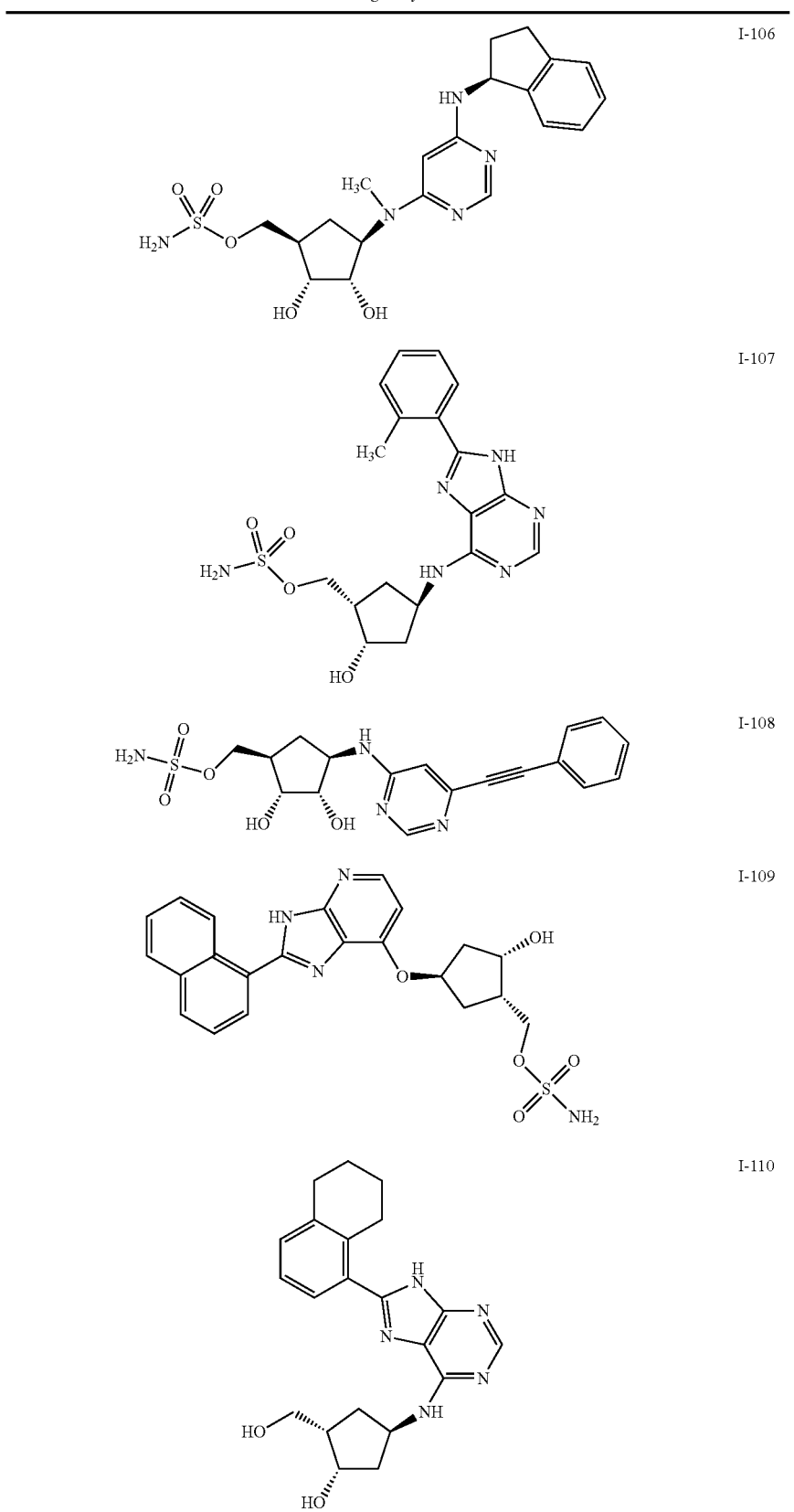
I-106
I-107
I-108
I-109
I-110

TABLE 1-continued
E1 Activating Enzyme Inhibitors
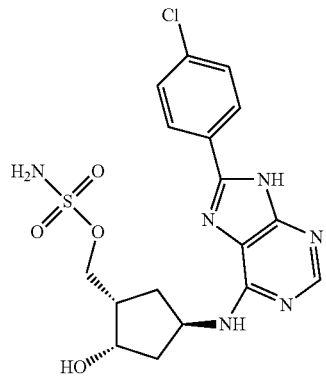 [SMILES: NS(=O)(=O)OC[C@@H]1C[C@@H](Nc2ncnc3[nH]c(-c4ccc(Cl)cc4)nc23)C[C@@H]1O]
I-111
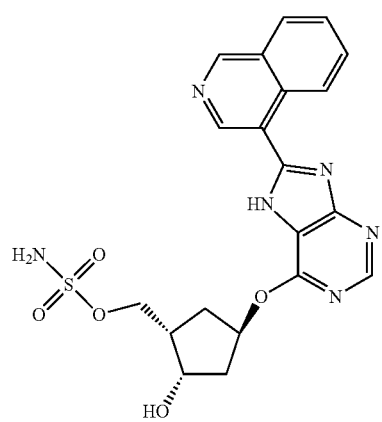 [SMILES: NS(=O)(=O)OC[C@@H]1C[C@@H](Oc2ncnc3nc(-c4cncc5ccccc45)[nH]c23)C[C@@H]1O]
I-112
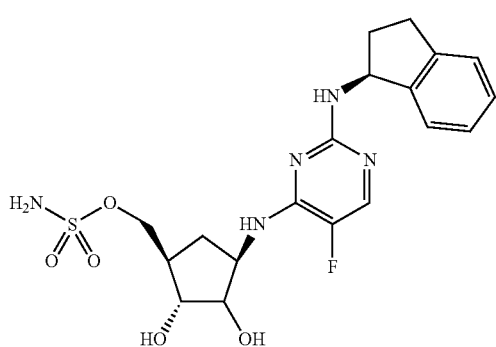 [SMILES: NS(=O)(=O)OC[C@H]1C[C@@H](Nc2nc(N[C@H]3CCc4ccccc43)ncc2F)C(O)[C@@H]1O]
I-113
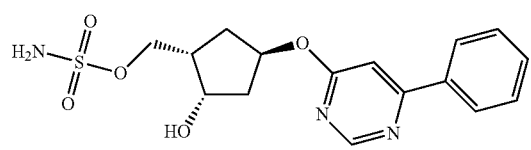 [SMILES: NS(=O)(=O)OC[C@@H]1C[C@@H](Oc2cc(-c3ccccc3)ncn2)C[C@@H]1O]
I-114

TABLE 1-continued
E1 Activating Enzyme Inhibitors
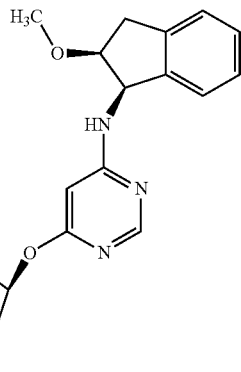
I-115
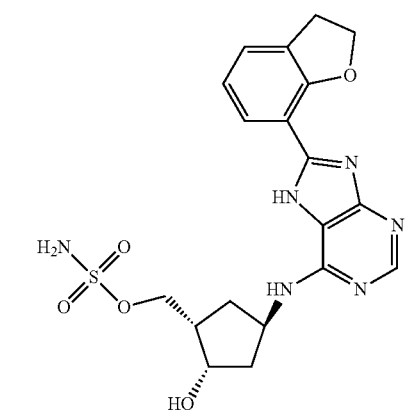 [SMILES: NS(=O)(=O)OC[C@@H]1C[C@@H](Nc2ncnc3nc(-c4cccc5c4OCC5)[nH]c23)C[C@@H]1O]
I-117
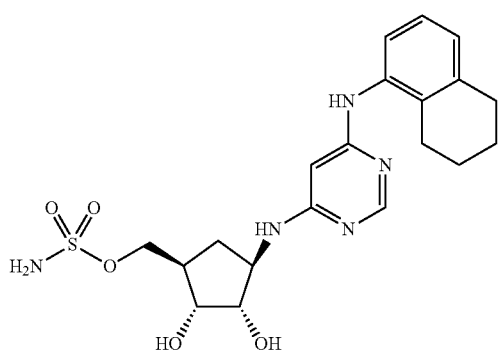 [SMILES: NS(=O)(=O)OC[C@H]1C[C@@H](Nc2cc(Nc3cccc4c3CCCC4)ncn2)[C@H](O)[C@@H]1O]
I-118
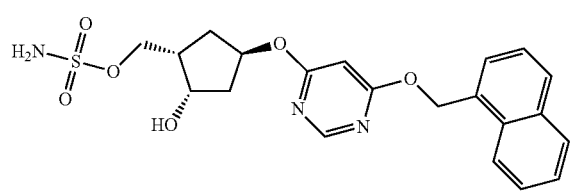 [SMILES: NS(=O)(=O)OC[C@@H]1C[C@@H](Oc2cc(OCc3cccc4ccccc34)ncn2)C[C@@H]1O]
I-119

TABLE 1-continued
E1 Activating Enzyme Inhibitors
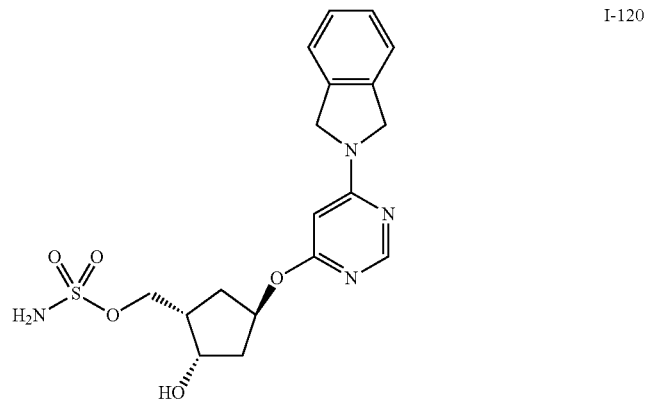
I-120
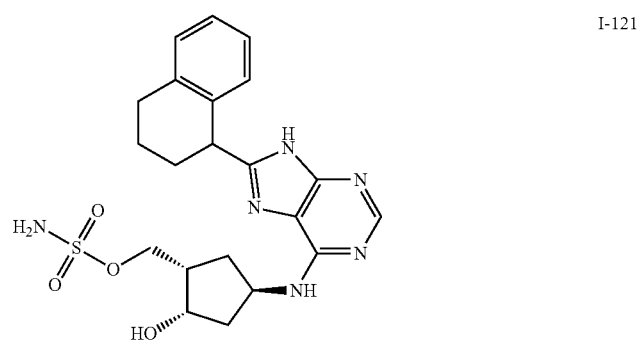
I-121
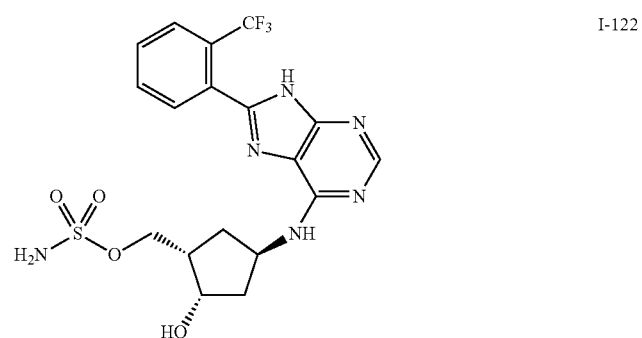
I-122
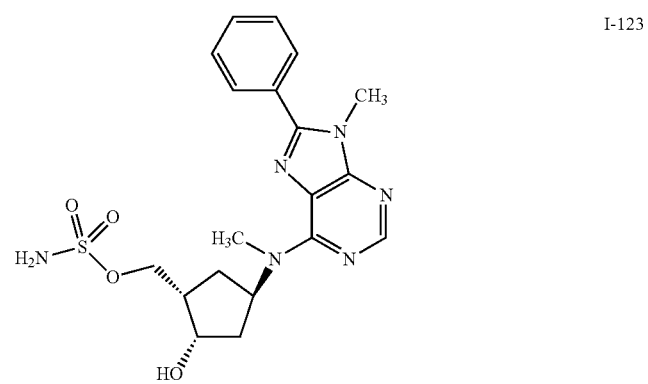
I-123

TABLE 1-continued
E1 Activating Enzyme Inhibitors
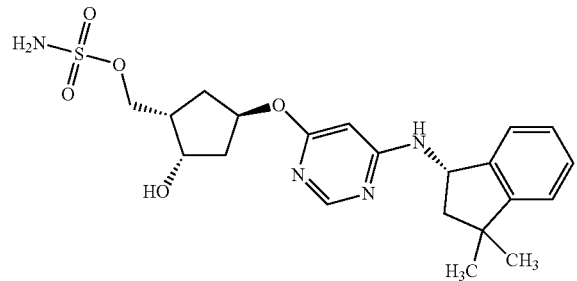 [SMILES: CC1(C)C[C@H](Nc2cc(O[C@@H]3C[C@@H](COS(N)(=O)=O)[C@@H](O)C3)ncn2)c2ccccc21]
I-124
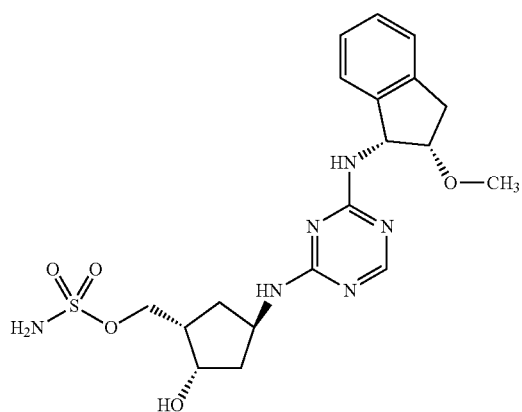 [SMILES: CO[C@H]1Cc2ccccc2[C@H]1Nc1ncnc(N[C@@H]2C[C@@H](COS(N)(=O)=O)[C@@H](O)C2)n1]
I-125
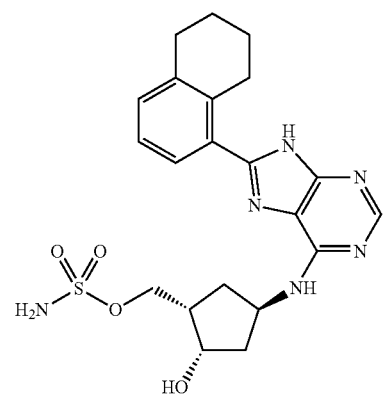 [SMILES: NS(=O)(=O)OC[C@@H]1C[C@@H](Nc2ncnc3[nH]c(-c4cccc5c4CCCC5)nc23)C[C@@H]1O]
I-126
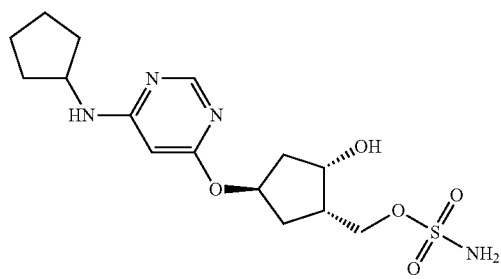 [SMILES: NS(=O)(=O)OC[C@@H]1C[C@@H](Oc2cc(NC3CCCC3)ncn2)C[C@@H]1O]
I-127

TABLE 1-continued
E1 Activating Enzyme Inhibitors
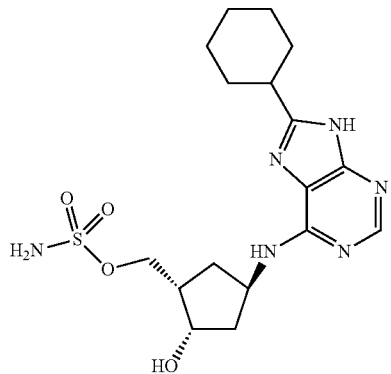 [SMILES: NS(=O)(=O)OC[C@@H]1C[C@@H](Nc2ncnc3[nH]c(C4CCCCC4)nc23)C[C@@H]1O]
I-128
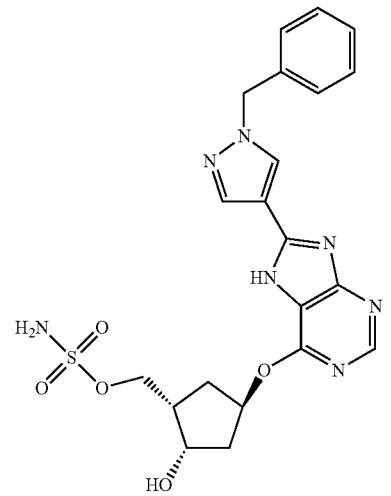 [SMILES: NS(=O)(=O)OC[C@@H]1C[C@@H](Oc2ncnc3nc(-c4cnn(Cc5ccccc5)c4)[nH]c23)C[C@@H]1O]
I-129
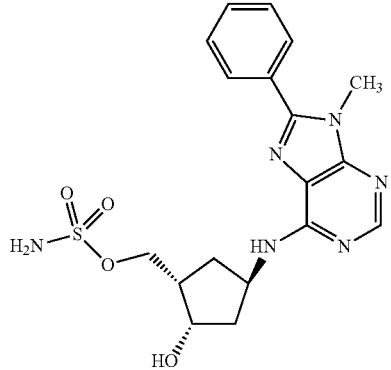 [SMILES: Cn1c(-c2ccccc2)nc2c(N[C@@H]3C[C@@H](COS(N)(=O)=O)[C@@H](O)C3)ncnc21]
I-130
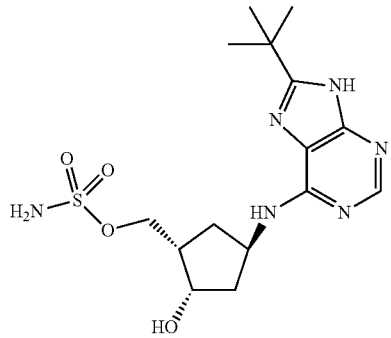 [SMILES: CC(C)(C)c1nc2c(N[C@@H]3C[C@@H](COS(N)(=O)=O)[C@@H](O)C3)ncnc2[nH]1]
I-131

TABLE 1-continued
E1 Activating Enzyme Inhibitors
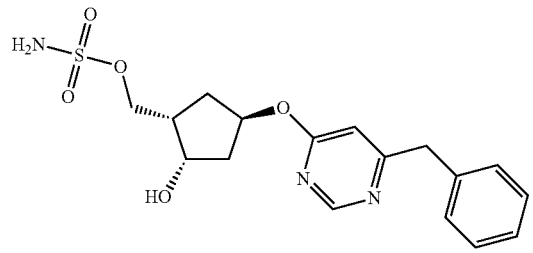 [SMILES: NS(=O)(=O)OC[C@@H]1C[C@@H](Oc2cc(Cc3ccccc3)ncn2)C[C@@H]1O]
I-132
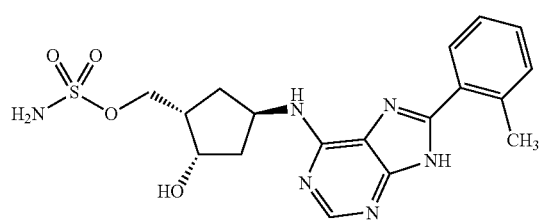 [SMILES: Cc1ccccc1-c1nc2c(N[C@@H]3C[C@@H](COS(N)(=O)=O)[C@@H](O)C3)ncnc2[nH]1]
I-133
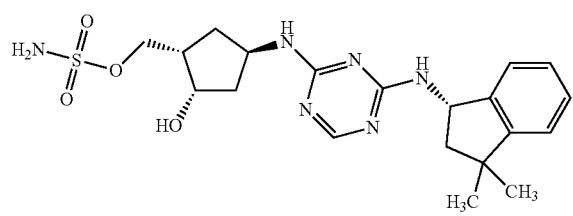 [SMILES: CC1(C)C[C@H](Nc2ncnc(N[C@@H]3C[C@@H](COS(N)(=O)=O)[C@@H](O)C3)n2)c2ccccc21]
I-134
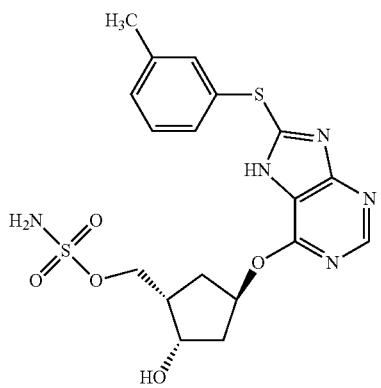 [SMILES: Cc1cccc(Sc2nc3ncnc(O[C@@H]4C[C@@H](COS(N)(=O)=O)[C@@H](O)C4)c3[nH]2)c1]
I-136
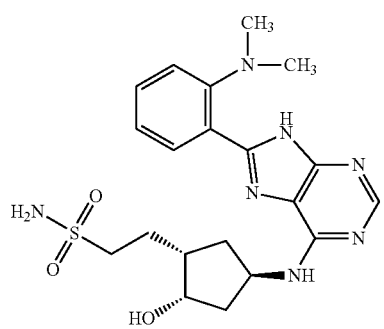 [SMILES: CN(C)c1ccccc1-c1nc2c(N[C@@H]3C[C@@H](CCS(N)(=O)=O)[C@@H](O)C3)ncnc2[nH]1]
I-137

TABLE 1-continued
E1 Activating Enzyme Inhibitors
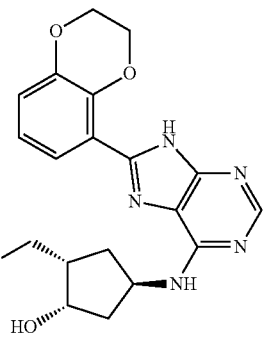
I-138
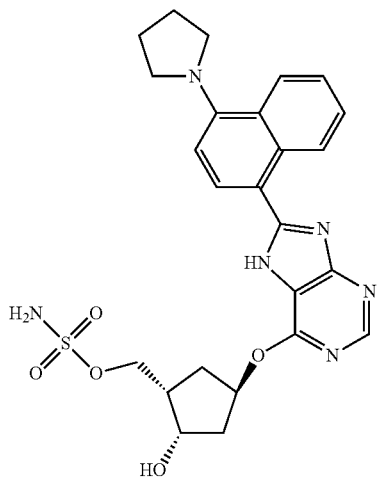 [SMILES: NS(=O)(=O)OC[C@@H]1C[C@@H](Oc2ncnc3nc(-c4ccc(N5CCCC5)c5ccccc45)[nH]c23)C[C@@H]1O]
I-139
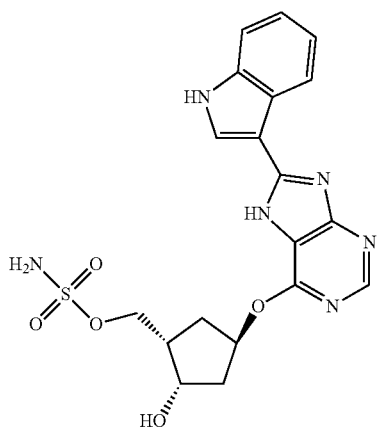 [SMILES: NS(=O)(=O)OC[C@@H]1C[C@@H](Oc2ncnc3nc(-c4c[nH]c5ccccc45)[nH]c23)C[C@@H]1O]
I-140
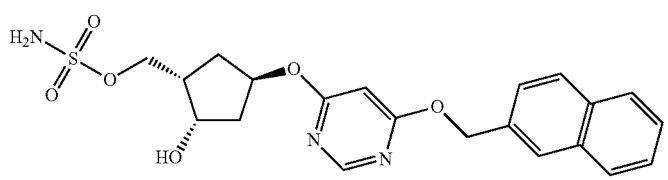 [SMILES: NS(=O)(=O)OC[C@@H]1C[C@@H](Oc2cc(OCc3ccc4ccccc4c3)ncn2)C[C@@H]1O]
I-141

TABLE 1-continued
E1 Activating Enzyme Inhibitors
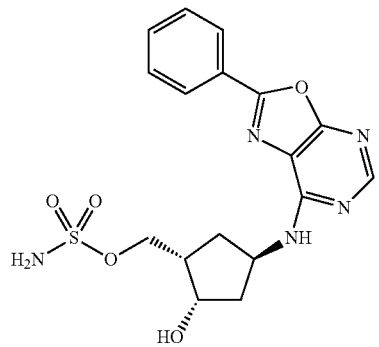 [SMILES: NS(=O)(=O)OC[C@@H]1C[C@@H](Nc2ncnc3oc(-c4ccccc4)nc23)C[C@@H]1O]
I-142
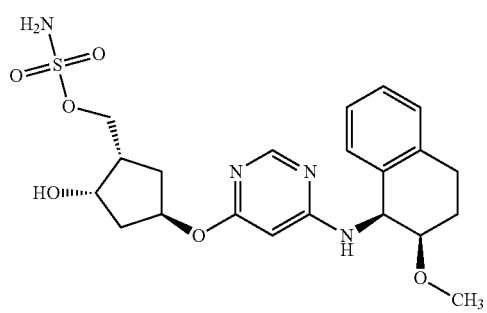 [SMILES: CO[C@@H]1CCc2ccccc2[C@@H]1Nc1cc(O[C@@H]2C[C@@H](COS(N)(=O)=O)[C@@H](O)C2)ncn1]
I-143
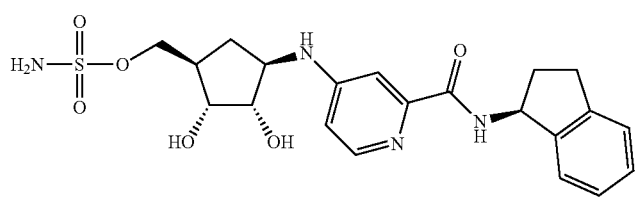 [SMILES: NS(=O)(=O)OC[C@H]1C[C@@H](Nc2ccnc(C(=O)N[C@H]3CCc4ccccc43)c2)[C@H](O)[C@@H]1O]
I-144
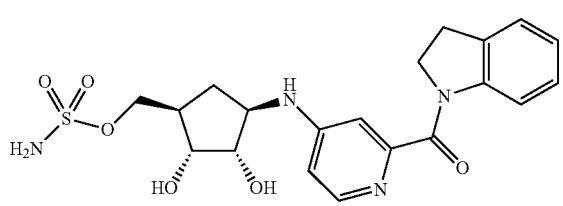 [SMILES: NS(=O)(=O)OC[C@H]1C[C@@H](Nc2ccnc(C(=O)N3CCc4ccccc43)c2)[C@H](O)[C@@H]1O]
I-145
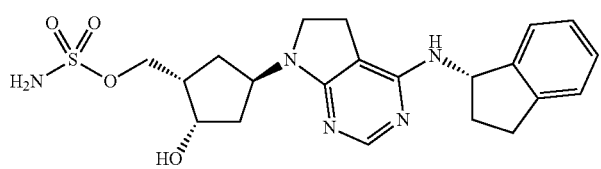 [SMILES: NS(=O)(=O)OC[C@@H]1C[C@@H](N2CCc3c(N[C@H]4CCc5ccccc54)ncnc32)C[C@@H]1O]
I-146

TABLE 1-continued
E1 Activating Enzyme Inhibitors
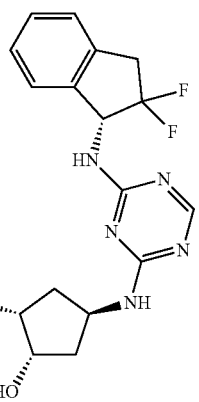 I-147
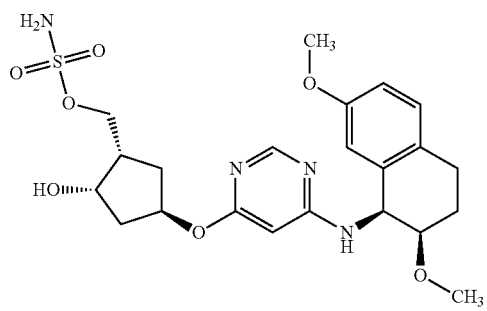 [SMILES: COc1ccc2c(c1)[C@H](Nc1cc(O[C@@H]3C[C@@H](COS(N)(=O)=O)[C@@H](O)C3)ncn1)[C@H](OC)CC2] I-148
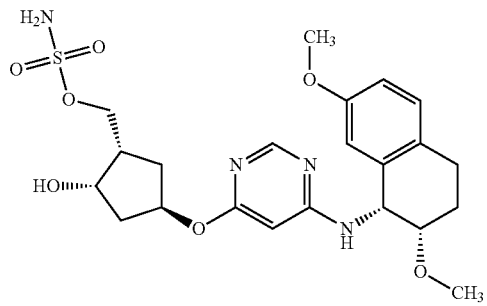 [SMILES: COc1ccc2c(c1)[C@@H](Nc1cc(O[C@@H]3C[C@@H](COS(N)(=O)=O)[C@@H](O)C3)ncn1)[C@@H](OC)CC2] I-149
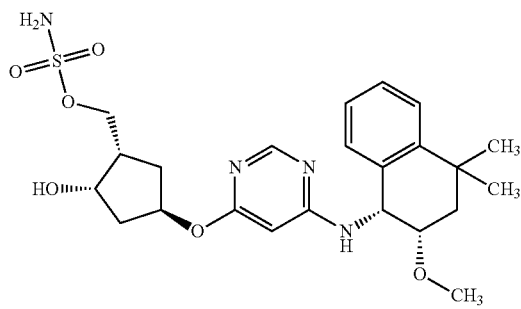 [SMILES: CO[C@H]1CC(C)(C)c2ccccc2[C@H]1Nc1cc(O[C@@H]2C[C@@H](COS(N)(=O)=O)[C@@H](O)C2)ncn1] I-150

TABLE 1-continued

E1 Activating Enzyme Inhibitors

I-151

I-152

I-153

The compounds in Table 1 above may also be identified by the following chemical names:

| | Chemical Name |
|---|---|
| I-1 | {(1R,2R,3S,4R)-4-[(6-{[(1S)-4-fluoro-2,3-dihydro-1H-inden-1-yl]amino}-pyrimidin-4-yl)-amino]-2,3-dihydroxycyclopentyl}methyl sulfamate; |
| I-2 | {(1R,2R,3S,4R)-2,3-dihydroxy-4-[(6-{[(1R,2S)-2-methoxy-2,3-dihydro-1H-inden-1-yl]-amino}pyrimidin-4-yl)amino]cyclopentyl}methyl sulfamate; |
| I-3 | [(1R,2R,3S,4R)-2,3-dihydroxy-4-(9H-purin-6-ylamino)cyclopentyl]methyl sulfamate; |
| I-4 | [(1R,2R,3S,4R)-4-({2-[(cyclohexylmethyl)amino]pyrimidin-4-yl}amino)-2,3-dihydroxycyclopentyl]methyl sulfamate |
| I-5 | [(1S,2S,4R)-4-({6-[(1S)-2,3-dihydro-1H-inden-1-ylamino]pyrimidin-4-yl}amino)-2-hydroxycyclopentyl]methyl sulfamate; |
| I-6 | {(1R,2R,3S,4R)-4-[(6-{[(1S)-4,7-difluoro-2,3-dihydro-1H-inden-1-yl]amino}-pyrimidin-4-yl)amino]-2,3-dihydroxycyclopentyl}methyl sulfamate; |
| I-7 | ((1R,2R,3S,4R)-4-{[2-(benzylamino)pyrimidin-4-yl]amino}-2,3-dihydroxycyclopentyl)methyl sulfamate |
| I-8 | [(1R,2R,3S,4R)-4-({6-[(1R)-2,3-dihydro-1H-inden-1-ylamino]pyrimidin-4-yl}-amino)-2,3-dihydroxycyclopentyl]methyl sulfamate; |

| | Chemical Name |
|---|---|
| I-9 | {(1R,2R,3S,4R)-2,3-dihydroxy-4-[(8-phenyl-9H-purin-6-yl)amino]cyclopentyl}-methyl sulfamate; |
| I-10 | [(1R,2R,3S,4R)-2,3-dihydroxy-4-({2-[(3-methyl-2,3-dihydro-1H-inden-1-yl)-amino]pyrimidin-4-yl}amino)cyclopentyl]methyl sulfamate; |
| I-11 | [(1S,2R,3S,4R)-4-({6-[(1S)-2,3-dihydro-1H-inden-1-ylamino]pyrimidin-4-yl}-amino)-2,3-dihydroxycyclopentyl]methyl sulfamate; |
| I-12 | [(1R,2R,3S,4R)-2,3-dihydroxy-4-({6-[(1S)-1,2,3,4-tetrahydronaphthalen-1-ylamino]pyrimidin-4-yl}amino)cyclopentyl]methyl sulfamate; |
| I-13 | {(1R,2R,3S,4R)-4-[(6-amino-2-methylpyrimidin-4-yl)amino]-2,3-dihydroxycyclopentyl}methyl sulfamate |
| I-14 | [(1R,2R,3S,4R)-4-({6-[(cyclohexylmethyl)amino]pyrimidin-4-yl}amino)-2,3-dihydroxycyclopentyl]methyl sulfamate; |
| I-15 | {(1R,2R,3S,4R)-4-[(2-{[(1S)-3,3-dimethyl-2,3-dihydro-1H-inden-1-yl]amino}-pyrimidin-4-yl)amino]-2,3-dihydroxycyclopentyl}methyl sulfamate; |
| I-16 | {(1R,2R,3S,4R)-2,3-dihydroxy-4-[(pyridin-3-ylcarbonyl)amino]cyclopentyl}-methyl sulfamate |
| I-17 | {(1R,2R,3S,4R)-4-[(6-{[(1S)-5,6-difluoro-2,3-dihydro-1H-inden-1-yl]amino}-pyrimidin-4-yl)amino]-2,3-dihydroxycyclopentyl}methyl sulfamate; |
| I-18 | [(1R,2R,3S,4R)-4-({6-[(1S)-2,3-dihydro-1H-inden-1-ylamino]-2-methylpyrimidin-4-yl}-amino)-2,3-dihydroxycyclopentyl]methyl sulfamate; |
| I-19 | {(1R,2R,3S,4R)-4-[(6-{[(1S)-5-chloro-2,3-dihydro-1H-inden-1-yl]amino}-pyrimidin-4-yl)-amino]-2,3-dihydroxycyclopentyl}methyl sulfamate; |
| I-20 | [(1R,2R,3S,4R)-4-({2-[benzyl(methyl)amino]pyrimidin-4-yl}amino)-2,3-dihydroxycyclopentyl]methyl sulfamate |
| I-21 | {(1R,2R,3S,4R)-4-[(6-{[(1S)-3,3-dimethyl-2,3-dihydro-1H-inden-1-yl]amino}-pyrimidin-4-yl)amino]-2,3-dihydroxycyclopentyl}methyl sulfamate; |
| I-22 | [(1R,2R,3S,4R)-4-({6-[benzyl(methyl)amino]pyrimidin-4-yl}amino)-2,3-dihydroxycyclopentyl]methyl sulfamate |
| I-23 | {(1R,2R,3S,4R)-2,3-dihydroxy-4-[(pyridin-2-ylcarbonyl)amino]cyclopentyl}-methyl sulfamate |
| I-24 | {(1R,2R,3S,4R)-4-[(6-{[(1S)-4-chloro-2,3-dihydro-1H-inden-1-yl]amino}-pyrimidin-4-yl)-amino]-2,3-dihydroxycyclopentyl}methyl sulfamate; |
| I-25 | [(1R,2S,4R)-4-({6-[(1S)-2,3-dihydro-1H-inden-1-ylamino]pyrimidin-4-yl}amino)-2-hydroxycyclopentyl]methyl sulfamate; |
| I-26 | [(1R,2R,3S,4R)-4-({4-[(1S)-2,3-dihydro-1H-inden-1-ylamino]-1,3,5-triazin-2-yl}-amino)-2,3-dihydroxycyclopentyl]methyl sulfamate; |
| I-27 | ((1R,2R,3S,4R)-4-{[6-(benzylamino)pyrimidin-4-yl]amino}-2,3-dihydroxycyclopentyl)-methyl sulfamate; |
| I-28 | [(1R,2R,3S,4R)-2,3-dihydroxy-4-(isonicotinoylamino)cyclopentyl]methyl sulfamate |
| I-29 | [(1R,2R,3S,4R)-4-({6-[(1S)-2,3-dihydro-1H-inden-1-ylamino]pyrimidin-4-yl}-amino)-2,3-dihydroxycyclopentyl]methyl sulfamate; |
| I-30 | ((1R,2R,3S,4R)-4-{[6-(benzylamino)-2-methylpyrimidin-4-yl]amino}-2,3-dihydroxycyclopentyl)methyl sulfamate |
| I-31 | [(1S,2S,4R)-4-({6-[(1S)-2,3-Dihydro-1H-inden-1-ylamino]pyrimidin-4-yl}oxy)-2-hydroxycyclopentyl]methyl sulfamate |
| I-32 | [(1S,2S,4R)-4-({6-[(1S)-2,3-dihydro-1H-inden-1-ylamino]-5-methylpyrimidin-4-yl}oxy)-2-hydroxycyclopentyl]methyl sulfamate; |
| I-33 | [(1S,2S,4S)-4-({6-[(1S)-2,3-dihydro-1H-inden-1-ylamino]pyrimidin-4-yl}methyl)-2-hydroxycyclopentyl]methyl sulfamate |
| I-34 | ((1S,2S,4R)-4-{[8-(2-chlorophenyl)-9H-purin-6-yl]amino}-2-hydroxycyclopentyl)methyl sulfamate; |
| I-35 | {(1S,2S,4R)-4-[(2-{[(1S)-5-chloro-3,3-dimethyl-2,3-dihydro-1H-inden-1-yl]-amino}-pyridin-4-yl)oxy]-2-hydroxycyclopentyl}methyl sulfamate |
| I-36 | {(1S,2S,4R)-2-hydroxy-4-[(7-methyl-8-phenyl-7H-purin-6-yl)-amino]cyclopentyl}methyl sulfamate |
| I-37 | ((1S,2S,4R)-2-hydroxy-4-{[8-(2-phenoxyphenyl)-9H-purin-6-yl]amino}-cyclopentyl)methyl sulfamate; |
| I-38 | {(1S,2S,4R)-2-hydroxy-4-[(6-phenyl-7H-pyrrolo[2,3-d]pyrimidin-4-yl)-amino]cyclopentyl}methyl sulfamate; |
| I-39 | {(1S,2S,4R)-4-[(8-dibenzo[b,d]furan-4-yl-9H-purin-6-yl)amino]-2-hydroxycyclopentyl}methyl sulfamate; |
| I-40 | [(1S,2S,4R)-2-hydroxy-4-({6-[(1S)-1,2,3,4-tetrahydronaphthalen-1-ylamino]pyrimidin-4-yl}oxy)cyclopentyl]methyl sulfamate; |
| I-41 | ((1S,2S,4R)-4-{[8-(2,3-dihydro-1,4-benzodioxin-5-yl)-9H-purin-6-yl]amino}-2-hydroxycyclopentyl)methyl sulfamate; |
| I-42 | [(1S,2S,4R)-2-hydroxy-4-({6-[(1-naphthylmethyl)amino]pyrimidin-4-yl}-oxy)cyclopentyl]methyl sulfamate; |
| I-43 | {(1S,2S,4R)-2-hydroxy-4-[(6-{[(1S,2S)-2-methyl-2,3-dihydro-1H-inden-1-yl]-amino}pyrimidin-4-yl)oxy]cyclopentyl}methyl sulfamate; |
| I-45 | [(1R,2R,3S,4R)-4-({4-[(1S)-2,3-dihydro-1H-inden-1-ylamino]-6-methyl-1,3,5-triazin-2-yl}amino)-2,3-dihydroxycyclopentyl]methyl sulfamate; |
| I-46 | ((1S,2S,4R)-2-hydroxy-4-{methyl[8-(1-naphthyl)-9H-purin-6-yl]amino}-cyclopentyl)methyl sulfamate; |
| I-47 | {(1S,2S,4R)-2-hydroxy-4-[(6-{[(1R,2S)-2-methoxy-2,3-dihydro-1H-inden-1-yl]-amino}pyrimidin-4-yl)amino]cyclopentyl}methyl sulfamate; |
| I-48 | {(1S,2S,4R)-4-[(8-biphenyl-2-yl-9H-purin-6-yl)amino]-2-hydroxycyclopentyl}-methyl sulfamate |

-continued

| | Chemical Name |
|---|---|
| I-49 | ((1S,2S,4R)-2-hydroxy-4-{[8-(1-naphthyl)-9H-purin-6-yl]amino}cyclopentyl)-methyl sulfamate; |
| I-53 | ((1S,2S,4R)-4-{[6-({(1S,2R)-2-[(dimethylamino)methyl]-2,3-dihydro-1H-inden-1-yl}amino)pyrimidin-4-yl]oxy}-2-hydroxycyclopentyl)methyl sulfamate |
| I-54 | [(1S,2S,4R)-4-({6-[(1S)-2,3-dihydro-1H-inden-1-ylamino]-2-oxo-2,3-dihydropyrimidin-4-yl}amino)-2-hydroxycyclopentyl]methyl sulfamate |
| I-55 | {(1R,2R,3S,4R)-2,3-dihydroxy-4-[(4-{[(1R,2S)-2-methoxy-2,3-dihydro-1H-inden-1-yl]amino}-1,3,5-triazin-2-yl)amino]cyclopentyl}methyl sulfamate; |
| I-56 | ((1S,2S,4R)-4-{[6-chloro-2-(1-naphthyl)-3H-imidazo[4,5-b]pyridin-7-yl]amino}-2-hydroxycyclopentyl)methyl sulfamate; |
| I-58 | [(1R,3R,4R)-3-({6-[(1S)-2,3-dihydro-1H-inden-1-ylamino]pyrimidin-4-yl}-amino)-4-hydroxycyclopentyl]methyl sulfamate |
| I-60 | ((1S,2S,4R)-4-{[8-(3-chlorophenyl)-9H-purin-6-yl]amino}-2-hydroxycyclopentyl)methyl sulfamate; |
| I-61 | ((1S,2S,4R)-4-{[6-(3,4-dihydroisoquinolin-2(1H)-yl)pyrimidin-4-yl]oxy}-2-hydroxycyclopentyl)methyl sulfamate |
| I-62 | [(1S,2S,4R)-2-hydroxy-4-({8-[2-(trifluoromethoxy)phenyl]-9H-purin-6-yl}-amino)cyclopentyl]methyl sulfamate; |
| I-63 | {(1S,2S,4R)-2-hydroxy-4-[(8-phenyl-9H-purin-6-yl)oxy]cyclopentyl}methyl sulfamate; |
| I-64 | [(1S,2S,4R)-4-({8-[4-(dimethylamino)-1-naphthyl]-9H-purin-6-yl}amino)-2-hydroxycyclopentyl]methyl sulfamate;. |
| I-65 | {(1S,2S,4R)-4-[(6-{[(1S)-3,3-dimethyl-2,3-dihydro-1H-inden-1-yl]amino}-pyrimidin-4-yl)amino]-2-hydroxycyclopentyl}methyl sulfamate; |
| I-66 | ((1S,2S,4R)-4-{[6-({(1S,2S)-2-[(dimethylamino)carbonyl]-2,3-dihydro-1H-inden-1-yl}amino)pyrimidin-4-yl]oxy}-2-hydroxycyclopentyl)methyl sulfamate |
| I-67 | ((1S,2S,4R)-4-{[8-(2,3-dimethoxyphenyl)-9H-purin-6-yl]amino}-2-hydroxycyclopentyl)methyl sulfamate; |
| I-68 | [(1S,2S,4R)-4-({8-[2-(benzyloxy)phenyl]-9H-purin-6-yl}amino)-2-hydroxycyclopentyl]methyl sulfamate; |
| I-69 | {(1S,2S,4R)-2-hydroxy-4-[(8-phenyl-9H-purin-6-yl)amino]cyclopentyl}methyl sulfamate; |
| I-71 | {(1S,2S,4R)-4-[(6-{[(1S)-3,3-dimethyl-2,3-dihydro-1H-inden-1-yl]amino}-5-fluoropyrimidin-4-yl)amino]-2-hydroxycyclopentyl}methyl sulfamate |
| I-73 | ((1S,2S,4R)-4-{[8-(7-chloroquinolin-4-yl)-7H-purin-6-yl]oxy}-2-hydroxycyclopentyl)methyl sulfamate; |
| I-74 | ((1S,2S,4R)-2-hydroxy-4-{[6-(1-naphthyl)-7H-pyrrolo[2,3-d]pyrimidin-4-yl]amino}cyclopentyl)methyl sulfamate; |
| I-76 | [(1S,3R,4R)-3-({6-[(1S)-2,3-dihydro-1H-inden-1-ylamino]pyrimidin-4-yl}amino)-4-hydroxycyclopentyl]methyl sulfamate |
| I-77 | {(1S,2S,4R)-2-hydroxy-4-[(6-{[(1S,2R)-1-methoxy-2,3-dihydro-1H-inden-2-yl]oxy}-pyrimidin-4-yl)oxy]cyclopentyl}methyl sulfamate |
| I-79 | {(1S,2S,4R)-2-hydroxy-4-[(6-{[(1R,2S)-1-methoxy-2,3-dihydro-1H-inden-2-yl]oxy}-pyrimidin-4-yl)oxy]cyclopentyl}methyl sulfamate |
| I-80 | {(1S,2S,4R)-4-[(9-benzyl-9H-purin-6-yl)oxy]-2-hydroxycyclopentyl}methyl sulfamate |
| I-81 | ((1S,2S,4R)-2-hydroxy-4-{[6-(2-phenylethyl)pyrimidin-4-yl]amino}cyclopentyl)methyl sulfamate |
| I-82 | N-({(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl)sulfamide |
| I-83 | {(1S,2S,4R)-4-[(5-fluoro-6-{[(1R,2S)-2-methoxy-2,3-dihydro-1H-inden-1-yl]amino}pyrimidin-4-yl)oxy]-2-hydroxycyclopentyl}methyl sulfamate; |
| I-84 | {(1S,2S,4R)-2-hydroxy-4-[(8-quinolin-8-yl-7H-purin-6-yl)amino]cyclopentyl}methyl sulfamate; |
| I-85 | {(1R,2R,3S,4R)-4-[(6-{[(1R,2R)-2-(benzyloxy)cyclopentyl]amino}pyrimidin-4-yl)amino]-2,3-dihydroxycyclopentyl}methyl sulfamate |
| I-86 | ((1R,2R,3S,4R)-2,3-dihydroxy-4-{[6-(2-phenylethyl)pyrimidin-4-yl]amino}cyclopentyl)-methyl sulfamate |
| I-87 | ((1S,2S,4R)-2-hydroxy-4-{[8-(1-naphthyl)-9H-purin-6-yl]oxy}cyclopentyl)methyl sulfamate; |
| I-88 | {(1S,2S,4R)-4-[(8-benzyl-9H-purin-6-yl)amino]-2-hydroxycyclopentyl}methyl sulfamate; |
| I-89 | [(1S,2S,4R)-4-({6-[(4-chlorobenzyl)oxy]pyrimidin-4-yl}oxy)-2-hydroxycyclopentyl]methyl sulfamate |
| I-90 | {(1S,2S,4R)-2-hydroxy-4-[(2-phenyl[1,3]oxazolo[5,4-d]pyrimidin-7-yl)amino]cyclopentyl}methyl sulfamate; |
| I-92 | {(1R,2R,3S,4R)-4-[(6-{[(1S,2S)-2-(benzyloxy)cyclopentyl]amino}pyrimidin-4-yl)amino]-2,3-dihydroxycyclopentyl}methyl sulfamate |
| I-93 | ((1S,2S,4R)-4-{[8-(2,6-dimethoxyphenyl)-9H-purin-6-yl]amino}-2-hydroxycyclopentyl)methyl sulfamate; |
| I-94 | [(1S,2S,4R)-4-({2-[(1S)-2,3-dihydro-1H-inden-1-ylamino]pyridin-4-yl}oxy)-2-hydroxycyclopentyl]methyl sulfamate |
| I-96 | {(1S,2S,4R)-2-hydroxy-4-[(6-{[(1R,2S)-2-methoxy-2,3-dihydro-1H-inden-1-yl]oxy}-pyrimidin-4-yl)oxy]cyclopentyl}methyl sulfamate |
| I-97 | [(1S,2S,4R)-2-hydroxy-4-(pyrimidin-4-yloxy)cyclopentyl]methyl sulfamate |
| I-98 | {(1S,2S,4R)-2-hydroxy-4-[(6-{[(1S,2R)-2-methoxy-2,3-dihydro-1H-inden-1-yl]oxy}-pyrimidin-4-yl)oxy]cyclopentyl}methyl sulfamate |
| I-99 | ((1S,2S,4R)-2-hydroxy-4-{[8-(3-methoxyphenyl)-9H-purin-6-yl]amino}cyclopentyl)methyl sulfamate; |
| I-100 | ((1S,2S,4R)-4-{[8-(2,2-dimethyl-2,3-dihydro-1-benzofuran-7-yl)-9H-purin-6-yl]amino}-2-hydroxycyclopentyl)methyl sulfamate; |

| | Chemical Name |
|---|---|
| I-101 | [(1S,2S,4R)-2-hydroxy-4-({8-[(3-methylphenyl)sulfonyl]-9H-purin-6-yl}oxy)cyclopentyl]methyl sulfamate; |
| I-102 | [(1S,2S,4R)-4-({8-[4-(benzyloxy)phenyl]-7H-purin-6-yl}amino)-2-hydroxycyclopentyl]methyl sulfamate; |
| I-103 | [(1S,2S,4R)-4-({8-[4-(dimethylamino)-1-naphthyl]-7H-purin-6-yl}oxy)-2-hydroxycyclopentyl]methyl sulfamate; |
| I-105 | {(1S,2S,4R)-4-[(8-biphenyl-3-yl-9H-purin-6-yl)amino]-2-hydroxycyclopentyl}methyl sulfamate; |
| I-106 | {(1R,2R,3S,4R)-4-[{6-[(1S)-2,3-dihydro-1H-inden-1-ylamino]pyrimidin-4-yl}(methyl)amino]-2,3-dihydroxycyclopentyl}methyl sulfamate; |
| I-107 | ((1S,2S,4R)-2-hydroxy-4-{[8-(2-methylphenyl)-9H-purin-6-yl]amino}cyclopentyl)methyl sulfamate; |
| I-108 | ((1R,2R,3S,4R)-2,3-dihydroxy-4-{[6-(phenylethynyl)pyrimidin-4-yl]amino}cyclopentyl)methyl sulfamate; |
| I-109 | ((1S,2S,4R)-2-hydroxy-4-{[2-(1-naphthyl)-3H-imidazo[4,5-b]pyridin-7-yl]oxy}cyclopentyl)methyl sulfamate; |
| I-110 | (1S,2S,4R)-2-(hydroxymethyl)-4-{[8-(5,6,7,8-tetrahydronaphthalen-1-yl)-9H-purin-6-yl]amino}cyclopentanol |
| I-111 | ((1S,2S,4R)-4-{[8-(4-chlorophenyl)-9H-purin-6-yl]amino}-2-hydroxycyclopentyl)methyl sulfamate; |
| I-112 | {(1S,2S,4R)-2-hydroxy-4-[(8-isoquinolin-4-yl-7H-purin-6-yl)oxy]cyclopentyl}methyl sulfamate; |
| I-113 | [(1R,2R,3S,4R)-4-({2-[(1S)-2,3-dihydro-1H-inden-1-ylamino]-5-fluoropyrimidin-4-yl}-amino)-2,3-dihydroxycyclopentyl]methyl sulfamate |
| I-114 | {(1S,2S,4R)-2-hydroxy-4-[(6-phenylpyrimidin-4-yl)oxy]cyclopentyl}methyl sulfamate |
| I-115 | {(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl sulfamate; |
| I-117 | ((1S,2S,4R)-4-{[8-(2,3-dihydro-1-benzofuran-7-yl)-7H-purin-6-yl]amino}-2-hydroxycyclopentyl)methyl sulfamate; |
| I-118 | ((1R,2R,3S,4R)-2,3-dihydroxy-4-{[6-(5,6,7,8-tetrahydronaphthalen-1-ylamino)pyrimidin-4-yl]amino}cyclopentyl)methyl sulfamate; |
| I-119 | ((1S,2S,4R)-2-hydroxy-4-{[6-(1-naphthylmethoxy)pyrimidin-4-yl]oxy}cyclopentyl)methyl sulfamate |
| I-120 | ((1S,2S,4R)-4-{[6-(1,3-dihydro-2H-isoindol-2-yl)pyrimidin-4-yl]oxy}-2-hydroxycyclopentyl)methyl sulfamate |
| I-121 | ((1S,2S,4R)-2-hydroxy-4-{[8-(1,2,3,4-tetrahydronaphthalen-1-yl)-9H-purin-6-yl]amino}cyclopentyl)methyl sulfamate; |
| I-122 | [(1S,2S,4R)-2-hydroxy-4-({8-[2-(trifluoromethyl)phenyl]-9H-purin-6-yl}amino)cyclopentyl]methyl sulfamate; |
| I-123 | {(1S,2S,4R)-2-hydroxy-4-[methyl(9-methyl-8-phenyl-9H-purin-6-yl)amino]cyclopentyl}-methyl sulfamate |
| I-124 | {(1S,2S,4R)-4-[(6-{[(1S)-3,3-dimethyl-2,3-dihydro-1H-inden-1-yl]amino}pyrimidin-4-yl)oxy]-2-hydroxycyclopentyl}methyl sulfamate; |
| I-125 | {(1S,2S,4R)-2-hydroxy-4-[(4-{[(1R,2S)-2-methoxy-2,3-dihydro-1H-inden-1-yl]amino}-1,3,5-triazin-2-yl)amino]cyclopentyl}methyl sulfamate; |
| I-126 | ((1S,2S,4R)-2-hydroxy-4-{[8-(5,6,7,8-tetrahydronaphthalen-1-yl)-9H-purin-6-yl]amino}cyclopentyl)methyl sulfamate; |
| I-127 | ((1S,2S,4R)-4-{[6-(cyclopentylamino)pyrimidin-4-yl]oxy}-2-hydroxycyclopentyl)methyl sulfamate |
| I-128 | {(1S,2S,4R)-4-[(8-cyclohexyl-9H-purin-6-yl)amino]-2-hydroxycyclopentyl}methyl sulfamate; |
| I-129 | ((1S,2S,4R)-4-{[8-(1-benzyl-1H-pyrazol-4-yl)-7H-purin-6-yl]oxy}-2-hydroxycyclopentyl)methyl sulfamate; |
| I-130 | {(1S,2S,4R)-2-hydroxy-4-[(9-methyl-8-phenyl-9H-purin-6-yl)amino]cyclopentyl}methyl sulfamate; |
| I-131 | {(1S,2S,4R)-4-[(8-tert-butyl-9H-purin-6-yl)amino]-2-hydroxycyclopentyl}methyl sulfamate; |
| I-132 | {(1S,2S,4R)-4-[(6-benzylpyrimidin-4-yl)oxy]-2-hydroxycyclopentyl}methyl sulfamate |
| I-133 | ((1S,2S,4R)-2-hydroxy-4-{[8-(2-methoxyphenyl)-9H-purin-6-yl]amino}cyclopentyl)methyl sulfamate; |
| I-134 | {(1S,2S,4R)-4-[(4-{[(1S)-3,3-dimethyl-2,3-dihydro-1H-inden-1-yl]amino}-1,3,5-triazin-2-yl)amino]-2-hydroxycyclopentyl}methyl sulfamate; |
| I-136 | [(1S,2S,4R)-2-hydroxy-4-({8-[(3-methylphenyl)sulfanyl]-7H-purin-6-yl}oxy)cyclopentyl]methyl sulfamate; |
| I-137 | [(1S,2S,4R)-4-({8-[2-(dimethylamino)phenyl]-9H-purin-6-yl}amino)-2-hydroxycyclopentyl]methyl sulfamate; |
| I-138 | (1S,2S,4R)-4-{[8-(2,3-dihydro-1,4-benzodioxin-5-yl)-9H-purin-6-yl]amino}-2-(hydroxymethyl)cyclopentanol |
| I-139 | ((1S,2S,4R)-2-hydroxy-4-{[8-(4-pyrrolidin-1-yl-1-naphthyl)-7H-purin-6-yl]oxy}cyclopentyl)methyl sulfamate; |
| I-140 | ((1S,2S,4R)-2-hydroxy-4-{[8-(1H-indol-3-yl)-7H-purin-6-yl]oxy}cyclopentyl)methyl sulfamate; |
| I-141 | ((1S,2S,4R)-2-hydroxy-4-{[6-(2-naphthylmethoxy)pyrimidin-4-yl]oxy}cyclopentyl)methyl sulfamate |
| I-142 | {(1S,2S,4R)-2-hydroxy-4-[(6-{[(1R,2S)-2-methoxy-1,2,3,4-tetrahydronaphthalen-1-yl]amino}pyrimidin-4-yl)oxy]cyclopentyl}methyl sulfamate; |

-continued

| Chemical Name |
|---|
| I-143 {(1S,2S,4R)-2-hydroxy-4-[(6-{[(1S,2R)-2-methoxy-1,2,3,4-tetrahydronaphthalen-1-yl]amino}pyrimidin-4-yl)oxy]cyclopentyl}methyl sulfamate; |
| I-144 {(1R,2R,3S,4R)-4-[(2-{[(1S)-2,3-dihydro-1H-inden-1-ylamino]carbonyl}pyridin-4-yl)-amino]-2,3-dihydroxycyclopentyl}methyl sulfamate |
| I-145 ((1R,2R,3S,4R)-4-{[2-(2,3-dihydro-1H-indol-1-ylcarbonyl)pyridin-4-yl]amino}-2,3-dihydroxycyclopentyl)methyl sulfamate |
| I-146 ((1S,2S,4R)-4-{4-[(1S)-2,3-dihydro-1H-inden-1-ylamino]-5,6-dihydro-7H-pyrrolo[2,3-d]pyrimidin-7-yl}-2-hydroxycyclopentyl)methyl sulfamate; |
| I-147 {(1S,2S,4R)-4-[(4-{[(1R)-2,2-difluoro-2,3-dihydro-1H-inden-1-yl]amino}-1,3,5-triazin-2-yl)amino]-2-hydroxycyclopentyl}methyl sulfamate; |
| I-148 {(1S,2S,4R)-4-[(6-{[(1S,2R)-2,7-dimethoxy-1,2,3,4-tetrahydronaphthalen-1-yl]amino}-pyrimidin-4-yl)oxy]-2-hydroxycyclopentyl}methyl sulfamate |
| I-149 {(1S,2S,4R)-4-[(6-{[(1R,2S)-2,7-dimethoxy-1,2,3,4-tetrahydronaphthalen-1-yl]amino}-pyrimidin-4-yl)oxy]-2-hydroxycyclopentyl}methyl sulfamate |
| I-150 {(1S,2S,4R)-2-hydroxy-4-[(6-{[(1R,2S)-2-methoxy-4,4-dimethyl-1,2,3,4-tetrahydronaphthalen-1-yl]amino}pyrimidin-4-yl)oxy]cyclopentyl}methyl sulfamate; |
| I-151 {(1S,2S,4R)-2-hydroxy-4-[(6-{[(1S,2R)-2-methoxy-4,4-dimethyl-1,2,3,4-tetrahydronaphthalen-1-yl]amino}pyrimidin-4-yl)oxy]cyclopentyl}methyl sulfamate; and |
| I-152 ((1S,3S)-3-{[8-(1-naphthyl)-9H-purin-6-yl]oxy}cyclopentyl)methyl sulfamate |
| I-153 [(1S,2S,4R)-4-({4-[(1S)-2,3-dihydro-1H-inden-1-ylamino]-1,3,5-triazin-2-yl}amino)-2-hydroxycyclopentyl]methyl sulfamate. |

General Synthetic Methodology

The compounds of the present invention can be prepared by methods known to one of ordinary skill in the art and/or by reference to the schemes shown below and the synthetic examples that follow. Exemplary synthetic routes are set forth in Schemes 1-21 below, and in the Examples.

As shown in Scheme 1, conversion of i to the compounds of formula iii is accomplished by coupling with the appropriately substituted pyrimidines at elevated temperature in protic solvents, such as EtOH or BuOH, using an appropriate base, such as DIPEA or Et$_3$N in the presence of microwave irradiation (Method A). Selective protection of the Scheme 1: General route for the synthesis of 2- and 6-substituted ((1R,2R,3S,4R)-4-[(pyrimidin-4-yl)amino]-2,3-dihydroxycyclopentyl)methyl sulfamates

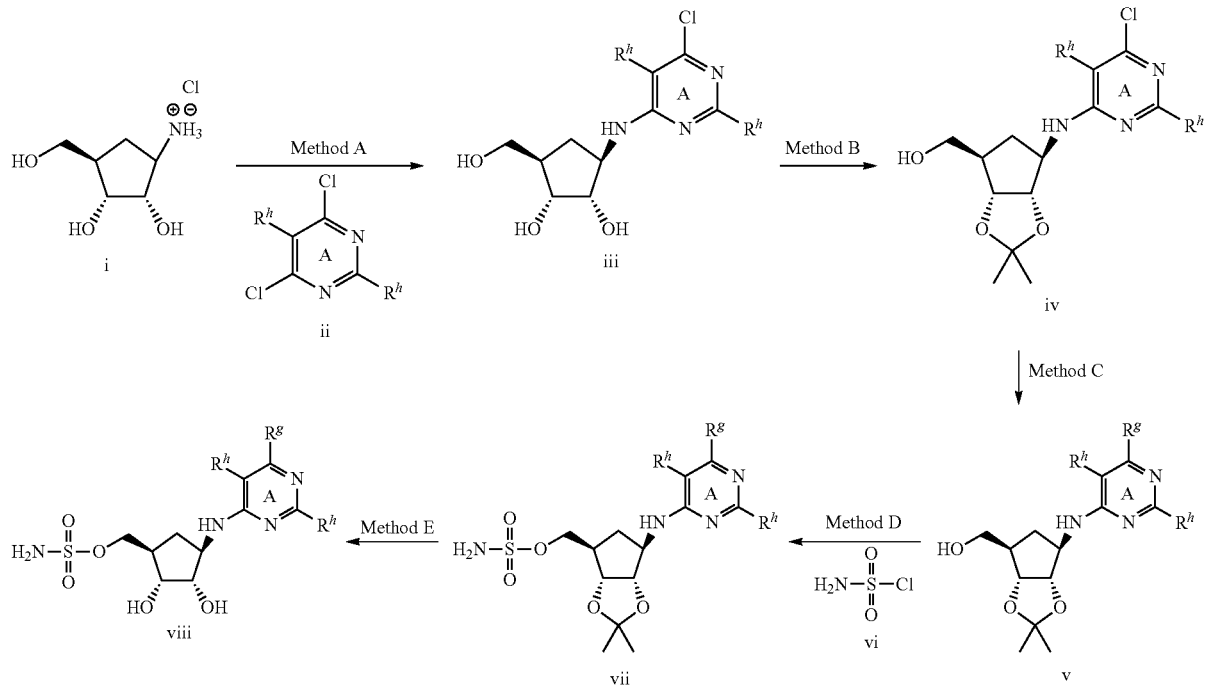

Scheme 1 above shows a general route for preparing compounds of formula (I-B), wherein W is —NH— and R$^c$ is —OH. Those of ordinary skill in the art will recognize that compounds of formula (I-B) wherein Ring A is other than pyrimidine can be prepared by the same general route, beginning with appropriate starting materials analogous to ii.

vicinal diol of iii is effected at this stage by treatment with 2,2-dimethoxypropane in the presence of an organic acid, such as p-TsOH in a solvent, such as MeOH or acetone (Method B). Displacement of the aryl chloride of formula iv is achieved by coupling with the appropriately substituted nucleophile, such as an amine, alcohol or thiol at elevated temperature using microwave irradiation in the absence of solvent (Method C). Further treatment with freshly prepared chlorosulfonamide vi affords the sulfamates vii (Method D). Cleavage of the acetal by treatment with a strong acid, such as TFA, in the presence of water according to Method E yields compounds of formula viii.

Scheme 2: Route for the synthesis of 6-substituted [(1S,2S,4R)-4-[(pyrimidin-4-yl)-amino]-2-mono and 2,3 dihydrocycyclopentyl]methyl sulfamates

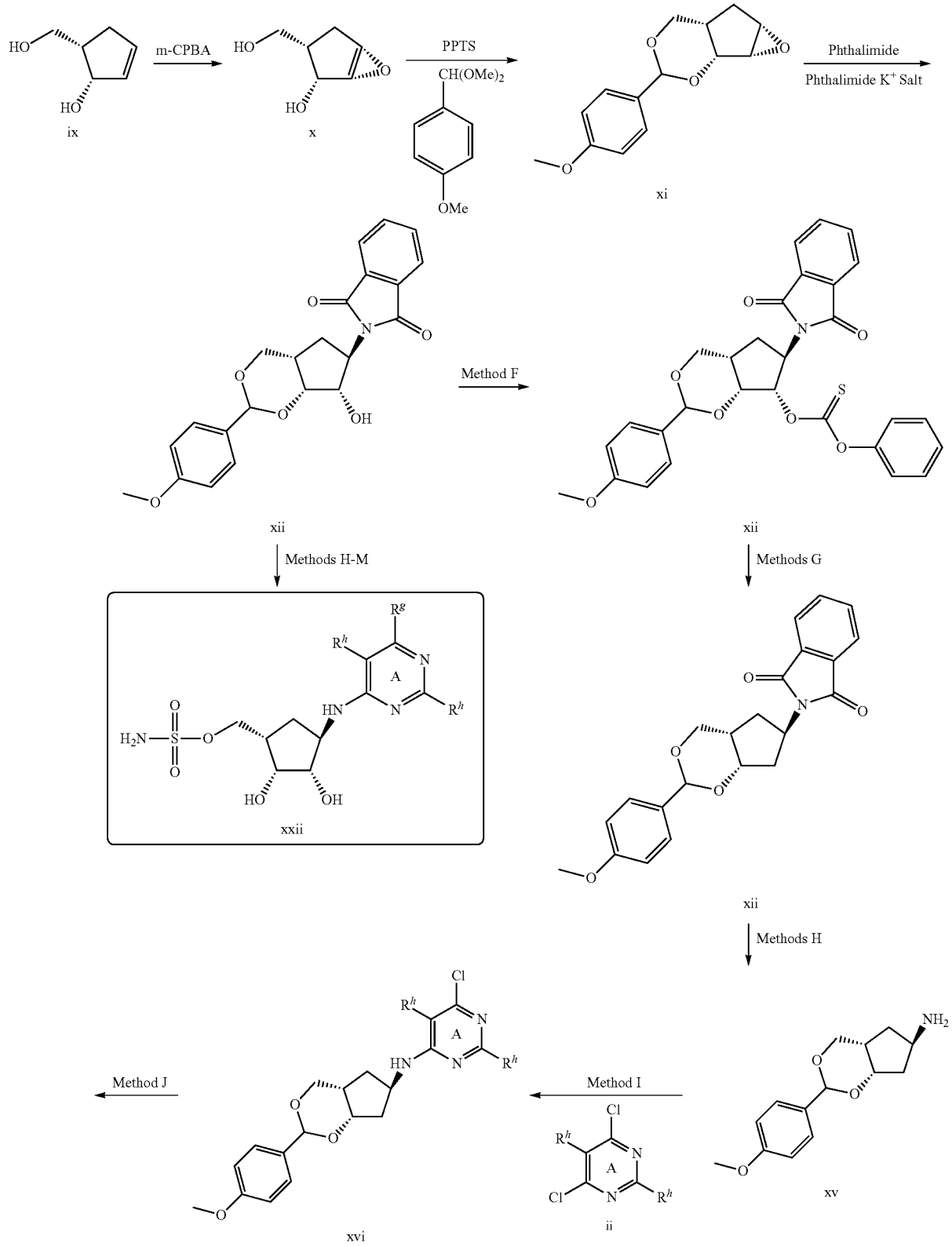

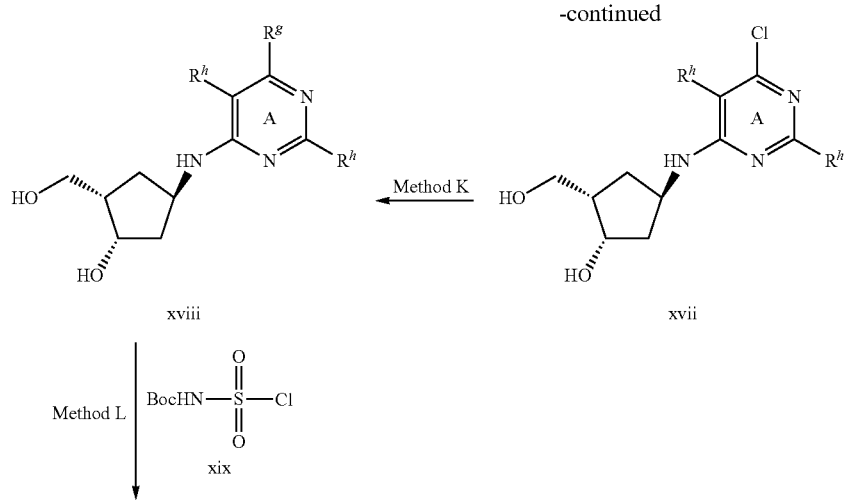

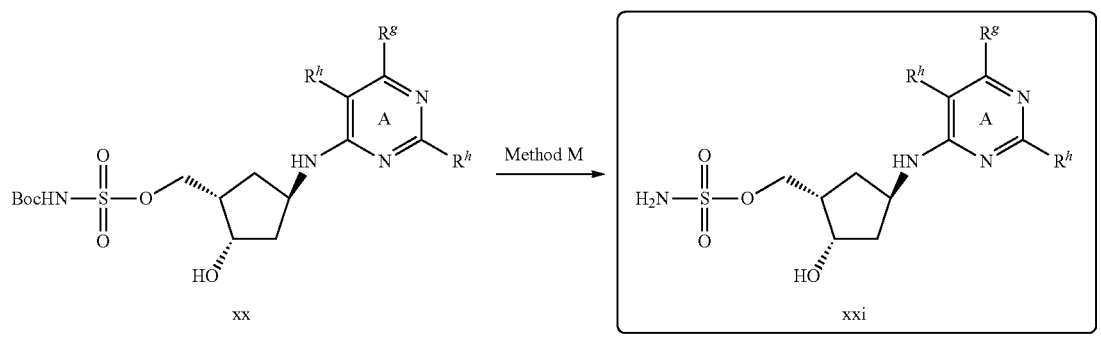

Compounds of formula (I-A) can be prepared by the methods described in Scheme 2. Methods for the synthesis of the intermediate alkene diol ix are known (*Nucleosides, Nucleotides & Nucleic Acids,* 2002, 21, 65-72). Upon treatment with m-CPBA, diol ix is converted to epoxy diol x. Subsequent protection of the diol using p-anisaldehyde dimethyl acetal in the presence of pyridinium p-toluenesulfonate provides epoxide xi. Opening of the epoxide using a mixture of phthalimide and phthalimide potassium salt in DMSO at elevated temperature affords alcohol xii. This alcohol is then alkylated by treatment with chlorophenyl-thionocarbonate and DMAP in DCM to afford thiocarbonate xiii (Method F). Deoxygenation at this stage is achieved by treatment with tris(trimethylsilyl)silane and air in toluene followed by $BEt_3$ in toluene to give xiv (Method G). Subsequent deprotection with hydrazine in EtOH at elevated temperature gives amine xv (Method H).

Conversion of amine xv to compounds of formula xvi is accomplished by coupling with the appropriately substituted pyrimidines at elevated temperature in protic solvents, such as EtOH or BuOH, using art appropriate base, such as $Et_3N$ in a sealed tube (Method I). Again, those of ordinary skill in the art will recognize that compounds of formula xxi and xxii wherein Ring A is other than pyrimidine can be prepared by the same general route, using a starting material analogous to ii.

The treatment of compounds having the general formula xvi with an amine, such as benzylamine, in the absence of solvent at elevated temperatures using microwave irradiation results in deprotection of the diol, and then repeating the process in the presence of a base, such as DIPEA or $Et_3N$ at elevated temperatures in a protic solvent, such as EtOH or BuOH using microwave irradiation affords substituted pyrimidines xviii (Methods J and K).

Methods for the synthesis of tert-butyl chlorosulfonylcarbamate xix are known (Hirayama et al., *Biorg. Med. Chem.,* 2002, 10, 1509-1523), and this reagent is reacted selectively with the primary alcohol using a hindered base, such as 2,6-di-tert-butyl-4-methylpyridine, in a solvent, such as ACN, to afford Boc sulfamates of formula xx (Method L). Removal of the siloxy group with a protic acid such as TFA (Method M) yields the compounds of formula xxi.

Alternatively, compound xii can be directly exposed to the conditions described in Methods H-M, to afford dihydroxy-cyclopentyl methyl sulfamates of formula xxii.

Scheme 3: General route for the synthesis of 4-amido substituted {(1R,2R,3S,4R,)-2,3-Dihydroxycyclopentyl}methyl sulfamates

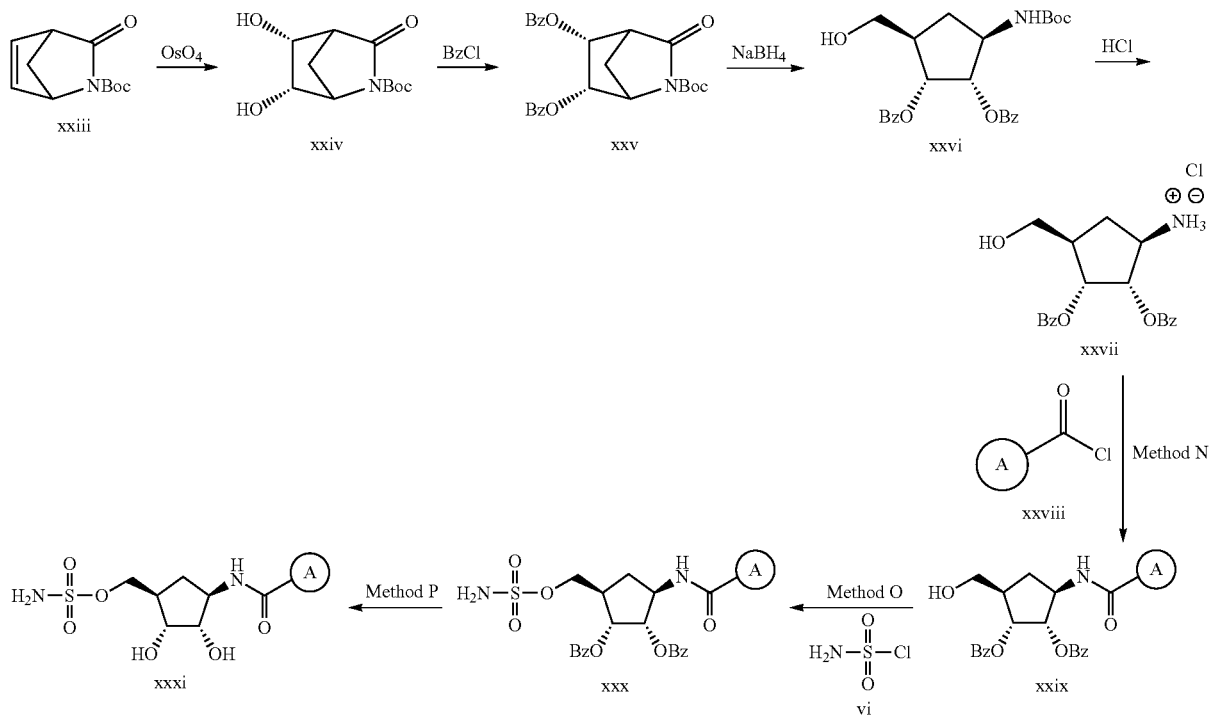

Compounds of formula (I-B), wherein W is —NHC(O)— can be prepared by the methods shown above in Scheme 3. Methods for the synthesis of bicyclic lactam xxiii are known (Daluge et al., *Nucleosides, Nucleotides & Nucleic Acids*, 2000, 19, 297-327). Dihydroxylation using osmium tetroxide in the presence of an organic N-oxide, such as N-methylmorpholine oxide, in a solvent, such as acetone, gives diol xxiv. Global protection of both alcohols using benzyl chloride and a base, such as $Et_3N$, and a catalyst, such as DMAP, in a solvent, such as DCM, gives compound xxv. The resulting bicyclic lactam is reduced using $NaBH_4$ to afford Boc-protected amine xxvi, which is then deprotected upon treatment with HCl in the absence of water. The resulting secondary amine hydrochloride xxvii is treated with an acyl chloride of formula xxviii in the presence of a base, such as $Et_3N$ or DIPEA, in an aprotic solvent, such as DCM to afford amides of formula xxix according to Method N. The primary alcohol of xxx is then sulfamoylated by treatment with chlorosulfonamide vi and a base, such as DBU, in a polar aprotic solvent, such as ACN (Method O). Global deprotection of both secondary alcohols using ammonia in a polar solvent, such as MeOH, yields final sulfamates of formula xxxi (Method P).

Scheme 4: Synthesis of 2- and 6-substituted [(1R,2S,4R)-4-[(pyrimidin-4-yl)amino]-2-hydroxycyclopentyl]methyl sulfamates

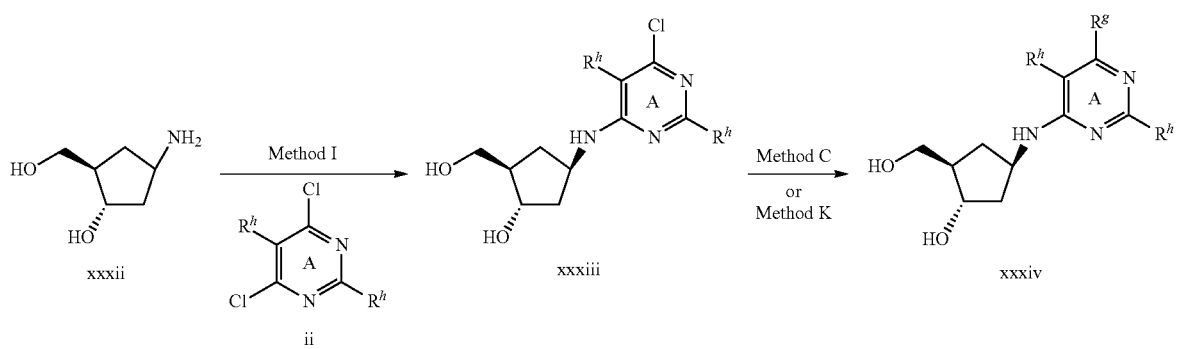

Compounds of formula (I-B), wherein W is —NH— and $R^c$ and $R^d$ are hydrogen can be prepared by the methods shown above in Scheme 4. Amino diol xxxii (Ober, M.; Muller, H.; Pieck, C.; Gierlich, J.; Carell, T. *J. Am. Chem. Soc.* 2005, 127, 18143-18149) is treated with dichloropyrimidines of formula ii according to Method I to give chloropyrimidines of formula xxxiii. Further reaction with an appropriately substituted nucleophile according to Method C or Method K gives compounds of formula xxxiv. These diols are subsequently selectively sulfamoylated and deprotected according to Methods L-M as outlined in Scheme 2.

Scheme 5: Synthesis of [(1R,2R,3S,4R)-4-({4-[(1S)-2,3-dihydro-1H-inden-1-ylamino]-1,3,5-triazin-2-yl}amino)-2,3-dihydroxycyclopentyl]methyl sulfamate

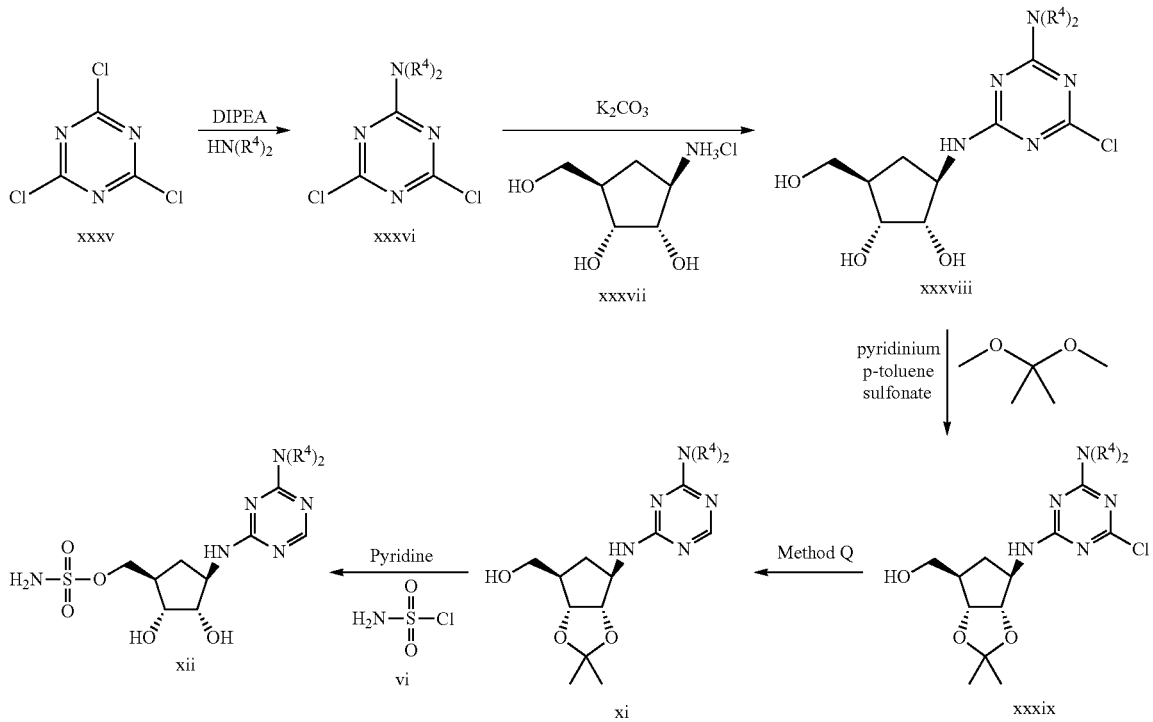

Compounds of formula (I-B), wherein Ring A is a triazine ring, can be prepared as shown in Scheme 5. Coupling of cyanuric chloride xxxv with a primary or secondary amine in a solvent such as THF using a base such as DIPEA at reduced temperature affords dichloride xxxvi. Displacement of one chloride with amine hydrochloride xxxvii, followed by selective protection of the vicinal hydroxyl groups using 2,2-dimethoxypropane in the presence of pyridinium p-toluene sulfonate affords alcohol xxxix. Removal of the remaining aryl chloride using hydrogen in the presence of palladium on carbon (Method Q), followed by sulfamoylation using chlorosulfonamide vi gives sulfamate xli.

Scheme 6: General route for the synthesis of 2- and 6-substituted ((1S,2S,4R)-4-[(pyrimidin-4-yl)oxy]-2-hydroxycyclopentyl)methyl sulfamates

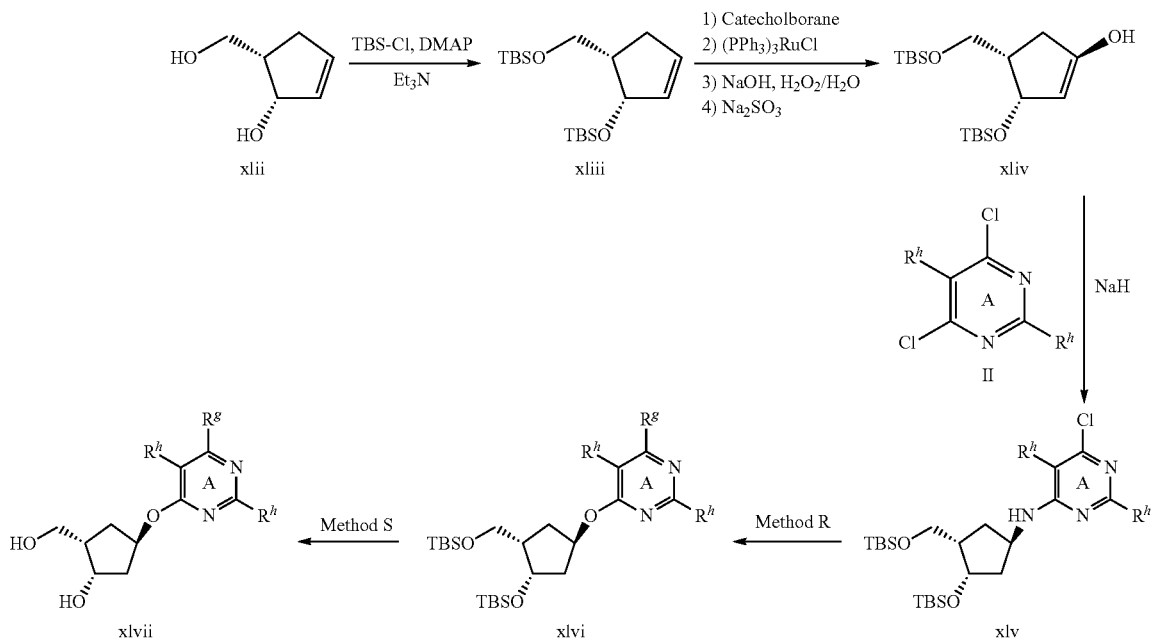

Compounds of formula (I-A), wherein W is —O— can be prepared as depicted above in Scheme 6. Methods for the synthesis of diol xlii are known (MacKeith et al., *Biorg. Med. Chem.*, 1994, 2, 387-394), and this reagent is bis-protected using TBS-Cl and Et₃N in the presence of DMAP at elevated temperatures. Subsequent hydroboration-oxidation using catecholborane and Wilkinson's catalyst followed by NaOH, hydrogen peroxide and finally sodium sulfite yields cyclopentanol xliv. This secondary alcohol is deprotonated with the use of sodium hydride, and then reacted with dichloropyrimidines of formula ii at reduced temperature to afford coupled chloropyrimidines of formula xlv. Displacement of the aryl chloride is achieved by coupling with the appropriately substituted nucleophile, such as an amine, alcohol or thiol at elevated temperature using microwave irradiation in a solvent, such as BuOH (Method R). Global deprotection of the silyl ethers using a fluoride reagent, such as TBAF according to Method S gives diols of formula xlvii. Compounds of formula xlvii are then selectively sulfamoylated and deprotected according to Methods L-M as outlined in Scheme 2.

Scheme 7: General route for synthesis of 2- and 6-substituted ((2R,3S,4R,5R)-5-[(pyrimidin-4-yl)amino]-3,4-dihydroxytetrahydrofuran-2-yl)methyl sulfamates

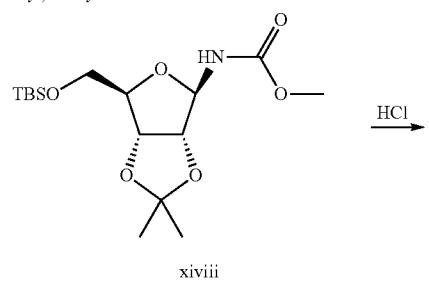

xlviii

HCl →

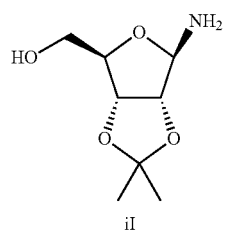

iI

Compounds of formula (I-B), wherein W is —NH— and Y=—O— can be prepared as shown above in Scheme 7. Methods for the synthesis of methyl carbamate xlviii are known (Nicolaou et al., *J. Am. Chem. Soc.*, 2004, 126, 6234-6235). Deprotection using an acid, such as HCl in the absence of water affords amino alcohol iI. Compound iI is then substituted with the appropriate substituents according to Methods A, then C-E and carried on to compounds of formula (I-B) according to Scheme 1.

Scheme 8: General route for synthesis of 2- and 6-substituted ((2R,3S,5R)-5-[(pyrimidin-4-yl)amino]-3-hydroxytetrahydrofuran-2-yl)methyl sulfamates

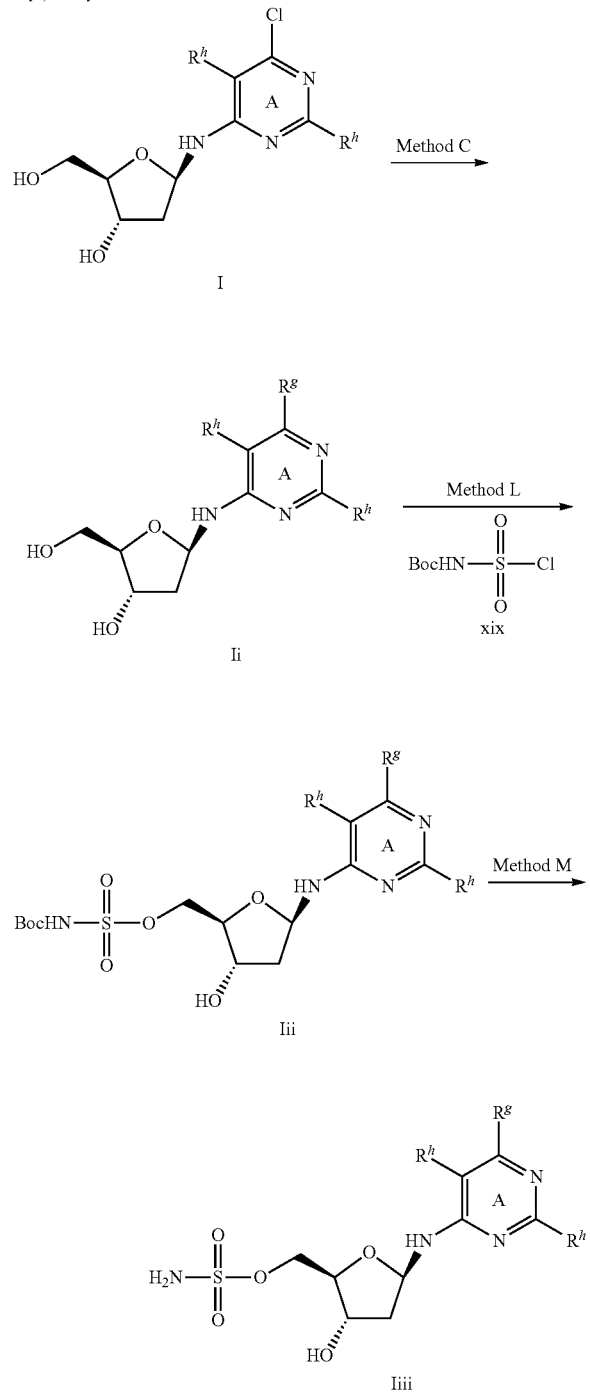

A general route for the synthesis of compounds of formula (I-B), wherein W is —NH—, Y=—O— and R^c is —H is outlined above in Scheme 8. Compounds of formula 1 are known (Kita, et al., *J. Org. Chem.*, 1988, 53, 554-561). Displacement of the aryl chloride using an appropriately substituted nucleophile according to Method C gives pyrimidines of formula li. Compound ii is then selectively sulfamoylated and deprotected to give the final compounds according to Scheme 2 (Methods L-M).

Scheme 9: General route for synthesis of 2- and 6-substituted ((1S,2S,4R)-4-[(pyrimidin-4-yl)sulfanyl]-2-mono and 2,3-dihydroxycyclopentyl)methyl sulfamates

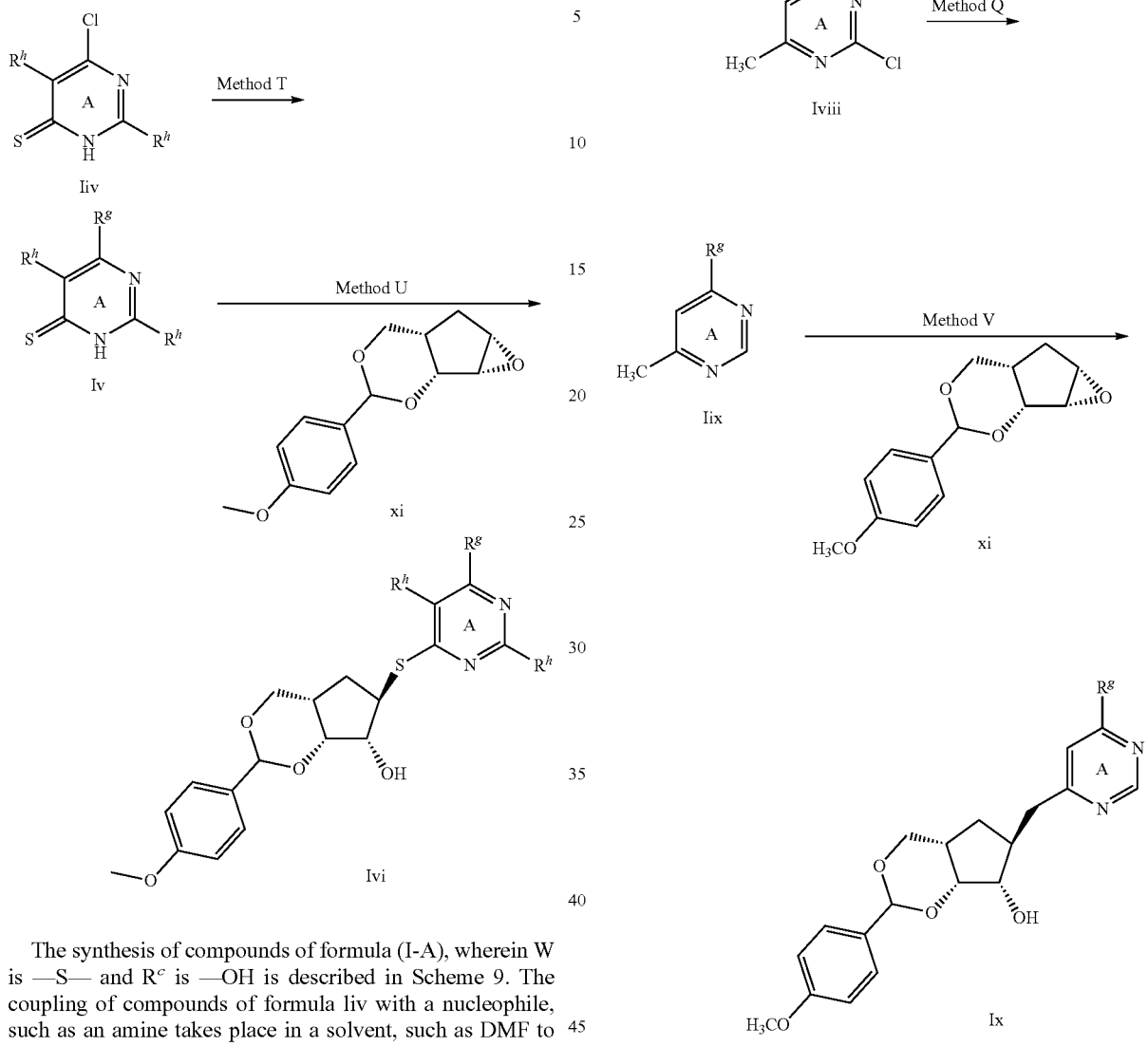

The synthesis of compounds of formula (I-A), wherein W is —S— and $R^c$ is —OH is described in Scheme 9. The coupling of compounds of formula lviv with a nucleophile, such as an amine takes place in a solvent, such as DMF to afford substituted compounds of formula lv (Method T). Subsequent opening of epoxide xi using a base, such as potassium carbonate in a solvent, such as DMF affords alcohol lvi (Method U). Compound lvi is then optionally deoxygenated (Methods F-G) and substituted with the appropriate substituents according to Methods J, then L-M and carried on to compounds of formula (I-A) according to Scheme 2.

Scheme 10: General route for synthesis of 2- and 6-substituted ((1S,2S,4S)-4-[(pyrimidin-4-yl)methyl]-2-mono and 2,3-dihydroxycyclopentyl)methyl sulfamates

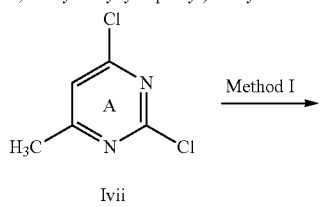

Compounds of formula (I-A), wherein W is —CH$_2$— can be prepared as shown above in Scheme 10. Methyl pyrimidines of formula lvii are coupled with a nucleophile, such as an amine according to Method I to give 2-chloropyrimidines of formula lviii. Hydro-dechlorination according to Method Q gives methylpyrimidines of formula lviii. Deprotonation of the methyl group of lviii is effected by treatment with a strong base, such as phenyllithium, and this carbanion is used to open epoxide xi (Method V). Resulting compounds of formula lix are then optionally deoxygenated (Methods F-G), deprotected and selectively sulfamoylated (Methods J, then L-M) carried on to compounds of formula (I-A) according to Scheme 2.

Scheme 11: General route for synthesis of 2- and 6-substituted ((2S,3S,5S)-5-[(pyrimidin-4-yl)methyl]-3-mono and 3,4-dihydroxytetrahydrofuran-2-yl)-methyl sulfamates Scheme 12: General route for synthesis of 2- and 6-substituted N-[((1R,2R,3S,4R)-4-[(pyrimidin-4-yl)amino]-2,3-dihydroxycyclopentyl)methyl]sulfamides

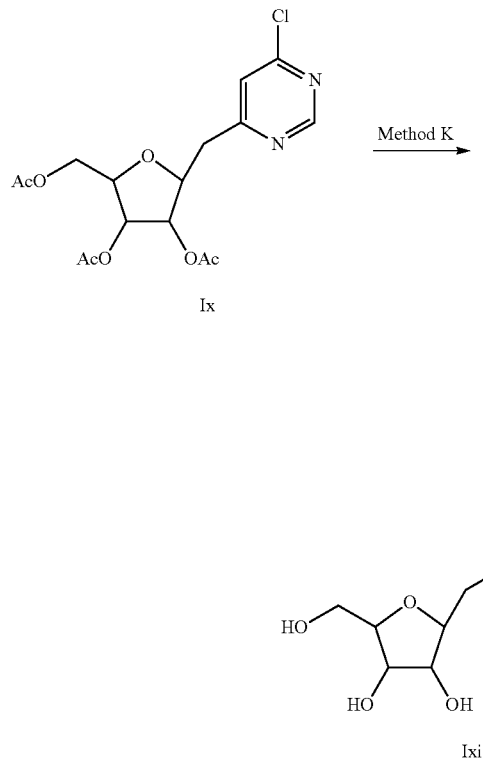

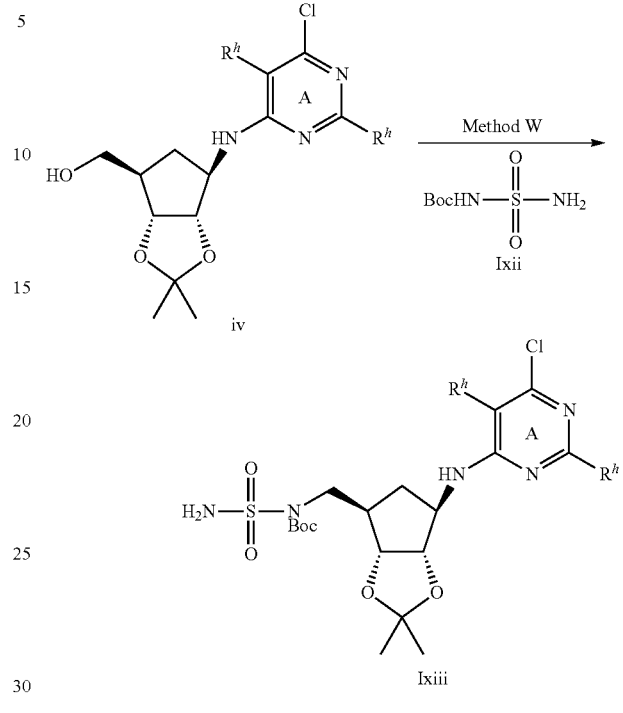

Compounds of formula (I), wherein W is —CH$_2$— and Y=—O— can be prepared above in Scheme 11. Compound lx is known (Renz, et al., *Liebigs Annalen der Chemie*, 1986, 6, 957-966). Coupling with an appropriately substituted nucleophile, such as an amine according to Method K gives the substituted, fully deprotected triol lxi. Compounds of formula lxi are then carried on according to Scheme 2 (Methods L-M).

Compounds of formula (I-B) wherein X=—NH— can be prepared by the methods outlined in Scheme 12. Methods for the synthesis of tert-butyl (aminosulfonyl)-carbamate lxii are known (Masui, et al., *Tet. Lett.*, 2004, 45, 1853-1856). Compounds of formula iv are coupled with this carbamate in the presence of an azodicarboxylate, such as diisobutyl azodicarboxylate in the presence of triphenylphosphine in a solvent, such as EtOAc to give Boc-protected compounds of formula lxiii (Method W). These compounds are then substituted with the appropriate substituents and globally deprotected to give compounds of formula (I-B) according to Methods T and E (Schemes 9 and 1).

Scheme 13: Route to the synthesis of 2- and 6-substituted 2-((1R,2R,3S,4R)-4-[(pyrimidin-4-yl)amino]-2,3-dihydroxycyclopentyl)ethanesulfonamides

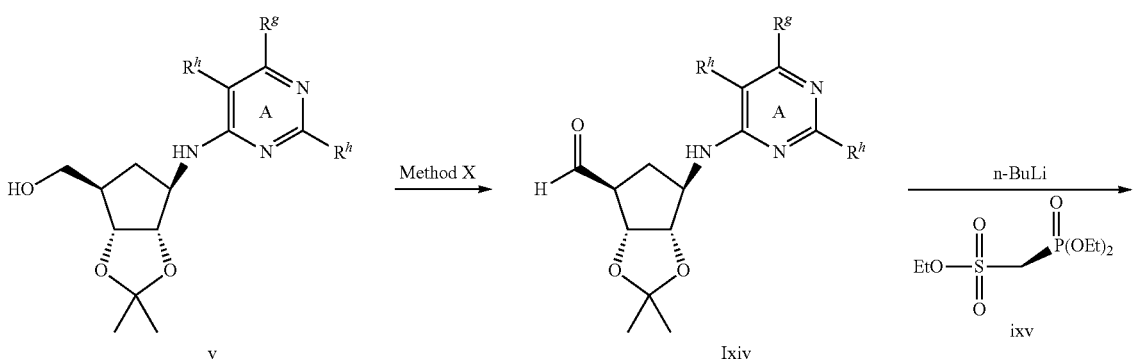

-continued

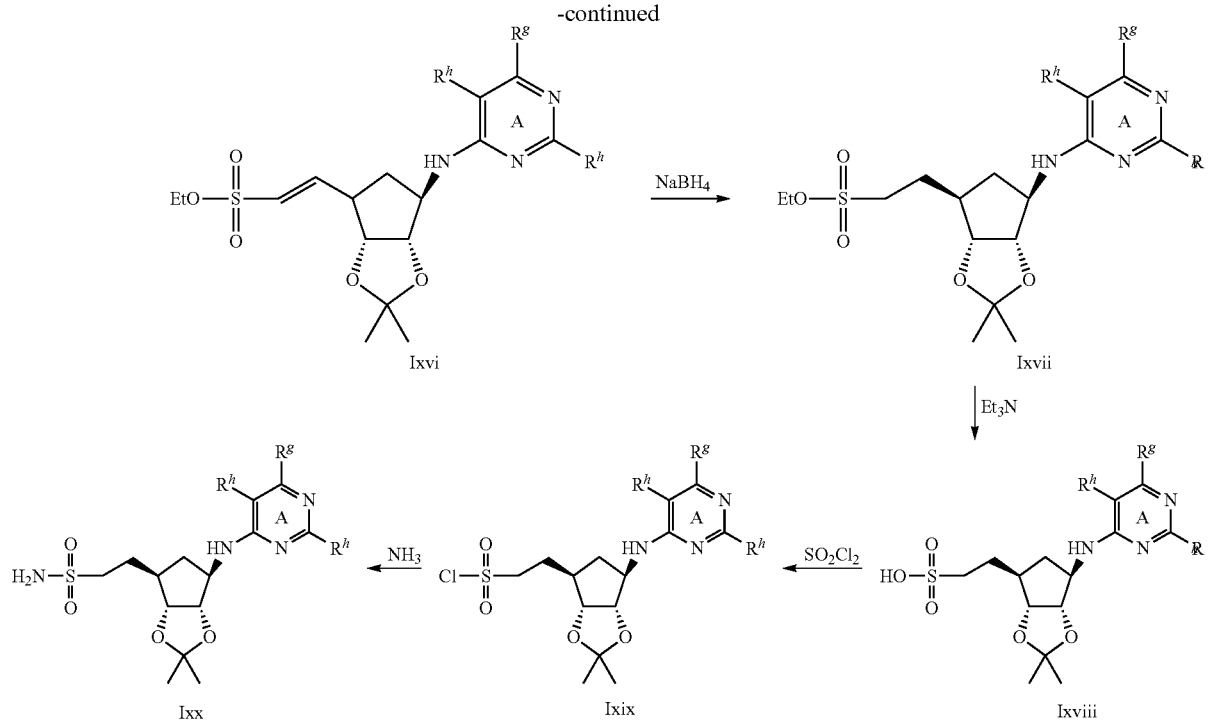

Compounds of formula (I-B) wherein $X=CH_2$ can be prepared by the methods outlined in Scheme 13. Compounds of formula v are oxidized using an oxidizing agent, such as Dess-Martin periodinane in a solvent, such as DCM (Method X). Methods for the synthesis of lxv are known (Carretero, et al., *Tetrahedron.*, 1987, 43, 5125-5134), and this compound is deprotonated using n-BuLi in THF and added to aldehyde lxiv to afford alkenes of formula lxvi. Reduction of the double bond using $NaBH_4$ in EtOH, followed by heating of the resulting sulfonate ester with $Et_3N$ in DCM using microwave irradiation yields sulfonic acid lxviii. Treatment with thionyl chloride at reduced temperature in DCM in the presence of a catalyst, such as DMF gives sulfonyl chlorides of formula lxix. Finally, treatment with ammonia in a solvent, such as 1,4-dioxane in the presence of DIPEA in DCM at reduced temperatures yields sulfonamides of formula lxx.

Scheme 14: Route to the synthesis of 2- and 6-substituted 2-((1R,2R,3S,4R)-4-[(pyrimidin-4-yl)amino]-2,3-dihydroxycyclopentyl)-1,1-difluoroethanesulfonamides

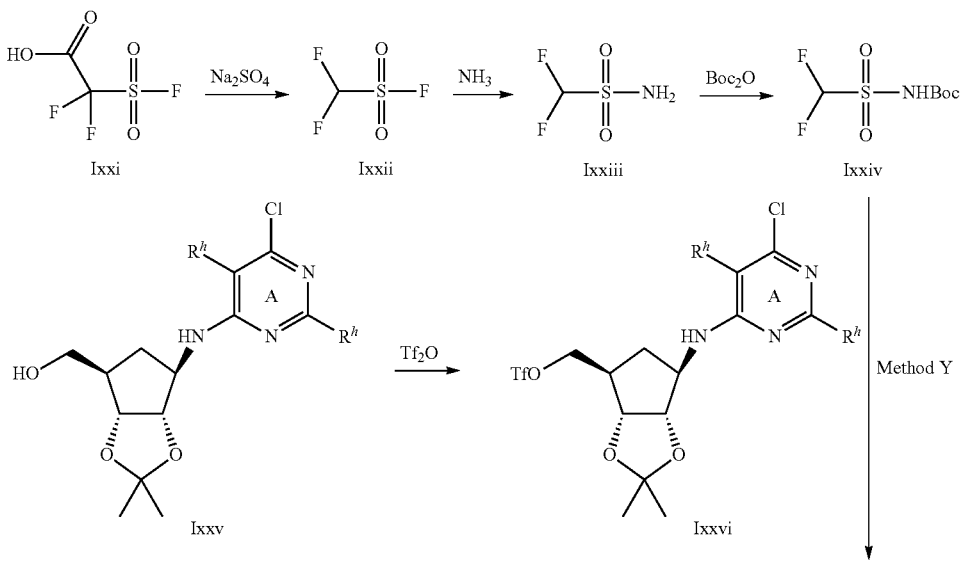

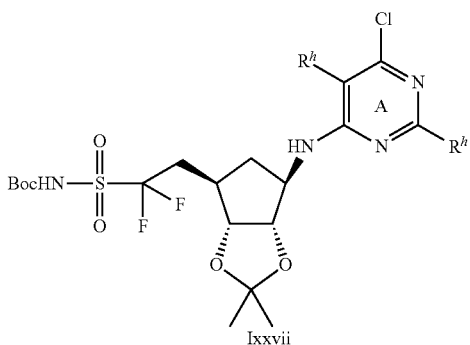

Compounds of formula (I-B) wherein X=CF₂ can be prepared by the methods outlined in Scheme 14. Carboxylic acid lxxi is decarboxylated using sodium sulfate in water to give sulfonyl fluoride lxxii, which is then converted to the corresponding sulfonamide using ammonia in 1,4-dioxane. Boc-protection of the nitrogen using Boc anhydride in the presence of DMAP and Et₃N in DCM yields Boc sulfonamide lxxiv. Deprotonation of the CF₂H group using a strong base, such as LiHMDS at reduced temperature in a solvent, such as THF followed by treatment with triflates of formula lxxvi (generated by treatment of alcohol lxxv with trifluoroacetic anhydride and Et₃N in DCM) gives compounds of formula lxxvii (Method Y). These compounds are then substituted with the appropriate substituents and globally deprotected to give compounds of formula (I-B) according to Methods T and E (Schemes 9 and 1).

Scheme 15: Route to the synthesis of 2- and 6-substituted 2-((1R,2R,3S,4R)-4-[(pyrimidin-4-yl)amino]-2,3-dihydroxycyclopentyl)-1-fluoroethanesulfonamides

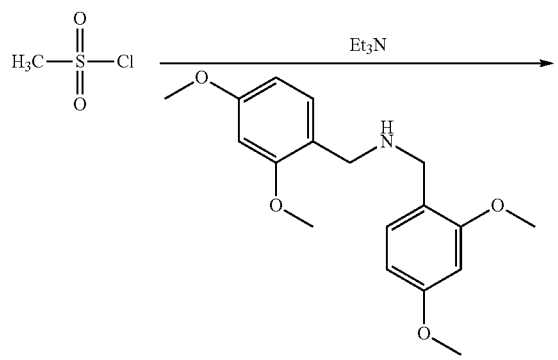

-continued

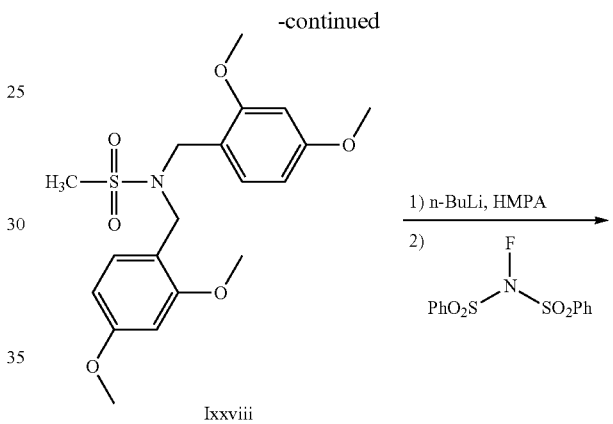

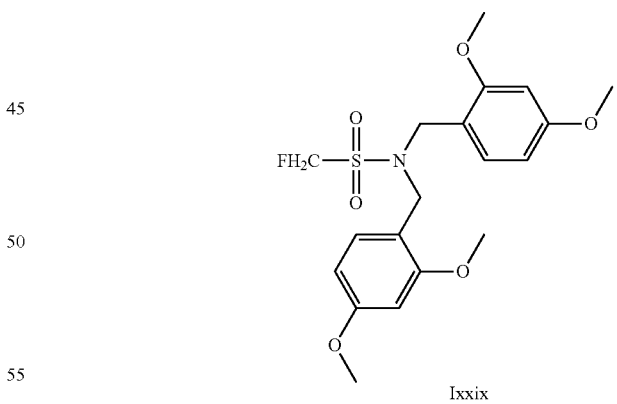

Compounds of formula (I) wherein X=CHF can be prepared by the methods outlined in Scheme 15. Methanesulfonyl chloride is coupled with bis(2,4-dimethoxybenzyl)-amine in the presence of Et₃N and DMAP in DCM to give sulfonamide lxxviii. Further treatment with n-BuLi and HMPA in THF at reduced temperature followed by N-fluorobenzenesulfonimide gives fluoromethylsulfonamide lxxix. This compound is then taken on to compounds of formula (I) by the procedures described in Scheme 14.

Scheme 16: Route to the synthesis of 2- and 6-substituted 2 ((1R,2R,4R)-2-hydroxy-4-(2-phenyl-3H-imidazo-pyridin-7-ylamino)cylcopentyl)methyl sulfamates

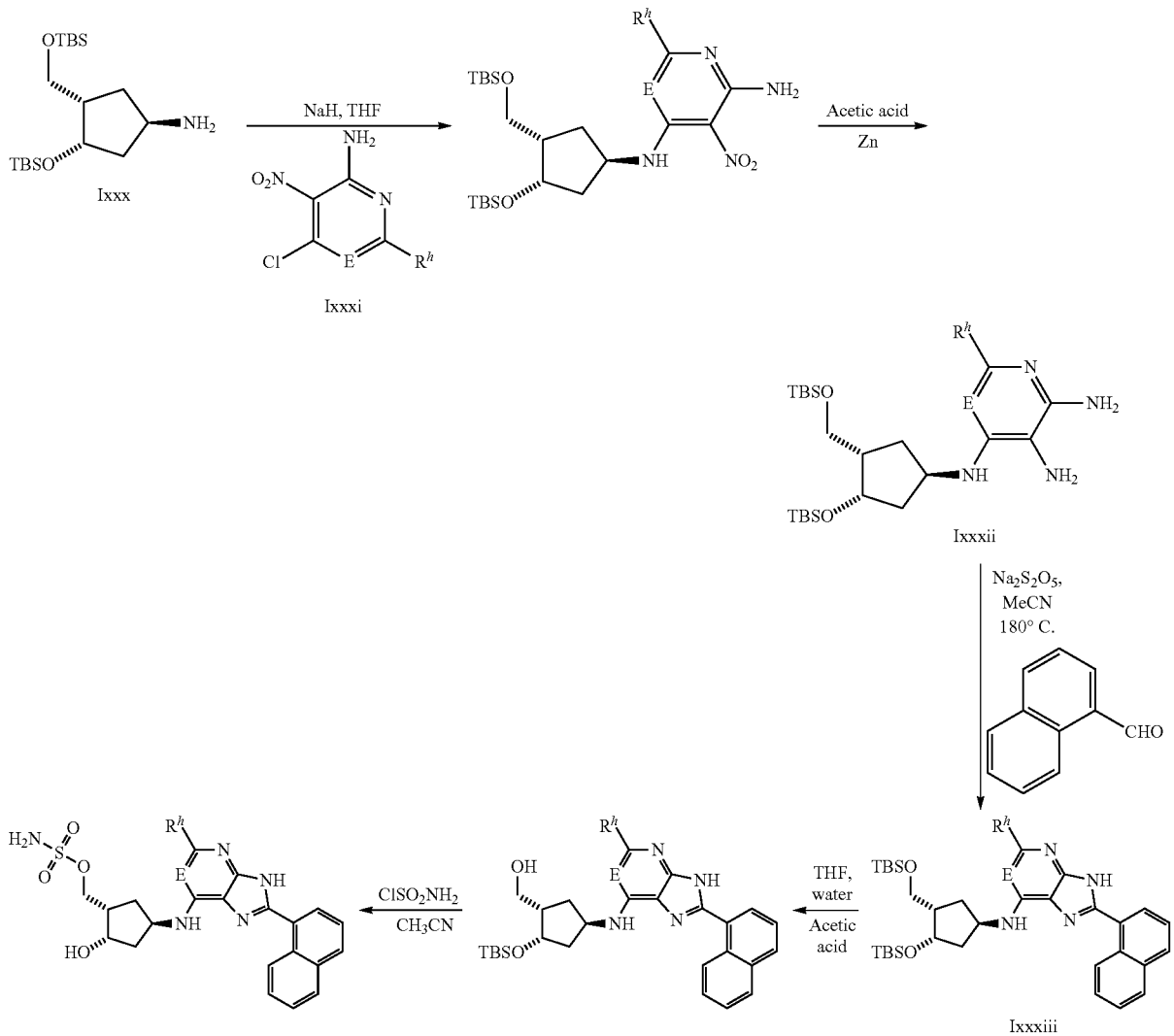

Compounds of formula (VII-A) wherein W=NH can be prepared by the methods outlined in Scheme 16. The sodium salt of lxxx, which is prepared as in Example 128a-c below, is condensed with a nitro aromatic lxxxi. Subsequently reduction with Zinc in acetic acid provides lxxxii. Oxidative coupling of an appropriate aldehyde such as napthaldehyde in the presence of $Na_2S_2O_5$ provides compounds of the general formula lxxxiii. Deprotection with acetic acid in water/THF (*Tetrahedron Lett.* 1998, 29, 6331) followed by sulfamation with chlorosulfonamide and concomitant deprotection of the secondary hydroxyl provides compounds of the general formula VII-A.

Scheme 17: Representative route to the synthesis of substituted ((1S,2S,4R)-2-hydroxy-4-(8-(sulfonyl)-9H-purin-6-yloxy)cyclopentyl)methyl sulfamates

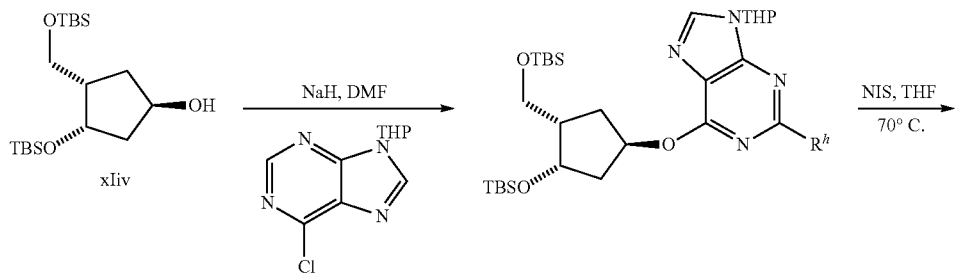

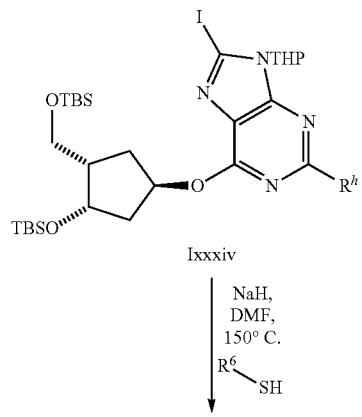

lxxxiv

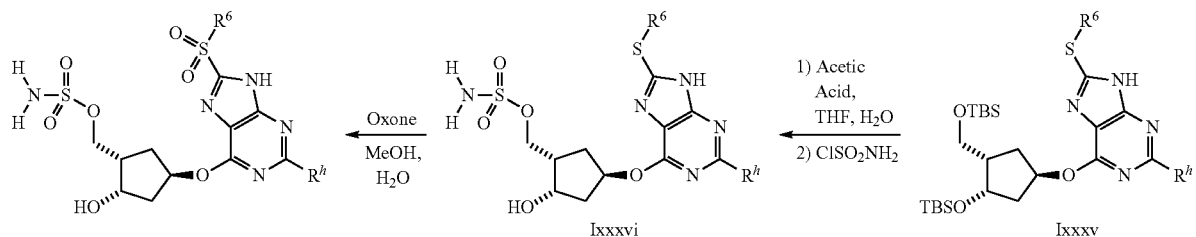

Compounds of formula (VII-A) wherein W=O and R^k=—SO_2R^6 can be prepared by the methods outlined in Scheme 17. The sodium salt of xliv is condensed with 6-chloro-9-(tetrahydro-2H-pyran-2-yl)-9H-purine, which is subsequently iodinated with NIS in THF to provide compound lxxxiv. The sodium salt of an aryl thiolate, such as 3-methylbenzenethiol, is condensed in DMF to provide the intermediate lxxxv which, after deprotection and sulfamation as previously described, provides compound lxxxvi. Exposure to oxidative conditions such as Oxone in aqueous methanol provides compounds of general formula VI.

Scheme 18: Route to the synthesis of 9-substituted ((1S,2S,4R)-4-(9H-purin-6-yloxy)-2-hydroxycyclopentyl)methyl sulfamates

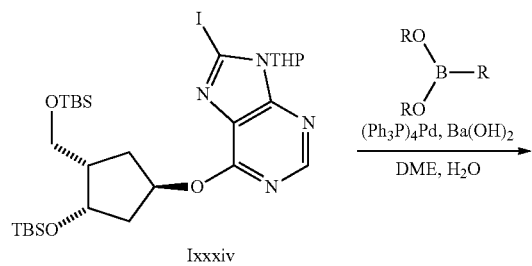

lxxxiv

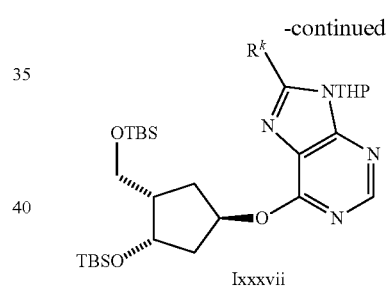

lxxxvii

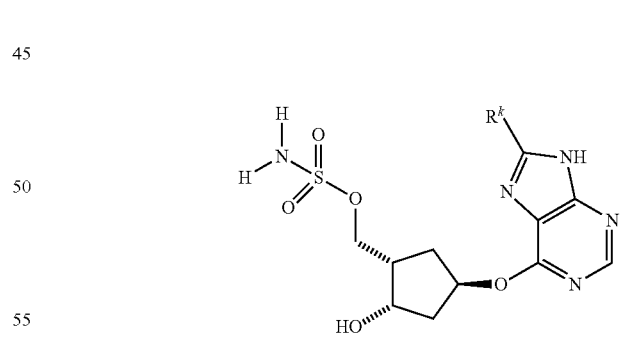

Compounds of formula (VII) wherein W=O and R^k=aryl and heteroaryl can be prepared by the methods outlined in Scheme 18. Pd-mediated coupling of intermediates of the form lxxxiv with boronic acids provides compounds of form lxxxvii. Deprotection followed by sulfamation with a chlorosulfonamide or diphenylcarbamoylsulfamoyl chloride (prepared in a manner similar to U.S. Pat. Appl. Publ. (2005), US 2005282797 A1) followed by removal of the secondary siloxy group with a protic acid, such as HCl, provides compounds of the general formula VII.

Scheme 19: Representative route to the synthesis of substituted ((1S,2S,4R)-2-hydroxy-4-(8-(sulfonyl)-9H-purin-6-yloxy)cyclopentyl)methyl sulfamates

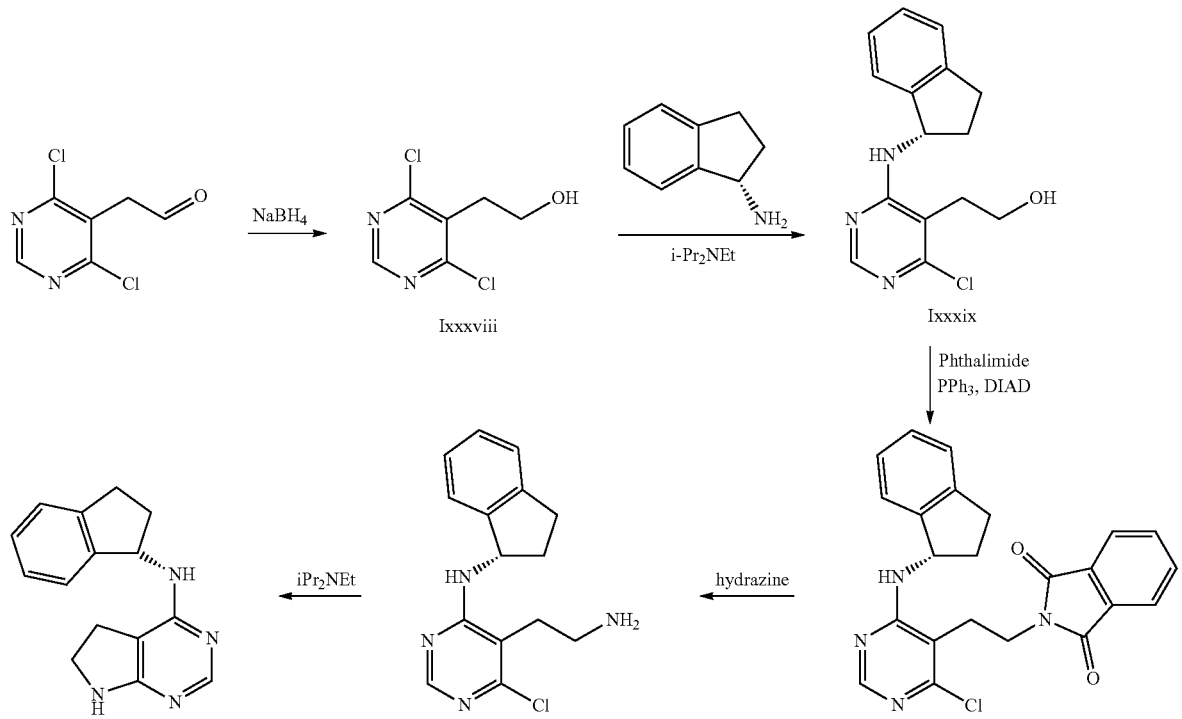

(S)—N-(2,3-dihydro-1H-inden-1-yl)indolin-4-amine is synthesized as illustrated in Scheme 19. Reduction of 2-(4,6-dichloropyrimidin-5-yl)acetaldehyde with sodium borohydride provides alcohol lxxxviii, which is subsequently condensed with an appropriate aminoindane such as (S)-2,3-dihydro-1H-inden-1-amine to provide the substituted pyrimidine lxxxix. Displacement under Mitsunobu type conditions with phthalimide and DIAD, followed by removal of the phthaloyl group with hydrazine, provides the amine intermediate xc. Cyclization under basic conditions provides the final compound (S)—N-(2,3-dihydro-1H-inden-1-yl)-6,7-dihydro-5H-pyrrolo[2,3-d]pyrimidin-4-amine.

Scheme 20: Synthesis of substituted ((1S,2S,4R)-2-hydroxy-4-(pyrimidin-4-ylamino)cyclpentyl)methyl sulfamates

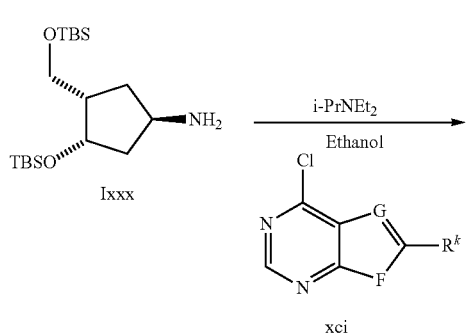

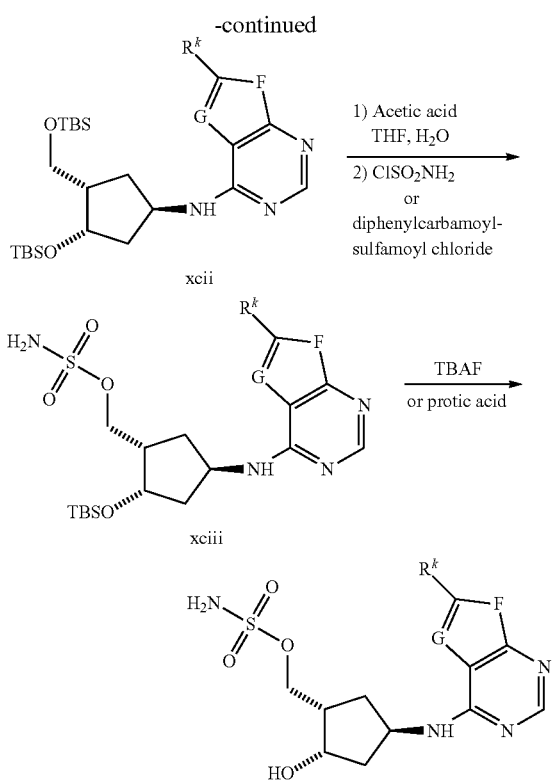

Compounds of formula (VI) wherein W=NH can be prepared by the methods outlined in Scheme 20. Amine lxxx is condensed with chlorosubstituted heterocycles of type xci to provide a product represented as xcii. Deprotection of the primary siloxy group with aqueous acetic acid followed by sulfamation with chlorosulfonamide or diphenylcarbamoylsulfamoyl chloride provides intermediates of form xciii. Removal of the primary hydroxyl group with a Fluoride source, such as TBAF, or protic acid, such as HCl provides the final compound of formula VI.

proteins (e.g., reduction of ubiquitination, neddylation, sumoylation), reduce intracellular signaling mediated by ubl conjugation, and/or reduce proteolysis mediated by ubl conjugation (e.g., inhibition of cullin-dependent ubiquitination and proteolysis (e.g., the ubiquitin-proteasome pathway)). Thus, the compounds of this invention may be

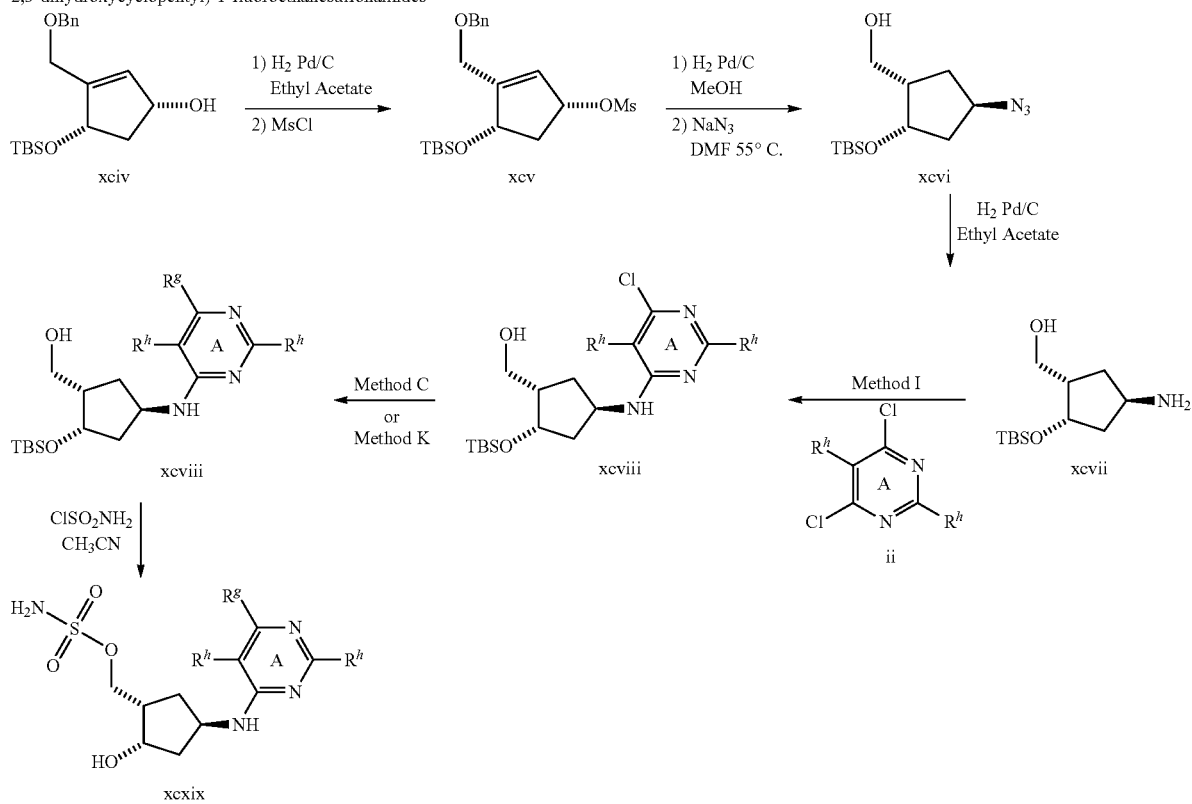

As shown in Scheme 21, conversion of xciv (Ruediger, E; Martel, A; Meanwell, N; Solomon, C; Turmel, B. *Tetrahedron Lett.* 2004, 45, 739-742) to the compounds of formula I-A wherein W=NH is accomplished by palladium catalyzed hydrogenation followed by mesylate formation to give xcv. Hydrogenolysis of the primary benzyl group followed by displacement of the mesylate using sodium azide in DMF yields xcvi. Exposure of xcvi to hydrogenation conditions yields the desired amino alcohol xcvii, which can subsequently be used in coupling reactions with a chloro-substituted heterocycle such as ii. Displacement of the aryl chloride of formula xcviii is achieved by coupling with the appropriately substituted nucleophile, such as an amine, alcohol or thiol at elevated temperature using microwave irradiation in the absence of solvent (see Method C). Further treatment with freshly prepared chlorosulfonamide vi followed by cleavage of the TBS-protecting group using a suitable reagent, such as TBAF, HF pyridine, or HCl. affords the sulfamates I-A as represented by xcxix.

Uses of Compounds of the Invention

The compounds of this invention are useful inhibitors of E1 enzyme activity. In particular, the compounds are designed to be inhibitors of NAE, UAE, and/or SAE. Inhibitors are meant to include compounds which reduce the promoting effects of E1 enzymes in ubl conjugation to target assayed for their ability to inhibit the E1 enzyme in vitro or in vivo, or in cells or animal models according to methods provided in further detail herein, or methods known in the art. The compounds may be assessed for their ability to bind or mediate E1 enzyme activity directly. Alternatively, the activity of compounds may be assessed through indirect cellular assays, or assays measuring downstream effects of E1 activation to assess inhibition of downstream effects of E1 inhibition (e.g., inhibition of cullin-dependent ubiquitination and proteolysis). For example, activity may be assessed by detection of ubl-conjugated substrates (e.g., ubl-conjugated E2s, neddylated cullins, ubiquitinated substrates, sumoylated substrates); detection of downstream protein substrate stabilization (e.g., stabilization of p27, stabilization of IκB); detection of inhibition of UPP activity; detection of downstream effects of protein E1 inhibition and substrate stabilization (e.g., reporter assays, e.g., NFκB reporter assays, p27 reporter assays). Assays for assessing activities are described below in the Experimental section and/or are known in the art.

One embodiment of this invention relates to a composition comprising a compound of this invention or a pharmaceutically acceptable salt thereof, and a pharmaceutically acceptable carrier. It will be appreciated that the compounds of this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the present compounds, similar to the metabolically labile esters or carbamates, which are capable of producing the parent compounds described herein in vivo, are within the scope of this invention.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and Remington: The Science and Practice of Pharmacy, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

In certain particular embodiments, the invention relates to a base addition salt of a compound of formula/formed by deprotonation of the sulfamate (X=O) moiety, the sulfamide (X=NH) moiety, or the sulfonamide (X=CH$_2$) moiety, as applicable. In some such embodiments, the invention relates to a sodium or potassium salt of a compound of formula I.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of the invention preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include, but are not limited to, ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as, but not limited to, an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes; e.g., to mask taste, to affect the site of dissolution or absorption, or to prolong drug action. Coatings may be applied to a tablet or to granulated particles for use in a capsule.

Alternatively, the pharmaceutical compositions of this invention may be administered the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). Preferably, the composition is formulated for administration to a patient having or at risk of developing or experiencing a recurrence of the relevant disorder being treated. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of compound or composition sufficient, upon single or multiple dose administration, to cause a detectable decrease in E1 enzyme activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of E1 enzyme inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

One embodiment of the invention relates to a method of inhibiting or decreasing E1 enzyme activity in a sample comprising contacting the sample with a compound of this invention, or composition comprising a compound of the invention. The sample, as used herein, includes, without limitation, sample comprising purified or partially purified E1 enzyme, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of E1 enzyme activity in a sample may be carried out in vitro or in vivo, in cellulo, or in situ.

In another embodiment, the invention provides a method for treating a patient having a disorder, a symptom of a disorder, at risk of developing, or experiencing a recurrence of a disorder, comprising administering to the patient a compound or pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Disease applications include those disorders in which inhibition of E1 enzyme activity is detrimental to survival and/or expansion of diseased cells or tissue (e.g., cells are sensitive to E1 inhibition; inhibition of E1 activity disrupts disease mechanisms; reduction of E1 activity stabilizes protein which are inhibitors of disease mechanisms; reduction of E1 activity results in inhibition of proteins which are activators of disease mechanisms). Disease applications are also intended to include any disorder, disease or condition which requires effective cullin and/or ubiquitination activity, which activity can be regulated by diminishing E1 enzyme activity (e.g., NAE, UAE activity).

For example, methods of the invention are useful in treatment of disorders involving cellular proliferation, including, but not limited to, disorders which require an effective cullin-dependent ubiquitination and proteolysis pathway (e.g., the ubiquitin proteasome pathway) for maintenance and/or progression of the disease state. The methods of the invention are useful in treatment of disorders mediated via proteins (e.g., NFκB activation, $p27^{Kip}$ activation, $p21^{WAF/CIP1}$ activation, p53 activation) which are regulated by E1 activity (e.g., NAE activity, UAE activity, SAE activity). Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or composition of the invention is used to treat a patient having or at risk of developing or experiencing a recurrence in a cancer selected from the group consisting of colorectal cancer, ovarian cancer, lung cancer, breast cancer, gastric cancer, prostate cancer, and pancreatic cancer. In certain preferred embodiments, the cancer is selected from the group consisting of lung cancer, colorectal cancer, ovarian cancer and hematologic cancers.

Depending on the particular disorder or condition to be treated, in some embodiments, the E1 enzyme inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The E1 inhibitor of the invention may be administered with the other therapeutic agent in a single dosage form or as a separate dosage form. When administered as a separate dosage form, the other therapeutic agent may be administered prior to, at the same time as, or following administration of the E1 inhibitor of the invention.

In some embodiments, the E1 enzyme inhibitor of the invention is administered in conjunction with a therapeutic agent selected from the group consisting of cytotoxic agents, radiotherapy, and immunotherapy appropriate for treatment of proliferative disorders and cancer. Non-limiting examples of cytotoxic agents suitable for use in combination with the E1 enzyme inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; including, e.g., CC-5013 and CC-4047; protein tyrosine kinase inhibitors, including, e.g., imatinib mesylate and gefitinib; proteasome inhibitors, including, e.g., bortezomib; thalidomide and related analogs; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, Il-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

In order that this invention be more fully understood, the following preparative and testing examples are set forth. These examples are for the purpose of illustration only and are not to be construed as limiting the scope of the invention in any way.

EXAMPLES

| Abbreviations | |
|---|---|
| AA | ammonium acetate |
| AcOH | acetic acid |
| ACN | acetonitrile |
| d | days |
| DBU | 1,8-diazabicyclo[5.4.0]undec-7-ene |
| DCM | dichloromethane |
| DEAD | diethylazodicarboxylate |
| DIAD | diisopropylazodicarboxylate |
| DIPEA | N,N-diisopropylethylamine |
| DMAP | N,N-dimethyl-4-aminopyridine |
| DMF | dimethylformamide |
| DMSO | dimethylsulfoxide |
| $Et_2O$ | diethyl ether |
| EtOAc | ethyl acetate |
| EtOH | ethanol |
| $Et_3N$ | triethylamine |
| FA | formic acid |
| $H_2O$ | water |
| h | hours |
| HCl | hydrochloric acid |
| LC/MS | liquid chromatography mass spectrum |
| MeOH | methanol |
| MeOD | $d_4$-methanol |
| $MgSO_4$ | magnesium sulfate |
| m-CPBA | meta-chloroperbenzoic acid |
| min | minutes |
| MS | mass spectrum |
| MWI | microwave irradiation |
| $Na_2CO_3$ | sodium carbonate |
| $NaHCO_3$ | sodium bicarbonate |
| NaOH | sodium hydroxide |
| NIS | N-iodosuccinimide |
| TBAF | tetra-n-butylammonium fluoride |
| TEA | triethylamine |
| p-TsOH | para-toluenesulfonic acid |
| rt | room temperature |
| TFA | trifluoroacetic acid |
| THF | tetrahydrofuran |

Analytical LC-MS Methods
Spectra were obtained on a Hewlett-Packard HP1100 using the following conditions:
FA Standard: Phenominex Luna 5 μm C18 50×4.6 mm column at 2.5 ml/min gradient of ACN containing 0 to 100 percent 0.1% Formic Acid in $H_2O$ for 3 min
AA Standard: Phenominex Luna 5 μm C18 50×4.6 mm column at 2.5 ml/min gradient of ACN containing 0 to 100 percent 10 mM Ammonium Acetate in $H_2O$ for 3 min.
FA Waters: Waters Symmetry C18 3.5 μm 4.6 mm×100 mm column at 1 ml/min gradient of ACN containing 0 to 95 percent 0.1% Formic Acid in $H_2O$ for 10 min
AA Waters: Waters Symmetry C18 3.5 μm 4.6 mm×100 nm column at 1 ml/min gradient of ACN containing 0 to 75 percent 0.1% 10 mM Ammonium Acetate in methanol for 10 min
FA Long: Waters Symmetry C18 3.5 μm 4.6 mm×100 mm column at 1 ml/min gradient of ACN containing 5 to 100 percent 0.1% Formic Acid in $H_2O$ for 12 min
AA Long: Waters Symmetry C18 3.5 μm 4.6 mm×100 mm column at 1 ml/min gradient of ACN containing 5 to 100 percent 10 mM Ammonium Acetate in $H_2O$ for 12 min.

Example 1

[(1R,2R,3S,4R)-4-({6-[(1S)-2,3-Dihydro-1H-inden-1-ylamino]pyrimidin-4-yl}amino)-2,3-dihydroxycyclopentyl]methyl sulfamate (Compound I-29)

Step a: (1R,2S,3R,5R)-3-[(6-Chloropyrimidin-4-yl)amino]-5-(hydroxymethyl)cyclopentane-1,2-diol A mixture of (1R,2S,3R,5R)-3-amino-5-(hydroxymethyl)cyclopentane-1,2-diol hydrochloride (200 mg, 1.09 mmol), 4,6-dichloropyrimidine (240. mg, 1.61 mmol) and $Et_3N$ (0.380 mL, 2.73 mmol) in EtOH (3.00 mL) was heated to 150° C. for 15 min using MWI. The crude mixture was purified via silica gel chromatography eluting with a gradient of 0 to 15% MeOH in DCM to afford the title compound (255 mg, 90%). LC/MS: $R_t$=1.13 min, $ES^+$ 260. (AA standard).

Step b: {(3aR,4R,6R,6aS)-6-[(6-Chloropyrimidin-4-yl)amino]-2,2-dimethyltetrahydro-3aH-cyclopenta[d][1,3]dioxol-4-yl}methanol A solution of (1R,2S,3R,5R)-3-[(6-chloropyrimidin-4-yl)amino]-5-(hydroxymethyl)cyclopentane-1,2-diol (255 mg, 0.982 mmol), p-toluenesulfonic acid monohydrate (187 mg, 0.982 mmol) and 2,2-dimethoxypropane (0.670 mL, 0.545 mmol) in MeOH (5.00 mL) was stirred overnight. The reaction was quenched via addition of saturated aqueous NaHCO$_3$ solution (10 mL) and MeOH was removed in vacuo. The aqueous mixture was extracted with DCM (4×20 mL) and the combined organics were concentrated in vacuo. The crude mixture was purified via silica gel chromatography eluting with a gradient of 0 to 10% MeOH in DCM to afford the title compound (135 mg, 45.8%). LC/MS: R$_t$=1.77 min, ES$^+$ 300. (AA standard).

Step c: [(3aR,4R,6R,6aS)-6-({6-[(1S)-2,3-Dihydro-1H-inden-1-ylamino]pyrimidin-4-yl}-amino)-2,2-dimethyltetrahydro-3aH-cyclopenta[d][1,3]dioxol-4-yl]methanol A mixture of {(3aR,4R,6R,6aS)-6-[(6-chloropyrimidin-4-yl)amino]-2,2-dimethyltetrahydro-3aH-cyclopenta[d][1,3]dioxol-4-yl}methanol (200 mg, 0.667 mmol) and (S)-(+)-1-aminoindan (0.188 mL, 1.47 mmol) were heated to 180° C. for 3 h in a sealed tube using MWI. The mixture was dissolved in DCM and the resulting suspension was washed with H$_2$O followed by saturated ammonium chloride solution. The organic layer was dried over MgSO$_4$, filtered and concentrated in vacuo. The residue was purified via silica gel chromatography eluting with a gradient of 0 to 10% MeOH in EtOAc to afford the title compound as an amorphous solid (218 mg, 82.4%). LC/MS: R$_t$=1.44 min, ES$^+$ 397 (AA standard).

Step d: [(3aR,4R,6R,6aS)-6-({6-[(1S)-2,3-Dihydro-1H-inden-1-ylamino]pyrimidin-4-yl}-amino)-2,2-dimethyltetrahydro-3aH-cyclopenta[d][1,3]dioxol-4-yl]methyl sulfamate A 2.00 M solution of chlorosulfonamide in ACN was prepared as follows: FA (2.30 mL, 61.0 mmol) was added dropwise, with stirring to chlorosulfonyl isocyanate (5.20 mL, 59.7 mmol) under an atmosphere of nitrogen at 0° C. After the addition was complete and the mixture had solidified, ACN (22.5 mL) was added. The resulting solution was left to stand under a vented source of nitrogen overnight at rt.

To a solution of [(3aR,4R,6R,6aS)-6-({6-[(1S)-2,3-dihydro-1H-inden-1-ylamino]pyrimidin-4-yl}amino)-2,2-dimethyltetrahydro-3aH-cyclopenta[d][1,3]dioxol-4-yl]-methanol (100. mg, 0.252 mmol) and Et$_3$N (0.0527 mL, 0.378 mmol) in DCM (2.50 mL) was added dropwise a 2.00 M solution of chlorosulfonamide in ACN (0.190 mL, 0.380 mmol) at 0° C. and the mixture was stirred for 2 h. The reaction was diluted with DCM, quenched with H$_2$O and the organic layer was separated, then concentrated in vacuo. The residue was purified via silica gel chromatography eluting with a gradient of 0 to 10% MeOH in DCM to afford the title compound (65.0 mg, 54%). LC/MS: R$_t$=1.58 min, ES$^+$ 476 (AA standard).

Step e: [(1R,2R,3S,4R)-4-({6-[(1S)-2,3-Dihydro-1H-inden-1-ylamino]pyrimidin-4-yl}-amino)-2,3-dihydroxycylopentyl]methyl sulfamate (Compound I-29)

A solution of [(3aR,4R,6R,6aS)-6-({6-[(1S)-2,3-dihydro-1H-inden-1-ylamino]pyrimidin-4-yl}amino)-2,2-dimethyl-tetrahydro-3aH-cyclopenta[d][1,3]dioxol-4-yl]-methyl sulfamate (60.0 mg, 0.126 mmol) was treated with a 9:1 mixture of trifluoroacetic acid in H$_2$O (5.00 mL, 58.4 mmol) and the mixture was stirred for 10 min before being concentrated in vacuo. The crude material was purified via reverse phase C18 preparative HPLC eluting with a gradient of 5 to 70% of 0.1% FA/95% ACN/5% H$_2$O in 0.1% FA/99% H2O/1% ACN over 16 min to afford the title compound (27.0 mg, 49%). $^1$H NMR (400 MHz, DMSO-d6, δ): 8.13 (s, 1H), 7.98 (s, 1H), 7.44 (s, 2H), 7.28-7.02 (m, 5H), 6.72 (bs, 1H), 5.53 (s, 1H), 5.41 (s, 1H), 4.63 (d, J=5.3 Hz, 1H), 4.09 (dd, J=5.1, 9.5 Hz, 1H), 3.97 (dd, J=7.0, 9.5 Hz, 1H), 3.81 (bs, 1H), 3.71-3.60 (m, 2H), 3.01-2.87 (m, 1H), 2.87-2.70 (m, 1H), 2.47-2.37 (m, 1H), 2.30-2.09 (m, 2H), 1.89-1.72 (m, 1H), 1.19-1.05 (n, 1H) ppm. LC/MS: R$_t$=1.13 min, ES$^+$ 436 (AA standard).

Example 2

{(1R,2R,3S,4R)-4-[(6-{[(1S)-3,3-Dimethyl-2,3-dihydro-1H-inden-1-yl]amino}-pyrimidin-4-yl)amino]-2,3-dihydroxycyclopentyl}methyl sulfamate (Compound I-21)

Step a: (2R)-2-{[(1S)-3,3-Dimethyl-2,3-dihydro-1H-inden-1-yl]amino}-2-phenylethanol To a solution of 3,3-dimethylindan-1-one (925 mg, 5.77 mmol) and (R)-(-)-2-phenylglycinol (893 mg, 6.51 mmol) in toluene (10.0 mL) was added p-toluenesulfonic acid monohydrate (62.5 mg, 0.328 mmol). The reaction was heated to reflux under an atmosphere of nitrogen for 90 min. At this point, the mixture was cooled and diluted with toluene (10.0 mL). The mixture was washed with saturated aqueous NaHCO$_3$ solution and H$_2$O. The organic layer was concentrated in vacuo and the residue was dissolved in THF (10.0 mL) and cooled to 0° C. AcOH (1.13 mL, 19.9 mmol) was added, followed by sodium borohydride (251 mg, 6.64 mmol) and the reaction was allowed to warm to 23° C. overnight. The mixture was partitioned between DCM and saturated aqueous NaHCO$_3$ solution. The organic layer was concentrated and silica gel chromatography eluting with a gradient of 5 to 35% EtOAc in DCM afforded the title compound (1.49 g, 74%). LC/MS: R$_t$=1.92 min, ES$^+$ 282 (AA standard).

Step b: (1S)-3,3-Dimethylindan-1-amine

A solution of (2R)-2-{[(1S)-3,3-dimethyl-2,3-dihydro-1H-inden-1-yl]amino}-2-phenylethanol (1.44 g, 5.13 mmol) in MeOH (40.0 mL) was added to a stirred solution of lead tetraacetate (3.75 g, 8.03 mmol) in MeOH (60.0 mL) at 0° C. dropwise over 20 min. After stirring for 45 min, the reaction was quenched via addition of a 10% solution of Na$_2$CO$_3$ in H$_2$O (76.0 mL) and the mixture was stirred for 10 min. DCM (200 mL) was then added and the layers were separated. The aqueous layer was extracted with DCM (50.0 mL). The combined organic layers were concentrated in vacuo and the residue was dissolved in EtOH (190. mL) and treated with a 10.4 M aqueous solution of HCl (5.70 mL, 59.3 mmol). The resulting mixture was then heated to reflux for 16 h. The cooled reaction was concentrated in vacuo and partitioned between H$_2$O (150. mL) and Et$_2$O (50.0 mL). The aqueous layer was adjusted to pH 10 via addition of Na$_2$CO$_3$ and extracted with Et$_2$O (3×50.0 mL). The combined organic layers were concentrated in vacuo and silica gel chromatography eluting with a gradient of 0 to 10%

MeOH in DCM to afford the title compound as a pale yellow oil (420. mg, 51%). ¹H NMR (CD₃OD, 300 MHz) δ: 7.34-7.14 (m, 4H), 4.45-4.37 (m, 1H), 2.38 (dd, J=7.1, 12.4 Hz, 1H), 1.73 (bs, 2H), 1.60 (dd, J=8.7, 12.4 Hz, 1H), 1.39 (s, 3H), 1.19 (s, 3H) ppm.

Step c: {(1R,2R,3S,4R)-4-[(6-{[(1S)-3,3-Dimethyl-2,3-dihydro-1H-inden-1-yl]amino}-pyrimidin-4-yl) amino]-2,3-dihydroxycyclopentyl}methyl sulfamate (Compound I-21

The title compound was prepared following the procedure described in Example 1a-e using (1S)-3,3-dimethylindan-1-amine in step c. ¹H NMR (CD₃OD, 400 MHz) δ: 7.95 (s, 1H), 7.28-7.15 (m, 4H), 5.62 (s, 1H), 5.38 (bs, 1H), 4.22-4.12 (m, 2H), 3.92 (bs, 1H), 3.88 (dd, J=5.5, 5.5 Hz, 1H), 3.78 (dd, J=5.5, 5.5 Hz, 1H), 2.46-2.27 (m, 3H), 1.84-1.76 (m, 1H), 1.39 (s, 3H), 1.35-1.27 (m, 2H), 1.25 (s, 3H) ppm. LC/MS: R$_t$=1.42 min, ES⁺ 464 (AA standard).

Example 3

{(1R,2R,3S,4R)-4-[(6-{[(1S)-4-Chloro-2,3-dihydro-1H-inden-1-yl]amino}-pyrimidin-4-yl)amino]-2,3-dihydroxycyclopentyl}methyl sulfamate (Compound I-24)

The title compound was prepared following the procedure described in Example 2a-c using 4-chloroindan-1-one in step a. ¹H NMR (CD₃OD, 400 MHz) δ: 8.01 (s, 1H), 7.26-7.15 (m, 4H), 5.69 (s, 1H), 5.44 (bs, 1H), 4.17 (dddd, J=5.2, 9.7, 9.7, 9.8 Hz, 2H), 3.95 (bs, 1H), 3.88 (t, J=5.4 Hz, 1H), 3.79 (t, J=5.6 Hz, 1H), 3.12-3.04 (m, 1H), 2.88 (ddd, J=8.2, 8.2, 16.4 Hz, 1H), 2.66-2.56 (m, 1H), 2.43-2.28 (m, 2H), 1.99-1.88 (m, 1H), 1.38-1.28 (m, 1H) ppm. LC/MS: R$_t$=1.08 min, ES⁺ 470. (FA standard).

Example 4

{(1R,2R,3S,4R)-4-[(6-{[(1S)-5,6-Difluoro-2,3-dihydro-1H-inden-1-yl]amino}-pyrimidin-4-yl) amino]-2,3-dihydroxycyclopentyl}methyl sulfamate (Compound I-17)

The title compound was prepared following the procedure described in Example 2a-c using 5,6-difluoroindan-1-one in step a. ¹H NMR (CD₃OD, 400 MHz) δ: 7.96 (s, 1H), 7.14-7.02 (m, 3H), 5.62-5.58 (m, 1H), 5.39 (s, 1H), 5.28 (bs, 1H), 4.22-4.13 (m, 2H), 3.89 (dd, J=5.5, 5.5 Hz, 1H), 3.78 (dd, J=5.4, 5.4 Hz, 1H), 3.00-2.91 (m, 1H), 2.88-2.77 (m, 1H), 2.64-2.55 (m, 1H), 2.44-232 (m, 1H), 1.97-1.86 (m, 1H), 1.43-1.20 (m, 2H) ppm. LC/MS: R$_t$=1.02 min, ES⁺ 472 (FA standard).

Example 5

{(1R,2R,3S,4R)-4-[(6-{[(1S)-4,7-Difluoro-2,3-dihydro-1H-inden-1-yl]amino}-pyrimidin-4-yl) amino]-2,3-dihydroxycyclopentyl}methyl sulfamate (Compound I-6)

The title compound was prepared following the procedure described in Example 2a-c using 4,7-difluoroindan-1-one in step a. ¹H NMR (CD₃OD, 400 MHz) δ: 7.95 (s, 1H), 7.02-6.86 (m, 2H), 5.62-5.50 (m, 2H), 4.23-4.12 (m, 2H), 3.92 (bs, 1H), 3.88 (dd, J=5.5, 5.5 Hz, 1H), 3.78 (dd, J=5.5, 5.5 Hz, 1H), 3.16-3.05 (m, 1H), 2.95-2.85 (m, 1H), 2.62- 2.50 (m, 1H), 2.45-2.28 (m, 2H), 2.11-2.00 (m, 1H), 1.37-1.25 (m, 1H) ppm. LC/MS: R$_t$=0.94 min, ES⁺ 472 (FA standard).

Example 6

{(1R,2R,3S,4R)-4-[(6-{[(1S)-4-Fluoro-2,3-dihydro-1H-inden-1-yl]amino}pyrimidin-4-yl)amino]-2,3-dihydroxycyclopentyl}methyl sulfamate (Compound I-1)

The title compound was prepared following the procedure described in Example 2a-c using 4-fluoroindan-1-one in step a. ¹H NMR (CD₃OD, 300 MHz) δ: 8.06 (s, 1H), 7.29-7.17 (m, 1H), 7.15-7.06 (m, 1H), 7.03-6.91 (m, 1H), 5.75 (s, 1H), 5.42 (bs, 1H), 4.27-4.11 (m, 1H), 4.08-3.89 (m, 2H), 3.89-3.80 (m, 1H), 3.16-3.02 (m, 1H), 2.96-2.80 (m, 1H), 2.73-2.55 (m, 1H), 2.47-2.27 (m, 2H), 2.06-1.89 (m, 1H), 1.47-1.23 (m, 1H) ppm. LC/MS: R$_t$=0.94 min, ES⁺ 454 (FA standard).

Example 7

[(1R,2R,3S,4R)-4-({6-[(1R)-2,3-Dihydro-1H-inden-1-ylamino]pyrimidin-4-yl}amino)-2,3-dihydroxycyclopentyl]methyl sulfamate (Compound I-8)

The title compound was prepared following the procedure described in Example 1a-e using (R)-(−)-1-aminoindan in step c. ¹H NMR (CD₃OD, 400 MHz) δ: 7.96 (s, 1H), 7.27-7.12 (m, 4H), 5.66 (s, 1H), 5.30 (bs, 1H), 4.23-4.13 (m, 2H), 3.95 (bs, 1H), 3.90 (dd, J=5.5, 5.5 Hz, 1H), 3.80 (dd, J=5.6, 5.6 Hz, 1H), 3.05-2.94 (m, 1H), 2.92-2.81 (m, 1H), 2.63-2.50 (m, 1H), 2.45-2.28 (m, 2H), 1.96-7.80 (m, 1H), 1.38-1.27 (m, 1H) ppm. LC/MS: R$_t$=1.07 min, ES⁺ 436 (FA standard).

Example 8

((1R,2R,3S,4R)-4-{6-(Benzylamino)pyrimidin-4-yl]amino}-2,3-dihydroxycyclopentyl)methyl sulfamate (Compound I-27)

The title compound was prepared following the procedure described in Example 1a-c using benzylamine in step c. ¹H NMR (CD₃OD, 300 MHz) δ: 7.92 (s, 1H), 7.35-7.16 (m, 5H), 5.49 (s, 1H), 4.42 (s, 2H), 4.21-4.07 (m, 2H), 3.91 (bs, 1H), 3.87 (dd, J=5.2, 5.2 Hz, 1H), 3.74 (dd, J=5.6, 5.6 Hz, 1H), 2.39-2.19 (m, 2H), 1.46-1.11 (m, 1H) ppm. LC/MS: R$_t$=1.14 min, ES⁻ 408 (AA standard).

Example 9

[(1R,2R,3S,4R)-4-({6-[Benzyl(methyl)amino]pyrimidin-4-yl}amino)-2,3-dihydroxycyclopentyl] methyl sulfamate (Compound I-22)

The title compound was prepared following the procedure described in Example 1a-e using N-methylbenzyl amine in step c. ¹H NMR (CD₃OD, 300 MHz) δ: 7.99 (s, 1H), 7.34-7.14 (m, 5H), 5.62 (s, 1H), 4.75 (s, 2H), 4.23-4.09 (m, 2H), 4.01-3.90 (m, 1H), 3.87 (dd, J=5.5, 5.5 Hz, 1H), 3.76 (dd, J=5.5, 5.5 Hz, 1H), 2.99 (s, 3H), 2.42-2.25 (m, 2H), 1.35-1.20 (1H) ppm. LC/MS: R$_t$=1.27 min, ES⁻ 422 (AA standard).

Example 10

{(1R,2R,3S,4R)-4-[(6-{[(1S)-5-Chloro-2,3-dihydro-1H-inden-1-yl]amino}pyrimidin-4-yl)amino]-2,3-dihydroxycyclopentyl}methyl sulfamate (Compound I-19)

The title compound was prepared following the procedure described in Example 2a-c using 5-chloroindan-1-one in step a. $^1$H NMR (CD$_3$OD, 400 MHz) δ: 7.94 (s, 1H), 7.34-7.18 (m, 2H), 7.18-7.12 (m, 1H), 5.62 (s, 1H), 5.30 (bs, 1H), 3.88 (dd, J=5.5, 5.5 Hz, 1H), 3.77 (dd, J=5.5, 5.5 Hz, 1H), 3.03-294 (m, 1H), 2.92-2.81 (m, 1H), 2.61-2.51 (m, 1H), 2.42-2.26 (m, 2H), 1.97-1.84 (m, 1H), 1.35-1.22 (m, 1H) ppm. LC/MS: $R_t$=1.44 min, ES$^-$ 470. (AA standard).

Example 11

[(1R,2R,3S,4R)-2,3-Dihydroxy-4-({6-[(1S)-1,2,3,4-tetrahydronaphthalen-1-ylamino]pyrimidin-4-yl}amino)cyclopentyl]methyl sulfamate (Compound I-12)

The title compound was prepared following the procedure described in Example 1a-e using (S)-(+)-1,2,3,4-tetrahydro-1-napthylamine in step c. $^1$H NMR (CD$_3$OD, 400 MHz) δ: 7.93 (s, 1H), 7.27-7.20 (m, 1H), 7.18-7.06 (m, 3H), 5.59 (s, 1H), 4.99 (bs, 1H), 4.23-4.11 (m, 2H), 3.92 (bs, 1H), 3.88 (dd, J=5.5, 5.5 Hz, 1H), 3.77 (dd, J=5.5, 5.5 Hz, 1H), 2.90-2.70 (m, 2H), 2.43-2.26 (m, 2H), 2.08-1.76 (m, 5H), 1.35-1.22 (m, 1H) ppm. LC/MS: $R_t$=1.33 min, ES$^+$ 450. (AA standard).

Example 12

{(1R,2R,3S,4R)-2,3-Dihydroxy-4-[(6-{[(1R,2S)-2-methoxy-2,3-dihydro-1H-inden-1-yl]amino}pyrimidin-4-yl)amino]cyclopentyl}methyl sulfamate (Compound I-2)

Step a: tert-Butyl [(1R,2S)-2-hydroxy-2,3-dihydro-1H-inden-1-yl]carbamate (1R,2S)-1-Aminoindan-2-ol (1.83 g, 12.3 mmol) was dissolved in DCM (70.0 mL) and TEA (3.42 mL, 24.5 mmol) was added. Di-tert-butyldicarbonate (2.81 g, 12.9 mmol) was added and the reaction mixture was stirred for 5 h. The solution was concentrated in vacuo and purified via silica gel chromatography eluting with a gradient of 0 to 100% EtOAc in hexanes to afford the title compound (3.12 g, 100%). LC/MS: $R_t$=1.55 min, ES$^+$ 250. (AA standard).

Step b: tert-Butyl [(1R,2S)-2-methoxy-2,3-dihydro-1H-inden-1-yl]carbamate

A mixture of tert-butyl [(1R,2S)-2-hydroxy-2,3-dihydro-1H-inden-1-yl]-carbamate (680. mg, 2.73 mmol), DMF (21.1), barium monoxide (5.02 g, 32.7 mmol), barium hydroxide (2.80 g, 16.4 mmol) and iodomethane (1.70 mL, 27.3 mmol) was stirred overnight. LC/MS showed no starting material. The reaction was quenched via addition of a saturated solution of NaHCO$_3$ and was extracted with DCM. The organic layer was washed with H$_2$O (3×), dried over sodium sulfate and concentrated in vacuo. The residue was purified via silica gel chromatography eluting with a gradient of 0 to 50% EtOAc in hexanes to afford the title compound (178 mg, 25%). LC/MS: $R_t$=1.24 min, ES$^+$ 264 (AA standard).

Step c: (1R,2S)-2-Methoxyindan-1-amine

To tert-butyl [(1R,2S)-2-methoxy-2,3-dihydro-1H-inden-1-yl]carbamate (253 mg, 0.961 mmol) was added a 4.00 M solution of HCl in 1,4-dioxane (5.00 mL) and the mixture was stirred for 10 min, after which a white solid crashed out. The suspension was concentrated in vacuo and co-evaporated with toluene to afford a white solid, which was dissolved in H$_2$O. The solution was adjusted to pH 10. via addition of Na$_2$CO$_3$. The mixture was then extracted with Et$_2$O (3×30 mL) and the organic extracts were concentrated in vacuo to afford the title compound (150. mg, 99%). LC/MS: $R_t$=0.85 min, ES$^+$ 164 (AA standard).

Step d: {(1R,2R,3S,4R)-2,3-Dihydroxy-4-[(6-{[(1R,2S)-2-methoxy-2,3-dihydro-1H-inden-1-yl]amino}pyrimidin-4-yl)amino]cyclopentyl}methyl sulfamate (Compound I-2)

The title compound was prepared following the procedure described in Example 2a-c using (1R,2S)-2-methoxyindan-1-amine in step a. $^1$H NMR (CD$_3$OD, 400 MHz) δ: 7.97 (s, 1H), 7.28-7.10 (m, 4H), 5.36 (bs, 1H), 4.21-4.10 (m, 3H), 3.93 (bs, 1H), 3.86 (t, J=5.4 Hz, 1H), 3.77 (t, J=5.6 Hz, 1H), 3.32 (s, 3H), 3.12-2.95 (m, 2H), 2.44-2.26 (m, 2H), 1.38-1.25 (m, 1H) ppm. LC/MS: $R_t$=0.94 min, ES$^+$ 466 (FA standard).

Example 13

[(1R,2R,3S,4R)-4-({6-[(Cyclohexylmethyl)amino]pyrimidin-4-yl}amino)-2,3-dihydroxycyclopentyl]methyl sulfamate (Compound I-14)

The title compound was prepared following the procedure described in Example 1a-e using cyclohexanemethylamine in step c. $^1$H NMR (CD$_3$OD, 400 MHz) δ: 8.08 (s, 1H), 5.69 (s, 1H), 4.22-4.13 (m, 2H), 4.00 (bs, 1H), 3.89 (dd, J=5.2, 5.2 Hz, 1H), 3.82 (dd, J=6.2, 6.5 Hz, 1H), 3.18-3.07 (m, 2H), 2.42-2.29 (m, 2H), 1.83-1.53 (m, 7H), 1.44-1.14 (m, 5H), 1.07-0.92 (m, 2H) ppm. LC/MS: $R_t$=1.31 min, ES$^-$ 414 (AA standard).

Example 14

[(1R,2R,3S,4R)-2,3-Dihydroxy-4-({2-[(3-methyl-2,3-dihydro-1H-inden-1-yl)-amino]pyrimidin-4-yl}amino)cyclopentyl]methyl sulfamate (Compound I-10)

Step a: 3-Methylindan-1-one oxime

To a solution of 3-methylindan-1-one (221 mg, 1.51 mmol) and hydroxylamine hydrochloride (295 mg, 4.25 mmol) in MeOH (4.00 mL) was added a solution of NaOH (200 mg, 5.00 mmol) in H$_2$O (2.00 mL) and the mixture was stirred at 80° C. for 2 h. The cooled reaction was concentrated in vacuo to remove most of the MeOH, and the residue was partitioned between DCM and H$_2$O. The organic layer was concentrated in vacuo to afford the title compound as a waxy solid (232 mg, 95%). LC/MS: $R_t$=1.51 min, ES$^+$ 162 (AA standard).

Step b: 3-Methylindan-1-amine

A mixture of -methylindan-1-one oxime (223 mg, 1.38 mmol) and 10% palladium on carbon (14.7 mg, 50% water wet) in MeOH (5.00 mL) was stirred under an atmosphere of hydrogen overnight. The mixture was then filtered through celite, washed through with MeOH and the combined filtrates were concentrated in vacuo to afford the title compound (195 mg, 96%). $^1$H NMR (CDCl$_3$, 300 MHz) δ: 739-7.14 (m, 4H), 4.26 (dd, J=7.2, 9.4 Hz, 1H), 3.13-2.96 (m, 1H), 2.71 (ddd, J=6.9, 6.9, 12.5 Hz, 1H), 1.75 (bs, 2H), 1.35 (d, J=6.8 Hz, 3H), 1.25 (ddd, J=9.9, 9.9, 11.7 Hz, 1H) ppm.

Step c: [(1R,2R,3S,4R)-2,3-Dihydroxy-4-({2-[(3-methyl-2,3-dihydro-1H-inden-1-yl)-amino]pyrimidin-4-yl}amino)cyclopentyl]methyl sulfamate (Compound I-10)

The title compound was prepared following the procedure described in Example 1a-e using 2,4-dichloropyrimidine in step a and 3-methylindan-1-amine in step c. $^1$H NMR (CD$_3$OD, 300 MHz) δ: 7.65-7.36 (m, 1H), 7.34-7.04 (m, 5H), 6.23-5.99 (m, 1H), 5.62 (bs, 1H), 4.53-4.36 (m, 1H), 4.22-4.09 (m, 2H), 3.94-3.81 (m, 2H), 3.25-3.08 (m, 1H), 2.94-2.76 (m, 1H), 1.66-1.44 (m, 1H), 1.44-1.20 (m, 6H) ppm. LC/MS: R$_t$=1.19 min, ES$^+$ 450. (AA standard).

Example 15

{(1R,2R,3S,4R)-4-[(2-{[(1S)-3,3-Dimethyl-2,3-dihydro-1H-inden-1-yl]amino}pyrimidin-4-yl)amino]-2,3-dihydroxycyclopentyl}methyl sulfamate (Compound I-15)

The title compound was prepared following the procedure described in Example 1a-e using 2,4-dichloropyrimidine in step a and (1S)-3,3-dimethylindan-1-amine in step c. $^1$H NMR (CD$_3$OD, 400 MHz) δ: 8.47 (s, 1H), 7.59 (s, 1H), 7.32-7.17 (m, 4H), 6.06 (bs, 1H), 5.64 (bs, 1H), 4.36 (bs, 1H), 4.21-4.09 (m, 2H), 3.91-3.81 (m, 2H), 2.47 (dd, J=7.3, 12.4 Hz, 1H), 2.41-2.23 (m, 2H), 1.91 (bs, 1H), 1.41 (s, 3H), 1.26 (s, 3H), 0.99-0.88 (m, 1H) ppm. LC/MS: R$_t$=1.24 min, ES$^+$ 464 (AA standard).

Example 16

[(1R,2R,3S,4R)-4-({2-[(Cyclohexylmethyl)amino]pyrimidin-4-yl}amino)-2,3-dihydroxycyclopentyl]methyl sulfamate (Compound I-4)

The title compound was prepared following the procedure described in Example 1a-e using 2,4-dichloropyrimidine in step a and cyclohexanemethylamine in step c. $^1$H NMR (CD$_3$OD, 400 MHz) δ: 7.50 (d, J=7.3 Hz, 1H), 6.04 (d, J=7.1 Hz, 1H), 4.42 (dd, J=7.9, 13.8 Hz, 1H), 4.22-1.43 (m, 2H), 3.93-9.85 (m, 2H), 3.68 (s, 1H), 2.48-2.28 (m, 2H), 1.84-1.55 (m, 7H), 1.37-1.13 (m, 5H), 1.07-0.93 (m, 2H) ppm. LC/MS: R$_t$=1.11 min, ES$^+$ 416 (AA standard).

Example 17

[(1R,2R,3S,4R)-4-({2-[Benzyl(methyl)amino]pyrimidin-4-yl}amino)-2,3-dihydroxycyclopentyl]methyl sulfamate (Compound I-20)

The title compound was prepared following the procedure described in Example 1a-e using 2,4-dichloropyrimidine in step a and N-methylbenzyl amine in step c. $^1$H NMR (CD$_3$OD, 400 MHz) δ: 7.59 (d, J=6.8 Hz, 1H), 7.38-7.25 (m, 5H), 6.14 (d, J=6.6 Hz, 1H), 5.03-4.95 (m, 1H), 4.37 (bs, 1H), 4.14 (d, J=4.6 Hz, 2H), 3.89-3.85 (m, 2H), 3.68 (s, 2H), 3.15 (s, 3H), 2.86 (s, 1H), 2.35-2.22 (m, 2H), 1.28 (bs, 1H) ppm. LC/MS: R$_t$=1.16 min, ES$^+$ 424 (AA standard).

Example 18

((1R,2R,3S,4R)-4-{[2-(Benzylamino)pyrimidin-4-yl]amino}-2,3-dihydroxycyclopentyl)methyl sulfamate (Compound I-7)

The title compound was prepared following the procedure described in Example 1a-e using 2,4-dichloropyrimidine in step a and benzylamine in step c. $^1$H NMR (CD$_3$OD, 400 MHz) δ: 7.58 (d, J=5.4 Hz, 1H), 7.36-7.26 (m, 4H), 7.24-7.18 (m, 1H), 5.90 (d, J=6.3 Hz, 1H), 4.63-4.47 (m, 2H), 4.26 (bs, 1H), 4.18-4.07 (m, 2H), 3.86 (dd, J=5.3, 5.3 Hz, 1H), 3.80 (dd, J=5.9, 6.3 Hz, 1H), 2.34-2.19 (m, 2H), 1.31-1.14 (m, 1H) ppm. LC/MS: R$_t$=1.07 min, ES$^+$ 410. (AA standard).

Example 19

[(1R,2R,3S,4R)-4-({6-[(1S)-2,3-Dihydro-1H-inden-1-ylamino]-2-methylpyrimidin-4-yl}amino)-2,3-dihydroxycyclopentyl]methyl sulfamate and {(1R,2R,3S,4R)-4-[(6-amino-2-methylpyrimidin-4-yl)amino]-2,3-dihydroxycyclopentyl}methyl sulfamate (Compounds I-18 and I-13)

The title compounds were prepared following the procedure described in Example 1a-e using 4,6-dichloro-2-methylpyrimidine in step a and (S)-(+)-1-aminoindan in step c. Analytical data for [(1R,2R,3S,4R)-4-({6-[(1S)-2,3-dihydro-1H-inden-1-ylamino]-2-methylpyrimidin-4-yl}amino)-2,3-dihydroxycyclopentyl]methyl sulfamate (Compound I-18): $^1$H NMR (CD$_3$OD, 400 MHz) δ: 7.31-7.14 (m, 4H), 5.54 (s, 1H), 5.29 (bs, 1H), 4.22-4.11 (m, 2H), 3.92 (bs, 1H), 3.90 (dd, J=5.2, 5.2 Hz, 1H), 3.78 (dd, J=5.7, 5.7 Hz, 1H), 3.06-2.96 (m, 1H), 2.93-2.82 (m, 1H), 2.63-2.52 (m, 1H), 2.40-2.31 (m, 2H), 2.29 (s, 3H), 1.98-1.85 (m, 2H), 1.43-1.24 (m, 2H) ppm. LC/MS: R$_t$=1.29 min, ES$^+$ 450. (AA standard). Analytical data for {(1R,2R,3S,4R)-4-[(6-amino-2-methylpyrimidin-4-yl)amino]-2,3-dihydroxycyclopentyl}-methyl sulfamate (Compound I-13): $^1$H NMR (CD$_3$OD, 400 MHz) δ: 7.45 (s, 1H), 5.49 (s, 1H), 4.25-4.11 (m, 2H), 3.95 (bs, 1H), 3.92 (dd, J=5.3, 5.8 Hz, 1H), 3.78 (dd, J=5.8, 5.8 Hz, 1H), 2.69 (s, 1H), 2.44-2.31 (m, 1H), 2.27 (s, 3H), 1.45-1.24 (m, 1H) ppm. LC/MS: R$_t$=0.76 min, ES$^+$ 334 (AA standard).

Example 20

((1R,2R,3S,4R)-4-{[6-(Benzylamino)-2-methylpyrimidin-4-yl]amino}-2,3-dihydroxycyclopentyl)methyl sulfamate (Compound I-30)

The title compound was prepared following the procedure described in Example 1a-e using 2,4-dichloropyrimidine in step a and benzylamine in step c. $^1$H NMR (CD$_3$OD, 300 MHz) δ: 7.41-7.31 (m, 4H), 7.31-7.22 (m, 1H), 5.55 (s, 1H), 4.52 (s, 2H), 4.21-4.09 (m, 2H), 3.87 (dd, J=4.9, 4.9 Hz, 1H), 3.79 (dd, J=5.9, 6.8 Hz, 1H), 2.42 (s, 3H), 2.37-2.21 (m, 2H), 1.41-1.21 (m, 2H) ppm. LC/MS: R$_t$=1.16 min, ES$^+$ 424 (AA standard).

Example 21

[(1R,2S,4R)-4-({6-[(1S)-2,3-Dihydro-1H-inden-1-ylamino]pyrimidin-4-yl}amino)-2-hydroxycyclopentyl]methyl sulfamate (Compound I-25)

Step a: (1S,2R,4R)-4-[(6-Chloropyrimidin-4-yl)amino]-2-(hydroxymethyl)cyclopentanol To a neat mixture of (1S,2R,4R)-4-amino-2-(hydroxymethyl)cyclopentanol (3.00 g, 22.9 mmol) and 4,6-dichloropyrimidine (3.70 g, 24.8 mmol) was added isopropyl alcohol (30.0 mL) and Et$_3$N (8.00 mL, 57.4 mmol) and the resulting mixture was heated to 90° C. for 1 h. The mixture was then cooled to 23° C., filtered and concentrated in vacuo. The residue was purified via silica gel chromatography eluting with a gradient of 5 to 7% MeOH in DCM, and the compound was recrystallized from EtOAc to afford the title compound as a white solid (3.30 g, 59%). LC/MS: R$_t$=0.84 min, ES$^+$ 244 (AA standard).

Step b: (1S,2R,4R)-4-({6-[(1S)-2,3-Dihydro-1H-inden-1-ylamino]pyrimidin-4-yl}amino)-2-(hydroxymethyl)cyclopentanol A mixture of (1S,2R,4R)-4-[(6-chloropyrimidin-4-yl)amino]-2-(hydroxymethyl)cyclopentanol (500. mg, 2.05 mmol), 1-butanol (4.00 mL) and (S)-(+)-1-aminoindan (0.806 mL, 6.16 mmol) was heated to 200° C. for 90 min in a sealed tube using MWI. The mixture was concentrated in vacuo and purified via silica gel chromatography eluting with a gradient of 5 to 25% MeOH in DCM to afford the title compound as an amorphous solid (513 mg, 73%). LC/MS: R$_t$=1.20 min, ES$^+$ 341 (AA standard).

Step c: tert-Butyl (chlorosulfonyl)carbamate

To a stirred solution of chlorosulfonyl isocyanate (3.20 mL, 36.0 mmol) in benzene (15.0 mL) in a water bath at 23° C. was added tert-butyl alcohol (3.50 mL, 36.2 mmol) dropwise via syringe under an atmosphere of nitrogen. After 2 h, the mixture was diluted with hexanes (30.0 mL) and the resulting white precipitate was filtered and washed with hexanes (3×20 mL). The collected solid was dried in a vacuum desiccator under house vacuum for 10 min to afford the title compound as a white solid (5.08 g, 65%). The product was stored under nitrogen in a freezer. $^1$H NMR (300 MHz, CDCl$_3$, δ): 8.44 (bs, 1H), 1.57 (s, 9H) ppm. LC/MS: R$_t$=0.939 min, ES$^+$ 215 (AA standard). Reference: F. Hirayama et al., *Biorg. Med. Chem.*, 2002, 10, 1509-1523.

Step d: tert-Butyl ({[(1R,2S,4R)-4-({6-[(1S)-2,3-dihydro-1H-inden-1-ylamino]pyrimidin-4-yl}amino)-2-hydroxycyclopentyl]methoxy}sulfonylcarbamate A neat mixture of (1S,2R,4R)-4-({6-[(1S)-2,3-dihydro-1H-inden-1-ylamino]pyrimidin-4-yl}amino)-2-(hydroxymethyl)cyclopentanol (100. mg, 0.294 mmol) and 2,6-di-tert-butyl-4-methylpyridine (181 mg, 0.881 mmol) was dissolved in ACN (5.00 mL) before tert-butyl (chlorosulfonyl)carbamate (95.0 mg, 0.441 mmol, as prepared in Example 21c) was added. The reaction was stirred for 2 h before being quenched via addition of MeOH (2 mL). The resulting mixture was concentrated in vacuo and purified via silica gel chromatography eluting with a gradient of 10 to 20% MeOH in DCM to afford the title compound as an amorphous solid (50.0 mg, 33%). LC/MS: R$_t$=1.24 min, ES$^+$ 520. (AA standard).

Step e: [(1R,2S,4R)-4-({6-[(1S)-2,3-Dihydro-1H-inden-1-ylamino]pyrimidin-4-yl}amino)-2-hydroxycyclopentyl]methyl sulfamate (Compound I-25)

To a solution of tert-butyl (([(1R,2S,4R)-4-({6-[(1S)-2,3-dihydro-1H-inden-1-ylamino]pyrimidin-4-yl}amino)-2-hydroxycyclopentyl]methoxy)sulfonyl)carbamate (50.0 mg, 0.0962 mmol) in DCM (2.00 mL) was added trifluoroacetic acid (0.500 mL, 6.49 mmol), and the mixture was stirred for 30 min. The mixture was concentrated in vacuo and the residue was purified via silica gel chromatography eluting with 10% MeOH in DCM, and the product was dissolved in MeOH and treated with solid NaHCO$_3$. The suspension was filtered and the filtrate was purified via silica gel chromatography eluting with 10% MeOH/DCM to afford the title compound as an amorphous solid (12.0 mg, 30%). $^1$H NMR (CD$_3$OD, 400 MHz) δ: 7.94 (s, 1H), 7.29-7.12 (m, 4H), 5.53 (s, 1H), 5.32 (bs, 1H), 4.23-4.08 (m, 4H), 3.06-2.96 (m, 1H), 2.93-2.82 (m, 1H), 2.61-2.50 (m, 1H), 2.45-2.34 (m, 1H), 2.26-2.15 (m, 1H), 2.08-1.98 (m, 1H), 1.95-1.78 (m, 2H), 1.37-1.25 (m, 2H) ppm. LC/MS: R$_t$=1.29 min, ES$^+$ 420. (AA standard).

Example 22

{(1R,2R,3S,4R)-2,3-Dihydroxy-4-[(8-phenyl-9H-purin-6-yl)amino]cyclopentyl}methyl sulfamate (Compound I-9)

The title compound was prepared following the procedure described in Example 1a-b, then 1d-e using 6-chloro-8-phenyl-9H-purine in step a. $^1$H NMR (DMSO-d6, 400 MHz) δ: 13.4 (s, 1H), 8.28-8.10 (m, 4H), 7.76-7.64 (m, 1H), 7.58-7.40 (m, 7H), 4.89-4.75 (m, 1H), 4.70-4.59 (m, 1H), 4.59-4.50 (m, 1H), 4.15-4.07 (m, 2H), 4.06-3.99 (m, 1H), 3.91 (bs, 1H), 3.80-3.74 (m, 2H), 3.17 (d, J=5.2 Hz, 1H), 2.34-2.15 (m, 3H), 1.37-1.21 (m, 2H) ppm. LC/MS: R$_t$=1.14 min, ES$^+$ 421 (AA standard).

Example 23

[(1R,2R,3S,4R)-2,3-Dihydroxy-4-(9H-purin-6-ylamino)cyclopentyl]methyl sulfamate (Compound I-3)

Step a: [(3aR,4R,6R,6aS)-6-Amino-2,2-dimethyltetrahydro-3aH-cyclopenta[d][1,3]dioxol-4-yl]methanol The title compound was prepared following the procedure described in Example 1b using (1R,2S,3R,5R)-3-amino-5-(hydroxymethyl)cyclopentane-1,2-diol hydrochloride. $^1$H NMR (CDCl$_3$, 300 MHz) δ: 4.76 (d, J=5.5 Hz, 1H), 4.20 (d, J=4.8 Hz, 1H), 3.70 (dd, J=3.9, 11.3 Hz, 1H), 3.56-3.47 (m, 2H), 3.05 (bs, 2H), 2.53-2.35 (m, 2H), 1.41 (s, 3H), 1.33-1.21 (m, 5H) ppm.

Step b: [(3aR,4R,6R,6aS)-2,2-Dimethyl-6-(9H-purin-6-ylamino)tetrahydro-3aH-cyclopenta[d][1,3]dioxol-4-yl]methanol The title compound was prepared following the procedure described in Example 1a using [(3aR,4R,6R,6aS)-6-amino- 2,2-dimethyltetrahydro-3aH-cyclopenta[d][1,3]dioxol-4-yl]methanol. LC/MS: R$_t$=1.39 min, ES$^+$ 306 (AA standard).

Step c: [(1R,2R,3S,4R)-2,3-Dihydroxy-4-(9H-purin-6-ylamino)cyclopentyl]methyl sulfamate (Compound I-3)

A suspension of [(3aR,4R,6R,6aS)-2,2-dimethyl-6-(9H-purin-6-ylamino)tetrahydro-3aH-cyclopenta[d][1,3]dioxol-4-yl]methanol (288 mg, 0.943 mmol) and Et$_3$N (0.400 mL, 2.87 mmol) in DCM (5.00 mL) was cooled to 0° C. A 2.00 M solution of chlorosulfonamide in ACN (0.94 mL, 1.88 mmol, as prepared in Example 1d) was added dropwise, and DMF (1.50 mL) was added to bring the mixture into solution. The solution was allowed to warm to 23° C. and was stirred for 5 h before being concentrated in vacuo to dryness. The crude mixture was treated with a 1.00 M solution of HCl in H$_2$O (5.00 mL, 5.00 mmol) and stirred for 10 min. The mixture was concentrated to dryness and purified via reverse phase C18 preparative HPLC eluting with a gradient of 0 to 40% of 0.1% FA/95% ACN/5% H$_2$O in 0.1% FA/99% H2O/1% ACN over 16 min to afford the title compound (95.0 mg, 29%). $^1$H NMR (DMSO-d6, 400 MHz) δ: 12.9 (bs, 1H), 8.25-8.01 (m, 2H), 7.68-7.29 (m, 3H), 5.12-4.30 (m, 3H), 4.10 (dd, J=5.8, 9.6 Hz, 1H), 4.01 (dd, J=7.0, 9.6 Hz, 1H), 3.85 (dd, J=5.6, 5.6 Hz, 1H), 3.75 (dd, J=5.2, 5.2 Hz, 1H), 2.35-2.13 (m, 2H), 1.33-1.19 (m, 1H) ppm. LC/MS: R$_t$=1.02 min, ES$^+$ 345 (AA standard).

Example 24

[(1S,2S,4R)-4-({6-[(1S)-2,3-Dihydro-1H-inden-1-ylamino]pyrimidin-4-yl}amino)-2-hydroxycyclopentyl]methyl sulfamate (Compound I-5)

Step a: (1R,2R,3S,5S)-3-(Hydroxymethyl)-6-oxabicyclo[3.1.0]hexan-2-ol (1S,5S)-5-(Hydroxymethyl)cyclopent-2-en-1-ol (3.19 g, 27.9 mmol) was dissolved in DCM (143 mL) and the solution was cooled to 0° C. 3-Chloroperbenzoic acid (7.52 g, 33.5 mmol) was added and the mixture was stirred at 23° C. for 4 h. TLC indicated complete conversion. Silica gel (20 g) was added, the mixture was concentrated to dryness and was purified via silica gel chromatography eluting with a gradient of 0 to 100% EtOAc in DCM to afford the title compound (2.75 g, 76%). $^1$H NMR (CDCl$_3$, 300 MHz) δ: 4.58 (d, J=8.1 Hz, 1H), 3.69 (s, 1H), 3.68 (s, 1H), 3.60 (s, 1H), 3.52 (s, 1H), 2.47-2.40 (m, 1H), 2.14 (ddd, J=1.5, 10.2, 15.3 Hz, 1H), 2.01 (dd, J=1.5, 15.3 Hz, 1H), 1.62 (bs, 2H) ppm. LC/MS: R$_t$=0.37 min, ES$^+$ 131 (AA standard).

Step b: (1aS,1bR,5aS,6aS)-3-(4-Methoxyphenyl)hexahydrooxireno[4,5]cyclopenta[1,2-d][1,3]dioxine (1R,2R,3S,5S)-3-(Hydroxymethyl)-6-oxabicyclo[3.1.0]hexan-2-ol (3.65 g, 21.0 mol) was dissolved in DCM (121 mL) and the solution was cooled to 0° C. 1-(Dimethoxymethyl)-4-methoxybenzene (10.7 mL, 63.1 mmol) was added followed by pyridinium p-toluenesulfonate (530. mg, 2.11 mmol). The mixture was stirred at 23° C. overnight. TLC indicated complete conversion. The reaction mixture was concentrated in vacuo and the residue was purified via silica gel chromatography eluting with a gradient of 0 to 50% EtOAc in hexanes to afford the title compound (4.10 g, 78%). $^1$H NMR (CDCl$_3$, 400 MHz) δ: 7.44 (d, J=8.8 Hz, 2H), 6.89 (d, J=8.8 Hz, 2H), 5.93 (1H, s), 4.58 (d, J=8.4 Hz, 1H), 4.05 (s, 1H), 4.03 (s, 1H), 3.80 (s, 3H), 3.71 (d, J=2.4 Hz, 1H), 3.51 (d, J=2.4 Hz, 1H), 2.50-2.48 (m, 1H), 1.87 (ddd, =1.6, 8.0, 14.8 Hz, 1H), 1.77 (d, J=14.8 Hz, 1H) ppm. LC/MS: R$_t$=1.68 min, ES$^+$ 249 (AA standard).

Step c: 2-[(4aS,6R,7S,7aR)-7-Hydroxy-2-(4-methoxyphenyl)hexahydrocyclopenta[d][1,3]dioxin-6-yl]-1H-isoindole-1,3(2H)-dione To a neat mixture of (1aS,1bR,5aS,6aS)-3-(4-methoxyphenyl)hexahydrooxireno[4,5]cyclopenta[1,2-d][1,3]dioxine (600. mg, 2.42 mmol), phthalimide (1.07 g, 7.25 mmol) and phthalimide potassium salt (1.34 g, 7.25 mmol) was added DMSO (15.0 mL) and the mixture was stirred at 120° C. for 18 h. The mixture was concentrated in vacuo, treated with H$_2$O and extracted with EtOAc. The organic layer was dried over MgSO$_4$, filtered and concentrated in vacuo. The residue was purified via silica gel chromatography eluting with a gradient of 0 to 15% EtOAc in DCM to afford the title compound as a white solid (602 mg, 63%). LC/MS: R$_t$=1.68 min, ES$^+$ 396 (AA standard).

Step d: O-[(4aS,6R,7S,7aR)-6-(1,3-Dioxo-1,3-dihydro-2H-isoindol-2-yl)-2-(4-methoxyphenyl)hexahydrocyclopenta[d][1,3]dioxin-7-yl] O-phenyl thiocarbonate To a stirred solution of 2-[(4aS,6R,7S,7aR)-7-hydroxy-2-(4-methoxyphenyl)-hexahydrocyclopenta[d][1,3]dioxin-6-yl]-1H-isoindole-1,3(2H)-dione (1.26 g, 3.19 mmol) in DCM (150. mL) was added DMAP (1.17 g, 9.54 mmol) and phenyl chlorothionoformate (0.661 mL, 4.78 mmol) under an atmosphere of argon. After 2 h, the mixture was concentrated in vacuo and the residue was purified via silica gel chromatography eluting with a gradient of 0 to 5% EtOAc in DCM to afford the title compound as a white amorphous solid (1.64 g, 97%). LC/MS: R$_t$=221 min, ES$^+$ 532 (AA standard).

Step e: 2-[(4aS,6R,7aS)-2-(4-Methoxyphenyl)hexahydrocyclopenta[d][1,3]dioxin-7-yl]-1H-isoindole-1,3(2H)-dione To a solution of O-[(4aS,6R,7S,7aR)-6-(1,3-dioxo-1,3-dihydro-2H-isoindol-2-yl)-2-(4-methoxyphenyl)hexahydrocyclopenta[d][1,3]dioxin-7-yl] O-phenyl thiocarbonate (56.9 mg, 0.107 mmol) in toluene (4.00 mL) was added tris(trimethylsilyl)silane (0.0700 mL, 0.227 mmol). Air (2.00 mL) was bubbled through the solution and a 1.00 M solution of triethylborane in hexane (0.0320 mL, 0.0320 mmol) was added and the reaction was stirred for 2 h. More tris(trimethylsilyl)silane (0.0700 mL, 0.227 mmol) and 1.00 M triethylborane in hexane (0.0300 mL, 0.0300 mmol) were added, and the mixture was stirred another 6 h. The mixture was then concentrated in vacuo and the residue was purified via silica gel chromatography eluting with a gradient of 0 to 20% EtOAc in DCM to afford the title compound (16.9 mg, 42%). LC/MS: R$_t$=2.03 min, ES$^+$ 380. (AA standard).

Step f: (4aS,6R,7aS)-2-(4-Methoxyphenyl)hexahydrocyclopenta[d][1,3]dioxin-6-amine A mixture of 2-[(4aS,6R,7aS)-2-(4-methoxyphenyl)-hexahydrocyclopenta[d][1,3]dioxin-6-yl]-1H-isoindole-1,3 (2H)-dione (390. mg, 1.03 mmol), EtOH (11.3 mL) and hydrazine (0.0362 mL, 1.13 mmol) was stirred at 90° C. for 18 h. The resulting mixture was purified via silica gel chromatography eluting with a gradient of 10 to 50% MeOH in DCM. LC/MS: $R_t$=1.08 min, ES$^+$ 250. (AA standard).

Step g: 6-Chloro-N-[(4a,6R,7aS)-2-(4-methoxyphenyl)-hexahydrocyclopenta[d][1,3]dioxin-6-yl]pyrimidin-4-amine A sealed tube containing (4aS,6R,7aS)-2-(4-methoxyphenyl)-hexahydrocyclopenta[d][1,3]dioxin-6-amine (120. mg, 0.481 mmol), 4,6-dichloropyrimidine (143 mg, 0.963 mmol), DIPEA (0.0920 mL, 0.528 mmol) and EtOH (30.0 mL) was heated to 110° C. for 20 h. The cooled mixture was concentrated in vacuo and the residue was purified via silica gel chromatography eluting with a gradient of 0 to 5% MeOH in DCM (120. mg, 69%). LC/MS: $R_t$=1.74 min, ES$^+$ 362 (AA standard).

Step h: (1 S,2S,4R)-4-[(6-Chloropyrimidin-4-yl)amino]-2-(hydroxymethyl)cyclopentanol A neat mixture of 6-chloro-N-[(4aS,6R,7aS)-2-(4-methoxyphenyl)-hexahydrocyclopenta[d][1,3]dioxin-6-yl]pyrimidin-4-amine (120. mg, 0.332 mmol) and (S)-(+)-1-aminoindan (0.170 mL, 1.33 mmol) was heated to 180° C. for 6 h in a sealed tube using MWI. The reaction was purified via silica gel chromatography eluting with a gradient of 0 to 15% MeOH in DCM to afford the title compound (33.1 mg, 41%). LC/MS: $R_t$=0.90 min, ES$^+$ 244 (AA standard).

Step i: (1 S,2S,4R)-4-({6-[(1S)-2,3-Dihydro-1H-inden-1-ylamino]pyrimidin-4-yl}amino)-2-(hydroxymethyl)cyclopentanol A mixture of (1S,2S,4R)-4-[(6-chloropyrimidin-4-yl)amino]-2-(hydroxymethyl)cyclopentanol (33.1 mg, 0.136 mmol), 6-chloro-N-[(4aS,6R,7aS)-2-(4-methoxyphenyl)hexahydrocyclopenta[d][1,3]dioxin-6-yl]pyrimidin-4-amine (81.6 mg, 0.226 mmol), (S)-(+)-1-aminoindan (0.222 mL, 1.73 mmol) and 1-butanol (1.00 mL) was heated to 180° C. for 6 h in a sealed tube using MWI. The reaction was purified via silica gel chromatography eluting with a gradient of 0 to 15% MeOH in DCM to afford the title compound (77.8 mg, 63%). LC/MS: $R_t$=1.29 min, ES$^+$ 341 (AA standard).

Step j: [(1S,2S,4R)-4-({6-[(1S)-2,3-Dihydro-1H-inden-4-ylamino]pyrimidin-4-yl}amino)-2-hydroxycyclopentyl]methyl sulfamate (Compound I-5)

The title compound was prepared following the procedure described in Example 21d-e using (1S,2S,4R)-4-({6-[(1S)-2,3-dihydro-1H-inden-1-ylamino]pyrimidin-4-yl}amino)-2-(hydroxymethyl)cyclopentanol and THF in step d. $^1$H NMR (CD$_3$OD, 400 MHz) δ: 7.94 (s, 1H), 7.38-7.12 (m, 5H), 5.51 (s, 1H), 5.32 (bs, 1H), 4.37-4.32 (m, 1H), 4.29 (dd, J=7.7, 9.7 Hz, 1H), 4.27-4.18 (m, 1H), 4.12 (dd, J=7.3, 9.7 Hz, 1H), 3.05-2.96 (m, 1H), 2.93-2.82 (m, 1H), 2.60-2.51 (m, 1H), 2.51-2.42 (m, 1H), 2.21 (ddd, J=1.8, 7.6, 13.9 Hz, 1H), 2.04-1.85 (m, 2H), 1.81 (ddd, J=4.9, 7.1, 13.8 Hz, 1H), 1.74-1.64 (m, 1H), 1.44 (s, 1H) ppm. LC/MS: $R_t$=1.38 min, ES$^+$ 420. (AA standard).

Example 25

[(1S,2R,3S,4R)-4-({6-[(1S)-2,3-Dihydro-1H-inden-1-ylamino]pyrimidin-4-yl}-amino)-2,3-dihydroxycyclopentyl]methyl sulfamate (Compound I-11)

The title compound was prepared following the procedure described in Example 24 steps a-c, followed by steps f-g, and finally steps i-j. $^1$H NMR (CD$_3$OD, 300 MHz) δ: 7.94 (s, 1H), 7.30-7.11 (m, 4H), 5.60 (s, 1H), 5.30 (bs, 1H), 4.32 (dd, J=7.9, 9.4 Hz, 1H), 4.14-3.96 (m, 3H), 3.89 (dd, J=3.8, 7.7 Hz, 1H), 3.08-2.95 (m, 1H), 2.87 (ddd, J=8.0, 8.0, 15.8 Hz, 1H), 2.62-2.44 (m, 2H), 2.15-2.01 (m, 1H), 1.96-1.81 (m, 1H), 1.70-1.57 (m, 1H) ppm. LC/MS: $R_t$=1.32 min, ES$^+$ 436 (AA standard).

Example 26

[(1R,2R,3S,4R)-4-({4-[(1S)-2,3-Dihydro-1H-inden-1-ylamino]-1,3,5-triazin-2-yl}amino)-2,3-dihydroxycyclopentyl]methyl sulfamate (Compound I-26)

Step a: 4,6-Dichloro-N-[(1S)-2,3-dihydro-1H-inden-1-yl]-1,3,5-triazin-2-amine

To a solution of cyanuric chloride (631 mg, 3.42 mmol) in THF (2.00 mL) at 0° C. was added (S)-(+)-1-aminoindan (0.385 mL, 3.00 mmol) and DIPEA (0.596 mL, 3.42 mmol) and the mixture was stirred at 0° C. for 2 h. The reaction was then poured into H$_2$O, extracted with DCM and the organic layer was dried over MgSO$_4$, filtered and concentrated in vacuo. The residue was purified via silica gel chromatography eluting with a gradient of 0 to 20% EtOAc in hexanes to afford the title compound as a yellow solid (738 mg, 87%). LC/MS: $R_t$=1.99 min, ES$^+$ 281 (FA standard).

Step b: (1R,2S,3R,5R)-3-({4-Chloro-6-[(1S)-2,3-dihydro-1H-inden-1-ylamino]-1,3,5-triazin-2-yl}amino)-5-(hydroxymethyl)cyclopentane-1,2-diol A mixture of 4,6-dichloro-N-[(1S)-2,3-dihydro-1H-inden-1-yl]-1,3,5-triazin-2-amine (735 mg, 2.61 mmol), (1R,2S,3R,5R)-3-amino-5-(hydroxymethyl)cyclopentane-1,2-diol hydrochloride (400. mg, 218 mmol), potassium carbonate (602 mg, 4.36 mmol) and 1,4-dioxane (3.60 mL) in a sealed tube was heated to 150° C. for 20 mins using MWI. Silica gel chromatography eluting with a gradient of 2 to 7% MeOH in DCM afforded the title compound as a white solid (750. mg, 88%). LC/MS: $R_t$=1.42 min, ES$^+$ 392 (FA standard).

Step c: [(3aR,4R,6R,6aS)-6-({4-Chloro-6-[(1S)-2,3-dihydro-1H-inden-1-ylamino]-1,3,5-triazin-2-yl}amino)-2,2-dimethyltetrahydro-3aH-cyclopenta[d][1,3]dioxol-4-yl]methanol The title compound was prepared following the procedure described in Example 1b using (1R,2S,3R,5R)-3-({4-chloro-6-[(1S)-2,3-dihydro-1H-inden-1-ylamino]-1,3,5-triazin-2-yl}amino)-5-(hydroxymethyl)cyclopentane-1,2-diol. LC/MS: $R_t$=1.81 min, ES$^+$ 432 (FA standard).

Step d: [(3aR,4R,6R,6aS)-6-({4-[(1S)-2,3-Dihydro-1H-inden-1-ylamino]-1,3,5-triazin-2-yl}amino)-2,2-dimethyltetrahydro-3aH-cyclopenta[d][1,3]dioxol-4-yl]methanol To a solution of [(3aR,4R,6R,6aS)-6-({4-Chloro-6-[(1S)-2,3-dihydro-1H-inden-1-ylamino]-1,3,5-triazin-2-yl}amino)-2,2-dimethyltetrahydro-3aH-cyclopenta[d][1,3]dioxol-4-yl]methanol (182 mg, 0.421 mmol) in EtOH (2.91 mL) was added 10% palladium on carbon (44.8 mg) and the mixture was placed under an atmosphere of hydrogen for 2 d. Filtration of the mixture through a pad of celite, followed by silica gel chromatography eluting with 5% MeOH in DCM afforded the title compound as a white solid (80.0 mg, 48%). LC/MS: $R_t$=1.24 min, ES$^+$ 398 (FA standard).

Step e: [(1R,2R,3S,4R)-4-({4-[(1S)-2,3-Dihydro-1H-inden-1-ylamino]-1,3,5-triazin-2-yl}amino)-2,3-dihydroxycyclopentyl]methyl sulfamate The title compound was prepared following the procedure described in Example 1d using [(3aR,4R,6R,6aS)-6-({4-[(1S)-2,3-Dihydro-1H-inden-1-ylamino]-1,3,5-triazin-2-yl}amino)-2,2-dimethyltetrahydro-3aH-cyclopenta[d][1,3]dioxol-4-yl]methanol and pyridine. $^1$H NMR (CD$_3$OD, 400 MHz) δ: 8.16-7.83 (m, 1H), 7.37-7.11 (m, 3H), 5.68-5.45 (m, 1H), 4.39-4.00 (m, 3H), 3.91-3.77 (m, 1H), 3.06-2.92 (m, 1H), 2.92-2.75 (m, 1H), 2.61-2.48 (m, 1H), 2.40-2.20 (m, 2H), 2.02-1.79 (m, 2H), 1.37-1.17 (m, 1H) ppm. LC/MS: $R_t$=1.07 min, ES$^+$ 437 (FA standard).

Example 27

[(1R,2R,3S,4R)-2,3-Dihydroxy-4-(isonicotinoylamino)cyclopentyl]methyl sulfamate (Compound I-28)

Step a: tert-Butyl (1R,4S,5R,6S)-5,6-dihydroxy-3-oxo-2-azabicyclo[2.2.1]heptane-2-carboxylate To a solution of tert-butyl (1R,4S)-3-oxo-2-azabicyclo[2.2.1]hept-5-ene-2-carboxylate (500. mg, 2.39 mmol) in acetone (20.0 mL) was added a 4% aqueous solution of osmium tetroxide in H$_2$O (0.015 mL, 0.00239 mmol). To the resulting mixture was added a 10.2 M aqueous solution of N-methylmorpholine N-oxide (0.262 mL, 2.67 mmol) dropwise over 1 h. At this point, a 0.240 M solution of aqueous sodium bisulfite (1.00 mL, 0.240 mmol) was added, the mixture was filtered through celite and concentrated in vacuo. The residue was purified via silica gel chromatography eluting with a gradient of 20 to 70% EtOAc in DCM to afford the title compound (420. mg, 72%). LC/MS: $R_t$=0.94 min, ES$^+$ 244 (FA standard).

Step b: tert-Butyl (1R,4S,5R,6S)-5,6-bis(benzoyloxy)-3-oxo-2-azabicyclo[2.2.1]heptane-2-carboxylate A solution of tert-butyl (1R,4S,5R,6S)-5,6-dihydroxy-3-oxo-2-azabicyclo[2.2.1]heptane-2-carboxylate (2.00 g, 8.22 mmol), pyridine (5.00 mL, 61.8 mmol), Et$_3$N (2.29 mL, 16.4 mmol) and DMAP (100. mg, 0.818 mmol) in DCM (5.00 mL) was cooled to 0° C. and benzoyl chloride (4.77 mL, 41.1 mmol) was added dropwise. The mixture was allowed to warm to 23° C. and stir for 2 h. The reaction was then diluted with DCM, washed with saturated aqueous NaHCO$_3$ (3×), copper (II) sulfate solution (3×) and water (3×). The organic layer was then dried over sodium sulfate, filtered and concentrated in vacuo. The residue was purified via silica gel chromatography eluting with a gradient of 5 to 40% EtOAc in hexanes to afford the title compound (2.92 g, 79%). LC/MS: $R_t$=2.15 min, ES$^+$ 452 (FA standard).

Step c: (1R,2S,3R,5R)-3-[(tert-Butoxycarbonyl)amino]-5-(hydroxymethyl)cyclopentane-1,2-diyl dibenzoate To a solution of tert-butyl (1R,4S,5R,6S)-5,6-bis(benzoyloxy)-3-oxo-2-azabicyclo[2.2.1]heptane-2-carboxylate (2.09 g, 4.62 mmol) in MeOH (60.0 mL) was added sodium borohydride (700. mg, 18.5 mmol) at 0° C. and the reaction was allowed to warm to rt. After 1.5 h, the mixture was quenched with 1.00 N HCl solution (20.0 mL), and concentrated in vacuo. The aqueous layer was extracted with DCM (3×50 mL) and the combined organic layers were washed with H$_2$O (100. mL), dried over MgSO$_4$ and concentrated in vacuo. The residue was purified via silica gel chromatography eluting with a gradient of 20 to 60% EtOAc in hexanes to afford the title compound (1.50 g, 80%). LC/MS: $R_t$=1.95 min, ES$^+$ 456 (FA standard).

Step d: (1R,2S,3R,5R)-3-Amino-5-(hydroxymethyl)cyclopentane-1,2-diyl dibenzoate hydrochloride (1R,2S,3R,5R)-3-[(tert-Butoxycarbonyl)amino]-5-(hydroxymethyl)-cyclopentane-1,2-diyl dibenzoate (1.42 g, 3.11 mmol) was treated with a 4.00 M solution of HQ in 1,4-dioxane (17.0 mL, 69.3 mmol) and the reaction was stirred for 35 min. The reaction mixture was concentrated in vacuo and Et$_2$O was added to precipitate the product, which was washed with Et$_2$O to afford the title compound as a white solid (1.05 g, 90%). LC/MS: $R_t$=1.06 min, ES$^+$ 356 (FA standard).

Step e: (1S,2R,3R,5R)-3-(Hydroxymethyl)-5-(isonicotinoylamino)cyclopentane-1,2-diyl dibenzoate A solution of (1R,2S,3R,5R)-3-amino-5-(hydroxymethyl) cyclopentane-1,2-diyl dibenzoate hydrochloride (150. mg, 0.380 mmol) in DCM (10.0 mL) at 0° C. was treated with Et$_3$N (0.170 mL, 1.22 mmol) and stirred for 20 min. Isonicotinoyl chloride (88.0 mg, 0.490 mmol) was then added and the mixture was stirred for 2 h. The reaction was treated with saturated aqueous solution of ammonium chloride (50 mL) and extracted with DCM (2×50 mL). The combined organic layers were dried over sodium sulfate, filtered and concentrated in vacuo. The resulting residue was purified via silica gel chromatography eluting with a gradient of 0 to 10% MeOH in DCM to afford the title compound (100. mg, 60%). LC/MS: $R_t$=1.49 min, ES$^+$ 461 (FA standard).

Step f: (1S,2R,3R,5R)-3-{[(Aminosulfonyl)oxy]methyl}-5-(isonicotinoylamino)cyclopentan-1,2-diyl dibenzoate To a solution of (1S,2R,3R,5R)-3-(hydroxymethyl)-5-(isonicotinoylamino)cyclopentane-1,2-diyl dibenzoate (160. mg, 0.350 mmol) in ACN (10.0 mL) at 0° C. was added DBU (0.0600 mL, 0.401 mmol) and the mixture was stirred for 15 min. A freshly prepared 1.40 M solution of chlorosulfonamide (0.500 mL, 0.700 mmol, as prepared in Example 1d) was then added dropwise via syringe and the mixture was stirred for 2.5 h at 0° C. before being allowed to warm to rt. The mixture was concentrated in vacuo and the residue was purified via silica gel chromatography eluting with a gradient of 0 to 10% MeOH in DCM to afford the title compound (50.0 mg, 27%). LC/MS: $R_t$=1.57 min, ES$^+$ 540. (FA standard).

Step g: [(1R,2R,3S,4R)-2,3-dihydroxy-4-(isonicotinoylamino)cyclopentyl]methyl sulfamate (Compound I-28)

A solution of (1S,2R,3R,5R)-3-{[(aminosulfonyl)oxy]methyl}-5-(isonicotinoylamino)cyclopentane-1,2-diyl dibenzoate (61.1 mg, 0.113 mmol) in a 7.00 M solution of ammonia in MeOH (1.50 mL, 10.5 mmol) was stirred for 2 days. The reaction mixture was then concentrated in vacuo and purified via reverse phase C18 preparative HPLC eluting with a gradient of 5 to 70% of 0.1% FA/95% ACN/5%

H₂O in 0.1% FA/99% H2O/1% ACN over 16 min to afford the title compound (15.0 mg, 40%). ¹H NMR (CD₃OD, 300 MHz) δ: 8.67 (m, 2H), 7.78 (m, 2H), 4.34-4.32 (m, 1H), 4.19-4.17 (m, 2H), 3.93-3.92 (m, 2H), 2.38-2.31 (m, 1H), 1.76-1.72 (m, 1H), 1.43-1.38 (m, 1H) ppm. LC/MS: R$_f$=0.76 min, ES⁺ 332 (FA standard).

Example 28

{(1R,2R,3S,4R)-2,3-Dihydroxy-4-[(pyridin-2-ylcarbonyl)amino]cyclopentyl}methyl sulfamate (Compound I-23)

The title compound was prepared following the procedure described in Example 27a-e using pyridine-2-carbonyl chloride in step c. ¹H NMR (CD₃OD, 300 MHz) δ: 8.62 (s, 1H), 8.09-8.06 (m, 1H), 7.97-7.94 (m, 1H), 7.55-7.51 (m, 1H), 4.34-4.32 (m, 1H), 4.19-4.18 (m, 2H), 3.95-3.93 (m, 2H), 2.64 (s, 1H), 2.38-2.35 (m, 2H) ppm. LC/MS: R$_f$=1.23 min, ES⁺ 332 (FA standard).

Example 29

{(1R,2R,3S,4R)-2,3-Dihydroxy-4-[(pyridin-3-ylcarbonyl)amino]cyclopentyl}-methyl sulfamate (Compound I-16)

The title compound was prepared following the procedure described in Example 27a-e using nicotinoyl chloride in step c. ¹H NMR (CD₃OD, 300 MHz) δ: 8.97 (s, 1H), 8.67-8.66 (m, 1H), 8.26-8.23 (m, 1H), 7.55-7.50 (m, 1H), 4.35-4.11 (m, 3H), 3.95-3.92 (m, 2H), 2.36-2.34 (m, 2H), 1.43-1.38 (m, 1H) ppm. LC/MS: R$_f$=0.83 min, ES⁺ 332 (FA standard).

The following additional compounds were also prepared.

Example 30

[(1S,2S,4R)-4-({6-[(1S)-2,3-Dihydro-1H-inden-1-ylamino]pyrimidin-4-yl}oxy)-2-hydroxycyclopentyl]methyl sulfamate (Compound I-31)

The title compound was prepared in a manner similar to Example 34 using (S)-2-aminoindane. The title compound was prepared as a 4:1 mixture of desired compound and (1S,2S,4R)-4-({6-[(1S)-2,3-dihydro-1H-inden-1-ylamino]pyrimidin-4-yl}oxy)-2-(hydroxymethyl)cyclopentyl sulfamate. Analytical data for [(1 S,2S,4R)-4-({6-[(1S)-2,3-Dihydro-1H-inden-1-ylamino]pyrimidin-4-yl}oxy)-2-hydroxycyclopentyl]methyl sulfamate: ¹H NMR (CD₃OD, 300 MHz) δ: 8.13 (s, 1H), 7.28-7.12 (m, 4H), 5.85 (s, 1H), 5.33-5.31 (m, 1H), 4.42-4.36 (m, 1H), 4.32 (dd, J=7.5, 9.7 Hz, 1H), 4.15 (dd, J=7.2, 9.7 Hz, 1H), 3.06-2.97 (m, 1H), 2.93-2.82 (m, 1H), 2.62-2.47 (m, 2H), 2.32-2.24 (m, 1H), 2.15 (s, 1H), 2.13-1.79 (m, 4H) ppm. LC/MS: R$_f$=1.38 min, ES⁺ 422 (FA standard). Analytical data for (1S,2S,4R)-4-({6-[(1 S)-2,3-dihydro-1H-inden-1-ylamino]pyrimidin-4-yl}oxy)-2-(hydroxymethyl)cyclopentyl sulfamate: ¹H NMR (CD₃OD, 300 MHz) δ: 8.13 (s, 1H), 7.28-7.12 (m, 4H), 5.85 (s, 1H), 5.33-5.31 (m, 1H), 5.14-5.07 (nm, 1H), 4.59 (s, 1H), 3.78 (dd, J=7.1, 11.0 Hz, 1H), 3.61 (dd, J=7.0, 11.1 Hz, 1H), 3.06-2.97 (m, 1H), 2.73-2.61 (m, 1H), 2.61-2.47 (m, 2H), 2.32-2.24 (m, 1H), 2.17 (s, 1H), 2.13-1.80 (m, 3H) ppm. LC/MS: R$_f$=1.38 min, ES⁺ 422 (FA standard).

Example 31

[(1S,2S,4R)-4-({6-[(1 S)-2,3-dihydro-H-inden-1-ylamino]-5-methylpyrimidin-4-yl}oxy)-2-hydroxy-cyclopentyl]methyl sulfamate (Compound I-32)

The title compound was prepared in a manner similar to Example 34 using (S)-2-aminoindane and 4,6-dichloro-5-methylpyrimidine. ¹H NMR (CD₃OD, 300 MHz) δ: 8.10 (s, 1H), 7.26-7.07 (m, 4H), 5.74 (t, J=7.9 Hz, 1H), 5.59-5.49 (m, 1H), 4.45-4.37 (m, 1H), 4.34 (dd, J=7.5, 9.8 Hz, 1H), 4.16 (dd, J=7.2, 9.7 Hz, 1H), 3.08-2.94 (m, 1H), 2.93-2.79 (m, 1H), 2.65-2.46 (m, 2H), 2.37-2.23 (m, 1H), 2.18-2.13 (m, 3H), 2.13-1.90 (m, 2H), 1.89 (s, 3H) ppm. LC/MS: R$_f$=1.55 min, ES⁺ 435 (FA standard).

Example 32

[(1S,2S,4S)-4-{(6-[(1S)-2,3-dihydro-1H-inden-1-ylamino]pyrimidin-4-yl}-methyl)-2-hydroxycyclopentyl]methyl sulfamate (Compound I-33)

The title compound was prepared according to Example 85. ¹H NMR (CD₃OD, 400 MHz) δ: 8.34 (s, 1H), 7.27-7.15 (m, 4H), 6.41 (bs, 1H), 5.65-5.48 (m, 1H), 4.30-4.25 (m, 2H), 4.09 (dd, J=4.1, 4.1 Hz, 1H), 3.07-3.00 (m, 1H), 2.94-2.85 (m, 1H), 2.72-2.55 (m, 4H), 2.43-2.35 (m, 1H), 1.93-1.85 (m, 2H), 1.75-1.67 (m, 1H), 1.58-1.51 (m, 2H) ppm. LC/MS: R$_f$=1.38 min, ES⁺ 419 (AA standard).

Example 33

((1S,3S)-3-{[8-(1-naphthyl)-9H-purin-6-yl]oxy}cyclopentyl)methyl sulfamate (Compound I-152)

Step a: 6-chloro-8-(1-naphthyl)-9H-purine

A mixture of 6-chloro-4,5-diaminopyrimidine (519 mg, 0.00359 mol) and 1-naphthalenecarboxylic acid (618 mg, 0.00359 mol) in phosphoryl chloride (2.0 mL, 0.021 mol) was heated at 110° C. under an atmosphere of nitrogen for 5.5 hours. The reaction was cooled and the residue was washed several times with ether. The residue was dissolved in CH₂Cl₂ and aqueous NaHCO₃. The layers were separated and the aqueous was extracted with EtOAc (1×) and CH₂Cl₂ (1×). The combined organics were washed with saturated aqueous NaHCO₃, brine, dried (Na₂SO₄), filtered, and collected in vacuo to obtain 810 mg (80%) of an orange solid. LC/MS: R$_f$=1.68 min, ES⁺ 261 (FA standard).

Step b: 6-chloro-8-(1-naphthyl)-9-(tetrahydro-2H-pyran-2-yl)-9H-purine

To a solution of 6-chloro-8-(1-naphthyl)-9H-purine (810 mg, 0.0029 mol) in THF (32.4 mL, 0.399 mol) was added pyridinium p-toluenesulfonate (70 mg, 0.0003 mol) and dihydropyran (11.0 mL, 0.121 mol) and the mixture was heated at 60° C. overnight. The reaction was cooled, quenched by addition of saturated aqueous NaHCO₃ and the mixture was extracted with EtOAc (3×). The organic layers were combined, dried (Na₂SO₄), filtered and concentrated. The dark residue was purified by flash chromatography (10 to 40% EtOAc/hexanes) to obtain 534.5 (51%) mg of a light yellow solid. LC/MS: R$_f$=2.03 min, ES⁺ 365 (FA standard).

Step c: (1 S,3S)-3-(hydroxymethyl cyclopentanol

To a solution of methyl (1S,3S)-3-hydroxycyclopentanecarboxylate (472.3 mg, 0.003276 mol) in THF (13.2 mL) at 0° C. was added LiAlH$_4$ (145 mg, 0.00382 mol) (WARNING: SIGNIFICANT GAS EVOLUTION). The mixture was stirred for 1 hour at 0° C., then quenched at 0° C. by dropwise addition of water (145 μL, 0.00805 mol), 15% aqueous NaOH (145 μL) and water (435 μL). The resulting gray suspension was stirred vigorously overnight. The resulting off white suspension was filtered through celite and rinsed with THF and MeOH. The combined organics were concentrated to obtain 4543 mg (>99%) an off-yellow solid. The material was carried on without further purification.

Step d: (1S,3S)-3-({[tert-butyl(dimethyl)silyl]oxy}methyl)cyclopentanol

To a solution of (1S,3S)-3-(hydroxymethyl)cyclopentanol (453.0 mg, 0.003276 mol) and 1H-imidazole (669 mg, 0.00983 mol) in DMF (35.8 mL) under an atmosphere of nitrogen was added tert-butyldimethylsilyl chloride (494 mg, 0.00328 mol). The mixture was stirred for 1.25 hours, then tert-butyldimethylsilyl chloride (49 mg, 0.00033 mol) was added. After an additional hour of stirring, the reaction was quenched with water, extracted with ethyl acetate (3×), dried with anhydrous Na$_2$SO$_4$, filtered, and concentrated. The residue was filtered through a plug of silica with 30% EtOAc/hexanes to obtain 234.1 mg (31%) of the title compound.

Step e: 6-{[(1S,3S)-3-({[tert-butyl(dimethyl)silyl]oxy}methyl)cyclopentyl]oxy}-8-(1-naphthyl)-9-(tetrahydro-2H-pyran-2-yl)-9H-purine To a solution of (1S,3S)-3-({[tert-butyl(dimethyl)silyl]oxy}methyl)-cyclopentanol (111.0 mg, 0.0004817 mol) (azeotroped with toluene) in DMF (3.6 mL) at 0° C. under an atmosphere of nitrogen was added sodium hydride (24.1 mg, 0.000602 mol). The mixture was stirred for 15 min. To this cold solution was added a solution of 6-chloro-8-(1-naphthyl)-9-(tetrahydro-2H-pyran-2-yl)-9H-purine (163 mg, 0.000401 mol) in DMF (1.8 mL). The flask was rinsed with DMF (1.0 mL)) and this was added to the reaction as well. The resulting mixture was stirred for 20 h. The reaction mixture was quenched with water and the mixture was extracted with EtOAc (3×). The combined organic layers were dried over Na$_2$SO$_4$, filtered and collected in vacuo. The residue was purified by flash chromatography (10 to 40% EtOAc/hexanes) to obtain 156.9 mg (70%) of the title compound as a white solid.

Step f: ((1S,3S)-3-{[8-(1-naphthyl)-9H-purin-6-yl]oxy}cyclopentyl)methanol

To a stirred solution of 6-{[(1S,3S)-3-({[tert-butyl(dimethyl)silyl]oxy}methyl)-cyclopentyl]oxy}-8-(1-naphthyl)-9-(tetrahydro-2H-pyran-2-yl)-9H-purine (156.9 mg, 0.0002808 mol) in THF (3.8 mL) was added water (3.8 mL) and AcOH (7.6 mL), and the reaction mixture was stirred for 7 hours. The reaction mixture was quenched by the slow addition of saturated NaHCO$_3$, and the resulting mixture was extracted with EtOAc (3×). The combined organic layers were washed with brine, dried (Na$_2$SO$_4$), filtered and concentrated. The residue was purified by flash chromatography (0 to 5% MeOH/CH$_2$Cl$_2$) to obtain 85.7 mg (85%) of the title compound as a white solid. LC/MS: R$_t$=1.51 min, ES$^+$ 361 (FA standard).

Step g: ((1S,3S)-3-{[8-(1-naphthyl)-9H-purin-6-yl]oxy}cyclopentyl)methyl sulfamate (Compound I-152)

To a solution of ((1S,3S)-3-{[8-(1-naphthyl)-9H-purin-6-yl]oxy}cyclopentyl)methanol (66.1 mg, 0.000183 mol) in DMA (8.12 mL) at 0° C. was added chlorosulfonamide (106 mg, 0.000917 mol) in CH$_3$CN (2.0 mL). The reaction was stirred at 0° C. for 10 mins, then 23° C. for 3 hours. The reaction was quenched with water and extracted with EtOAc (3×). The combined organics were washed with water (2×), dried (Na$_2$SO$_4$), filtered, and concentrated. The residue was purified by flash chromatography (0 to 6% MeOH/CH$_2$Cl$_2$) to obtain 56.3 mg (70%) of the title compound as a white solid. $^1$H NMR (CD$_3$OD, 400 MHz) δ: 8.52-8.48 (m, 2H), 8.10-8.07 (m, 1H), 8.01-7.98 (m, 1H), 7.90-7.87 (m, 1H), 7.65-7.57 (m, 3H), 5.89-5.85 (m, 1H), 4.12-4.07 (m, 2H), 2.75-2.66 (m, 1H), 2.30-2.21 (m, 2H), 2.16-2.01 (m, 2H), 1.93-1.85 (m, 1H), 1.62-1.53 (m, 1H) ppm. LC/MS: R$_t$=1.38 min, ES$^+$ 442 (FA standard).

Example 34

{(1S,2S,4R)-2-hydroxy-4-[(6-{[(1R,2S)-2-methoxy-2,3-dihydro-1H-inden-1-yl]-amino}pyrimidin-4-yl)oxy]cyclopentyl}methyl sulfamate (Compound I-115)

Step h: 4-{[(1R,3S,4S)-3-{[tert-butyl(dimethyl)silyl]oxy}4-({[tert-butyl(dimethyl)silyl]oxy}methyl)cyclopentyl]oxy}-6-chloropyrimidine To a suspension of sodium hydride (75.6 mg, 0.00189 mol) in THF (2 mL) at 0° C. under an atmosphere of nitrogen was added (1R,3S,4S)-3-{[tert-butyl(dimethyl)silyl]oxy}-4-({[tert-butyl(dimethyl)silyl]oxy}methyl)cyclopentanol (0.60 g, 0.0017 mol) in 1.5 mL THF dropwise at 0° C. The mixture was stirred at 0° C. for 10 min. To this was next added 4,6-dichloro-pyrimidine (0.225 g, 0.00151 mol) in 2 mL THF at 0° C. The suspension was stirred at 0° C. for 2 hrs. The reaction was quenched with 9 mL saturated aqueous NH$_4$Cl and extracted with t-BuOMe (3×). The organic layers were combined and washed with brine, dried over anhydrous MgSO$_4$ and then concentrated to give 0.804 g of an oil. The residue was purified by flash chromatography (0 to 10% EtOAc/hexanes) to give 0.63 g (80%) of the title compound.

Step b: 6-{[(1R,3S,4S)-3-{[tert-butyl(dimethyl)silyl]oxy}-4-({[tert-butyl(dimethyl)silyl]oxy}methyl)cyclopentyl]oxy}-N-[(1R,2S)-2-methoxy-2,3-dihydro-1H-inden-1-yl]-pyrimidin-4-amine A mixture of 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (260.0 mg, 0.0005494 mol), (1R,2S)-2-methoxyindan-1-amine (0.359 g, 0.00220 mol) and triethylamine (115 μL, 0.000824 mol) in 1-butanol (0.97 mL, 0.011 mol) was subjected to microwave irradiation (300 watts, 200° C.) for 30 minutes. The resulting dark brown mixture was filtered and concentrated. The residue was purified by flash chromatography (0 to 15% EtOAc/hexanes) to give 0.26 g (79%) of the title compound. LC/MS: R$_t$=3.42 min, ES$^+$ 600 (AA standard).

Step c: {(1S,2S,4R)-2-{[tert-butyl(dimethyl)silyl]oxy}-4-[(6-{[(1R,2S)-2-methoxy-2,3-dihydro-1H-inden-1-yl]amino}pyrimidin-4-yl)oxy]cyclopentyl}methanol A solution of 6-{[(1R,3S,4S)-3-{[tert-butyl(dimethyl)silyl]oxy}-4-({[tert-butyl(dimethyl)silyl]oxy}methyl)cyclopentyl]oxy}-N-[(1R,2S)-2-methoxy-2,3-dihydro-1H-inden- 1-yl]pyrimidin-4-amine (0.32 g, 0.00053 mol) in THF (2.88 mL), water (2.88 mL), and acetic acid (8.64 mL) was stirred for 3 days. The reaction was concentrated and azeotroped 2× with toluene. The residue was purified by flash chromatography (30 to 80% EtOAc/hexanes) give 0.20 g (77%) of the title compound. LC/MS: $R_t$=1.59 min, ES$^+$ 486 (FA standard).

Step d: {(1S,2S,4R)-2-{[tert-butyl(dimethyl)silyl]oxy}-4-[(6-{[(1R,2S)-2-methoxy-2,3-dihydro-1H-inden-1-yl]amino}pyrimidin-4-yl)oxy]cyclopentyl}methyl sulfamate The title compound was prepared following the procedure described in Example 1 step d. LC/MS: $R_t$=2.16 min, ES$^+$ 565 (FA standard).

Step e: {(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl sulfamate (Compound I-115)

To a solution of {(1S,2S,4R)-2-{[tert-butyl(dimethyl)silyl]oxy}-4-[(6-{[(1R,2S)-2-methoxy-2,3-dihydro-1H-inden-1-yl]amino}pyrimidin-4-yl)oxy]cyclopentyl}methyl sulfamate (0.239 g, 0.000423 mol) in pyridine (3.44 mL) and THF (3.44 mL) was added pyridine hydrofluoride (0.953 mL, 0.0106 mol) dropwise. After stirring the reaction for 2 hours, an additional amount of pyridine hydrofluoride (0.50 mL, 0.0055 mol) was added. After 2.75 hours the reaction was quenched by slow dropwise addition of saturated aqueous NaHCO$_3$ and extracted with EtOAc (4×). The combined organic phases were dried (Na$_2$SO$_4$), filtered and concentrated. The residue was purified by flash chromatography (0 to 10% MeOH/CH$_2$Cl$_2$) and then by preparative plate chromatography (EtOAc) to obtain 100 mg (52%) of the title compound. $^1$H NMR (CD$_3$OD, 400 MHz) δ: 8.15 (s, 1H), 7.24-7.15 (m, 4H), 5.98 (s, 1H), 5.34 (bs, 1H), 4.41-4.38 (m, 1H), 4.32 (dd, 1H, J=7.5, 9.7 Hz), 4.24-4.20 (m, 1H), 4.17 (dd, 1H, J=7.3, 9.8 Hz), 3.35 (s, 3H), 3.13-3.00 (m, 3H), 2.57-2.48 (m, 1H), 2.31-2.25 (m, 1H) 2.12-1.93 (m, 4H) ppm. LC/MS: $R_t$=1.33 min, ES$^+$ 451 (FA standard).

Example 35

{(1S,2S,4R)-2-hydroxy-4-[(4-{[(1R,2S)-2-methoxy-2,3-dihydro-1H-inden-1-yl]-amino}-1,3,5-triazin-2-yl)amino]cyclopentyl}methyl sulfamate (Compound I-125)

Step a: (1S,3S,4S)-3-[(benzyloxy)methyl]-4-{[tert-butyl(dimethyl)silyl]oxy}cyclopentanol A suspension of (1R,4S)-3-[(benzyloxy)methyl]-4-{[tert-butyl(dimethyl)silyl]-oxy}cyclopent-2-en-1-ol (7.54 g, 0.0225 mol) (Ruediger, E; Martel, A; Meanwell, N; Solomon, C; Turmel, B. *Tetrahedron Lett.* 2004, 45, 739-742), sodium carbonate (5.7 g, 0.054 mol) and 10% Pd/C (2 g, 0.002 mol) in EtOAc (90 mL) was stirred under an atmosphere of hydrogen for three hours. The reaction flask was purged with nitrogen and the mixture was filtered through celite with EtOAc. The filtrate was concentrated to obtain 7.16 g (76%) of the title compound as a 4:1 mixture of diastereomers (desired:undesired).

Step b: (1S,3S,4S)-3-[(benzyloxy)methyl]-4-{[tert-butyl(dimethyl)silyl]oxy}cyclopentyl methanesulfonate To a stirred solution of (1S,3S,4S)-3-[(benzyloxy)methyl]-4-{[tert-butyl(dimethyl)silyl]oxy}cyclopentanol (2.04 g, 0.00606 mol) in CH$_2$Cl$_2$ (96 mL) was added pyridine (2.4 mL, 0.030 mol), DMAP (100 mg, 0.001 mol), and methanesulfonyl chloride (700 µL, 0.0091 mol) under an atmosphere of nitrogen, The mixture was stirred 23° C. for 45 minutes, then warmed to 40° C. for 3 hours. To the reaction was added DMAP (100 mg, 0.001 mol) and methanesulfonyl chloride (700 µL, 0.0091 mol). After stirring for 40 min, the reaction was cooled then concentrated in vacuo. The residue was purified by flash chromatography (0 to 15% EtOAc/hexanes) to obtain 1.39 g (55%) of the title compound as one diastereomer (separated undesired diastereomer from step a).

Step c: ({(1S,2S,4R)-4-azido-2-[(benzyloxy)methyl]cyclopentyl}oxy)(tert-butyl)-dimethylsilane To a solution of (1S,3S,4S)-3-[(benzyloxy)methyl]-4-{[tert-butyl(dimethyl)-silyl]oxy}cyclopentanol (138.9 mg, 0.0004127 mol) and PPh$_3$ (118 mg, 0.000451 mol) in THF (2.7 mL) at 0° C. was slowly added DEAD (71.1 µL, 0.000451 mol). The reaction was stirred for 5 minutes, then diphenylphosphonic azide (97.4 µL, 0.000452 mol) was added dropwise. The mixture was stirred for one hour. The reaction was partitioned with water and EtOAc. The layers were separated and the aqueous extracted with EtOAc (2×). The combined organics were washed with brine (1×), dried (Na$_2$SO$_4$), filtered, and collected in vacuo. The residue was purified by flash chromatography (0 to 10% EtOAc/hexanes) to obtain 93.5 mg (63%) of the title compound.

Step d: (1R,3S,4S)-3-[(benzyloxy)methyl]-4-{[tert-butyl(dimethyl)silyl]oxy}cyclopentanamine A suspension of ({(1S,2S,4R)-4-azido-2-[(benzyloxy)methyl]cyclopentyl}oxy)(tert-butyl)dimethylsilane (2.20 g, 0.00608 mol) and 10% Pd/C (0.16 g, 0.00015 mol) in EtOAc (23.9 mL) was stirred under an atmosphere of hydrogen overnight. The reaction was purged with nitrogen and the mixture filtered through celite with EtOAc. The filtrate was concentrated to obtain 2.01 g (98%) of the title compound.

Step e: 4,6-dichloro-N-[(1R,2S)-2-methoxy-2,3-dihydro-1H-inden-1-yl]-1,3,5-triazin-2-amine To a solution of (1R,2S)-2-methoxyindan-1-amine (242.8 mg, 0.001488 mol) in THF (1 mL) was added cyanuric chloride (313 mg, 0.00170 mol) at 0° C., followed by DIPEA (300 µL, 0.002 mol) and the reaction was stirred at 0° C. for 1.5 hours. The reaction was poured into water and extracted with CH$_2$Cl$_2$. The organic layer was dried (Na$_2$SO$_4$), filtered and concentrated. The residue was purified by flash chromatography (0 to 15% EtOAc/hexanes) to obtain 229.1 mg (49%) of the title compound. LC/MS: $R_t$=2.03 min, ES$^+$ 311 (FA standard).

Step f: N-((1R,3S,4S)-3-[(benzyloxy)methyl]-4-{[tert-butyl(dimethyl)silyl]oxy}cyclopentyl-6-chloro-N'-[(1R,2S)-2-methoxy-2,3-dihydro-1H-inden-1-yl]-3,5-triazine-2,4-diamine To a solution of (1R,3S,4S)-3-[(benzyloxy)methyl]-4-{[tert-butyl(dimethyl)-silyl]oxy}cyclopentanamine (486.5 mg, 0.001450 mol) and triethylamine (0.55 mL, 0.0040 mol) in THF (2.1 mL) was added 4,6-dichloro-N-[(1R,2S)-2-methoxy-2,3-dihydro-1H-inden-1-yl]-1,3,5-triazin-2-amine (410 mg, 0.0013 mol) and the mixture was stirred for 2 hours. The reaction was concentrated and the residue was purified by flash chromatography (0 to 25% EtOAc/hexanes) to obtain 250 mg (31%) of the title compound. LC/MS: $R_t$=2.96 min, ES$^+$ 610 (FA standard).

step g: {(1S,2S,4R)-2-{[tert-butyl(dimethyl)silyl]
oxy}-4-[(4-{[(1R,2S)-2-methoxy-2,3-dihydro-1H-
inden-1-yl]amino}-1,3,5-triazin-2-yl)amino]
cyclopentyl}methanol A suspension of N-((1R,3S,4S)-3-[(benzyloxy)methyl]-4-{[tert-butyl(dimethyl)-silyl]oxy}cyclopentyl)-6-chloro-N'-[(1R,2S)-2-methoxy-2,3-dihydro-1H-inden-1-yl]-1,3,5-triazine-2,4-diamine (250 mg, 0.00041 mol) and 10% Pd/C (44 mg, 0.000041 mol) in methanol (1.61 mL) was stirred under an atmosphere of hydrogen for 2 days. The reaction was purged with nitrogen and filtered through celite with EtOAc. The filtrate was concentrated to obtain a yellow oil. The oil was taken up in CH$_2$Cl$_2$ and saturated NaHCO$_3$. The layers were separated and the aqueous was extracted with CH$_2$Cl$_2$ (1×). The combined organics were dried over Na$_2$SO$_4$, filtered, and concentrated. The residue was purified by flash chromatography (0 to 10% MeOH/CH$_2$Cl$_2$) to obtain 114 mg (57%) of the title compound. LC/MS: $R_t$=1.68 min, ES$^+$ 486 (FA standard).

Step h: {(1S,2S,4R)-2-hydroxy-4-[(4-{[(1R,2S)-2-
methoxy-2,3-dihydro-H-inden-1-yl]-amino}-1,3,5-
triazin-2-yl)amino]cyclopentyl}methyl sulfamate The title compound was prepared following the procedure described in Example 34 steps d-e. $^1$H NMR (compound exists as a ~1:1 mixture of rotamers by $^1$H NMR) (CD$_3$OD, 400 MHz) δ: 8.03 and 7.92 [(d, J=4.6 Hz and s), 1H], 7.25-7.15 (m, 4H), 5.69 and 5.57 [(d, J=5.1 Hz and m), 1H], 4.67-4.54 (m, 1H), 4.31-4.19 (m, 3H), 4.13-4.06 (m, 1H), 3.37 (s, 3H), 4.13-2.98 (m, 2H), 2.53-2.43 (m, 1H), 2.19-2.14 (m, 1H), 2.06-1.98 (m, 1H), 1.85-1.72 (m, 2H) ppm. LC/MS: $R_t$=1.07 min, ES$^+$ 451 (FA standard).

Example 36

[(1S,2S,4R)-4-({4-[(1 S)-2,3-dihydro-1H-inden-1-yl
amino]-1,3,5-triazin-2-yl}amino)-2-hydroxycyclo-
pentyl]methyl sulfamate (Compound I-153)

The title compound was prepared in a fashion analogous to Example 35. $^1$H NMR (compound exists as a ~1:1 mixture of rotamers by $^1$H NMR) (CD$_3$OD, 400 MHz) δ: 8.03-8.00 and 7.91 [(m and s), 1H], 7.26-7.14 (m, 4H), 5.66-5.50 (m, 1H), 4.65-4.57 (m, 1H), 4.33-4.25 (m, 2H), 4.12-4.08 (m, 1H), 3.04-2.99 (m, 1H), 2.92-2.80 (m, 1H), 2.61-2.44 (m, 2H), 2.22-2.16 (m, 1H), 2.04-1.71 (m, 4H) ppm. LC/MS: $R_t$=1.07 min, ES$^+$ 421 (FA standard).

Example 37

[(1S,2S,4R)-2-hydroxy-4-({6-[(1S)-1,2,3,4-tetrahy-
dronaphthalen-1-ylamino]pyrimidin-4-yl}oxy)cyclo-
pentyl]methyl sulfamate (Compound I-40)

The title compound was prepared in a fashion analogous to Example 34, steps a-c (using (S)-(+)-1,2,3,4-tetrahydro-1-naphthylamine in step b) and Example 65, step d to obtain the title compound. $^1$H NMR (CD$_3$OD, 400 MHz) δ: 8.12 (s, 1H), 7.22-7.08 (m, 4H), 5.77 (s, 1H), 5.30 (bs, 1H), 4.40-4.28 (m, 2H), 4.17-4.13 (m, 1H), 2.89-2.71 (m, 2H), 2.54-2.47 (m, 1H), 2.29-2.21 (m, 1H), 2.10-1.79 (m, 8H) ppm. LC/MS: $R_t$=6.66 min, ES$^+$ 435 (FA long).

Example 38

((1S,2S,4R)-4-{[6-(1,3-dihydro-2H-isoindol-2-yl)
pyrimidin-4-yl]oxy}-2-hydroxycyclopentyl)methyl
sulfamate (Compound I-120)

The title compound was prepared in a fashion analogous to Example 34, steps a-c (using isoindoline in step b) and Example 65, step d to obtain the title compound. $^1$H NMR (D6-DMSO, 300 MHz) δ: 8.27 (s, 1H), 7.40-7.29 (m, 4H), 5.81 (s, 1H), 5.47 (bs, 1H), 4.81 (d, 1H, J=4.4 Hz), 4.74 (bs, 4H), 4.24-4.18 (m, 2H), 4.03-3.97 (m, 1H), 2.38 (bs, 1H), 2.22-2.14 (m, 1H), 2.01-1.77 (m, 3H) ppm. LC/MS: $R_t$=6.40 min, ES$^+$ 407 (FA long).

Example 39

((1S,2S,4R)-4-{[6-(3,4-dihydroisoquinolin-2(1H)-yl)
pyrimidin-4-yl]oxy}-2-hydroxycyclopentyl)methyl
sulfamate (Compound I-61)

The title compound was prepared in a fashion analogous to Example 34, steps a-c (using tetrahydroisoquinoline in step b) and Example 65, step d to obtain the title compound. $^1$H NMR (CD$_3$OD, 400 MHz) δ: 8.17 (s, 1H), 7.17-7.14 (m, 4H), 5.93 (s, 1H), 4.63 (s, 2H), 4.39-4.30 (m, 2H), 4.18-4.13 (m, 1H), 3.78-3.75 (m, 2H), 3.30 (s, 1H), 2.90-2.87 (m, 2H), 2.54-2.47 (m, 1H), 2.30-2.24 (m, 1H), 2.09-1.91 (m, 3H) ppm. LC/MS: $R_t$=7.05 min, ES+ 421 (FA long).

Example 40

[(1S,2S,4R)-2-hydroxy-4-(pyrimidin-4-yloxy)cyclo-
pentyl]methyl sulfamate (Compound I-97)

Step a: 4-{[(1R,3S,4S)-3-{[tert-butyl(dimethyl)silyl]
oxy}-4-({[tert-butyl(dimethyl)silyl]oxy}methyl)
cyclopentyl]oxy}pyrimidine A suspension of 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (115.5 mg, 0.0002441 mol), sodium carbonate (62 mg, 0.00058 mol) and 10% Pd/C (26 mg, 0.000024 mol) in methanol (1.1 mL) was stirred under an atmosphere of hydrogen for 2 days. The reaction was purged with nitrogen and filtered through celite with EtOAc. The filtrate was concentrated and the residue was purified by flash chromatography (0 to 15% EtOAc/hexanes) to obtain 80 mg (70%) of the title compound.

Step b: [(1S,2S,4R)-2-hydroxy-4-(pyrimidin-4-
yloxy)cyclopentyl]methyl sulfamate The title compound was prepared in a fashion analogous to Example 34, step b and Example 65, step d to obtain the title compound. $^1$H NMR (CD$_3$OD, 400 MHz) δ: 8.70 (s, 1H), 8.40 (d, J=6.1 Hz, 1H), 6.83 (dd, J=1, 6.1 Hz, 1H), 5.66-5.61 (m, 1H), 4.41-4.38 (m, 1H), 4.33 (dd, J=7.3, 9.8 Hz), 4.16 (dd, J=7.2, 9.7 Hz), 2.58-2.48 (m, 1H), 2.36-2.30

(m, 1H), 2.11-2.03 (m, 2H), 2.00-1.94 (m, 1H) ppm. LC/MS: $R_t$=4.08 min, ES+ 290 (FA long).

Example 41

[(1S,2S,4R)-4-({6-[(4-chlorobenzyl)oxy]pyrimidin-4-yl}oxy)-2-hydroxycyclopentyl]methyl sulfamate (Compound I-89)

Step a: 4-{[(1R,3S,4S)-3-({[tert-butyl(dimethyl)silyl]oxy}methyl)-4-(1,1,2,2-tetramethylpropoxy)cyclopentyl]oxy}-6-[(4-chlorobenzyl)oxy]pyrimidine To a solution of 4-{[(1R,3S,4S)-3-{[tert-butyl(dimethyl)silyl]oxy-4-({[tert-butyl(dimethyl)silyl]oxy}methyl)cyclopentyl]oxy}-6-chloropyrimidine (0.205 g, 0.000433 mol) and 4-chlorobenzyl alcohol (0.130 g, 0.000910 mol) in DMF (1 mL) under at atmosphere of nitrogen was added sodium hydride (36.4 mg, 0.000910 mol) (60% in oil). The reaction was stirred for 3.5 hours. The reaction was quenched with water and extracted with EtOAc. The organic layer was washed with brine, dried (MgSO$_4$), filtered and concentrated. The residue by purified by flash chromatography (0 to 7% EtOAc/hexanes) to obtain 98 mg (40%) of the title compound.

Step b: [(1S,2S,4R)-4-({6-(4-chlorobenzyl)oxy}pyrimidin-4-yl}oxy)-2-hydroxycyclopentyl]methyl sulfamate The title compound was prepared in a fashion analogous to Example 34, step b and Example 65, step d (followed by TBAF removal of secondary silyl group) to obtain the title compound. $^1$H NMR (CD$_3$OD, 400 MHz) δ: 6.82 (s, 1H), 5.88-5.79 (m, 4H), 4.62 (s, 1H), 3.98-3.95 (bs, 1H), 3.81 (s, 2H), 2.84-2.75 (m, 2H), 2.64-2.58 (m, 1H), 1.04-0.91 (m, 1H), 0.79-0.72 (m, 1H), 0.63-0.37 (m, 3H) ppm. LC/MS: $R_t$=8.62 min, ES+ 430 (FA long).

Example 42

N-({(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl)sulfamide (Compound I-82)

Step a: tert-butyl (aminosulfonyl)({(1S,2S,4R)-2-{[tert-butyl(dimethyl)silyl]oxy}-4-[(6-{[(1R,2S)-2-methoxy-2,3-dihydro-1H-inden-1-yl]amino}pyrimidin-4-yl)-oxy]cyclopentyl}methyl)carbamate To a solution of {(1S,2S,4R)-2-{[tert-butyl(dimethyl)silyl]oxy}-4-[(6-{[(1R,2S)-2-methoxy-2,3-dihydro-1H-inden-1-yl]amino}pyrimidin-4-yl)oxy]cyclopentyl}methanol (105.3 mg, 0.0002168 mol), N-Boc-sulfonamide (58.9 mg, 0.000300 mol) and triphenylphosphine (85.3 mg, 0.000325 mol) in EtOAc (4.15 mL) under an atmosphere of nitrogen was added diethyl azodicarboxylate (51.9 µL, 0.000330 mol). The mixture was stirred for four hours. The solvent was removed and the orange residue was purified by flash chromatography (10 to 50% EtOAc/hexanes) to obtain 135.2 mg (94%) of the title compound.

Step b: tert-butyl (aminosulfonyl)({(1S,2S,4R)-2-hydroxy-4-[(6-{[(1R,2S)-2-methoxy-2,3-dihydro-1H-inden-1-yl]amino}pyrimidin-4-yl)oxy]cyclopentyl}methyl)carbamate To a solution of tert-butyl (aminosulfonyl)({(1S,2S,4R)-2-{[tert-butyl(dimethyl)silyl]oxy}-4-[(6-{[(1R,2S)-2-methoxy-2,3-dihydro-1H-inden-1-yl]amino}pyrimidin-4-yl)oxy]cyclopentyl}methyl)carbamate (331.5 mg, 0.0004094 mol) in THF (1.84 mL, 0.0228 mol) and pyridine (1.84 mL) at 0° C. was added pyridine hydrofluoride (0.25 mL, 0.0028 mol) dropwise. The mixture was allowed to slowly warm to 23° C. and stirred for 19 hours. To the reaction was added pyridine hydrofluoride (0.25 mL, 0.0028 mol) and the mixture was stirred an additional 6 hours. The reaction was quenched by the dropwise addition of saturated aqueous NaHCO$_3$. The mixture was partitioned with additional saturated aqueous NaHCO$_3$ and EtOAc, separated, and the aqueous was extracted with EtOAc (2×) and CH$_2$Cl$_2$ (2×). The combined organics were washed with brine, dried over Na$_2$SO$_4$, filtered and concentrated. The residue was purified by flash chromatography (30 to 70% EtOAc/hexanes) to collect 34.5 mg (15%) of the title compound. LC/MS: $R_t$=1.64 min, ES+ 550 (FA standard).

Step c: N-({(1S,2S,4R)-2-hydroxy-4-[(6-{[(1R,2S)-2-methoxy-2,3-dihydro-1H-inden-1-yl]-amino]pyrimidin-4-yl)oxy}cyclopentyl}methyl)sulfamide To a solution of tert-butyl (aminosulfonyl)({(1S,2S,4R)-2-hydroxy-4-[(6-{[(1R,2S)-2-methoxy-2,3-dihydro-1H-inden-1-yl]amino}pyrimidin-4-yl)oxy]cyclopentyl}-methyl) carbamate (34.5 mg, 0.0000628 mol) in CH$_2$Cl$_2$ (1.4 mL) was added trifluoroacetic acid (0.70 mL, 0.0091 mol) and the mixture was stirred for 15 minutes. The mixture was diluted with toluene and evaporated to dryness. The residue was purified by flash chromatography (0 to 10% MeOH/CH$_2$Cl$_2$) to obtain 23.8 mg (84%) of the title compound as a white residue. $^1$H NMR (CD$_3$OD, 400 MHz) δ: 8.15 (s, 1H), 7.24-7.14 (m, 4H), 5.98 (s, 1H), 5.57 (bs, 1H), 5.29 (bs, 1H), 4.38-4.35 (m, 1H), 4.23-4.20 (n, 1H), 3.34 (s, 3H), 3.25-3.20 (m, 1H), 3.13-3.00 (m, 3H), 2.42-2.33 (m, 1H), 2.29-2.24 (m, 1H), 2.10-1.94 (m, 3H) ppm. LC/MS: $R_t$=1.16 min, ES+ 450 (FA standard).

Example 43

[(1R,2R,3S,4R)-4-({4-[(1S)-2,3-dihydro-1H-inden-1-ylamino]-6-methyl-1,3,5-triazin-2-yl}amino)-2,3-dihydroxycyclopentyl]methyl sulfamate (Compound I-45)

Step a: 4-chloro-N-[(1S)-2,3-dihydro-1H-inden-1-yl]-6-methyl-1,3,5-triazin-2-amine To a solution of 2,4-dichloro-6-methyl-1,3,5-triazine (0.90 g, 0.0055 mol) in DMF (3.50 mL) and toluene (1.5 mL) at 0° C. was added (S)-(+)-1-aminoindan (0.64 mL, 0.0050 mol) followed by DIPEA (0.991 mL, 0.00569 mol). The mixture was stirred at 0° C. for 30 min. The reaction was poured into water and extracted with CH$_2$Cl$_2$. The organic layer was dried over MgSO$_4$, filtered and concentrated. The residue was purified by flash chromatography (0 to 15% EtOAc/hexanes) to afford 0.69 g (53%) of the title compound.

Step b: N-[(3aS,4R,6S,6aR)-6-({[tert-butyl(dimethyl)silyl]oxy}methyl)-2,2-dimethyltetrahydro-3aH-cyclopenta[d][1,3]dioxol-4-yl]-N'-[(1S)-2,3-dihydro-1H-inden-1-yl]-6-methyl-1,3,5-triazine-2,4-diamine A mixture of (3aS,4R,6R,6aR)-6-({[tert-butyl(dimethyl)silyl]oxy}methyl)-2,2-dimethyltetrahydro-3aH-cyclopenta[d][1,3]dioxol-4-amine (141.8 mg, 0.0004703 mol), 4-chloro-N-[(1S)-2,3-dihydro-1H-inden-1-yl]-6-methyl-1,3,5-triazin-2-amine (127.1 mg, 0.0004876 mol) and potassium carbonate (0.130 g, 0.000940 mol) in 1,4-dioxane (0.77 mL) was subjected to microwave irradiation (300 watts, 160° C.) for 30 minutes. The mixture was filtered with $CH_2Cl_2$ and concentrated. The residue was purified by flash chromatography (10 to 100% EtOAc/hexanes) to obtain 60 mg (24%) of the title compound. LC/MS: $R_t$=2.03 min, ES+ 279 (FA standard).

Step c: [(3aR,4R,6R,6aS)-6-({4-[(1S)-2,3-dihydro-1H-inden-1-ylamino]-6-methyl-1,3,5-triazin-2-yl}amino)-2,2-dimethyltetrahydro-3aH-cyclopenta[d][1,3]dioxol-4-yl]methanol To a solution of N-[(3aS,4R,6S,6aR)-6-({[tert-butyl(dimethyl)silyl]oxy}methyl)-2,2-dimethyltetrahydro-3aH-cyclopenta[d][1,3]dioxol-4-yl]-N'-[(1 S)-2,3-dihydro-1H-inden-1-yl]-6-methyl-1,3,5-triazine-2,4-diamine (0.23 g, 0.00044 mol) in THF (1 mL) was added 1.00 M of TBAF in THF (1.31 mL). The reaction was stirred for 30 minutes. The solution was concentrated and the residue purified by flash chromatography (0 to 4% MeOH/EtOAc) to afford 210 mg (>99%) of the title compound. LC/MS: $R_t$=1.24 min, ES+ 412 (FA standard).

Step d: [(1R,2R,3S,4R)-4-({4-[(1S)-2,3-dihydro-1H-inden-1-ylamino]-6-methyl-1,3,5-triazin-2-yl}amino)-2,3-dihydroxycyclopentyl]methyl sulfamate The title compound was prepared in a fashion analogous to Example 65, step d. $^1$H NMR (CD$_3$OD, 400 MHz) δ: 7.29-7.16 (m, 4H), 5.65 (t, J=7.5 Hz, 1H), 4.35 (dd, J=7.7, 14.9 Hz, 1H), 4.14 (s, 1H), 3.92-3.84 (m, 1H), 3.10-3.00 (m, 1H), 2.95-2.84 (m, 1H), 2.63-2.52 (m, 1H), 2.35-2.33 (m, 2H), 2.30 (s, 3H), 2.08-1.90 (m, 1H), 1.39-1.28 (m, 1H) ppm. LC/MS: $R_t$=1.13 min, ES+ 451 (FA standard).

Example 44

{(1S,2S,4R)-2-hydroxy-4-[(6-{[(1R,2S)-2-methoxy-2,3-dihydro-1H-inden-1-yl]-amino}pyrimidin-4-yl)amino]cyclopentyl}methyl sulfamate (Compound I-47)

Step d: N-[(1R,3S,4S)-3-({[tert-butyl(dimethyl)silyl]oxy}-4-({[tert-butyl(dimethyl)silyl]oxy}methyl)cyclopentyl]-6-chloropyrimidin-4-amine To a solution of (1R,3S,4S)-3-{[tert-butyl(dimethyl)silyl]oxy}-4-({[tert-butyl(dimethyl)silyl]oxy}methyl)cyclopentanamine (0.400 g, 1.11 mmol) in EtOH (3.0 mL) was added 4,6-dichloro-pyrimidine (0.199 g, 1.33 mmol) and Et$_3$N (0.310 mL, 2.22 mmol). The reaction was heated to 140° C. for 1 h in a sealed tube using microwave irradiation then concentrated in vacuo. The residue was dissolved in CH$_2$Cl$_2$ and purified by flash chromatography (CH$_2$Cl$_2$) to afford the title compound (0.300 g, 57%).

Step b: N-[(1R,3S,4S)-3-{[tert-butyl(dimethyl)silyl]oxy}-4-({[tert-butyl(dimethyl)silyl]oxy}-methyl)cyclopentyl]-N'-[(1R,2S)-2-methoxy-2,3-dihydro-1H-inden-1-yl]pyrimidine-4,6-diamine A mixture of N-[(1R,3S,4S)-3-{[tert-butyl(dimethyl)silyl]oxy}-4-({[tert-butyl(dimethyl)silyl]oxy}methyl)cyclopentyl]-6-chloropyrimidin-4-amine (0.114 g, 2.42 mmol), (1R,2S)-2-methoxyindan-1-amine (0.170 g, 1.04 mmol) and Na$_2$CO$_3$ (0.10 g, 0.97 mmol) was heated to 180° C. for 2 h in a sealed tube using an oil bath. The reaction was cooled and filtered. The filtrate was concentrated in vacuo. The residue was purified by flash chromatography (50 to 60% EtOAc/hexanes) to afford the title compound as a beige foam (0.066 g, 46%). LC/MS: $R_t$=2.20 min, ES+ 599 (Formic Acid).

Step c: {(1R,2R,4S)-2-{[tert-butyl(dimethyl)silyl]oxy}-4-[(6-{[(1S,2R)-2-methoxy-2,3-dihydro-1H-inden-1-yl]amino}pyrimidin-4-yl)amino]cyclopentyl}methanol To a solution of N-[(1R,3S,4S)-3-{[tert-butyl(dimethyl)silyl]oxy}-4-({[tert-butyl(dimethyl)silyl]oxy}methyl)cyclopentyl]-N-[(1R,2S)-2-methoxy-2,3-dihydro-1H-inden-1-yl]pyrimidine-4,6-diamine (0.188 g, 0.314 mmol) in THF (1.70 mL) and H$_2$O (1.70 mL) was added AcOH (5.08 mL). The solution was stirred overnight then concentrated in vacuo and purified by flash chromatography (0 to 5% MeOH/EtOAc) to obtain the title compound (0.112 g, 74%). LC/MS: $R_t$=1.46 min, ES+ 485 (Formic Acid).

Step d: {(1R,2R,4S)-2-hydroxy-4-[(6-{[(1S,2R)-2-methoxy-2,3-dihydro-1H-inden-1-yl]amino}pyrimidin-4-yl)amino]cyclopentyl}methyl sulfamate (Compound I-47)

A solution of {(1R,2R,4S)-2-{[tert-butyl(dimethyl)silyl]oxy}-4-[(6-{[(1S,2R)-2-methoxy-2,3-dihydro-1H-inden-1-yl]amino}pyrimidin-4-yl)amino]cyclopentyl}methanol (0.112 g, 0.231 mmol) (azetroped with toluene) and pyridine (0.0374 mL, 0.462 mmol) in anhydrous acetonitrile (2.3 mL) was cooled to 0° C. A 2 N solution of chlorosulfonamide in acetonitrile (0.116 mL) was added dropwise and the reaction was stirred for 3 h. Additional 2 N solution of chlorosulfonamide in acetonitrile (0.026 mL) and pyridine (0.0041 g, 0.052 mol) were added and the reaction was stirred for 1 h then quenched with methanol. The solution was concentrated in vacuo and purified by flash chromatography (0 to 10% MeOH/DCM) to afford the title compound as a white solid (0.059 g, 57%). $^1$H NMR (CD$_3$OD, 400 MHz, δ): 8.26 (s, 1H); 8.01 (s, 1H); 7.26-7.16 (m, 3H); 5.70 (s, 1H); 5.47-5.33 (bs, 1H); 4.35 (t, J=4.5 Hz, 1H); 4.31 (d, J=7.5 Hz, 1H); 4.28 (d, J=7.5 Hz, 1H); 4.25-4.21 (m, 1H); 4.15-4.11 (dd, J=7.3 Hz; J=2.5 Hz, 1H); 3.36 (s, 3H); 3.16-3.00 (m, 2H); 2.54-2.45 (m, 1H); 2.26-2.19 (m, 1H); 2.10-1.98 (m, 1H); 1.87-1.78 (m, 1H); 1.77-1.69 (m, 1H). LC/MS: $R_t$=1.11 min, ES+ 450 (FA standard).

Example 45

{(1S,2S,4R)-4-[(6-{[(1S)-3,3-dimethyl-2,3-dihydro-1H-inden-1-yl]amino}pyrimidin-4-yl)oxy]-2-hydroxycyclopentyl}methyl sulfamate (Compound I-124)

The title compound was prepared in a fashion analogous to Example 34 steps a-e using (1S)-3,3-dimethylindan-1- amine in step b to obtain the title compound. $^1$H NMR (CD$_3$OD, 400 MHz, δ): 8.14 (s, 1H); 7.28-7.15 (m, 4H); 5.83 (s, 1H); 5.59 (bs, 1H); 5.31 (bs, 1H); 4.39 (dt, J=5.0 Hz; J=2.0 Hz, 1H); 4.32 (dd, J=7.3 Hz; J=2.5 Hz, 1H); 4.16 (dd, J=733 Hz; J=2.5 Hz, 1H); 2.57-2.47 (m, 1H); 2.46-2.39 (m, 1H); 2.31-2.24 (m, 1H); 2.12-1.90 (m, 3H); 1.82-1.75 (m, 1H); 1.39 (s, 3H); 1.25 (s, 3H). LC/MS: R$_t$=1.51 min, ES$^+$ 449 (FA standard).

Example 46

{(1S,2S,4R)-4-[(4-{[(1S)-3,3-dimethyl-2,3-dihydro-1H-inden-1-yl]amino}-1,3,5-triazin-2-yl)amino]-2-hydroxycyclopentyl}methyl sulfamate (Compound I-134)

Step a: 46-dichloro-N-[(1S)-3,3-dimethyl-2,3-dihydro-1H-inden-1-yl]-1,3,5-triazin-2-amine To a solution of (1S)-3,3-dimethylindan-1-amine (0.67 g, 4.2 mmol) in THF (3 mL) cooled to 0° C. was added cyanuric chloride (0.874 g, 4.74 mmol) resulting in a white solid. DIPEA (0.724 mL, 4.16 mmol) was added and the yellow mixture was stirred for 1.5 hours. The reaction was quenched with H$_2$O and extracted with DCM (3×). The combined organic layers were dried (Na$_2$SO$_4$), filtered and collected in vacuo to give a pale yellow oil. The residue was purified by flash chromatography (0 to 25% EtOAc/hexanes) to afford the title compound (0.771 g, 60%) as a white solid. LC/MS: R$_t$=2.20 min, ES$^+$ 310 (FA standard).

Step b: N-[(1R,3S,4S)-3-{[(tert-butyl(dimethyl)silyl]oxy}-4-({[tert-butyl(dimethyl)silyl]oxy}methyl)cyclopentyl]-6-chloro-N'-[(1S)-3,3-dimethyl-2,3-dihydro-1H-inden-1-yl]-1,3,5-triazine-2,4-diamine To a solution of (1R,3S,4S)-3-{[tert-butyl(dimethyl)silyl]oxy}-4-({[tert-butyl(dimethyl)silyl]oxy}methyl)cyclopentanamine (0.200 g, 0.556 mmol), TEA (0.21 mL, 1.50 mmol) in THF (0.80 mL) was added 4,6-dichloro-N-[(1S)-3,3-dimethyl-2,3-dihydro-1H-inden-1-yl]-1,3,5-triazin-2-amine (0.160 g, 0.500 mol). The reaction was stirred for 3.5 h then concentrated in vacuo. The residue was purified by preparative TLC (10% EtOAc/hexanes) followed by DCM. The relevant band was cut and washed using acetone, filtered, and concentrated in vacuo to afford the title compound (0.228 g, 71%). LC/MS: R$_t$=2.77 min, ES$^+$ 633 (FA standard).

Step c: {(1R,2R,4S)-2-{[tert-butyl(dimethyl)silyl]oxy}-4-[(4-chloro-6-{[(1R)-3,3-dimethyl-2,3-dihydro-1H-inden-1-yl]amino}-1,3,5-triazin-2-yl)amino]cyclopentyl}methanol The title compound was prepared following the procedure described in Example 44 step c using N-[(1R,3S,4S)-3-{[tert-butyl(dimethyl)silyl]oxy}-4-({[tert-butyl (dimethyl)silyl]oxy}methyl)cyclopentyl]-6-chloro-N'-[(1 S)-3,3-dimethyl-2,3-dihydro-1H-inden-1-yl]-1,35-triazine-2,4-diamine. LC/MS: R$_t$=2.20 min, ES$^+$ 518, 520 (FA standard).

Step d: {(1S,2S,4R)-2-{[tert-Butyl(dimethyl)silyl]oxy}-4-[(4-{[(1S)-3,3-dimethyl-2,3-dihydro-1H-inden-1-yl]amino}-1,3,5-triazin-2-yl)amino]cyclopentyl}methanol To a solution of {(1R,2R,4S)-2-{[tert-butyl(dimethyl)silyl]oxy}-4-[(4-chloro-6-{[(1R)-3,3-dimethyl-2,3-dihydro-1H-inden-1-yl]amino}-1,3,5-triazin-2-yl)amino]cyclopentyl}methanol (0.083 g, 0.16 mmol) in EtOH (1.11 mL) was added Pd (10% on carbon) (0.0170 g, 0.0160 mmol) and the mixture was stirred under an atmosphere of hydrogen for 4 d. The reaction was purged with nitrogen for 30 minutes then Pd(OH)$_2$ (20% on carbon dry weight) (0.022 g, 0.016 mmol) was added and the mixture was stirred for 4 h under an atmosphere of hydrogen. Filtration of the mixture through a pad of celite, followed by flash chromatography (50-100% EtOAc/hexanes) afforded the title compound (0.027 g, 35%). LC/MS: R$_t$=1.81 min, ES$^+$ 484 (FA standard).

Step e: {(1S,2S,4R)-4-[(4-{[(1S)-3,3-dimethyl-2,3-dihydro-1H-inden-1-yl]amino}-1,3,5-triazin-2-yl)amino]-2-hydroxycyclopentyl}methyl sulfamate (Compound I-134)

The title compound was prepared following the procedure described in Example 44 step d using {(1S,2S,4R)-2-{[tert-butyl(dimethyl)silyl]oxy}-4-[(4-{[(1S)-3,3-dimethyl-2,3-dihydro-1H-inden-1-yl]amino}-1,3,5-triazin-2-yl)amino]cyclopentyl}methanol. $^1$H NMR (CD$_3$OD, 400 MHz, δ): 8.17-7.81 (m, 1H); 7.27-7.15 (m, 4H); 5.71-5.57 (m, 1H); 4.65-4.49 (m, 1H); 4.36-4.23 (m, 2H); 4.20-4.00 (m, 1H); 2.53-2.33 (m, 2H); 2.25-2.10 (m, 1H); 2.06-1.68 (m, 4H); 1.39 (s, 3H); 1.24 (s, 3H). LC/MS: R$_t$=1.90 min ES$^+$ 449 (FA standard).

Example 47

{(1R,2R,3S,4R)-2,3-dihydroxy-4-[(4-{[(1R,2S)-2-methoxy-2,3-dihydro-1H-inden-1-yl]amino}-1,3,5-triazin-2-yl)amino]cyclopentyl}methyl sulfamate (Compound I-55)

The title compound was prepared following the procedure described in Example 46 (step e) using {(3aR,4R,6R,6aS)-6-[(4-{[(1R,2S)-2-methoxy-2,3-dihydro-1H-inden-1-yl]amino}-1,3,5-triazin-2-yl)amino]-2,2-dimethyltetrahydro-3aH-cyclopenta[d][1,3]dioxol-4-yl}methanol (prepared as in Example 26). $^1$H NMR (CD$_3$OD, 400 MHz, δ): 8.10-7.95 (m, 1H); 7.30-7.14 (m, 4H); 5.72-5.56 (m, 1H); 4.36-4.08 (m, 4H); 3.95-3.78 (m, 2H); 3.37 (s, 3H); 3.15-2.93 (m, 2H); 2.42-2.17 (m, 2H); 1.37-1.78 (m, 1H). LC/MS: R$_t$=1.07 min ES$^+$ 467 (FA standard).

Example 48

((1R,2R,3S,4R)-2,3-dihydroxy-4-{[6-(phenylethynyl)pyrimidin-4-yl]amino}cyclopentyl)methyl sulfamate (Compound I-108)

Step a: (1R,2S,3R,5R)-3-[(6-chloropyrimidin-4-yl)amino]-5-(hydroxymethyl) cyclopentane-1,2-diol To a solution of (1R,2S,3R,5R)-3-amino-5-(hydroxymethyl)cyclopentane-1,2-diol.HCl (1.00 g, 5.44 mmol) and 2-amino-4,6-dichloropyrimidine (0.982 g, 5.99 mmol) in isopropyl alcohol (8 mL) was added Et$_3$N (1.90 mL, 13.6 mmol). The reaction was heated to 90° C. for 1 h in an oil bath then cooled, filtered and concentrated in vacuo. The residue was dissolved in CH$_2$Cl$_2$ and purified by flash chromatography (20 to 50% MeOH/CH$_2$Cl$_2$) to afford the title compound as an off-white solid (2.025 g, >99%). LC/MS: R$_t$=0.81 min ES$^+$ 260 (FA standard).

Step b: (1S,2R,3R,5R)-5-hydroxymethyl)-5-[(6-iodopyrimidin-4-yl)amino]cyclopentane-1,2-diol To a solution of (1R,2S,3R,5R)-3-[(6-chloropyrimidin-4-yl)amino]-5-(hydroxymethyl)cyclopentane-1,2-diol (1.880 g, 7.239 mmol) in hydroiodic acid (23.9 mL) was added sodium iodide (5.42 g, 36.2 mmol). The mixture heated to 70° C. for 10 min then concentrated and azeotroped using toluene (3×). The residue was dissolved in acetone and NaHCO$_3$ was added. The suspension was filtered and the filtrate was concentrated in vacuo to obtain the title compound (24 g, >99%). LC/MS: R$_t$=0.76 min ES$^+$ 352 (FA standard).

Step c: {(3aR,4R,6R,6aS)-6-[(6-iodopyrimidin-4-yl)amino]-2,2-dimethyltetrahydro-3aH-cyclopenta[d][1,3]dioxol-4-yl}methanol The title compound was prepared following the procedure described in Example 1 step b using (1S,2R,3R,5R)-3-(hydroxymethyl)-5-[(6-iodopyrimidin-4-yl)-amino]cyclopentane-1,2-diol. LC/MS: R$_t$ 1.24 min ES$^+$ 392 (FA standard).

Step d: N-[(3aS,4R,6R,6aR)-6-({[tert-butyl(dimethyl)silyl]oxy}methyl)-2,2-dimethyltetrahydro-3aH-cyclopenta[d][1,3]dioxol-4-yl]-6-iodopyrimidin-4-amine To a solution of {(3aR,4R,6R,6aS)-6-[(6-iodopyrimidin-4-yl)amino]-2,2-dimethyltetrahydro-3aH-cyclopenta[d][1,3]dioxol-4-yl}methanol (1.321 g, 3.38 mmol) and 1H-imidazole (0.552 g, 8.10 mmol) in DMF (16.9 mL) was added tert-butyldimethylsilyl chloride (0.534 g, 3.54 mmol) and the reaction was stirred overnight. The solution was diluted with H$_2$O and extracted with EtOAc (3×). The combined organic layers were washed with brine, dried (Na$_2$SO$_4$), filtered, and concentrated in vacuo. The crude mixture was purified by flash chromatography (10 to 40% EtOAc/hexanes) to afford the title compound (1.465 g, 86%). LC/MS: R$_t$=2.47 min ES$^+$ 506 (FA Standard).

Step e: N-[(3aS,4R,6R,6aR)-6-({[tert-butyl(dimethyl)silyl]oxy}methyl-2,2-dimethyltetrahydro-3aH-cyclopenta[d][1,3]dioxol-4-yl]-6-(phenylethynyl)-pyrimidin-4-amine To a solution of N-[(3aS,4R,6R,6aR)-6-({[tert-butyl(dimethyl)silyl]oxy}methyl)-2,2-dimethyltetrahydro-3aH-cyclopenta[d][1,3]dioxol-4-yl]-6-iodopyrimidin-4-amine (0.300 g, 0.594 mmol) in DMF (2.46 mL) was added CuI (0.0113 g, 0.0594 mmol) and bis(triphenylphosphine)palladium(II) chloride (0.0292 g, 0.0415 mmol). The tube was sealed and flushed with argon. Et$_3$N (0.165 mL, 1.19 mol) was added and the reaction was stirred for 1 h. Phenylacetylene (0.216 mL, 1.96 mmol) was added and the reaction was stirred overnight. The suspension was filtered and the filtrate was concentrated in vacuo. The crude mixture was purified by flash chromatography (10 to 40% EtOAc/hexanes) to afford the title compound as a yellow oil (0.238 g, 84%). LC/MS: R$_t$=2.47 min, ES$^+$ 480 (FA standard).

Step f: ((3aR,4R,6R,6aS)-2,2-dimethyl-6-{[6-(phenylethynyl)pyrimidin-4-yl]amino}-tetrahydro-3aH-cyclopenta[d][1,3]dioxol-4-yl)methanol To a solution of N-[(3aS,4R,6R,6aR)-6-({[tert-butyl(dimethyl)silyl]oxy}methyl)-2,2-dimethyltetrahydro-3aH-cyclopenta[d][1,3]dioxol-4-yl]-6-(phenylethynyl)pyrimidin-4-amine (0.275 g, 0.573 mmol) in THF (2 mL) and pyridine (2 mL) in a teflon vial was added pyridine hydrofluoride (1.3 mL, 0.014 mol) dropwise. The reaction was stirred for 1.5 h then quenched using a saturated aqueous Na$_2$CO$_3$ solution (15 mL) and EtOAc. The aqueous layer was extracted with EtOAc (3×20 mL). The combined organic layers were dried (Na$_2$SO$_4$), filtered and concentrated in vacuo. The residue was purified by flash chromatography (0 to 5% MeOH/EtOAc) to afford the title compound as a yellow solid (0.172 g, 82%). LC/MS: R$_t$=1.29 min, ES$^+$ 366 (FA standard).

Step g: ((1R,2R,3S,4R)-2,3-dihydroxy-4-{[6-(phenylethynyl)pyrimidin-4-yl]amino}cyclopentyl)methyl sulfamate (Compound I-108)

The title compound was prepared following the procedure described in Example 1 steps d-e using ((3aR,4R,6R,6aS)-2,2-dimethyl-6-{[6-(phenylethynyl)pyrimidin-4-yl]amino}tetrahydro-3aH-cyclopenta[d][1,3]dioxol-4-yl)methanol. $^1$H NMR (CD$_3$OD, 400 MHz, δ): 8.36 (s, 1H); 7.80-7.54 (m, 2H); 7.45-7.38 (m, 3H); 6.69 (bs, 1H); 4.33 (bs, 1H); 4.23-4.14 (m, 2H); 3.92-3.88 (m, 1H); 3.86-3.81 (m, 1H); 3.32-3.28 (m, 2H); 2.46-2.30 (m, 2H); 1.39-1.27 (m, 1H). LC/MS: R$_t$=1.09 min, ES$^+$ 405 (FA standard).

Example 49

[(1S,2S,4R)-2-hydroxy-4-({6-[(1-naphthylmethyl)amino]pyrimidin-4-yl}-oxy)cyclopentyl]methyl sulfamate (Compound I-42)

The title compound was prepared in a fashion analogous to Example 34 steps a-e using 1-naphthalenemethylamine in step b to obtain the title compound. $^1$H NMR (CD$_3$OD, 400 MHz, δ): 8.13 (s, 1H); 8.04 (d, J=9.0 Hz, 1H); 7.87 (d, J=7.5 Hz, 1H); 7.79 (d, J=8.0 Hz, 1H); 7.54-7.39 (m, 5H); 5.75 (s, 1H); 5.31-5.26 (m, 1H); 4.94 (s, 2H); 4.39-4.25 (m, 2H); 4.17-4.06 (m, 1H); 2.52-2.42 (m, 1H); 2.26-2.19 (m, 1H); 2.05-1.84 (m, 2H). LC/MS: R$_t$=1.59 min, ES$^+$ 445 (FA standard).

Example 50

[(1S,2S,4R)-2-hydroxy-4-({6-[(1-naphthylmethyl)amino]pyrimidin-4-yl}oxy)cyclopentyl]methyl sulfamate (Compound I-119)

Step a: 4-{[(1R,3S,4S)-3-{[(tert-butyl(dimethyl)silyl]oxy}-4-{([tert-butyl(dimethyl)silyl]oxy}methyl)cyclopentyl]oxy}-6-(1-naphthylmethoxy)pyrimidine To a solution of 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (0.200 g, 0.423 mmol) and 1-naphthalenemethanol (0.140 g, 0.888 mmol) in DMF (1 mL) was added sodium hydride (0.0355 g, 0.888 mmol) and stirred for 3 h. The mixture was diluted with H$_2$O and extracted with EtOAc. The combined organic layers were washed with brine, dried (Na$_2$SO$_4$), filtered, and concentrated in vacuo. The residue was purified by flash chromatography (0 to 20% EtOAc/hexanes) to afford the title compound (0.139 g, 55%).

Step b: [(1S,2S,4R)-2-hydroxy-4-({6-[(1-naphthyl-methyl)amino]pyrimidin-4-yl}oxy)cyclopentyl] methyl sulfamate The title compound was prepared following the procedure described in Example 44 (steps c-d) and Example 48 (step f) using 4-{[(1R,3S,4S)-3-{[tert-butyl(dimethyl)-silyl]oxy}-4-({[tert-butyl(dimethyl)silyl]oxy}methyl)cyclopentyl]oxy}-6-(1-naphthylmethoxy) pyrimidine. $^1$H NMR (CD$_3$OD, 400 MHz, δ): 8.39 (s, 1H); 8.01 (d, J=8.8 Hz, 1H); 7.88-7.81 (m, 2H); 7.57 (d, J=7.0 Hz, 1H); 7.53-7.40 (m, 3H); 6.14 (s, 1H); 5.79 (s, 2H); 5.50-5.42 (m, 1H); 4.35-4.31 (m, 1H); 4.30-4.25 (m, 1H); 4.15-4.03 (m, 1H); 2.53-2.42 (m, 1H); 2.30-2.21 (m, 1H); 2.08-1.87 (m, 3H). LC/MS: R$_t$=1.82 min, ES$^+$ 446 (FA standard).

Example 51

((1S,2S,4R)-2-hydroxy-4-{[6-(2-phenylethyl)pyrimidin-4-yl]amino}cyclopentyl)methyl sulfamate (Compound I-81)

Step a: N-[(1R,3S,4S)-3-{[tert-butyl(dimethyl)silyl]oxy}-4-({[tert-butyl(dimethyl)silyl]oxy}methyl)cyclopentyl]-6-iodopyrimidin-4-amine The title compound was prepared following the procedure described in Example 44 step a using 4,6-diiodopyrimidine heating to 150° C. for 300 sec.

Step b: N-[(1R,3S,4S)-3-{[tert-butyl(dimethyl)silyl]oxy}-4-({[tert-butyl(dimethyl)silyl]oxy}methyl)cyclopentyl]-6-(phenylethynyl)pyrimidin-4-amine The title compound was prepared following the procedure described in Example 48 step e. LC/MS: R$_t$=3.56 min, ES$^+$ 538 (FA standard).

Step c: N-[(1R,3S,4S)-3-{[tert-butyl(dimethyl)silyl]oxy}-4-({[tert-butyl(dimethyl)silyl]oxy}methyl)cyclopentyl]-6-(2-phenylethyl)pyrimidin-4-amine The title compound was prepared following the procedure described in Example 3d using N-[(1R,3S,4S)-3-{[tert-butyl(dimethyl)silyl]oxy}-4-({[tert-butyl(dimethyl)-silyl]oxy}methyl)cyclopentyl]-6-(phenylethynyl)pyrimidin-4-amine and Pd(OH)$_2$ on carbon (20% dry weight). LC/MS: R$_t$=2.30 min, ES$^+$ 542 (FA standard).

Step d: ((1S,2S,4R)-2-hydroxy-4-{[6-(2-phenylethyl)pyrimidin-4-yl]amino}cyclopentyl)methyl sulfamate (Compound I-81)

The title compound was prepared following the procedure described in Example 46 steps c and e and Example 48 step f. $^1$H NMR (CD$_3$OD, 400 MHz, δ): 8.30 (s, 1H); 7.26-7.20 (m, 2H); 7.18-7.13 (m, 3H); 6.18 (s, 1H); 4.35-4.26 (m, 2H); 4.15-4.06 (m, 1H); 2.97-2.90 (m, 2H); 2.85-2.76 (m, 2H); 2.51-2.41 (m, 1H); 2.24-2.15 (m, 1H); 1.82-1.73 (m, 1H); 1.70-1.60 (m, 1H); 0.94-0.85 (m, 1H). LC/MS: R$_t$=1.38 min, ES$^+$ 393 (FA standard).

Example 52

((1S,2S,4R)-2-hydroxy-4-{[6-(2-naphthylmethoxy)pyrimidin-4-yl]oxy}cyclopentyl)methyl sulfamate (Compound I-141)

The title compound was prepared following the procedure described in Example 50 using 2-naphthalenemethanol. $^1$H NMR (CD$_3$OD, 400 MHz, δ): 8.39 (s, 1H); 7.88 (s, 1H); 7.86-7.81 (m, 3H); 7.52 (dd, J=8.5 Hz, J=1.76 Hz, 1H); 7.49-7.44 (m, 2H); 6.19 (s, 1H); 5.53-5.48 (m, 1H); 4.38-4.35 (m, 1H); 4.34-4.29 (m, 1H); 4.17-4.12 (m, 1H); 2.56-2.46 (m, 1H); 2.32-2.26 (m, 1H); 2.09-1.91 (m, 3H). LC/MS: R$_t$=1.82 min ES$^+$ 446 (FA standard).

Example 53

{(1S,2S,4R)-2-hydroxy-4-[(6-{[(1R,2S)-2-methoxy-2,3-dihydro-1H-inden-1-yl]oxy}pyrimidin-4-yl)oxy]cyclopentyl}methyl sulfamate (Compound I-96)

Step a: (1R,2S)-1-[(6-chloropyrimidin-4-yl)oxy]indan-2-ol and (1R,2S)-2-[(6-chloropyrimidin-4-yl)oxy]indan-1-ol The title compounds were prepared following the procedure described in Example 34 step a using (1R,2S)-indane-1,2-diol (0.5 g, 3.00 mmol) (Yanagimachi, K. S; Stafford, D; Dexter, A; Sinskey, A; Drew, S; Stephanopoulos, G. *European Journal of Biochemistry*. 2001, 268, 4950-4960) as a 1.2:1 ratio of 2-O-pyrimidine to 1-O-pyrimidine.

Step b: 4-chloro-6-{[(1R,2S)-2-methoxy-2,3-dihydro-1H-inden-1-yl]oxy}pyrimidine and 4-chloro-6-{[(1R,2S)-1-methoxy-2,3-dihydro-1H-inden-2-yl]oxy}pyrimidine and 4-chloro-6-{[(1R,2S)-1-methoxy-2,3-dihydro-1H-inden-2-yl]oxy}pyrimidine To a flame dried flask containing 4 Å molecular sieves (0.700 g) cooled under nitrogen and equipped with a reflux condenser was added silver(I) oxide (3 g, 10.0 mmol), (1R,2S)-1-[(6-chloropyrimidin-4-yl)oxy]indan-2-ol (0.365 g, 1.39 mmol), and Et$_2$O (10 mL). MeI (3.08 mL, 49.5 mmol) was pre-purified through an alumina plug and added to the mixture. The reaction was heated to 40° C. for 2 h. The reaction was diluted with Et$_2$O, filtered through a pad of celite and concentrated in vacuo. The residue was purified by flash chromatography (15 to 30% EtOAc/hexanes) to obtain the title compounds as a 1:1 mixture (0.540 g, 70%).

Step c: 4-{[(1R,3S,4S)-3-{[tert-butyl(dimethyl)silyl]oxy}-4-({[tert-butyl(dimethyl)silyl]oxy}methyl)cyclopentyl]oxy}-6-{[(1R,2S)-2-methoxy-2,3-dihydro-1H-inden-1-yl]oxy}pyrimidine, and tert-butyl{[(1S,2S,4R)-2-{[tert-butyl(dimethyl)silyl]oxy}-4-(3-{[(1R,2S)-1-methoxy-2,3-dihydro-1H-inden-2-yl]oxy}phenoxy)cyclopentyl]methoxy}dimethylsilane, and 4-{[(1R,3S,4S)-3-{[tert-butyl(dimethyl)silyl]oxy}-4-({[tert-butyl(dimethyl)silyl]oxy}methyl)cyclopentyl]oxy}-6-{[(1S,2R)-2-methoxy-2,3-dihydro-1H-inden-1-yl]oxy}pyrimidine, and tert-butyl{[(1S,2S,4R)-2-{[tert-butyl(dimethyl)silyl]oxy}-4-(3-{[(1S,2R)-1-methoxy-2,3-dihydro-1H-inden-2-yl]oxy}phenoxy)cyclopentyl]methoxy}dimethylsilane To a solution of (1R,3S,4S)-3-{[tert-butyl(dimethyl)silyl]oxy}-4-({[tert-butyl(dimethyl)silyl]oxy}methyl)cyclopentanol (0.334 g, 0.928 mmol) and sodium hydride (0.0779 g, 1.95 mmol) in DMF (3 mL) was added 4-chloro-6-{[(1R,2S)-2-methoxy-2,3-dihydro-1H-inden-1-yl]oxy}pyrimidine (0.539 g, 1.95 mmol). The mixture was stirred for 5 h then quenched with H$_2$O and extracted with EtOAc (3×). The combined organic layers were washed with brine, dried (MgSO$_4$) and concentrated in vacuo. The residue was purified by flash chromatography (0 to 30% EtOAc/hexanes) to obtain the title compounds (0.124 g, 22%).

Step d: {(1S,2S,4R)-2-hydroxy-4-[(6-{[(1R,2S)-2-methoxy-2,3-dihydro-1H-inden-1-yl]oxy}pyrimidin-4-yl)oxy]cyclopentyl}methyl sulfamate, and {(1S,2S,4R)-2-hydroxy-4-[(6-{[(1R,2S)-1-methoxy-2,3-dihydro-1H-inden-2-yl]oxy}pyrimidin-4-yl)-oxy]cyclopentyl}methyl sulfamate, and {(1S,2S,4R)-2-hydroxy-4-[(6-[{(1S 2R)-2-methoxy-2,3-dihydro-1H-inden-1-yl]oxy}pyrimidin-4-yl)oxy]cyclopentyl}methyl sulfamate, and {(1S,2S,4R)-2-hydroxy-4-[(6-{[(1S,2R)-1-methoxy-2,3-dihydro-1H-inden-2-yl]oxy}pyrimidin-4-yl)oxy]cyclopentyl}methyl sulfamate (Compounds I-96, I-79, I-98, I-77)

The title compounds were prepared using the procedure described in Example 51 step d using 4-{[(1R,3S,4S)-3-{[tert-butyl(dimethyl)silyl]oxy}-4-({[tert-butyl(dimethyl)silyl]oxy}methyl)cyclopentyl]oxy}-6-{[(1R,2S)-2-methoxy-2,3-dihydro-1H-inden-1-yl]oxy}-pyrimidine, and tert-butyl{[(1S,2S,4R)-2-{[tert-butyl(dimethyl)silyl]oxy}-4-(3-{[(1R,2S)-1-methoxy-2,3-dihydro-1H-inden-2-yl]oxy}phenoxy)cyclopentyl]methoxy}dimethylsilane, and 4-{[(1R,3S,4S)-3-{[tert-butyl(dimethyl)silyl]oxy}-4-({[tert-butyl (dimethyl) silyl]oxy}methyl)cyclopentyl]oxy}-6-{[(1S,2R)-2-methoxy-2,3-dihydro-1H-inden-1-yl]oxy}pyrimidine, and tert-butyl{[(1 S,2S,4R)-2-{[tert-butyl(dimethyl)silyl]oxy}-4-(3-{[(1S,2R)-1-methoxy-2,3-dihydro-1H-inden-2-yl]oxy}phenoxy)cyclopentyl]methoxy}dimethylsilane.

Example 54

{(1S,2S,4R)-2-hydroxy-4-[(6-{[(1R,2S)-2-methoxy-2,3-dihydro-1H-inden-1-yl]oxy}pyrimidin-4-yl)oxy]cyclopentyl}methyl sulfamate (Compound I-96)

$^1$H NMR (CD$_3$OD, 400 MHz, δ): 8.44 (s, 1H); 7.45 (d, J=7.3 Hz, 1H); 7.32-7.25 (m, 2H); 7.23-7.17 (m, 1H); 6.53 (d, J=5.0 Hz, 1H); 6.12 (s, 1H); 5.52-5.47 (m, 1H); 4.39-4.36 (m, 1H); 4.35-4.27 (m, 2H); 4.14 (dd, J=9.8 Hz, J=2.5 Hz, 1H); 3.37 (s, 3H); 3.20-3.06 (m, 2H); 2.56-2.47 (m, 1H); 2.34-2.25 (m, 1H); 2.11-1.89 (m, 3H). LC/MS: R$_t$=1.64 min, ES$^+$ 452 (FA standard).

Example 55

{(1S,2S,4R)-2-hydroxy-4-[(6-{[(1R,2S)-1-methoxy-2,3-dihydro-1H-inden-2-yl]-oxy}pyrimidin-4-yl)oxy]cyclopentyl}methyl sulfamate (Compound I-79)

$^1$H NMR (CD$_3$OD, 400 MHz, δ): 8.40 (s, 1H); 7.40 (d, J=7.3 Hz, 1H); 7.33-7.23 (m, 3H); 6.13 (s, 1H); 5.78 (q, J=5.77 Hz, J=5.52 Hz, 1H); 5.54-5.47 (m, 1H); 4.94 (d, J=4.77 Hz, 1H); 4.41-4.36 (m, 1H); 4.35-4.29 (m, 1H); 4.18-4.12 (m, 1H); 3.38 (s, 3H); 3.28-3.23 (m, 1H); 3.20-3.12 (m, 1H); 2.57-2.47 (m, 1H); 2.33-2.25 (m, 1H); 2.10-1.90 (m, 3H). LC/MS: R$_t$=1.64 min, ES$^+$ 452 (FA standard).

Example 56

{(1S,2S,4R)-2-hydroxy-4-[(6-{[(1S,2R)-2-methoxy-2,3-dihydro-1H-inden-1-yl]-oxy}pyrimidin-4-yl)oxy]cyclopentyl}methyl sulfamate (Compound I-98)

$^1$H NMR (CD$_3$OD, 400 MHz, δ): 8.44 (s, 1H); 7.45 (d, J=7.5 Hz, 1H); 7.32-7.25 (m, 2H); 7.23-7.16 (m, 1H); 6.53 (d, J=5.0 Hz, 1H); 6.12 (s, 1H); 5.53-5.47 (n, 1H); 4.40-4.35 (m, 1H); 4.34-4.27 (m, 2H); 4.15 (dd, J=7.3 Hz, J=5.1 Hz, 1H); 3.37 (s, 3H); 3.19-3.06 (m, 2H); 2.56-2.47 (m, 1H); 2.33-2.25 (m, 1H); 2.10-1.90 (m, 3H). LC/MS: R$_t$=1.65 min, ES$^+$ 452 (FA standard).

Example 57

{(1S,2S,4R)-2-hydroxy-4-[(6-{[(1S,2R)-1-methoxy-2,3-dihydro-1H-inden-2-yl]-oxy}pyrimidin-4-yl)oxy]cyclopentyl}methyl sulfamate (Compound I-77)

$^1$H NMR (CD$_3$OD, 400 MHz, δ): 8.40 (s, 1H); 7.41 (d, J=7.0 Hz, 1H); 7.33-7.23 (m, 3H); 6.13 (s, 1H); 5.81-5.76 (m, 1H); 5.55-5.48 (m, 1H); 4.94 (d, J=5.0 Hz, 1H); 4.41-4.36 (m, 1H); 4.32 (dd, J=9.8 Hz; J=2.3 Hz, 1H); 4.15 (dd, J=9.8 Hz; J=2.5 Hz, 1H); 3.38 (s, 3H); 3.28-3.22 (m, 1H); 3.20-3.12 (m, 1H); 2.57-2.47 (n, 1H); 2.33-2.26 (m, 1H); 2.10-1.93 (m, 3H). LC/MS: R$_t$=1.64 min, ES$^+$ 452 (FA Standard).

Example 58

{(1S,2S,4R)-2-hydroxy-4-[(6-phenylpyrimidin-4-yl)oxy]cyclopentyl}methyl sulfamate (Compound I-114)

Step a: 4-{[(1R,3S,4S)-3-{[tert-butyl(dimethyl)silyl]oxy}-4-({[tert-butyl(dimethyl)silyl]oxy}methyl)cyclopentyl]oxy}-6-phenylpyrimidine A flask containing 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (0.300 g, 0.634 mmol), phenylboronic acid (0.0696 g, 0.570 mmol), a 2.00 M solution of K$_2$CO$_3$ in H$_2$O (0.317 mL), EtOH (0.0944 mL) and toluene (1.417 mL) was purged with argon for 20 minutes. Tetrakis(triphenylphosphine)palladium(0) (0.0264 g, 0.0229 mmol) was added and the mixture was refluxed overnight. The reaction was cooled and diluted with H$_2$O. The aqueous layer was extracted with CH$_2$Cl$_2$ (3×). The combined organics were washed with brine, dried (MgSO$_4$) and concentrated in vacuo. The residue was purified by flash chromatography (0 to 10% EtOAc/hexanes) to afford the title compound (0.224 g, 76%).

Step b: {(1S,2S,4R)-2-hydroxy-4-[(6-phenylpyrimidin-4-yl)oxy]cyclopentyl}methyl sulfamate (Compound I-114)

The title compound was prepared as described in Example 46 steps c and e and Example 48 step f using 4-{[(1R,3S,4S)-3-{[tert-butyl(dimethyl)silyl]oxy}-4-({[tert-butyl(dimethyl)silyl]oxy}methyl)cyclopentyl]oxy}-6-phenylpyrimidine. $^1$H NMR (CD$_3$OD, 400 MHz, δ): 8.73 (s, 1H); 8.03-7.98 (m, 2H); 7.51-7.47 (m, 3H); 7.21 (s, 1H); 5.70-5.65 (m, 1H); 4.44-4.39 (m, 1H); 4.35 (dd, J=7.5 Hz, J=2.3 Hz, 1H); 4.17 (dd, J=7.3 Hz, J=2.5 Hz, 1H); 3.30 (q, J=3.3 Hz, J=1.6 Hz, 1H); 2.62-2.51 (m, 1H); 2.38-2.30 (m, 1H); 2.17-1.96 (m, 3H). LC/MS: R$_t$=1.55 min, ES$^+$ 366 (FA standard).

Example 59

{(1S,2S,4R)-4-[(6-benzylpyrimidin-4-yl)oxy]-2-hydroxycyclopentyl}methyl sulfamate (Compound I-132)

Step a: 4-benzyl-6-{[(1R,3S,4S)-3-{[tert-butyl(dimethyl)silyl]oxy}-4-({[tert-butyl(dimethyl)silyl]oxy}methyl)cyclopentyl]oxy}pyrimidine To a solution of 4-{[(1R,3S,4S)-3-{[tert-butyl(dimethyl)silyl]oxy}-4-({[tert-butyl(dimethyl)silyl]oxy}methyl)cyclopentyl]oxy}-6-chloropyrimidine (0.264 g, 0.559 mmol) and ferric acetylacetonate (0.0395 g, 0.112 mmol) in THF (9 mL) was added a 1.00 M solution of benzylmagnesium bromide in THF (2.52 mL) and the mixture was stirred overnight. The reaction was quenched using NH$_4$Cl and extracted with EtOAc (3×). The combined organic layers were dried (Na$_2$SO$_4$), filtered and concentrated in vacuo. The residue was purified by flash chromatography (0 to 15% EtOAc/hexanes) to afford the title compound as a clear oil. (0.254 g, 86%).

Step b: {(1S,2S,4R)-4-[(6-benzylpyrimidin-4-yl)oxy]-2-hydroxycyclopentyl}methyl sulfamate (Compound I-132)

The title compound was prepared as described in Example 46 steps c and e and Example 48 step f using 4-benzyl-6-{[(1R,3S,4S)-3-{[tert-butyl(dimethyl)silyl]oxy}-4-({[tert-butyl(dimethyl)silyl]oxy}methyl)cyclopentyl]oxy}pyrimidine. $^1$H NMR (CD$_3$OD, 400 MHz, δ): 8.69 (s, 1H); 7.38-7.22 (m, 6H); 6.41 (s, 1H); 5.65-5.58 (m, 1H); 4.52-4.47 (m, 1H); 4.45-4.39 (m, 1H); 4.31-4.25 (m, 1H); 4.03 (s, 2H); 2.63-2.53 (m, 1H); 2.37-2.28 (m, 1H); 2.16-1.84 (m, 4H). LC/MS: R$_t$=1.42 min, ES$^+$ 380 (FA standard).

Example 60

((1R,2R,3S,4R)-2,3-dihydroxy-4-{[6-(2-phenylethyl)pyrimidin-4-yl]amino}cyclopentyl)methyl sulfamate (Compound I-86)

Step a: ((3aR,4R,6R,6aS)-2,2-dimethyl-6-{[6-(2-phenylethyl)pyrimidin-4-yl]amino}tetrahydro-3aH-cyclopenta[d][1,3]dioxol-4-yl)methanol The title compound was prepared following the procedure described in Example 46 step d using ((3aR,4R,6R,6aS)-2,2-dimethyl-6-{[6-(phenylethynyl)pyrimidin-4-yl]amino}tetrahydro-3aH-cyclopenta[d][1,3]dioxol-4-yl)methanol.

Step b: ((1R,2R,3S,4R)-2,3-dihydroxy-4-{[6-(2-phenylethyl)pyrimidin-4-yl]amino}cyclopentyl)methyl sulfamate (Compound I-86)

The title compound was prepared following the procedure described in Example 48 step g using ((3aR,4R,6R,6aS)-2,2-dimethyl-6-{[6-(2-phenylethyl)pyrimidin-4-yl]amino}tetrahydro-3aH-cyclopenta[d][1,3]dioxol-4-yl)methanol. $^1$H NMR (CD$_3$OD, 400 MHz, δ): 8.45 (s, 1H); 7.30-7.16 (m, 5H); 6.41 (bs, 1H); 4.41 (bs, 1H); 4.19-4.12 (m, 2H); 3.90-3.85 (m, 1H); 3.83-3.78 (m, 1H); 3.38 (s, 2H); 3.03-2.86 (m, 4H); 2.41-2.29 (m, 2H); 1.37-1.26 (m, 1H). LC/MS: R$_t$=0.99 min, ES$^+$ 409 (FA standard).

Example 61

[(1S,3R,4R)-3-({6-[(1S)-2,3-dihydro-1H-inden-1-ylamino]pyrimidin-4-yl}amino)-4-hydroxycyclopentyl]methyl sulfamate (Compound I-76)

Step a: (1R,2R,4R)-2-amino-4-(hydroxymethyl)cyclopentanol

A solution of (1R,3R,5S)-6-oxabicyclo[3.1.0]hex-3-ylmethanol (0.419 g, 3.67 mmol) (Feeya, David. *Journal of Organic Chemistry*, 1981, 46, 3512-3519) in ammonium hydroxide (7.22 mL) was heated to 65° C. overnight. The solution was concentrated in vacuo and azeotroped with toluene (3×) to afford the title compound as a clear oil (0.473 g, 98%).

Step b: (1R,2R,4R)-4-({[tert-butyl(dimethyl)silyl]oxy}methyl)-2-({6-[(1S)-2,3-dihydro-1H-inden-1-ylamino]pyrimidin-4-yl}amino)cyclopentanol The title compound was prepared following the procedure described in Example 48 steps c-d using (1R,2R,4R)-2-amino-4-(hydroxymethyl)cyclopentanol.

Step c: (1R,2R,4R)-4-({[tert-butyl(dimethyl)silyl]oxy}methyl)-2-({6-[(1S)-2,3-dihydro-1H-inden-1-ylamino]pyrimidin-4-yl}amino)cyclopentyl acetate To a solution of (1R,2R,4R)-4-({[tert-butyl(dimethyl)silyl]oxy}methyl)-2-({6-[(1S)-2,3-dihydro-1H-inden-1-ylamino]pyrimidin-4-yl}amino)cyclopentanol (0.193 g, 0.424 mmol), N,N-dimethylaminopyridine (4.7 mg, 0.039 mmol) and pyridine (0.281 mL, 3.48 mmol) in DCM (2.1 mL) was added acetic anhydride (0.044 mL, 0.46 mmol) and the mixture stirred overnight. The reaction was diluted with CH$_2$CL$_2$ (10 mL) and H$_2$O (20 mL) then stirred for 10 m. The organic layer was separated and the aqueous layer was extracted with CH$_2$CL$_2$ and combined organics were washed with H$_2$O. The organic layer was dried (MgSO$_4$), filtered and concentrated in vacuo to obtain the title compound. LC/MS: R$_t$=1.74 min, ES$^+$ 498 (FA Standard).

Step d: [(1S,3R,4R)-3-({6-[(1S)-2,3-dihydro-1H-inden-1-ylamino]pyrimidin-4-yl}amino)-4-hydroxycyclopentyl]methyl sulfamate (Compound I-76)

The title compound was prepared following the procedure described in Example 57 step d using (1R,2R,4R)-4-({[tert-butyl(dimethyl)silyl]oxy}methyl)-2-({6-[(1S)-2,3-dihydro-1H-inden-1-ylamino]pyrimidin-4-yl}amino)cyclopentyl acetate. $^1$H NMR (CD$_3$OD, 400 MHz, δ): 7.95 (s, 1H); 7.28-7.14 (m, 4H); 5.66-5.61 (m, 1H); 5.30 (bs, 1H); 4.07 (s, 1H); 4.05 (s, 1H); 4.02 (q, J=5.3 Hz, 1H); 3.82 (bs, 1H); 3.05-2.96 (m, 1H); 2.92-2.82 (m, 1H); 2.63-2.52 (m, 2H); 2.41-2.30 (m, 1H); 1.39-1.28 (m, 1H). LC/MS: R$_t$=0.94 min, ES$^+$ 420 (FA standard).

Example 62

[(1R,3R,4R)-3-({6-[(1S)-2,3-dihydro-1H-inden-1-ylamino]pyrimidin-4-yl}amino)-4-hydroxycyclopentyl]methyl sulfamate (Compound I-58)

The title compound was prepared following the procedure described in Example 59 steps a-d using (1S,2S,4R)-2-amino-4-(hydroxymethyl)cyclopentanol. $^1$H NMR (CD$_3$OD, 400 MHz, δ): 7.95 (s, 1H); 7.29-7.13 (m, 5H); 5.61 (d, J=5.0 Hz, 1H); 5.30 (bs, 1H); 4.08 (s, 1H); 4.06 (s, 1H); 4.01 (q, J=6.3 Hz, 1H); 3.82 (bs, 1H); 3.04-2.95 (m, 1H); 2.92-2.83 (m, 1H); 2.61-2.46 (m, 2H); 2.25-2.17 (m, 1H); 2.06-1.96 (m, 1H); 1.93-1.82 (m, 1H); 1.80-1.70 (m, 1H); 1.49-1.40 (m, 1H). LC/MS: R$_t$=0.94 min, ES$^+$ 420 (FA standard).

Example 63

{(1R,2R,3S,4R)-4-[{6-[(1S)-2,3-dihydro-1H-inden-1-ylamino]pyrimidin-4-yl}(methyl)amino]-2,3-dihydroxycyclopentyl}methyl sulfamate (Compound I-106)

Step a: N-[(3aS,4R,6R,6aR)-6-({[tert-butyl(dimethyl)silyl]oxy}methyl)-2,2-dimethyltetrahydro-3aH-cyclopenta[d][1,3]dioxol-4-yl]-6-chloro-N-methylpyrimidin-4-amine To a mixed solution of N-[(3aS,4R,6R,6aR)-6-({[tert-butyl(dimethyl)silyl]oxy}methyl)-2,2-dimethyltetrahydro-3aH-cyclopenta[d][1,3]dioxol-4-yl]-6-chloropyrimidin-4-amine (405 mg, 0.98 mmol) in THF (10.0 mL) and DMF (2.50 mL) was added sodium hydride (47.0 mg, 1.17 mmol) under an atmosphere of Argon, and the mixture was stirred for 15 minutes. Methyl iodide (0.08 mL, 1.27 mmol) was added to the mixture, and the resulting mixture was stirred for 1 h. After quenching by addition of brine (20.0 mL), the mixture was extracted with ethyl acetate (3×40.0 mL). The organic layers were combined, dried over MgSO$_4$, filtered, and evaporated under vacuum. The residue was purified via silica gel column chromatography eluting with a gradient of 5 to 15% ethyl acetate in DCM to afford the title compound (381 mg, 91%) as a colorless oil. LC/MS: R$_t$=2.55 min, ES$^+$ 428.3 (AA standard).

Step b: {(3aR,4R,6R,6aS)-6-[(6-chloropyrimidin-4-yl)(methyl)amino]-2,2-dimethyltetrahydro-3aH-cyclopenta[d][1,3]dioxol-4-yl}methanol To a stirred solution of N-[(3aS,4R,6R,6aR)-6-({[tert-butyl(dimethyl)silyl]oxy}-methyl)-2,2-dimethyltetrahydro-3aH-cyclopenta[d][1,3]dioxol-4-yl]-6-chloro-N-methylpyrimidin-4-amine (400 mg, 0.93 mmol) in THF (10.0 mL) was added 1M solution of tetra-n-butylammonium fluoride in THF (1.00 mL, 1.00 mmol), and the mixture was stirred for 2 h. After quenching by addition of brine (20.0 mL), the resulting mixture was extracted with ethyl acetate (3×40.0 mL). The organic layers were combined, dried over MgSO$_4$, filtered, and evaporated under vacuum. The residue was purified via silica gel column chromatography eluting with a gradient of 40 to 100% ethyl acetate in DCM to afford the title compound (261 mg, 89%) as a colorless oil. LC/MS: R$_t$=1.24 min, ES$^+$ 314.2 (AA standard).

Step c: {(3aR,4R,6R,6aS)-6-[{6-[(1S)-2,3-dihydro-1H-inden-1-ylamino]pyrimidin-4-yl}(methyl)amino]-2,2-dimethyltetrahydro-3aH-cyclopenta[d][1,3]dioxol-4-yl}methanol {(3aR,4R,6R,6aS)-6-[(6-chloropyrimidin-4-yl)(methyl)amino]-2,2-dimethyltetrahydro-3aH-cyclopenta[d][1,3]dioxol-4-yl}methanol (130 mg, 0.41 mmol) was weighed into a microwave reaction tube and dissolved in 1-butanol (1.50 mL). To this solution was added N,N-diisopropylethylamine (0.22 mL, 1.24 mmol) and (S)-(+)-1-aminoindan (0.16 mL, 1.24 mmol) and the mixture was heated in a sealed tube under microwave irradiation at 200° C. for 4 h. The reaction mixture was concentrated under vacuum, and the residue was purified via silica gel column chromatography eluting with a gradient of 2 to 5% methanol in DCM to afford the title compound (40.5 mg, 24%) as a colorless oil. LC/MS: R$_t$=1.49 min, ES$^+$ 411.5 (AA standard).

Step d: {(3aR,4R,6R,6aS)-6-[{6-[(1S)-2,3-dihydro-1H-inden-1-ylamino]pyrimidin-4-yl}(methyl)amino]-2,2-dimethyltetrahydro-3aH-cyclopenta[d][1,3]dioxol-4-yl}methyl sulfamate The title compound was prepared following the procedure described in Example 1 step d. LC/MS: R$_t$=1.68 min, ES$^+$ 490.3 (AA standard).

Step e: {(1R,2R,3S,4R)-4-[{6-[(1S)-2,3-dihydro-1H-inden-1-ylamino]pyrimidin-4-yl}(methyl)amino]-2,3-dihydroxycyclopentyl}methyl sulfamate (Compound I-106)

To a stirred solution of {(3aR,4R,6R,6aS)-6-[{6-[(1S)-2,3-dihydro-1H-inden-1-yl}amino]pyrimidin-4-yl}(methyl)amino]-2,2-dimethyltetrahydro-3aH-cyclopenta[d][1,3]dioxol-4-yl)methyl sulfamate (12.0 mg, 0.02 mmol) in methanol (3.00 mL) was added 1.00 M hydrochloric acid (0.10 mL), and the mixture was stirred for 8 h. After quenching by addition of saturated NaHCO$_3$ solution, the resulting mixture was evaporated under vacuum. The residue was purified via silica gel column chromatography eluting with a gradient of 5 to 10% methanol in DCM to afford the title compound (7.80 mg, 71%). $^1$H-NMR (400 MHz, CD$_3$OD) δ: 8.01 (s, 1H), 7.27-7.13 (m, 4H), 5.67 (s, 1H), 5.42-5.34 (m, 1H), 4.88-4.75 (m, 1H), 4.17 (d, 2H, J=5.6 Hz), 4.04 (dd, 1H, J=8.8, 6.1 Hz), 3.88 (dd, 1H, =5.8, 4.1 Hz), 3.05-2.96 (m, 1H), 2.89 (s, 3H), 2.93-2.83 (m, 1H), 2.62-2.52 (m, 1H), 2.34-2.24 (m, 1H), 2.01 (dt, 1H, d=13.0, 8.3 Hz), 1.94-1.83 (m, 1H), 1.44 (ddd, 1H, J=13.0, 10.8, 9.1). LC/MS: R$_t$=5.79 min, ES$^+$ 450.2 (AA Waters).

Example 64

[(1R,2R,3S,4R)-4-({2-[(1S)-2,3-dihydro-1H-inden-1-ylamino]-5-fluoropyrimidin-4-yl}amino)-2,3-dihydroxycyclopentyl]methyl sulfamate (Compound I-113)

Step a: (1R,2S,3R,5R)-3-[(2-chloro-5-fluoropyrimidin-4-yl)amino]-5-(hydroxymethyl)cyclopentane-1,2-diol The title compound was prepared following the procedure described in Example 1 using 2,4-dichloro-5-fluoropyrimidine in step a. LC/MS: R$_t$=0.89 min, ES$^+$278.0 (FA standard).

Step b: {(3aR,4R,6R,6aS)-6-[(2-chloro-5-fluoropyrimidin-4-yl)amino]-2,2-dimethyltetrahydro-3aH-cyclopenta[d][1,3]dioxol-4-yl}methanol The title compound was prepared following the procedure described in Example 1 using (1R,2S,3R,5R)-3-[(2-chloro-5-fluoropyrimidin-4-yl)amino]-5-(hydroxymethyl)cyclopentane-1,2-diol in step b. LC/MS: R$_t$=1.42 min, ES$^+$ 318.1 (FA standard).

Step c: [(3aR,4R,6R,6aS)-6-({2-[(1S)-2,3-dihydro-1H-inden-1-ylamino]-5-fluoropyrimidin-4-yl}amino)-2,2-dimethyltetrahydro-3aH-cyclopenta[d][1,3]dioxol-4-yl]methanol The title compound was prepared following the procedure described in Example 1 using {(3aR,4R,6R,6aS)-6-[(2-chloro-5-fluoropyrimidin-4-yl)amino]-2,2-dimethyltetrahydro-3aH-cyclopenta[d][1,3]dioxol-4-yl}methanol in step c. LC/MS: $R_t$=1.20 min, $ES^+$ 415.6 (FA standard).

Step d: [(1R,2R,3S,4R)-4-({2-[(1S)-2,3-dihydro-1H-inden-1-ylamino]-5-fluoropyrimidin-4-yl}amino)-2,3-dihydroxycyclopentyl]methyl sulfamate (Compound I-113)

The title compound was prepared following the procedure described in Example 65 step d. (63.5 mg, 62%) $^1$H-NMR (400 MHz, CD$_3$OD) δ: 8.29 (bs, 1H), 7.65 (d, 1H, J=4.6 Hz), 7.29-7.13 (m, 4H), 5.43 (t, 1H, J=7.3 Hz), 4.44-4.37 (m, 1H), 4.17 (dd, 1H, J=9.8, 5.1 Hz), 4.13 (dd, 1H, J=9.8, 5.3 Hz), 3.93-3.86 (m, 2H), 3.01 (ddd, 1H, J=16.0, 8.8, 3.5 Hz), 2.87 (dt, 1H, J=16.0, 8.0 Hz), 2.62-2.53 (m, 1H), 2.35-2.24 (m, 2H), 1.98-1.87 (m, 1H), 1.40-1.27 (m, 1H). LC/MS: $R_t$=4.21 min, $ES^+$ 454.2 (FA long).

Example 65

{(1S,2S,4R)-4-[(5-fluoro-6-{[(1R,2S)-2-methoxy-2,3-dihydro-1H-inden-1-yl]-amino}pyrimidin-4-yl)oxy]-2-hydroxycyclopentyl}methyl sulfamate (Compound I-83)

Step a: 4-{[(1R,3S,4S)-3-{[tert-butyl(dimethyl)silyl]oxy}-4-({[tert-butyl(dimethyl)silyl]-oxy}methyl)cyclopentyl]oxy}-6-chloro-5-fluoropyrimidine To a stirred suspension of sodium hydride (37.4 mg, 0.93 mmol) in THF (5.00 mL) was added a solution of (1R,3S,4S)-3-{[tert-butyl(dimethyl)silyl]oxy}-4-({[tert-butyl(dimethyl)silyl]oxy}methyl)cyclopentanol (285 mg, 0.79 mmol) in THF (2.50 mL) at 0° C. under an atmosphere of Argon, and the mixture was stirred for 15 minutes. To this cooled suspension was added a solution of 4,6-dichloro-5-fluoropyrimidine (120 mg, 0.72 mmol) in THF (2.50 mL) at 0° C., and the resulting mixture was stirred for 19 h at 23° C. After quenching by addition of saturated NH$_4$Cl solution (50.0 mL), the mixture was extracted with ethyl acetate (3×70.0 mL). The organic layers were combined, dried over MgSO$_4$, filtered, and evaporated under vacuum. The residue was purified via silica gel column chromatography eluting with a gradient of 5 to 7% ethyl acetate in hexanes to afford the title compound (295 mg, 79%). $^1$H-NMR (400 MHz, CDCl$_3$) δ: 8.32 (s, 1H), 5.67-5.61 (m, 1H), 4.41-4.37 (m, 1H), 3.73 (dd, 1H, J=9.8, 7.1 Hz), 3.59 (dd, 1H, J=9.8, 6.6 Hz), 2.33-2.25 (m, 1H), 2.10-1.96 (m, 2H), 1.90 (ddd, 1H, J=13.8, 7.7, 1.8 Hz), 1.55 (s, 18H), 0.89 (s, 6H), 0.88 (s, 6H).

Step b: 6-{[(1R,3S,4S)-3-{[tert-butyl(dimethyl)silyl]oxy}-4-({[tert-butyl(dimethyl)silyl]-oxy}methyl)cyclopentyl]oxy}-5-fluoro-N-[(1R,2S)-2-methoxy-2,3-dihydro-1H-inden-1-yl]pyrimidin-4-amine 4-{[(1R,3S,4S)-3-{[tert-butyl(dimethyl)silyl]oxy}-4-({[tert-butyl(dimethyl)silyl]-oxy}methyl)cyclopentyl]oxy}-6-chloro-5-fluoropyrimidine (260 mg, 0.53 mmol), (1R,2S)-2-methoxyindan-1-amine (364 mg, 2.12 mmol), and sodium carbonate (224 mg, 2.12 mmol) was weighed into a microwave reaction tube. This mixture was heated in a sealed tube under microwave irradiation at 180° C. for 2 h. The reaction mixture was diluted with DCM (100 mL), and the suspension was filtered. The filtrate was washed with saturated NH4Cl solution (100 mL), and the organic layer was dried over MgSO$_4$. This suspension was filtered, and evaporated under vacuum. The residue was purified via silica gel column chromatography eluting with a gradient of 0 to 10% methanol in DCM to afford the title compound (313 mg, 91%).

Step c: {(1S,2S,4R)-2-{[tert-butyl(dimethyl)silyl]oxy}-4-[(5-fluoro-6-{[(1R,2S)-2-methoxy-2,3-dihydro-1H-inden-1-yl]amino}pyrimidin-4-yl)oxy]cyclopentyl}methanol The title compound was prepared following the procedure described in Example 34 using 6-{[(1R,3S,4S)-3-{[tert-butyl(dimethyl)silyl]oxy}-4-({[tert-butyl(dimethyl)-silyl]oxy}methyl)cyclopentyl]oxy}-5-fluoro-N-[(1R,2S)-2-methoxy-2,3-dihydro-1H-inden-1-yl]pyrimidin-4-amine in step c. LC/MS: $R_t$=2.60 min, $ES^+$ 504.5 (FA standard).

Step d: {(1S,2S,4R)-4-[(5-fluoro-6-{[(1R,2S)-2-methoxy-2,3-dihydro-1H-inden-1-yl]amino}-pyrimidin-4-yl)oxy]-2-hydroxcyclopentyl}methyl sulfamate (Compound I-83)

To a stirred solution of {(1S,2S,4R)-2-{[tert-butyl(dimethyl)silyl]oxy}-4-[(5-fluoro-6-{[(1R,2S)-2-methoxy-2,3-dihydro-1H-inden-1-yl]amino}pyrimidin-4-yl)-oxy]cyclopentyl}methanol (190 mg, 0.36 mmol) in THF (5.40 mL) was added triethylamine (0.08 mL, 0.54 mmol) and [(diphenylamino)carbonyl]sulfamoyl chloride (186 mg, 0.54 mmol) at 0° C. under an atmosphere of Argon, and the mixture was stirred for 30 min. The reaction mixture was added 1.00 M Hydrochloric acid in (5.40 mL) at 23° C., and the resulting mixture was stirred for 16 h. The reaction mixture was quenched by addition of saturated NaHCO$_3$ solution (80.0 mL) and extracted with ethyl acetate (3×100 mL). The organic layers were combined, dried over MgSO$_4$, filtered, and evaporated under vacuum. The residue was purified via silica gel column chromatography eluting with a gradient of 0 to 10% methanol in DCM to afford the title compound (91.0 mg, 51%). $^1$H-NMR (400 MHz, CD$_3$OD) δ: 8.01 (s, 1H), 7.25-7.13 (m, 4H), 5.72 (d, 1H, J=6.5 Hz), 5.65-5.58 (m, 1H), 4.43-4.38 (m, 1H), 4.33 (dd, 1H, J=9.7, 7.6 Hz), 4.22 (dt, 1H, J=5.0, 2.4 Hz), 4.16 (dd, 1H, J=9.7, 7.3 Hz), 3.35 (s, 3H), 3.14 (dd, 1H, J=16.6, 2.4 Hz), 3.02 (dd, 1H, J=16.6, 5.0 Hz), 2.60-2.49 (m, 1H), 2.31 (ddd, 1H, d=14.8, 6.8, 2.3 Hz), 2.12 (ddd, 1H, J=14.8, 5.0, 4.7), 2.08-1.95 (m, 2H). LC/MS: $R_t$=6.76, $ES^+$ 469.3 (FA long).

Example 66

{(1S,2S,4R)-4-[(6-{[(1S)-3,3-dimethyl-2,3-dihydro-1H-inden-1-yl]amino}-5-fluoropyrimidin-4-yl)amino]-2-hydroxycyclopentyl}methyl sulfamate (Compound I-71)

Step a: N-[(1R,3S,4S)-3-{[tert-butyl(dimethyl)silyl]oxy}-4-({[tert-butyl(dimethyl)silyl]oxy}-methyl)cyclopentyl]-6-chloro-5-fluoropyrimidin-4-amine A solution of 4,6-dichloro-5-fluoropyrimidine (102 mg, 0.61 mmol), (1R,3S,4S)-3-{[tert-butyl(dimethyl)silyl]oxy}-

4-({[tert-butyl(dimethyl)silyl]oxy}methyl)-cyclopentanamine (200 mg, 0.56 mmol), and triethylamine (0.16 mL, 1.11 mmol) in ethanol (2.00 mL) was heated in a sealed tube under microwave irradiation at 140° C. for 1 h. The reaction mixture was concentrated under vacuum, and the residue was purified by flash chromatography (0 to 15% ethyl acetate/hexanes) to afford the title compound (213 mg, 70%) as a light yellow solid. LC/MS: $R_t$=2.60 min, ES⁺ 490.5 (AA standard).

Step b: N-[(1R,3S,4S)-3-{[tert-butyl(dimethyl)silyl]oxy}-4-({[tert-butyl(dimethyl)silyl]oxy}-methyl)cyclopentyl]-N'-[(1 S)-3,3-dimethyl-2,3-dihydro-1H-inden-1-yl]-5-fluoropyrimidine-4,6-diamine A mixture of N-[(1R,3S,4S)-3-{[tert-butyl(dimethyl)silyl]oxy}-4-({[tert-butyl(dimethyl)silyl]oxy}methyl)cyclopentyl]-6-chloro-5-fluoropyrimidin-4-amine (205 mg, 0.38 mmol), (1S)-3,3-dimethylindan-1-amine (243 mg, 1.51 mmol), and sodium carbonate (160 mg, 1.51 mmol) was stirred at 180° C. for 3 h in an oil bath. The reaction mixture was diluted with DCM and the suspension was filtered. The filtrate was concentrated under vacuum and the residue was purified by flash chromatography (5 to 10% ethyl acetate/hexanes) to afford the title compound (213 mg, 70%) as a colorless amorphous solid.

Step c: {(1S,2S,4R)-2-{[tert-butyl(dimethyl silyl]oxy}-4-[(6-{[(1S)-3,3-dimethyl-2,3-dihydro-1H-inden-1-yl]amino}-5-fluoropyrimidin-4-yl)amino]cyclopentyl}-methanol The title compound was prepared following the procedure described in Example 34 step c. LC/MS: $R_t$=2.51 min, ES⁺ 501.5 (AA standard).

Step d: {(1S,2S,4R)-4-[(6-{[(1S)-3,3-dimethyl-2,3-dihydro-1H-inden-1-yl]amino}-5-fluoropyrimidin-4-yl)amino]-2-hydroxycyclopentyl}methyl sulfamate (Compound I-71)

The title compound was prepared following the procedure described in Example 65 step d. (63.5 mg, 62%). ¹H-NMR (400 MHz, CD₃OD) δ: 7.84 (d, 1H, J=1.2 Hz), 7.25-7.15 (m, 4H), 5.68 (dd, 1H, J=8.8, 7.7 Hz), 4.67 (ddd, 1H, J=16.3, 8.0, 4.3 Hz), 4.37-4.33 (m, 1H), 4.31 (dd, 1H, J=9.8, 7.8 Hz), 4.13 (dd, 1H, J=9.8, 7.1 Hz), 2.58-2.47 (m, 1H), 2.40 (dd, 1H, J=12.3, 7.3 Hz), 2.22 (ddd, 1H, J=13.8, 7.8, 1.8 Hz), 2.04 (ddd, 1H, J=13.5, 10.1, 4.5 Hz), 1.91-1.81 (m, 2H), 1.73 (ddd, 1H, J=13.5, 8.7, 4.0 Hz), 1.40 (s, 3H), 1.23 (s, 3H). LC/MS: $R_t$=7.53 min, ES⁺ 466.2 (FA long).

Example 67

((1R,2R,3S,4R)-2,3-dihydroxy-4-{[6-(5,6,7,8-tetrahydronaphthalen-1-ylamino)-pyrimidin-4-yl]amino}cyclopentyl)methyl sulfamate (Compound I-118)

Step a: (1S,2R,3R,5R)-3-(hydroxymethyl)-5-{[6-(5,6,78-tetrahydronaphthalen-1-ylamino)pyrimidin-4-yl]amino}cyclopentane-1,2-diol The title compound was prepared following the procedure described in Example 1 steps a and c using 5,6,7,8-tetrahydro-1-naphthylamine in step c. LC/MS: $R_t$=1.29 min, ES⁺ 371.3 (AA standard).

Step b: ((3aR,4R,6R,6aS)-2,2-dimethyl-6-{[6-(5,6,7,8-tetrahydronaphthalen-1-ylamino)pyrimidin-4-yl]amino}tetrahydro-3aH-cyclopenta[d][1,3]dioxol-4-yl)-methanol To a stirred solution of (1S,2R,3R,5R)-3-(hydroxymethyl)-5-{[6-(5,6,7,8-tetrahydronaphthalen-1-ylamino)pyrimidin-4-yl]amino}cyclopentane-1,2-diol (70.0 mg, 0.19 mmol) in acetone (5.00 mL) was added 2,2-dimethoxypropane (0.21 mL, 1.70 mmol) and pyridinium p-toluenesulfonate (57.0 mg, 0.23 mmol), and the mixture was stirred for 55 h. The reaction mixture was quenched by addition of saturated NaHCO₃ solution (50.0 mL) and then extracted with ethyl acetate (3×50.0 mL). The organic layers were combined, dried over MgSO₄, filtered, and evaporated under vacuum. The residue was purified by flash chromatography (2 to 10% Methanol/DCM) to afford the title compound (72.0 mg, 85%) as a light yellow amorphous solid. LC/MS: $R_t$=1.59 min, ES⁺ 411.3 (AA standard).

Step c: ((1R,2R,3S,4R)-2,3-dihydroxy-4-{[6-(5,6,7,8-tetrahydronaphthalen-1-ylamino)pyrimidin-4-yl]amino}cyclopentyl)methyl sulfamate (Compound I-118)

The title compound was prepared following the procedure described in Example 65 step d. ¹H-NMR (400 MHz, CD₃OD) δ: 7.96 (s, 1H), 7.13-7.02 (m, 2H), 6.97 (d, 1H, J=7.2 Hz), 5.46 (s, 1H), 4.18-4.08 (m, 2H), 4.02-3.87 (m, 1H), 3.85 (dd, 1H, J=5.5, 4.0 Hz), 3.73 (dd, 1H, J=5.8, 5.5 Hz), 2.82-2.76 (m, 2H), 2.65-2.59 (m, 2H), 2.37-2.25 (m, 2H), 1.82-1.74 (m, 4H), 1.30-1.20 (m, 1H). LC/MS: $R_t$=5.04 min, ES⁺ 450.2 (FA long)

Example 68

{(1S,2S,4R)-4-[(6-{[(1S)-3,3-dimethyl-2,3-dihydro-1H-inden-1-yl]amino}pyrimidin-4-yl)amino]-2-hydroxycyclopentyl}methyl sulfamate (Compound I-65)

Step a: (1S,3S,4S)-3-[(benzyloxy)methyl]-4-{[tert-butyl (dimethyl)silyl]oxy}cyclopentanol A suspension of (1R,4S)-3-[(benzyloxy)methyl]-4-{[tert-butyl(dimethyl)silyl]-oxy}cyclopent-2-en-1-ol (1.47 g, 0.00439 mol), sodium carbonate (1.1 g, 0.010 mol) and 10% Pd/C (0.3 g, 0.0003 mol) in EtOAc (20 mL, 0.2 mol) was stirred under an atmosphere of Hydrogen overnight. The reaction was purged with nitrogen and filtered through celite with EtOAc. The filtrate was concentrated to obtain 1.45 g (98%) of the title compound as a 5:1 mixture of diastereomers (desired:undesired).

Step b: (1S,3S,4S)-3-[(benzyloxy)methyl]-4-{[tert-butyl(dimethyl)silyl]oxy}cyclopentyl methanesulfonate The title compound was prepared following the procedure described in Example 35 step b.

Step c: (1S,3S,4S)-3-{[tert-butyl(dimethyl)silyl]oxy}-4-(hydroxymethyl)cyclopentyl methanesulfonate A suspension of (1S,3S,4S)-3-[(benzyloxy)methyl]-4-{[tert-butyl(dimethyl)silyl]-oxy}cyclopentyl methanesulfonate (690 mg, 0.0017 mol) and Palladium hydroxide, 20 wt. % Pd on carbon (160 mg, 0.00012 mol) in methanol (10 mL, 0.2 mol) was stirred under an atmosphere of hydrogen for 2 hours. The reaction was purged with nitrogen and filtered the mixture through celite with DCM. The filtrate was concentrated to obtain 350 mg (65%).

Step d: ((1S,2S,4R)-4-azido-2-{[tert-butyl(dimethyl)silyl]oxy}cyclopentyl)methanol To a solution of (1S,3S,4S)-3-{[tert-butyl(dimethyl)silyl]oxy}-4-(hydroxymethyl)-cyclopentyl methanesulfonate (0.470 g, 0.00145 mol) in N,N-Dimethylformamide (6 mL, 0.08 mol) was added sodium azide (0.4 g, 0.006 mol) 23° C., and the mixture was heated at 55° C. for 3 hours. The reaction was cooled to 23° C., quenched by addition of water and extracted with Et₂O (3×), dried (Na₂SO₄), filtered and concentrated. The residue was purified by flash chromatography (10 to 25% ethyl acetate/hexane) to obtain 211 mg (53.7%).

Step e: ((1S,2S,4R)-4-amino-2-{[tert-butyl(dimethyl)silyl]oxy}cyclopentyl)methanol A suspension of ((1S,2S,4R)-4-azido-2-{[tert-butyl(dimethyl)silyl]oxy}-cyclopentyl)methanol (0.211 g, 0.000777 mol) and 10% Pd/C (0.047 g, 0.000044 mol) in EtOAc (6 mL, 0.06 mol) was stirred under an atmosphere of Hydrogen overnight. The reaction was purged with nitrogen and filtered the mixture through celite with DCM. The filtrate was concentrated to obtain 167 mg (87.5%) of the title compound.

Step f: {(1S,2S,4R)-2-{[tert-butyl(dimethyl)silyl]oxy}-4-[(6-chloropyrimidin-4-yl)amino]-cyclopentyl}methanol A mixture of ((1S,2S,4R)-4-amino-2-{[tert-butyl(dimethyl)silyl]oxy}cyclopentyl)-methanol (0.132 g, 0.000538 mol), pyrimidine, 4,6-dichloro- (0.096 g, 0.00064 mol) and triethylamine (0.1 mL, 0.001 mol) in ethanol (1.5 mL, 0.025 mol) was subjected to microwave irradiation (140° C.) for 60 minutes. The resulting dark brown mixture was concentrated. The residue was purified by flash chromatography (0 to 10% MeOH/DCM) to give 158 mg (82%).

Step g: {(1S,2S,4R)-4-[(6-{[(1S)-3,3-dimethyl-2,3-dihydro-1H-inden-1-yl]amino}pyrimidin-4-yl)amino]-2-hydroxycyclopentyl}methyl sulfamate (Compound I-65)

The title compound was prepared following the procedure described in Example 44 (steps b and d) using (1S)-3,3-dimethylindan-1-amine. $^1$H NMR (CD₃OD, 400 MHz) δ: 8.15 (s, 1H), 7.33-7.21 (m, 4H), 5.66 (s, 1H), 4.39-4.36 (m, 1H), 4.31 (dd, J=7.3, 9.7 Hz, 1H), 4.13 (dd, J=7.4, 9.7 Hz, 1H), 2.53-2.44 (m, 2H), 2.27-2.22 (m, 1H), 2.08-2.01 (m, 1H), 1.91-1.84 (m, 2H), 1.78-1.72 (m, 1H), 1.41 (s, 3H), 1.27 (s, 3H) ppm. LC/MS: $R_t$=1.54 min, ES$^+$ 448.38 (AA standard).

Example 69

{(1S,2S,4R)-2-hydroxy-4-[(6-{[(1S,2S)-2-methyl-2,3-dihydro-1H-inden-1-yl]-amino}pyrimidin-4-yl)oxy]cyclopentyl}methylsulfamate (Compound I-43)

The title compound was prepared following the procedure described in Example 34 using (1S,2S)-2-methyl-2,3-dihydro-1H-inden-1-amine (Zhang, Z.; Zhu, G.; Jiang, Q.; Xiao, D.; Zhang, Z. *J. Org. Chem.* 1999, 64, 1774) in step b. $^1$H NMR (400 MHz, CD₃OD) δ: 8.13 (s, 1H), 7.28-7.14 (m, 4H), 5.88 (s, 1H), 5.56 (bs, 1H), 5.32 (bs, 1H), 4.40-4.30 (m, 2H), 4.18-4.12 (m, 1H), 3.10-3.02 (m, 1H), 2.90-2.78 (m, 1H), 2.68-2.62 (m, 1H), 2.57-2.47 (m, 1H), 2.31-2.23 (m, 1H), 2.11-1.91 (m, 3H), 0.91 (d, J=7.03 Hz, 3H) ppm. LC/MS: $R_t$=1.65 min, ES$^+$ 435 (AA standard).

Example 70

{(1S,2S,4R)-4-[(4-{[(1R)-2,2-Difluoro-2,3-dihydro-1H-inden-1-yl]amino}-1,3,5-triazin-2-yl)amino]-2-hydroxycyclopentyl}methyl sulfamate (Compound I-147)

The title compound was prepared following the procedure in Example 46 steps a-d using (1R)-5-chloro-2,2-difluoroindan-1-amine in step a. The sulfamation was carried out according to the procedure in Example 65 step d to give the title compound. $^1$H NMR (CD₃OD 400 MHz) δ: 8.05 (d, 0.5H), 7.95 (s, 0.5H), 7.30-7.28 (m, 4H), 6.06-5.89 (m, 1H), 4.62-4.59 (m, 1H), 4.27-4.24 (m, 2H), 4.14-4.08 (m, 1H), 3.50-3.41 (m, 2H), 2.49 (bs, 1H), 2.22-2.14 (m, 1H), 2.05-1.97 (m, 1H), 1.87-1.80 (m, 1H), 1.76-1.70 (m, 1H) ppm. LC/MS: $R_t$=5.61 min, ES$^+$ 457 (FA long).

Example 71

{(1S,2S,4R)-2-hydroxy-4-[(6-{[(1R,2S)-2-methoxy-1,2,3,4-tetrahydronaphthalen-1-yl]amino}pyrimidin-4-yl)oxy]cyclopentyl}methyl sulfamate (Compounds I-142 and I-143)

The title compound was prepared as a 1:1 mixture of diastereomers following the procedures in Example 34. Rel-(1R,2S)-2-methoxy-1,2,3,4-tetrahydronaphthalen-1-amine, generated by adapting the following literature precedent. Marcune, B. F.; Karady, S.; Reider, P. J.; Miller, R. A.; Biba, M.; DiMichele, L.; Reamer, R. A. *J. Org. Chem.* 2003, 68, 8088-8091, was used as a coupling partner in step b. The mixture was then separated by chiral HPLC (Chiralpak AD 20×250, eluent 85/15/0.1% hex/EtOH/DEA at 20 mL/min). Analytical data for {(1S,2S,4R)-2-hydroxy-4-[(6-{[(1R,2S)-2-methoxy-1,2,3,4-tetrahydronaphthalen-1-yl]amino}pyrimidin-4-yl)oxy]cyclopentyl}methyl sulfamate (Compound I-142): $^1$H NMR (CD₃OD, 400 MHz) δ: 8.13 (d, J=0.8 Hz, 1H), 7.20 (d, J=7.3 Hz, 1H), 7.15-7.01 (m, 3H), 5.93 (s, 1H), 5.48 (bs, 1H), 5.34-5.31 (m, 1H), 4.40-4.37 (m, 1H), 4.32 (dd, J=7.6, 9.8 Hz, 1H), 4.15 (dd, J=7.5, 9.6 Hz, 1H), 3.77-3.74 (m, 1H), 3.41 (s, 3H), 3.00-2.92 (m, 1H), 2.78-2.71 (m, 1H), 2.55-2.48 (m, 1H), 2.31-2.19 (m, 2H), 2.12-1.90 (m, 4H) ppm. LC/MS: $R_t$=6.22 min, ES$^+$ 465 (FA long). Analytical data for {(1S,2S,4R)-2-hydroxy-4-[(6-{[(1S,2R)-2-methoxy-1,2,3,4-tetrahydronaphthalen-1-yl]amino}pyrimidin-4-yl)-oxy]cyclopentyl}methyl sulfamate (Compound I-143): $^1$H NMR (CD₃OD, 400 MHz) δ: 8.13 (d, J=0.8 Hz, 1H), 7.19 (d, J=7.3 Hz, 1N), 7.15-7.08 (m, 3H), 5.93 (s, 1H), 5.50 (bs, 1H), 5.34-5.31 (m, 1H), 4.40-4.37 (m, 1H), 4.32 (dd, J=7.2, 9.8 Hz, 1H), 4.16 (dd, J=7.3, 9.8 Hz, 1H), 3.77-3.74 (m, 1H), 3.41 (s, 3H), 3.00-2.92 (m, 1H), 2.78-2.71 (m, 1H), 2.55-2.49 (m, 1H), 2.31-2.19 (m, 2H), 2.12-1.90 (m, 4H) ppm. LC/MS: $R_t$=6.09 min, ES$^+$ 465 (FA long).

Example 72

{(1R,2R,3S,4R)-4-[(6-{[(1R,2R)-2-(benzyloxy)cyclopentyl]amino}pyrimidin-4-yl)amino]-2,3-dihydroxycyclopentyl}methyl sulfamate (Compound I-85)

The title compound was prepared following the procedure described in Example 1, steps a-c using (1R,2R)-(+)-2-benzyloxycyclopentylamine and Example 65, step d. $^1$H-NMR (400 MHz, CD$_3$OD) δ: 7.90 (s, 1H), 7.34-7.22 (m, 5H), 5.59 (s, 1H), 4.58 (d, 1H, J=14.5 Hz), 4.55 (d, 1H, J=14.5 Hz), 4.18 (dd, 1H, J=9.8, 4.8 Hz), 4.13 (dd, 1H, J=9.8, 5.5 Hz), 4.05-3.96 (m, 1H), 3.95-3.84 (m, 3H), 3.76 (t, 1H, J=5.5 Hz), 2.41-2.25 (m, 2H), 2.20-2.10 (m, 2H), 1.99-1.90 (m, 1H), 1.83-1.68 (m, 3H), 1.56-1.45 (m, 1H), 1.29 (dt, 1H, J=12.5, 8.3 Hz). LC/MS: R$_t$=5.17 min, ES$^+$ 473.2 (FA long)

Example 73

{(1R,2R,3S,4R)-4-[(6-{[(1S,2S)-2-(benzyloxy)cyclopentyl]amino}pyrimidin-4-yl)amino]-2,3-dihydroxycyclopentyl}methyl sulfamate (Compound I-92)

The title compound was prepared following the procedure described in Example 1, steps a-c using (1S,2S)-(+)-2-benzyloxycyclopentylamine and Example 65, step d. $^1$H-NMR (400 MHz, CD$_3$OD) δ: 7.91 (s, 1H), 7.33-7.21 (m, 5H), 5.57 (s, 1H), 4.57 (s, 2H), 4.19 (dd, 1H, J=9.6, 4.7 Hz), 4.14 (dd, 1H, J=9.6, 5.5 Hz), 4.06-3.90 (m, 2H), 3.90-3.83 (m, 2H), 3.77 (t, 1H, J=5.5 Hz), 2.45-2.28 (m, 2H), 2.20-2.10 (m, 2H), 2.00-1.88 (m, 1H), 1.82-1.68 (m, 3H), 1.54-1.43 (m, 1H), 1.31 (dt, 1H, J=12.6, 8.4 Hz). LC/MS: R$_t$=1.16 min, ES$^+$ 494.2 (FA standard).

Example 74

((1R,2R,4S)-4-{[6-({(1R,2R)-2-[(dimethylamino)carbonyl]-2,3-dihydro-1H-inden-1-yl}amino)pyrimidin-4-yl]oxy}-2-hydroxycyclopentyl)methyl rel-sulfamate (Compound I-66)

Step a: tert-butyl rel-(2aR,7bR)-2-oxo-2,2a,3,7b-tetrahydro-1H-indeno[1,2-b]azete-1-carboxylate To a mixed solution of rel-(2aR,7bR)-1,2a,3,7b-tetrahydro-2H-indeno[1,2-b]azet-2-one (1.20 g, 7.54 mmol) and N,N-dimethylaminopyridine (0.20 g, 2.00 mmol) in acetonitrile (24.0 mL) was added di-tert-butyldicarbonate (3.29 g, 15.1 mmol) at 0° C. under an atmosphere of Argon, and the mixture was stirred for 1 h at 23° C. The reaction mixture was added DCM (ca. 200 mL) and then the organic layer was washed with saturated NaHCO$_3$ solution and brine. After drying over MgSO$_4$, the suspension was filtered and the filtrate was evaporated under vacuum. The residue was purified by flash chromatography (10 to 30% ethyl acetate/hexanes) to afford the title compound (1.85 g, 90%) as a light pink solid. $^1$H-NMR (400 MHz, CDCl$_3$) δ: 7.58 (d, 1H, J=7.5 Hz), 7.36-7.23 (m, 3H), 5.34 (d, 1H, J=5.0 Hz), 3.98 (ddd, 1H, J=10.5, 5.0, 2.4 Hz), 3.38 (dd, 1H, J=17.4, 1.2 Hz), 3.13 (dd, 1H, J=17.4, 10.5 Hz), 1.52 (s, 9H).

Step b: tert-butyl rel-{(1R,2R)-2-[(dimethylamino)carbonyl]-2,3-dihydro-1H-inden-1-yl}-carbamate To tert-butyl rel-(2aR,7bR)-2-oxo-2,2a,3,7b-tetrahydro-1H-indeno[1,2-b]azete-1-carboxylate (200 mg, 0.77 mmol) was added 2.00 M dimethylamine in THF (1.90 mL, 3.80 mmol) in the sealed tube, and the mixture was microwaved at 120° C. for 30 minutes. The reaction mixture was concentrated under vacuum, and then the residue was washed with small amount of hexane to give the title compound (226 mg, 91%) as a white solid.

Step c: rel-(1R,2R)-1-amino-N,N-dimethylindane-2-carboxamide

To a stirred solution of tert-butyl rel-{(1R,2R)-2-[(dimethylamino)carbonyl]-2,3-dihydro-1H-inden-1-yl}carbamate (690 mg, 2.15 mmol) in DCM (25.0 mL) was added zinc dibromide (970 mg, 4.31 mmol) and ethanol (0.25 mL, 4.31 mmol), and the mixture was stirred for 18 h. The reaction mixture was quenched by addition of water (20.0 mL) and the resulting mixture was stirred for 2 h. To this mixture was added 1.00 M NaOH (30.0 mL) and extracted with DCM (3×100 mL). The organic layers were combined, dried over MgSO$_4$, filtered, and evaporated under vacuum. The residue was purified by flash chromatography (10 to 30% Methanol/DCM) to afford the title compound (438 mg, 95%) as a colorless oil. LC/MS: R$_t$=0.89 min, ES$^+$ 205.2 (AA standard).

Step d: ((1R,2R,4S)-4-{[6-({(1R,2R)-2-[(dimethylamino)carbonyl]-2,3-dihydro-1H-inden-1-yl}amino)pyrimidin-4-yl]oxy}-2-hydroxycyclopentyl)methyl rel-sulfamate (Compound I-66)

The title compound was prepared following the procedure described in Example 34, steps a-c and Example 65, step d. $^1$H-NMR (400 MHz, CD$_3$OD) δ: 8.18 (s, 1H), 7.28-7.16 (m, 4H), 6.14-5.94 (bs, 1H), 5.81-5.71 (bs, 1H), 5.31-5.23 (bs, 1H), 4.39-4.35 (m, 1H), 4.31 (dd, 1H, J=9.7, 7.5 Hz), 4.13 (dd, 1H, J=9.7, 7.3 Hz), 3.98 (dd, 1H, J=15.6, 7.8 Hz), 3.53 (dd, 1H, J=16.1, 7.3 Hz), 3.17 (s, 3H), 3.01 (dd, 1H, J=16.1, 8.1 Hz), 2.73 (s, 3H), 2.56-2.44 (m, 1H), 2.29-2.20 (m, 1H), 2.04-1.88 (m, 3H). LC/MS: R$_t$=5.70 min, ES$^+$ 492.2 (FA long).

Example 75

((1R,2R,4S)-4-{[6-({(1R,2S)-2-[(dimethylamino)methyl]-2,3-dihydro-1H-inden-1-yl}amino)pyrimidin-4-yl]oxy}-2-hydroxycyclopentyl)methyl rel-sulfamate (Compound I-53)

Step a: rel-(1R,2S)-2-[(dimethylamino)methyl]indan-1-amine

To a stirred suspension of lithium tetrahydroaluminate (256 mg, 6.74 mmol) in THF (20.0 mL) was added a solution of rel-(1R,2R)-1-amino-N,N-dimethylindane-2-carboxamide (580 mg, 2.70 mmol) in THF (10.0 mL) at 0° C. under an atmosphere of Argon, and then the mixture was stirred for 1 h at 60° C. following by stirring for 14 h at 23° C. The reaction mixture was quenched by addition of water and 1.00 M NaOH (5.00 mL), and the resulting mixture was stirred for 2 h. This suspension was filtered through a Celite pad, and the filtrate was concentrated in vacuo. The residue was purified by flash chromatography (5 to 20% Methanol/DCM with 1% NH$_4$OH) to afford the title compound (438 mg, 95%) as a light brown oil.

Step b: ((1R,2R,4S)-4-{[6-({(1R,2S)-2-[(dimethyl-amino)methyl]-2,3-dihydro-1H-inden-1-yl}amino)pyrimidin-4-yl]oxy}-2-hydroxycyclopentyl)methyl rel-sulfamate (Compound I-53)

The title compound was prepared following the procedure described in Example 34, steps a-c using rel-(1R,2S)-2-[(dimethylamino)methyl]indan-1-amine and Example 65, step d. $^1$H-NMR (400 MHz, CD$_3$OD) δ: 8.14 (s, 1H), 7.28-7.14 (m, 4H), 5.90-5.78 (bs, 1H), 5.70-5.40 (bs, 1H), 5.38-5.28 (bs, 1H), 4.41-4.36 (m, 1H), 4.32 (dd, 1H, J=9.8, 7.5 Hz), 4.15 (dd, 1H, J=9.8, 7.3 Hz), 3.09-3.00 (m, 1H), 2.94-2.82 (m, 2H), 2.57-2.46 (m, 1H), 2.37 (br d, 2H, J=6.2 Hz), 2.30-2.20 (m, 1H), 2.22 (s, 6H), 2.11-1.91 (m, 3H). LC/MS: R$_t$=4.34 min, ES$^+$ 478.2 (FA long).

Example 76

{(1S,2S,4R)-4-[(2-{[(1S)-5-chloro-3,3-dimethyl-2,3-dihydro-1H-inden-1-yl]amino}pyridin-4-yl)oxy]-2-hydroxycyclopentyl}methyl sulfamate (Compound I-35)

Step a: 1-(4-chlorophenyl)-3-methylbutan-2-ol

To a suspension of magnesium (2.98 g, 0.123 mol) in ether (30 mL) was added iodine (0.165 g, 0.000651 mol). To this was slowly added a solution of 4-chlorobenzyl bromide (24.00 g, 0.1168 mol) in ether (100 mL). Upon addition of approximately 1 mL of solution an exotherm was noted and the mixture reached reflux. The addition of solution was slowly continued to maintain a gentle reflux (~90 min). On completion of addition, the reaction was heated for 30 minutes at 45° C. The reaction was then cooled to 0° C. Isobutyraldehyde (12.7 mL, 0.140 mol) in ether (10 mL) was then added slowly over 2 hours. On completion of the addition the reaction was allowed to warm to 23° C. and stirred overnight. The reaction was quenched with ice (~200 g) and acidified with 2M HCl (~100 ml). This was extracted twice with ether and the organic phase was evaporated. The residue was purified by flash chromatography (0 to 10% MeOH/CH$_2$Cl$_2$) to afford the title compound (9.89 g, 43%).

Step b: 6-chloro-1,1-dimethylindane

To a solution of concentrated sulfuric acid (3.00 mL, 0.056 mol) in water (0.28 mL, 0.0156 mol) was added 1-(4-chlorophenyl)-3-methylbutan-2-ol (1.00 g, 0.00503 mol) over 30 minutes. Additional sulfuric acid was added to dissolve the solid. The mixture was stirred for 2 hours. The mixture was poured onto ice then extracted with ether. The organic phase was washed (water), dried (MgSO$_4$), filtered, and concentrated. The residue was filtered through a plug of silica with CH$_2$Cl$_2$ to afford the title compound (0.568 g, 63%).

Step c: 5-chloro-3,3-dimethylindan-1-one

To a solution of 6-chloro-1,1-dimethylindane (6.00 g, 0.0332 mol) in acetone (100 mL, 2 mol) was added 1.5 M of magnesium sulfate in water (30 mL) and potassium permanganate (12.3 g, 0.0780 mol). The reaction was stirred overnight, the resulting deposit was filtered, and the solution was concentrated to a reduced volume. The solution was extracted with EtOAc (3×100 ml) and the organic layer was concentrated. Purification by flash chromatography (10% EtOAc/hexanes) afforded the title compound (4.33 g, 67%) as a white solid.

Step d: (2R)-2-{[(1S)-5-chloro-3,3-dimethyl-2,3-dihydro-1H-inden-1-yl]amino}-2-phenylethanol To a mixture of 5-chloro-3,3-dimethylindan-1-one (4.33 g, 0.0222 mol) and (R)-(−)-2-phenylglycinol (3.2 g, 0.0234 mol) in toluene (200 mL) was added p-toluenesulfonic acid monohydrate (241 mg, 0.00127 mol). The reaction was stirred at reflux (140° C.) under an atmosphere of nitrogen overnight, cooled and diluted with toluene. The mixture was washed with saturated aqueous NaHCO$_3$ and water and the organic phase was concentrated. The residue was dissolved in THF (200 mL) under an atmosphere of nitrogen and cooled at 0° C. To this was added acetic acid (3.79 mL, 0.0667 mol) and sodium borohydride (1.26 g, 0.0334 mol). The reaction was stirred under at atmosphere of nitrogen overnight. The reaction was partitioned between CH$_2$Cl$_2$ and saturated aqueous NaHCO$_3$ solution, separated, and the organic phase was evaporated. The residue was purified by flash chromatography (20 to 100% EtOAc/hexanes) to afford the title compound (6.25 g, 90%) as a white solid.

Step e: (1S)-5-chloro-3,3-dimethylindan-1-amine.HCl

To a solution of lead(IV) acetate (9.92 g, 0.0212 mol) in methanol (80 mL) at 0° C. under an atmosphere of nitrogen was added (2R)-2-{[(1S)-5-chloro-3,3-dimethyl-2,3-dihydro-1H-inden-1-yl]amino}-2-phenylethanol (4.288 g, 0.01358 mol) as a solution in methanol (80 mL) dropwise over 10 min. On completion of the addition, the mixture was warmed to 23° C. and stirred for 90 mins. To this was added 0.943 M of sodium carbonate in water (194 mL) and the mixture stirred for 10 min. CH$_2$Cl$_2$ (500 mL) was added and the mixture was filtered and washed with CH$_2$Cl$_2$. The filtrates were collected, the organic phase was separated and the aqueous extracted with CH$_2$Cl$_2$ (25 ml). The combined organics were evaporated to dryness. The residue was dissolved in ethanol (500 mL) and 10.4 M of hydrochloric acid in water (15.6 mL) was added. The mixture was heated to reflux (95° C.) overnight. The mixture was cooled, evaporated and the residue was treated with ether and sonicated. The solid was isolated by filtration, washed with ether and dried to yield the title compound (2.704 g, 86%) as the HCl salt.

Step f: 4-{[(1R,3S,4S)-3-{[tert-butyl(dimethyl)silyl]oxy}-4-({[tert-butyl(dimethyl)silyl]-oxy}methyl)cyclopentyl]oxy}-N-[(1S)-5-chloro-3,3-dimethyl-2,3-dihydro-1H-inden-1-yl]pyridin-2-amine To a mixture of [1,3-bis(2,6-diisopropylphenyl)imidazolidin-2-yl](chloro)[(2,3-η)-(1Z)-1-phenylprop-1-ene-2,3-diyl]palladium(2+) (3.4 mg, 0.0000052 mol) and potassium tert-butoxide (32.0 mg, 0.000286 mol) under an atmosphere of argon was added 4-{[(1R,3S,4S)-3-{[tert-butyl(dimethyl)silyl]oxy}-4-({[tert-butyl(dimethyl)silyl]oxy}methyl)-cyclopentyl]oxy}-2-chloropyridine (0.1226 g, 0.0002596 mol) in 1.00 ml DME, followed by (1S)-5-chloro-3,3-dimethyl-indan-1-amine (0.048 g, 0.00025 mol) in 1 ml DME. The mixture was stirred overnight, and the solution was poured into 50 ml EtOAc, washed with 10 ml water and concentrated. The residue was purified by preparative plate chromatography (70% EtOAc/hexanes) to afford the title compound (28.0 mg, 18.0%).

Step g: {(1S,2S,4R)-2-{[tert-butyl(dimethyl)silyl]oxy}-4-[(2-{[(1S)-5-chloro-3,3-dimethyl-2,3-dihydro-1H-inden-1-yl]amino}pyridin-4-yl)oxy]cyclopentyl)methanol The title compound was prepared by a method analogous to Example 34, step c.

Step h: {(1S,2S,4R)-2-1[tert-butyl(dimethyl)silyl]oxy}-4-[(2-{[(1S)-5-chloro-3,3-dimethyl-2,3-dihydro-1H-inden-1-yl]amino}pyridin-4-yl)oxy]cyclopentyl}methyl sulfamate To a solution of {(1S,2S,4R)-2-[tert-butyl(dimethyl)silyl]oxy}-4-[(2-{[(1S)-5-chloro-3,3-dimethyl-2,3-dihydro-1H-inden-1-yl]amino}pyridin-4-yl)oxy]cyclopentyl)-methanol (28.1 mg, 0.0000543 mol) in DMA (1.00 mL) was added chlorosulfonamide (0.0251 g, 0.000217 mol) in 0.50 ml acetonitrile. The mixture was stirred for 30 min then poured into 50 ml EtOAc and 1.00 ml Et$_3$N. The layers were separated and the organic layer was washed (water) and concentrated. The residue was purified by preparative plate chromatography (85% EtOAc/hexanes) to afford the title compound (28.7 mg, 89%) as a white solid.

Step i: {(1S,2S,4R)-4-[(2-{[(1S)-5-chloro-3,3-dimethyl-2,3-dihydro-1H-inden-1-yl]amino}-pyridin-4-yl)oxy]-2-hydroxycyclopentyl}methyl sulfamate A solution of {(1S,2S,4R)-2-{[tert-butyl(dimethyl)silyl]oxy}-4-[(2-{[(1S)-5-chloro-3,3-dimethyl-2,3-dihydro-1H-inden-1-yl]amino}pyridin-4-yl)oxy]cyclopentyl}methyl sulfamate (0.0287 g, 0.0000481 mol) in 3.0% (V/V) HCl in ethanol (25.0 ml) was stirred for 4 hrs. The reaction was concentrated and dissolved in 50 ml EtOAc and 1.00 ml triethylamine. The solution was washed with water, concentrated, and the residue was isolated by preparative plate chromatography (5% MeOH/EtOAc) to afford the title compound (16.5 mg, 71%) as a white solid. $^1$H NMR (CDCl$_3$, 400 MHz) δ: 7.92 (d, 1H, J=5.8 Hz), 7.22-7.20 (m, 1H), 7.17-7.14 (m, 2H), 6.16 (dd, 1H, J=6.0 Hz, J=2.3 Hz) 5.85 (d, 1H, J=2.0 Hz), 5.30 (m, 1H), 4.92 (m, 1H), 4.70 (d, 1H, J=8.5 Hz), 4.50 (dt, 1H, J=5.0 Hz, J=1.9 Hz), 4.40 (dd, 1H, J=7.3 Hz, J=2.5 Hz), 4.28 (dd, 1H, J=7.3 Hz, J=2.5 Hz), 2.60 (bs, 1H), 2.50 (q, 1H, J=7.0 Hz), 2.31-2.25 (m, 1H), 2.18-2.12 (m, 1H), 1.95-1.87 (m, 2H), 1.79 (m, 1H), 1.25 (s, 6H). LC/MS: R$_t$=1.81 min, ES+ 482 (AA standard).

Example 77

((1S,2S,4R)-2-hydroxy-4-{[2-(1-naphthyl)-3H-imidazo[4,5-b]pyridin-7-yl]oxy}-cyclopentyl)methyl sulfamate (Compound I-109)

Step a: 2-amino-4-chloro-3-nitropyridine

To a solution of 2-amino-4-chloropyridine (5.00 g, 0.0389 mol) in sulfuric acid (40.8 mL) with stirring at 0° C. was added a solution of nitric acid (2.72 g, 0.0389 mol) and sulfuric acid (3.89 g, 0.0389 mol). The mixture was stirred (1 hr) then poured into 200 g ice and 100 ml water. The solid was filtered and collected. The solution was neutralized with 28% NH in water to pH ~5. The solution was extracted with EtOAc (3×300 ml). The solid also was dissolved in EtOAc and neutralized with 28% NH$_3$ in H$_2$O. The organic layers were combined, concentrated with 30 g silica gel, and purified by flash chromatography (20 to 60% EtOAc/hexanes) to afford the title compound (2.40 g, 36%) as a yellow solid.

Step b: 4-{[(1R,3S,4S)-3-{[tert-butyl(dimethyl)silyl]oxy}-4-({[tert-butyl(dimethyl)silyl]-oxy}methyl)cyclopentyl]oxy}-3-nitropyridin-2-amine To a solution of (1R,3S,4S)-3-{[tert-butyl(dimethyl)silyl]oxy}-4-({[tert-butyl(dimethyl)silyl]oxy}methyl)cyclopentanol (0.782 g, 0.00217 mol) in THF (30.0 mL) was added NaH (0.156 g, 0.00650 mol) and the mixture was stirred for 1 h. To this was added 2-amino-4-chloro-3-nitropyridine (0.376 g, 0.00217 mol) and the mixture was stirred overnight. The solution was concentrated and the residue was purified by flash chromatography (25% EtOAc/hexanes) to afford the title compound (0.381 g, 35%) as a yellow solid.

Step c: 4-{[(1R,3S,4S)-3-{[tert-butyl(dimethyl)silyl]oxy}-4-({[tert-butyl(dimethyl)silyl]-oxy}methyl)cyclopentyl]oxy}pyridine-2,3-diamine To a solution of 4-{[(1R,3S,4S)-3-{[tert-butyl(dimethyl)silyl]oxy}-4-({[tert-butyl(dimethyl)silyl]oxy}methyl)cyclopentyl]oxy}-3-nitropyridin-2-amine (0.361 g, 0.000725 mol) in CH$_2$Cl$_2$ (6.00 mL) and acetic acid (3.00 mL) was added zinc (0.474 g, 0.00725 mol) and the mixture was stirred for 30 min. The suspension was filtered and the filtrate was concentrated. The residue was dissolved in 50 ml EtOAc and 3 ml Et$_3$N then washed with water (2×10 mL). The organic layer was dried (MgSO$_4$) and concentrated to afford the crude product (0.297 g, 88%).

Step d: 7-{[(1R,3S,4S)-3-{[tert-butyl(dimethyl)silyl]oxy}-4-({[tert-butyl(dimethyl)silyl]-oxy}methyl)cyclopentyl]oxy}-2-(1-naphthyl)-3H-imidazo[4,5-b]pyridine A mixture of 1-naphthalenecarboxaldehyde (115 mg, 0.000738 mol), 4-{[(1R,3S,4S)-3-{[tert-butyl(dimethyl)silyl]oxy}-4-({[tert-butyl(dimethyl)silyl]oxy}methyl)cyclopentyl]oxy}pyridine-2,3-diamine (115.1 mg, 0.0002460 mol) and sodium metabisulfite (0.140 g, 0.000738 mol) in acetonitrile (2.00 mL) was subject to microwave irradiation at 180° C. for 25 mins. The mixture was filtered and the filtrate was concentrated. The residue was purified by preparative plate chromatography (25% EtOAc/hexanes) to afford the title compound (0.101 g, 68%) as a white solid.

Step e: ((1S,2S,4R)-2-{[tert-butyl(dimethyl)silyl]oxy}-4-{[2-(1-naphthyl)-3H-imidazo[4,5-b]pyridin-7-yl]oxy}cyclopentyl)methanol The title compound was prepared by a method analogous to Example 34, step C.

Step f: ((1S,2S,4R)-2-hydroxy-4-{[2-(1-naphthyl)-3H-imidazo[4,5-b]pyridin-7-yl]oxy}-cyclopentyl)methyl sulfamate (Compound I-109)

To a solution of ((1S,2S,4R)-2-{[tert-butyl(dimethyl)silyl]oxy}-4-{[2-(1-naphthyl)-3H-imidazo[4,5-b]pyridin-7-yl]oxy}cyclopentyl)methanol (0.0624 g, 0.000127 mol) in DMA (2.00 mL) was added chlorosulfonamide (0.0736 g, 0.000637 mol) and the mixture was stirred for 10 min. To this was added 12 M of hydrochloric acid in water (2.00 mL) dropwise at 0° C. and the mixture was stirred for 10 min. The mixture was added dropwise to 50 mL of a 2N Na$_2$CO$_3$ solution, and was extracted by CH$_2$Cl$_2$ (3×30 ml). The combined organic layers were concentrated and the residue was purified by flash chromatography (0 to 10% MeOH/ EtOAc) to provide the title compound (14.5 mg, 25%) as a white solid. $^1$H NMR (CD$_3$OD, 400 MHz) δ: 8.49 (m, 1H), 8.28 (m, 1H), 8.06 (d, 1H, J=8.3 Hz), 7.97 (m, 1H), 7.87 (dd, 1H, J=7.0 Hz, J=1.0 Hz) 7.63-7.54 (m, 3H), 6.89 (d, 1H, J=5.8 Hz) 5.40 (bs, 1H), 4.45 (dt, 1H, J=4.9 Hz, J=1.9 Hz), 4.35 (dd, 1H, J=7.2 Hz, J=2.5 Hz), 4.19 (dd, 1H, J=7.2 Hz, J=2.5 Hz), 2.62 (m, 1H), 2.44-2.39 (m, 1H), 2.31-2.25 (m, 1H), 2.18-2.14 (m, 2H). LC/MS: R$_t$=1.55 min, ES+ 455 (AA standard).

Example 78

((1S,2S,4R)-4-{[6-chloro-2-(1-naphthyl)-3H-imidazo[4,5-b]pyridin-7-yl]-amino}-2-hydroxycyclopentyl)methyl sulfamate (Compound I-56)

Step a: N(4)-[(1R,3S,4S)-3-{[tert-butyl(dimethyl) silyl]oxy}-4-({[tert-butyl(dimethyl)silyl]-oxy}methyl)cyclopentyl]-5-chloro-3-nitropyridine-2, 4-diamine A solution of 4,5-dichloro-3-nitropyridin-2-amine (0.0365 g, 0.000175 mol) (Johansson, H; Lawitz, K; Nikitidis, G; Sjoe, P; Storm, P. PCT Int. Application WO2004/ 016611), (1R,3S,4S)-3-{[tert-butyl(dimethyl)silyl]oxy}-4-({[tert-butyl(dimethyl)silyl]-oxy}methyl)cyclopentanamine (0.0947 g, 0.000263 mol) and DIPEA (0.0907 g, 0.000702 mol) in ethanol (10.0 mL) was refluxed overnight. The reaction was concentrated and purified by flash chromatography (30% EtOAc/hexanes) to afford the title compound (0.0768 g, 82%) as a yellow solid.

Step b: N(4)-[(1R,3S,4S)-3-{[tert-butyl(dimethyl silyl]oxy}-4-({[tert-butyl(dimethyl)silyl]-oxy}methyl)cyclopentyl]-5-chloropyridine-2,3,4-triamine N(4)-[(1R,3S,4S)-3-{[tert-butyl(dimethyl)silyl]oxy}-4-({[tert-butyl(dimethyl)-silyl]oxy}methyl)cyclopentyl]-5-chloro-3-nitropyridine-2,4-diamine (0.875 g, 0.00165 mol) and zinc (0.431 g, 0.00659 mol) was added to acetic acid (40.0 mL, 0.704 mol) with stirring for 10 mins. The mixture was stirred for 10 min and the solid was filtered off. The filtrate was concentrated, dissolved in EtOAc (50 mL) washed with water (2×10). To the organic phase was added 2 ml Et$_3$N and the mixture was washed with 10 mL water. The organic layer was concentrated and purified by flash chromatography (30% EtOAc/hexanes) to afford the title compound (0.746 g, 90%) as a white solid.

Step c: ((1S,2S,4R)-4-{[6-chloro-2-(1-naphthyl)-3H-imidazo[4,5-b]pyridin-7-yl]amino}-2-hydroxycyclopentyl)methyl sulfamate (Compound I-56)

The title compound was prepared in an analogous fashion to Example 77, steps d-f. $^1$H NMR (CD$_3$OD, 400 MHz) δ: 9.13 (d, 1H, J=9.9), 8.05-7.92 (m, 4H), 7.65-7.57 (m, 3H), 5.82 (bs, 1H), 4.41 (dt, 1H, J=5.0 Hz, J=1.9 Hz), 4.32 (dd, 1H, J=7.3 Hz, J=2.5 Hz), 4.17 (dd, 1H, J=7.3 Hz, J=2.5 Hz), 3.25 (q, 2H, J=7.8 Hz), 2.40-2.28 (m, 2H), 2.05-1.94 (m, 2H). LC/MS: R$_t$=1.68 min, ES+ 488 (AA standard).

Example 79

((1S,2S,4R)-4-{[6-(cyclopentylamino)pyrimidin-4-yl]oxy}-2-hydroxycyclopentyl)methyl sulfamate (Compound I-127)

The title compound was prepared in a manner analogous to Example 34, step b using cyclopentanamine and Example 76, steps g-i. $^1$H NMR (CD$_3$OD, 400 MHz) δ: 8.08 (s, 1H), 5.74 (s, 1H), 5.31 (bs, 1H), 4.38 (dt, 1H, J=5.0 Hz, J=1.9 Hz), 4.30 (dd, 1H, J=7.2 Hz, J=2.5 Hz), 4.15 (dd, 1H, J=7.2 Hz, J=2.5 Hz), 2.51 (m, 1H), 2.34-2.26 (m, 1H), 2.09-1.96 (m, 6H), 1.76 (m, 2H), 1.64 (m, 2H), 1.51 (m, 2H). LC/MS: R$_t$=1.46 min ES+ 373 (AA standard).

Example 80

[(1S,2S,4R)-4-({2-[(1S)-2,3-dihydro-1H-inden-1-yl amino]pyridin-4-yl}oxy)-2-hydroxycyclopentyl] methyl sulfamate (Compound I-94)

Step a: 4-{[(1R,3S,4S)-3-{[tert-butyl(dimethyl)silyl] oxy}-4-{[tert-butyl(dimethyl)silyl]oxy}methyl)cyclopentyl]oxy}-2-chloropyridine To a solution of (1R,3S,4S)-3-{[tert-butyl(dimethyl)silyl] oxy}-4-({[tert-butyl(dimethyl)silyl]oxy}methyl)cyclopentanol (973.5 mg, 0.002699 mol) in DMF (8.00 mL, 0.103 mol) was added NaH (202 mg, 0.00504 mol) (60% in oil). After stirring the mixture for 10 minutes, 2-chloro-4-nitropyridine (400.0 mg, 0.00252 mol) was added and the mixture was stirred overnight. The reaction was quenched with water and extracted with (3×50 ml EtOAc). The combined organic layers were dried (Na$_2$SO$_4$), filtered and concentrated in vacuo. The residue was purified by flash chromatography (0 to 10% EtOAc/hexanes) to obtain the title compound (0.9859 g, 83%) as a clear oil.

Step b: 4-{[(1R,3S,4S)-3-{[tert-butyl(dimethyl)silyl] oxy}-4-({[tert-butyl(dimethyl)silyl]-oxy}methyl) cyclopentyl]oxy}-N-[(1S)-2,3-dihydro-1H-inden-1-yl]pyridin-2-amine To a mixture of [1,3-bis(2,6-diisopropylphenyl)imidazolidin-2-yl](chloro)[(2,3-η)-(1Z)-1-phenylprop-1-ene-2,3-diyl]palladium(2+) (7.8 mg, 0.000012 mol) and potassium tert-butoxide (73.7 mg, 0.000656 mol) under an atmosphere of argon was added 4-{[(1R,3S,4S)-3-{[tert-butyl(dimethyl) silyl]oxy}-4-({[tert-butyl(dimethyl)silyl]oxy}methyl)-cyclopentyl]oxy}-2-chloropyridine (281.8 mg, 0.0005968 mol) in 1 ml DME. The solution was stirred for 5 mins, then (S)-(+)-1-aminoindane (0.10 mL, 0.000776 mol) in 1.0 ml DME was added dropwise over 15 min. The solution was stirred overnight, then dissolved in 50 mL EtOAc, washed with water, and concentrated. The residue was purified by flash chromatography (30% EtOAc/hexanes) to afford the title compound (0.3219 g, 95%) as a white solid.

Step c: [(1S,2S,4R)-4-({2-[(1S)-2,3-dihydro-1H-inden-1-yl amino]pyridin-4-yl}oxy)-2-hydroxycyclopentyl]methyl sulfamate (Compound I-94)

The title compound was prepared in a manner analogous to Example 76, steps g-i. $^1$H NMR (CDCl$_3$, 400 MHz) δ:

7.75 (d, 1H, J=6.0 Hz), 7.27-7.13 (m, 3H), 6.16 (dd, 1H, J=6.3 Hz, J=2.4 Hz), 5.33 (t, 1H, J=7.5 Hz), 4.95 (m, 1H), 4.50 (dt, 1H, J=5.1 Hz, J=2.0 Hz), 4.31 (dd, 1H, J=7.3 Hz, J=2.4 Hz), 4.15 (dd, 1H, J=7.3 Hz, J=2.4 Hz), 3.03-2.96 (m, 1H), 2.86 (m, 1H), 2.61-2.46 (m, 2H), 2.29-2.23 (m, 1H), 2.10-2.03 (m, 1H), 2.00-1.95 (m, 1H), 1.90-1.80 (m, 1H), 1.15-1.10 (m, 2H).

Example 81

{(1S,2S,4R)-4-[(6-{([(1R,2S)-2,7-dimethoxy-1,2,3,4-tetrahydronaphthalen-1-yl]-amino}pyrimidin-4-yl)oxy]-2-hydroxycyclopentyl}methyl sulfamate (Compound I-149)

The title compound was prepared as a 1:1 mixture of with the compound in example 82 according to Example 34, steps a-d, followed by HCl-mediated desilylation. Rel-(1R,2S)-2,7-dimethoxy-1,2,3,4-tetrahydronaphthalen-1-amine, prepared according to the reference found in Example 71, was used as a coupling partner in step b. The title compound was then isolated via chiral HPLC (Chiralcel OD 20×250, eluent 88/12/0.2% hex/EtOH/DEA at 20 mL/min). $^1$H NMR (CD$_3$OD, 400 MHz) δ: 8.14 (d, J=0.7 Hz, 1H), 7.00 (d, J=8.3 Hz, 1H), 6.76-6.71 (m, 2H), 5.94 (s, 1H), 5.32 (bs, 1H), 4.39 (ddd, J=2.2, 5.2, 5.2 Hz, 1H), 4.32 (dd, J=7.4, 9.8 Hz, 1H), 4.15 (dd, J=7.3, 9.8 Hz, 1H), 3.73 (ddd, J=2.1, 3.8, 6.4 Hz, 1H), 3.67 (s, 3H), 3.40 (s, 3H), 2.93-2.80 (m, 2H), 2.67 (ddd, J=5.6, 5.6, 11.6 Hz, 1H), 2.58-2.46 (m, 1H), 2.28 (ddd, J=2.2, 6.8, 14.8 Hz, 1H), 2.25-2.16 (m, 1H), 2.12-1.87 (m, 4H). LC/MS: R$_t$=1.25 min, ES$^+$ 495 (FA standard).

Example 82

{(1S,2S,4R)-4-[(6-{[(1S,2R)-2,7-dimethoxy-1,2,3,4-tetrahydronaphthalen-1-yl]-amino}pyrimidin-4-yl)oxy]-2-hydroxycyclopentyl}methyl sulfamate (Compound I-148)

The title compound was prepared as a 1:1 mixture of with the compound in example 81 according to Example 34, steps a-d, followed by HCl-mediated desilylation. Rel-(1R,2S)-2,7-dimethoxy-1,2,3,4-tetrahydronaphthalen-1-amine, prepared according to the reference found in Example 71, was used as a coupling partner in step b. The title compound was then isolated via chiral HPLC (Chiralcel OD 20×250, eluent 88/12/0.2% hex/EtOH/DEA at 20 mL/min). $^1$H NMR (CD$_3$OD, 400 MHz) δ: 8.14 (d, J=0.7 Hz, 1H), 7.00 (d, J=8.3 Hz, 1H), 6.76-6.71 (m, 2H), 5.94 (s, 1H), 5.32 (bs, 1H), 4.39 (ddd, J=2.1, 5.1, 5.1 Hz, 1H), 4.32 (dd, J=7.5, 9.8 Hz, 1H), 4.15 (dd, J=7.3, 9.8 Hz, 1H), 3.74 (ddd, J=2.1, 3.9, 6.6 Hz, 1H), 3.67 (s, 3H), 3.40 (s, 3H), 2.95-2.82 (m, 2H), 2.67 (ddd, J=5.7, 5.7, 11.5 Hz, 1H), 2.58-2.47 (m, 1H), 2.28 (ddd, J=2.2, 6.8, 14.8 Hz, 1H), 2.25-2.16 (m, 1H), 2.12-1.87 (m, 4H). LC/MS: R$_t$=1.25 min, ES$^+$ 495 (FA standard).

Example 83

{(1S,2S,4R)-2-hydroxy-4-[(6-{[(1S,2R)-2-methoxy-4,4-dimethyl-1,2,3,4-tetrahydronaphthalen-1-yl]amino}pyrimidin-4-yl)oxy]cyclopentyl}methyl sulfamate (Compound I-151)

The title compound was prepared as a 1:1 mixture of with the compound in example 84 according to example 34, steps a-d, followed by HC-mediated desilylation and then treatment with 1.0 equivalents of potassium hydroxide as a solution in methanol to afford the corresponding potassium salt. Rel-(1R,2S)-2-methoxy-4,4-dimethyl-1,2,3,4-tetrahydronaphthalen-1-amine, prepared according to the reference found in Example 71, was used as a coupling partner in step b. The title compound was then isolated via chiral HPLC (Chiralpak AD 20×250, eluent 85/15/0.1% hex/EtOH/DEA at 20 mL/min). $^1$H NMR (CD$_3$OD, 400 MHz) δ: 8.13 (s, 1H), 7.39-7.34 (m, 1H), 7.25-7.18 (m, 2H), 7.13-7.06 (m, 1H), 5.90 (s, 1H), 5.64 (bs, 1H), 5.24 (bs, 1H), 4.40 (ddd, J=1.7, 5.6, 5.6 Hz, 1H), 4.14 (ddd, J=1.3, 8.5, 10.0 Hz, 1H), 4.00 (ddd, J=2.0, 6.4, 10.0 Hz, 1H), 3.78 (ddd, J=3.0, 4.1, 10.4 Hz, 1H), 3.42 (s, 3H), 2.53-2.38 (m, 1H), 2.26 (dddd, J=1.8, 1.8, 6.7, Hz, 1H), 2.12-1.81 (m, 4H), 1.77 (dd, J=2.0, 13.6 Hz, 1H), 1.43 (s, 3H), 1.31 (s, 3H). LC/MS: R$_t$=1.61 min, ES$^+$ 493 (FA standard).

Example 84

{(1 S,2S,4R)-2-hydroxy-4-[(6-{[(1R,2S)-2-methoxy-4,4-dimethyl-1,2,3,4-tetrahydronaphthalen-1-yl]amino}pyrimidin-4-yl)oxy]cyclopentyl}methyl sulfamate (Compound I-150)

The title compound was prepared as a 1:1 mixture of with the compound in example 83 according to example 34, steps a-d, followed by HO-mediated desilylation and then treatment with 1.0 equivalents of potassium hydroxide as a solution in methanol to afford the corresponding potassium salt. Rel-(1R,2S)-2-methoxy-4,4-dimethyl-1,2,3,4-tetrahydronaphthalen-1-amine, prepared according to the reference found in Example 71, was used as a coupling partner in step b. The title compound was then isolated via chiral HPLC (Chiralpak AD 20×250, eluent 85/15/0.1% hex/EtOH/DEA at 20 mL/min). $^1$H NMR (CD$_3$OD, 400 MHz) δ: 8.14 (s, 1H), 7.40-7.35 (m, 1H), 7.26-7.18 (m, 2H), 7.13-7.07 (m, 1H), 5.91 (s, 1H), 5.65 (bs, 1H), 5.25 (bs, 1H), 4.40 (ddd, J=1.7, 5.6, 5.6 Hz, 1H), 4.14 (ddd, J=1.3, 8.5, 10.0 Hz, 1H), 4.00 (ddd, J=1.8, 6.4, 9.9 Hz, 1H), 3.79 (ddd, J=3.4, 3.4, 10.4 Hz, 1H), 3.42 (s, 3H), 2.52-2.38 (m, 1H), 2.32-2.21 (m, 1H), 2.12-1.81 (m, 4H), 1.78 (dd, J=2.0, 13.5 Hz, 1H), 1.43 (s, 3H), 1.32 (s, 3H). LC/MS: R$_t$=1.61 min, ES$^+$ 493 (FA standard).

Example 85

[(1S,2S,4S)-4-({6-[(1S)-2,3-dihydro-1H-inden-1-ylamino]pyrimidin-4-yl}methyl)-2-hydroxycyclopentyl]methyl sulfamate (I-33)

Step a: 2-Chloro-N-[(1S)-2,3-dihydro-1H-inden-1-yl]-6-methylpyrimidine-4-amine 2,4-Dichloro-6-methylpyrimidine (2.54 g, 0.156 mol) was dissolved in ethanol (100 mL) and N,N-Diisporopylethylamine (4.07 mL, 0.23 mol) was added followed by (S)-1-Aminoindan (2.00 mL, 0.156 mol). The solution was heated to reflux for 2 hours, TLC indicated complete conversion. The solvent was removed in vacuo and the residue was purified using chromatography on silica gel using gradient 0 to 50% ethyl acetate in hexane to afford the title compound (1.95 g, 46%). LC/MS: R$_t$=1.90 min, ES$^+$ 260 (AA standard).

Step b: N-[(1S)-2,3-dihydro-1H-inden-1-yl]-6-methylpyrimidine-4-amine

2-Chloro-N-[(1S)-2,3-dihydro-1H-inden-1-yl]-6-methylpyrimidine-4-amine (1.95 g, 7.5 mmol) was dissolved in ethanol (5 mL) and 10% Pd/C (0.140 g, 0.13 mmol) was added. The flask was filled with hydrogen and stirred overnight. At that time, TLC indicated complete conversion. Palladium was filtered off and the solvent was removed in vacuo. The residue was purified using chromatography on silica gel using gradient 50 to 100% ethyl acetate in hexane to afford the title compound (1.65 g, 93%). LC/MS: $R_t$=1.51 min, ES$^+$ 226 (AA standard).

Step c: (4aS,6S,7S,7aR)-6-{6-[(1S)-2,3-Dihydro-1H-inden-1-ylamino]-pyrimidin-4-yl}-methyl)-2-(4-methoxyphenyl)hexahydrocyclopenta[d][1,3]dioxin-7-ol N-[(1S)-2,3-dihydro-1H-inden-1-yl]-6-methylpyrimidine-4-amine (0.575 g, 2.55 mmol) was dissolved in THF (24 mL) and 1.8M Phenyllithium in di-n-butyl ether (2.98 mL, 5.36 mmol) was added and stirred for 1 hour. The mixture was cooled to 0° C. and a solution of (1aS,1bR,5aS,6aS)-3-(4-methoxyphenyl)hexahydrooxireno[4,5]cyclopenta[1,2-d][1,3]dioxine (0.634 g, 2.55 mmol) in THF (15 mL) was slowly added. The mixture was stirred at 0° C. for 45 minutes and 23° C. for 2 hours. At that time, LCMS indicated ~70% conversion. The reaction was quenched using saturated ammonium chloride (30 mL), extracted with ethyl acetate (3×20 mL), dried with anhydrous magnesium sulfate, filtered, and evaporated in vacuo. The residue was purified using chromatography on silica gel using gradient 50 to 100% ethyl acetate in hexane to afford the title compound (0.465 g, 38%). LC/MS: $R_t$=1.77 min, ES$^+$ 474 (AA standard).

Step d: O-[(4aS,6S,7S,7aR)-6-{[(1S)-2,3-Dihydro-1H-inden-1-ylamino]-pyrimidin-4-yl}-methyl)-2-(4-methoxyphenyl)hexahydrocyclopenta[d][1,3]dioxin-7-yl] O-phenyl thiocarbonate (4aS,6S,7S,7aR)-6-{6-[(1 S)-2,3-Dihydro-1H-inden-1-ylamino]-pyrimidin-4-yl}methyl)-2-(4-methoxyphenyl) hexahydrocyclopenta[d][1,3]dioxin-7-ol (0.465 g, 0.98 mmol) was dissolved in DCM (17 mL) under an atmosphere of argon and 4-(dimethylamino)-pyridine (0.24 g, 1.96 mmol) was added followed by phenyl chlorothionocarbonate (0.204 mL, 1.47 mmol). The mixture was stirred for 1 hour. The solvent was concentrated in vacuo and the residue was purified via silica gel chromatography eluting with a gradient of 50 to 100% EtOAc in hexanes on a column pre-treated with 1% TEA in hexanes to afford the title compound (0.508 g, 84%). LC/MS: $R_t$=2.38 min, ES$^+$ 610 (AA standard).

Step e: N-[(1S)-2,3-Dihydro-1H-inden-1-yl]-6-{[(4aS,6S,7aS)-2-(4-methoxyphenyl)-hexahydrocyclopenta[d][1,3]dioxin-6-yl]methyl}pyrimidin-4-amine O-[(4aS,6S,7S,7aR)-6-{[(1S)-2,3-Dihydro-1H-inden-1-ylamino]-pyrimidin-4-yl}methyl)-2-(4-methoxyphenyl) hexahydrocyclopenta[d][1,3]dioxin-7-yl] O-phenyl thiocarbonate (0.508 g, 0.83 mmol) was dissolved in toluene (14 mL) under an atmosphere of nitrogen and tri-n-butyltin hydride (0.448 mL, 1.67 mmol) was added followed by 2,2'-azo-bis-isobutyronitrile (0.027 mg, 0.17 mmol). The solution was heated to reflux for 1 hour, the mixture was cooled down, the solvent was concentrated to 30 mL and the residue was purified via silica gel chromatography eluting with a gradient of 50 to 100% EtOAc in hexanes to afford the title compound (0.280 g, 73%). LC/MS: $R_t$=1.94 min, ES$^+$ 458 (AA standard).

Step f: (1 S,2S,4S)-4-({6-[(1S)-2,3-Dihydro-1H-inden-1-ylamino]pyrimidin-4-yl}methyl)-2-(hydroxymethyl)cyclopentanol N-[(1S)-2,3-Dihydro-1H-inden-1-yl]-6-{[(4aS,6S,7aS)-2-(4-methoxyphenyl)-hexahydrocyclopenta[d][1,3]dioxin-6-yl]methyl}pyrimidin-4-amine (0.280 g, 0.61 mmol) was dissolved in THF (2 mL), water (2 mL) and AcOH (6 mL, 0.106 mmol) were added. The mixture was stirred under an atmosphere of argon for 60 h. The mixture was concentrated under reduced pressure and the residue was purified via silica gel chromatography eluting with a gradient of 0 to 10% MeOH in DCM to afford the title compound (0.190 g, 91%). LC/MS: $R_t$=1.29 min, ES$^+$ 340 (AA standard).

Step g: [(1S,2S,4S)-4-({6-[(1S)-2,3-dihydro-1H-inden-1-ylamino]pyrimidin-4-yl}methyl)-2-hydroxycyclopentyl]methyl sulfamate (I-33)

The title compound was prepared following the procedure described in Example 65, step d. $^1$H NMR (CD$_3$OD, 400 MHz, δ): 8.34 (s, 1H), 7.27-7.15 (m, 4H), 6.41 (bs, 1H), 5.65-5.48 (m, 1H), 4.30-4.25 (m, 2H), 4.09 (dd, J=4.1, 4.1 Hz, 1H), 3.07-3.00 (m, 1H), 2.94-2.85 (m, 1H), 2.72-2.55 (m, 4H), 2.43-2.35 (m, 1H), 1.93-1.85 (m, 2H), 1.75-1.67 (m, 1H), 1.58-1.51 (m, 2H). LC/MS: $R_t$=1.38 min, ES$^+$ 419 (AA standard).

Example 86

((1S,2S,4R)-4-{4-[(1S)-2,3-Dihydro-1H-inden-1-ylamino]-5,6-dihydro-7H-pyrrolo[2,3-d]pyrimidin-7-yl}-2-hydroxycyclopentyl)methyl sulfamate (Compound I-146)

Step a: 2-(4,6-dichloropyrimidin-5-yl)ethanol (4,6-dichloropyrimidin-5-yl)acetaldehyde (2.96 g, 15.5 mmol) was dissolved in methanol (60 mL) and cooled at 0° C. Sodium tetrahydroborate (0.879 g, 23.2 mmol) was added and the mixture was stirred for 1 hour. TLC indicated complete conversion. The reaction was quenched with water (20 mL), methanol was removed in vacuo and the residue was extracted with ethyl acetate (3×30 mL). The combined organic extracts were dried with magnesium sulfate, filtered and evaporated. The residue was purified using chromatography on silica gel using gradient 0 to 100% ethyl acetate in methylene chloride to afford the title compound (1.90 g, 63%). LC/MS: $R_t$=0.93 min, ES$^+$ 194 (AA standard).

Step b: 2-{4-chloro-6-[(1S-2,3-dihydro-1H-inden-1-ylamino]pyrimidin-5-yl}ethanol 2-(4,6-dichloropyrimidin-5-yl)ethanol (1.90 g, 9.84 mmol) was dissolved in 1-butanol (97 mL) and N,N-Diisopropylethylamine (3.43 mL, 19.7 mmol) and (S)-1-Aminoindane (1.26 mL, 9.84 mmol) were added. The solution was heated at 130° C. for 3 days. Solvent was removed in vacuo and the residue was purified using chromatography on silica gel using gradient 0 to 100% ethyl acetate in methylene chloride to afford the title compound (2.80 g, 98%). LC/MS: $R_t$=1.63 min, ES$^+$ 290 (AA standard).

Step c: 2-(2-{4-chloro-6-[(1S)-2,3-dihydro-1H-inden-1-ylamino]pyrimidin-5-yl}ethyl)-1H-isoindole-1,3(2H)-dione 2-{4-chloro-6-[(1 S)-2,3-dihydro-1H-inden-1-ylamino] pyrimidin-5-yl}ethanol (2.80 g, 9.66 mmol), phthalimide (1.56 g, 10.6 mmol) and triphenylphosphine (2.79 g, 10.6 mmol) were dissolved in THF (105 mL) and the solution was cooled at 0° C. DIAD (2.09 mL, 10.6 mmol) was added dropwise and the mixture was stirred 23° C. for 1 hour. The solvent was removed in vacuo and the residue was purified using chromatography on silica gel using gradient 10 to 50% ethyl acetate in hexane to afford the title compound (3.50 g, 86%). LC/MS: $R_t$=2.12 min, $ES^+$ 419 (AA standard).

Step d: 5-(2-aminoethyl)-6-chloro-N-[(1)-2,3-dihydro-1H-inden-1-yl]pyrimidin-4-amine 2-(2-{4-chloro-6-[(1S)-2,3-dihydro-1H-inden-1-ylamino] pyrimidin-5-yl}ethyl)-1H-isoindole-1,3(2H)-dione (3.50 g, 8.32 mmol) was suspended in ethanol (102 mL) and hydrazine hydrate (1.62 mL, 33.3 mmol) was added. The mixture was heated to reflux for 1 hour. At that time, LCMS indicated complete conversion. The mixture was cooled to 23° C., crystals were filtered off, the residue was evaporated in vacuo and purified using chromatography on silica gel using gradient 0 to 20% MeOH in methylene chloride to afford the title compound (1.20 g, 50%). LC/MS: $R_t$=1.29 min, $ES^+$ 289 (AA standard).

Step e: N-[(1S)-2,3-dihydro-1H-inden-1-yl]-6,7-dihydro-5H-pyrrolo[2,3-d]pyrimidin-4-amine 5-(2-aminoethyl)-6-chloro-N-[(1 S)-2,3-dihydro-1H-inden-1-yl]pyrimidin-4-amine (1.00 g, 3.46 mmol) and N,N-diisopropylethylamine (1.21 mL, 6.92 mmol) were dissolved in 1,4-dioxane (19 mL) and the solution was heated in a pressure tube at 160° C. for 48 hours. At that time, LCMS indicated complete conversion. Solvent was removed in vacuo and the residue was purified using chromatography on silica gel using gradient 0 to 20% MeOH in methylene chloride to afford the title compound (0.81 g, 93%). LC/MS: $R_t$=1.55 main, $ES^+$ 253 (AA standard).

Step f: 7-[(1R,3S,4S)-3-{[tert-butyl(dimethyl)silyl]oxy}-4-{[tert-butyl(dimethyl)silyl]oxy}-methyl)cyclopentenyl-N-[(1S)-2,3-Dihydro-1H-inden-1-yl]-6,7-dihydro-5H-pyrrolo[2,3-d]pyrimidin-4-amine N-[(1S)-2,3-dihydro-1H-inden-1-yl]-6,7-dihydro-5H-pyrrolo[2,3-d]pyrimidin-4-amine (0.460 mg, 1.82 mmol) was dissolved in DMF (20 mL) and NaH (60%, 0.146 g, 3.65 mmol) was added. The mixture was heated at 60° C. for 5 minutes. (1S,3S,4S)-3-{[tert-butyl(dimethyl)silyl]oxy}-4-{[tert-butyl(dimethyl)silyl]oxy}methyl)cyclopentenyl methanesulfonate (0.800 g, 1.82 mmol) in DMF (10 mL) was added and the resulting mixture was heated at 100° C. for 2 hours. The solution was cooled to 23° C., quenched with saturated brine (20 mL), extracted with ethyl acetate (3×30 mL), dried with magnesium sulfate, filtered and evaporated in vacuo. The residue was purified using chromatography on silica gel using gradient 0 to 30% ethyl acetate in hexane to afford the title compound (0.22 g, 20%). LC/MS: $R_t$=7.17 min, $ES^+$ 596 (AA Nonpolar: Phenominex Luna 5 um C18 50×4.6 mm column at 2.5 ml/min gradient of ACN containing 50 to 0% 10 mM Ammonium Acetate in $H_2O$ for 3 min.)

Step g: ((1S,2S,4R)-4-{4-[(1S)-2,3-Dihydro-1H-inden-1-ylamino]-5,6-dihydro-7H-pyrrolo-[2,3-d]pyrimidin-7-yl}-2-hydroxycyclopentyl)methyl sulfamate (Compound I-146)

The title compound was prepared following the procedures described in Example 34, step c and Example 65, step d. $^1$H NMR (CD$_3$OD, 400 MHz) δ: 7.93 (s, 1H), 7.23-7.12 (m, 4H), 5.64-5.60 (m, 1H), 4.87-4.83 (m, 1H), 4.34-4.31 (m, 1H), 4.29 (dd, J=7.6, 9.6 Hz, 1H), 4.13 (dd, J=7.2, 9.6 Hz, 1H), 3.58-3.53 (m, 2H), 3.03-2.95 (m, 1H), 2.90-2.77 (m, 3H), 2.59-2.42 (m, 2H), 2.00-1.97 (m, 2H), 1.91-1.82 (m, 3H). LC/MS: $R_t$=4.98 min, $ES^+$ 446 (FA long).

Example 87

((1R,2R,3S,4R)-4-{[2-2,3-dihydro-1H-indol-1-ylcarbonyl)pyridine-4-yl}amino}-2,3-dihydroxycyclopentyl)methylsulfamate (Compound I-145)

$^1$H NMR (400 MHz, CD$_3$OD) δ: 8.20-8.00 (m, 2H), 7.30-6.70 (m, 5H), 4.26-4.02 (m, 3H), 3.88-3.78 (m, 2H), 3.17-3.11 (m, 2H) 2.50-2.30 (m, 2H), 1.40-1.20 (m, 3H), ppm. LC/MS: $R_t$=0.95 min, $ES^+$ 449 (AA standard).

Example 88

{(1R,2R,3S,4R)-4-[(2-{[(1S)-2,3-dihydro-1H-inden-1-ylamino]carbonyl}pyridine-4-yl)amino]-2,3-dihydroxycyclopentyl}methylsulfamate (Compound I-144)

$^1$H NMR (CD$_3$OD, 300 MHz) δ: 8.05 (d, J=7.5 Hz, 1H), 7.50 (bs, 1H), 7.32-7.16 (m, 4H), 6.97-6.92 (m, 1H), 5.64 (t, J=7.54 Hz, 1H), 4.17 (d, J=5.09 Hz, 2H), 4.09-3.80 (m, 3H), 3.15-3.04 (m, 1H), 3.00-2.87 (m, 1H), 2.66-2.54 (m, 1H), 2.45-2.29 (m, 2H), 2.11-1.97 (m, 1H), 1.44-1.34 (m, 1H) ppm. LC/MS: $R_t$=1.35 min, $ES^+$ 463 (AA standard).

Example 89

((1S,2S,4R)-4-([8-(3-chlorophenyl)-9H-purin-6-yl]amino)-2-hydroxycyclopentyl)methyl sulfamate (Compound I-60)

Step a: 6-chloro-4,5-diaminopyrimidine

A suspension of 5-Amino-4,6-dichloropyrimidine (3 g, 0.02 mol) in ammonia (25 mL, 7N/MeOH, 0.175 mole) was heated at 118° C. overnight (under pressure). The reaction was cooled to 23° C., filtered and washed with ethanol to obtain 1.92 g (70%).

Step b: 6-chloro-8-(3-chlorophenyl)-9H-purine

To a mixture of 6-Chloro-4,5-diaminopyrimidine (0.70 g, 4.84 mmol) and 3-chlorobenzoic acid (0.76 g, 4.84 mmol) in the flask was added phosphoryl chloride (40.0 mL), and the resulting mixture was stirred for 16 h at 100° C. The reaction mixture was evaporated to remove excess phosphoryl chloride, and the residue was added to water (20 mL). The precipitate was filtered and purified by flash chromatography (0 to 5% Methanol/DCM) to afford the title compound (1.28 g, 31%) as a yellow solid. LC/MS: $R_t$=1.59 min, $ES^+$ 265.0 (FA standard).

Step c: N-[(1R,3S,4S)-3-{[tert-butyl(dimethyl)silyl] oxy}-4-({[tert-butyl(dimethyl)silyl]oxy}-methyl) cyclopentyl]-8-(3-chlorophenyl)-9H-purin-6-amine A solution of 6-chloro-8-(3-chlorophenyl)-9H-purine (155 mg, 0.58 mmol), (1R,3S,4S)-3-{[tert-butyl(dimethyl)silyl]oxy}-4-({[tert-butyl (dimethyl)silyl]oxy}methyl)-cyclopentanamine (200 mg, 0.56 mmol) (Example 128, steps a-c), and N,N-diisopropylethylamine (0.20 mL, 1.17 mmol) in ethanol (2.00 mL) was microwaved at 160° C. for 30 minutes. The reaction mixture was concentrated under vacuum, and the residue was purified by flash chromatography (0 to 5% Methanol/DCM) to afford the title compound (275 mg, 76%) as a light yellow solid.

Step d: ((1S,2S,4R)-2-{[tert-butyl(dimethyl)silyl] oxy}-4-{[8-(3-chlorophenyl)-9H-purin-6-yl] amino}cyclopentyl)methanol The title compound was prepared following the procedure described in Example 34, step c. LC/MS: $R_t$=2.07 min, ES$^+$ 474.2 (AA standard).

Step e: ((1S,2S,4R)-4-{[8-(3-chlorophenyl)-9H-purin-6-yl]amino}-2-hydroxycyclopentyl)methyl sulfamate (Compound I-60)

The title compound was prepared following the procedure described in Example 65, step d. $^1$H-NMR (400 MHz, CD$_3$OD) δ: 8.22 (s, 1H), 8.09 (s, 1H), 8.00-7.94 (m, 1H), 7.54-7.48 (m, 2H), 4.93-4.84 (m, 1H), 4.44-4.40 (m, 1H), 4.35 (dd, 1H, J=9.7, 7.8 Hz), 4.17 (dd, 1H, J=9.7, 7.3 Hz), 2.64-2.54 (m, 1H), 2.35 (ddd, 1H, J=14.0, 7.6, 1.2 Hz), 2.20-2.10 (m, 1H), 1.96 (ddd, 1H, J=14.0, 7.0, 4.8 Hz), 1.86 (ddd, 1H, J=13.0, 8.2, 3.8 Hz). LC/MS: $R_t$=5.48 min, ES$^+$ 439.1 (FA long)

Example 90

((1S,2S,4R)-4-[8-(2,6-dimethoxyphenyl)-9H-purin-6-yl]amino)-2-hydroxycyclopentyl)methyl sulfamate (Compound I-93)

The title compound was prepared following the procedure described in Example 89 (steps a-e) using 2,6-dimethoxybenzoic acid. $^1$H-NMR (400 MHz, CD$_3$OD) δ: 8.21 (s, 1H), 7.46 (t, 1H, J=8.6 Hz), 6.78 (d, 2H, J=8.6 Hz), 4.90-4.79 (m, 1H), 4.43-4.38 (m, 1H), 4.34 (dd, 1H, J=9.6, 7.5 Hz), 4.17 (dd, 1H, J=9.6, 7.3 Hz), 3.81 (s, 6H), 2.62-2.52 (m, 1H), 2.34 (ddd, 1H, J=14.0, 7.5, 1.7 Hz), 2.15 (ddd, 1H, J=13.8, 10.3, 8.9), 1.93 (ddd, 1H, J=14.0, 6.5, 5.3 Hz), 1.84 (ddd, 1H, J=13.8, 8.6, 3.8 Hz). LC/MS: $R_t$=4.30 min, ES$^+$ 465.2 (FA long).

Example 91

[(1S,2S,4R)-2-hydroxy-4-({8-[2-(trifluoromethyl) phenyl]-9H-purin-6-yl}amino)cyclopentyl]methyl sulfamate (Compound I-122)

The title compound was prepared following the procedure described in Example 89 (steps a-e) using aza-Trifluoro-o-toluic acid. $^1$H-NMR (400 MHz, CD$_3$OD) δ: 8.26 (s, 1H), 7.92 (dd, 1H, J=7.0, 1.9 Hz), 7.82-7.71 (m, 3H), 4.96-4.85 (m, 1H), 4.43-4.38 (m, 1H), 4.34 (dd, 1H, J=9.8, 7.4 Hz), 4.16 (dd, 1H, J=9.8, 7.3 Hz), 2.63-2.52 (m, 1H), 2.34 (ddd, 1H, J=14.0, 7.5, 1.8 Hz), 2.15 (ddd, 1H, J=13.5, 10.6, 8.8 Hz), 1.95 (ddd, 1H, J=14.0, 7.1, 5.0 Hz), 1.85 (ddd, 1H, J=13.5, 8.6, 3.8 Hz). LC/MS: $R_t$=5.17 min, ES$^+$ 473.2 (FA long).

Example 92

((1S,2S,4R)-2-hydroxy-4-{[8-(2-phenoxyphenyl)-9H-purin-6-yl]amino}-cyclopentyl)methyl sulfamate (Compound I-37)

The title compound was prepared following the procedure described in Example 89 (steps a-e) using 2-phenoxybenzoic acid. $^1$H-NMR (400 MHz, THF-d8) δ: 8.40 (br d, 1H, J=7.5 Hz), 8.18 (bs, 1H), 7.43-7.34 (m, 3H), 7.25-7.13 (m, 4H), 6.94 (d, 1H, J=8.3 Hz), 6.87 (br d, 1H, J=7.5 Hz), 5.17-4.93 (m, 1H), 4.41-4.35 (m, 1H), 4.35 (dd, 1H, J=9.8, 7.7 Hz), 4.13 (dd, 1H, J=9.8, 7.3 Hz), 2.63-2.52 (m, 1H), 2.35-2.25 (m, 1H), 2.20-2.06 (m, 1H), 2.01-1.91 (m, 1H), 1.87 (ddd, 1H, J=13.3, 8.8, 4.4 Hz). LC/MS: $R_t$=5.83 min, ES$^+$ 497.2 (FA long).

Example 93

((1S,2S,4R)-2-hydroxy-4-{[8-(1-naphthyl)-9H-purin-6-yl]amino}cyclopentyl)-methyl sulfamate (Compound I-49)

The title compound was prepared following the procedure described in Example 89 (steps a-e) using 1-naphthalenecarboxylic acid. $^1$H-NMR (400 MHz, CD$_3$OD) δ: 8.70-8.55 (bs, 1H), 8.26 (s, 1H), 8.02 (d, 1H, J=8.3 Hz), 7.98-7.93 (m, 1H), 7.84 (dd, 1H, J=7.1, 1.1 Hz), 7.61-7.52 (m, 3H), 5.01-4.80 (m, 1H), 4.41-4.37 (m, 1H), 4.34 (dd, 1H, J=9.5, 7.6 Hz), 4.16 (dd, 1H, J=9.5, 7.3 Hz), 2.61-2.50 (m, 1H), 2.34 (ddd, 1H, J=14.0, 7.6, 1.5 Hz), 2.20-2.10 (m, 1H), 1.94 (ddd, 1H, J=14.0, 7.0, 4.9 Hz), 1.84 (ddd, 1H, J=13.1, 8.3, 3.8 Hz). LC/MS: $R_t$=5.48 min, ES$^+$ 455.1 (FA long).

Example 94

((1S,2S,4R)-4-[(8-dibenzo[b,d]furan-4-yl-9H-purin-6-yl)amino]-2-hydroxycyclopentyl)methyl sulfamate (Compound I-39)

The title compound was prepared following the procedure described in Example 89 (steps a-e) using dibenzofuran-4-carboxylic acid. $^1$H-NMR (400 MHz, CD$_3$OD) δ: 8.25 (s, 1H), 8.15-8.07 (m, 2H), 8.04 (d, 1H, J=7.9 Hz), 7.74 (d, 1H, J=8.2 Hz), 7.56-7.50 (m, 1H), 7.46 (t, 1H, J=7.6 Hz), 7.40 (dd, 1H, J=7.9, 7.2 Hz), 4.91-4.77 (m, 1H), 4.47-4.43 (m, 1H), 4.38 (dd, 1H, J=9.8, 7.5 Hz), 4.20 (dd, 1H, J=9.8, 7.2 Hz), 2.67-2.56 (m, 1H), 2.38 (ddd, 1H, J=14.0, 7.8, 1.2 Hz), 2.24-2.13 (m, 1H), 1.99 (ddd, 1H, J=14.0, 6.7, 5.0 Hz), 1.89 (ddd, 1H, J=13.0, 8.4, 3.7 Hz). LC/MS: $R_t$=5.74 min, ES$^+$ 495.0 (FA long).

Example 95

{(1S,2S,4R)-4-[(8-Biphenyl-3-yl-9H-purin-6-yl) amino]-2-hydroxycyclopentyl}-methyl sulfamate (Compound I-105)

The title compound was prepared following the procedure described in Example 89 (steps a-e) using biphenyl-3-carboxylic acid. $^1$H-NMR (400 MHz, THF-d8) δ: 12.38-12.25 (bs, 1H), 10.95-10.80 (bs, 1H), 8.38 (t, 1H, J=1.8 Hz), 8.17 (s, 1H), 8.05 (d, 1H, J=7.3 Hz), 7.72-7.68 (m, 3H), 7.55

(t, 1H, J=7.6 Hz), 7.48-7.43 (m, 2H), 7.35 (tt, 1H, J=7.3, 1.3 Hz), 6.87 (br d, 1H, J=6.5 Hz), 6.57-6.45 (bs, 2H), 5.15-4.90 (m, 1H), 437-4.31 (m, 1H), 4.31 (dd, 1H, J=9.5, 7.8 Hz), 4.09 (dd, 1H, J=9.5, 7.3 Hz), 3.95-3.85 (bs, 1H), 2.31-2.21 (m, 1H), 2.16-2.04 (m, 1H), 1.94 (ddd, 1H, J=13.1, 8.0, 4.4 Hz), 1.84 (ddd, 1H, J=13.3, 8.8, 4.2 Hz). LC/MS: $R_t$=6.17 min, ES$^+$ 481.0 (FA long).

Example 96

((1S,2S,4R)-2-hydroxy-4-{[8-(5,6,7,8-tetrahy-dronaphthalen-1-yl)-9H-purin-6-yl]amino}cyclopentyl)methyl sulfamate (Compound I-126)

The title compound was prepared following the procedure described in Example 89 (steps a-e) using 5,6,7,8-tetrahydro-naphthalene-1-carboxylic acid. $^1$H-NMR (400 MHz, CD$_3$OD) δ: 8.22 (s, 1H), 7.38-7.32 (m, 1H), 7.25-7.19 (m, 2H), 4.92-4.82 (m, 11H), 4.42-4.38 (m, 1H), 4.34 (dd, 1H, J=9.5, 7.8 Hz), 4.16 (dd, 1H, J=9.5, 7.3 Hz), 2.93-2.83 (m, 4H), 2.62-2.51 (m, 1H), 2.33 (ddd, 1H, J=13.8, 7.5, 1.8 Hz), 2.15 (ddd, 1H, J=13.5, 10.3, 8.8 Hz), 1.94 (ddd, 1H, J=13.8, 7.1, 4.8 Hz), 1.88-1.73 (m, 5H). LC/MS: $R_t$=5.22 min, ES$^+$ 459.1 (FA long).

Example 97

((1S,2S,4R)-2-hydroxy-4-{[8-(1-naphthyl)-9H-purin-6-yl]oxy}cyclopentyl)-methyl sulfamate (Compound I-87)

The title compound was prepared following the procedures described in Example 33 (steps a-b, e-f) and Example 65 (step d) using (1R,3S,4S)-3-{[tert-butyl(dimethyl)-silyl]oxy}-4-({[tert-butyl(dimethyl)silyl]oxy}methyl)cyclopentanol. $^1$H-NMR (400 MHz, CD$_3$OD) δ: 8.53-8.46 (m, 1H), 8.52 (s, 1H), 8.08 (d, 1H, J=8.0 Hz), 8.01-7.96 (m, 1H), 7.88 (dd, 1H, J=7.3, 1.2 Hz), 7.65-7.55 (m, 3H), 5.98-5.91 (m, 1H), 4.90-4.85 (m, 1H), 4.48-4.43 (m, 1H), 4.36 (dd, 1H, J=9.8, 7.5 Hz), 4.20 (dd, 1H, J=9.8, 7.2 Hz), 2.71-2.60 (m, 1H), 2.44 (ddd, 1H, J=15.0, 6.7, 1.9 Hz), 2.27 (ddd, 1H, J=15.0, 5.0, 4.5 Hz), 2.20-2.13 (m, 1H). LC/MS: $R_t$=6.48 min, ES$^+$ 456.0 (FA long).

Example 98

1(1S,2S,4R)-4-[(8-biphenyl-2-yl-9H-purin-6-yl)amino]-2-hydroxycyclopentyl)-methyl sulfamate (Compound I-48)

The title compound was prepared following the procedure described in Example 89 (steps a-e) using 2-biphenylcarboxylic acid. $^1$H-NMR (400 MHz, CD$_3$OD) δ: 8.14 (s, 1H), 7.73 (dd, 1H, J=7.6, 1.1 Hz), 7.65-7.60 (m, 1H), 7.57-7.50 (m, 2H), 7.30-7.24 (m, 3H), 7.22-7.18 (m, 2H), 4.88-4.77 (m, 1H), 4.41-4.36 (m, 1H), 4.33 (dd, 1H, J=9.7, 7.5 Hz), 4.15 (dd, 1H, J=9.7, 7.5 Hz), 2.60-2.48 (m, 1H), 2.34-2.25 (m, 1H), 2.16-2.04 (m, 1H), 1.94-1.85 (m, 1H), 1.84-1.74 (m, 1H). LC/MS: $R_t$=5.43 min, ES$^+$ 481.0 (FA long).

Example 99

((1S,2S,4R)-4-{[8-(2,2-dimethyl-2,3-dihydro-1-benzofuran-7-yl)-9H-purin-6-yl]amino}-2-hydroxycyclopentyl)methyl sulfamate (Compound I-100)

The title compound was prepared following the procedure described in Example 89 (steps a-e) using 2,2-dimethyl-2, 3-dihydro-1-benzofuran-7-carboxylic acid. $^1$H-NMR (400 MHz, CD$_3$OD) δ: 8.30-8.19 (m, 1H), 8.06-8.02 and 7.90-7.80 (each bs, total 1H), 7.34-7.28 (m, 1H), 6.99 (t, 1H, J=6.5 Hz), 4.90-4.80 (m, 1H), 4.45-4.40 (m, 1H), 4.35 (dd, 1H, J=9.7, 7.7 Hz), 4.18 (dd, 1H, J=9.7, 7.5 Hz), 3.15 (bs, 2H), 2.64-2.52 (m, 1H), 2.44-2.30 (m, 1H), 2.23-2.10 (m, 1H), 2.01-1.90 (m, 1H), 1.86 (ddd, 1H, J=13.0, 8.2, 3.7 Hz), 1.64 (bs, 3H), 1.61 (s, 3H). LC/MS: $R_t$=5.17 min, ES$^+$ 475.3 (FA long).

Example 100

[(1S,2S,4R)-4-({8-[4-(dimethylamino)-1-naphthyl]-9H-purin-6-yl}amino)-2-hydroxycyclopentyl]methyl sulfamate (Compound I-64)

The title compound was prepared following the procedure described in Example 89 (steps a-e) using 4-dimethylaminonaphthalene-1-carboxylic acid. $^1$H-NMR (400 MHz, CD$_3$OD) δ: 8.70-8.58 (bs, 1H), 8.34-8.28 (m, 1H), 8.25 (s, 1H), 7.77 (d, 1H, J=7.9 Hz), 7.60-7.53 (m, 1H), 7.21 (d, 1H, J=7.9 Hz), 4.98-4.84 (m, 1H), 4.44-4.39 (m, 1H), 4.35 (dd, 1H, J=9.8, 7.6 Hz), 4.17 (dd, 1H, J=9.8, 7.3 Hz), 2.64-2.53 (m, 1H), 2.35 (ddd, 1H, J=14.0, 7.6, 1.6 Hz), 2.22-2.12 (m, 1H), 1.97 (ddd, 1H, J=14.0, 7.0, 5.0 Hz), 1.87 (ddd, 1H, J=12.5, 8.6, 3.5 Hz). LC/MS: $R_t$=5.39 min, ES$^+$ 498.0 (FA long).

Example 101

((1S,2S,4R)-2-hydroxy-4-{[8-(3-methoxyphenyl)-9H-purin-6-yl]amino}cyclopentyl)methyl sulfamate (Compound I-99)

The title compound was prepared following the procedure described in Example 89 (steps a-e) using 3-Methoxybenzoic acid. $^1$H-NMR (400 MHz, MeOD, δ): 8.22 (s, 1H), 7.62 (m, 2H), 7.43 (t, J=7.9 Hz, 1H), 7.07 (dd, J=2.3 Hz, 8.3 Hz, 1H), 4.42 (t, J=4.3 Hz, 1H), 4.35 (dd, J=7.7 Hz, 9.7 Hz, 1H), 4.17 (dd, J=7.3 Hz, 9.7 Hz, 1H), 3.89 (s, 1H), 2.59 (m, 1H), 2.35 (ddd, J=1.1 Hz, 7.6 Hz, 14.2 Hz, 1H), 2.16 (td, 1H, J=9.4 Hz, 13.3 Hz), 1.96 (ddd, J=5.1 Hz, J=6.9 Hz, J=14.0 Hz, 1H), 1.86 (ddd, J=3.8 Hz, 8.5 Hz, 13.1 Hz, 1H). LC/MS: $R_t$=1.33 min, ES$^+$ 435 (AA standard).

Example 102

{(1S,2S,4R)-4-[(8-benzyl-9H-purin-6-yl)amino]-2-hydroxycyclopentyl}methyl sulfamate (Compound I-88)

The title compound was prepared following the procedure described in Example 89 (steps a-e) using Benzeneacetic acid. $^1$H-NMR (400 MHz, CD$_3$OD) δ: 8.17 (s, 1H), 7.35-7.21 (m, 5H), 4.84-4.71 (m, 1H), 4.40-4.35 (m, 1H), 4.33 (dd, J=7.5, 9.8 Hz, 1H), 4.19 (s, 2H), 4.14 (dd, J=7.3, 9.8 Hz, 1H), 2.59-2.45 (m, 1H), 2.34-2.23 (m, 1H), 2.17-2.04 (m, 1H), 1.92-1.82 (m, 1H), 1.82-1.72 (m, 1H) ppm. LC/MS: $R_t$=3.94 min, ES$^+$ 419 (FA Waters).

Example 103

((1S,2S,4R)-2-hydroxy-4-{[8-(1,2,3,4-tetrahydronaphthalen-1-yl)-9H-purin-6-yl]amino}cyclopentyl)methyl sulfamate (Compound I-121)

The title compound was prepared following the procedure described in Example 89 (steps a-e) using 1,2,3,4-Tetrahydro-1-naphthalenyl hydroperoxide. $^1$H NMR (400 MHz, CD$_3$OD) δ: 8.17 (s, 1H), 7.26-7.03 (m, 3H), 6.93-6.83 (m, 1H), 4.82-4.70 (m, 1H), 4.47-4.28 (m, 3H), 4.17-4.10 (m, 1H), 3.00-2.79 (m, 2H), 2.57-2.43 (m, 1H), 2.33-2.04 (m, 4H), 1.98-1.68 (m, 5H) ppm. LC/MS: R$_t$=4.30 min, ES$^+$ 459 (FA Waters).

Example 104

[(1S,2S,4R)-4-({8-[2-(dimethylamino)phenyl]-9H-purin-6-yl}amino)-2-hydroxycyclopentyl]methyl sulfamate (Compound I-137)

The title compound was prepared following the procedure described in Example 89 (steps a-e) using 2-Dimethylaminobenzoic acid. $^1$H NMR (400 MHz, CD$_3$OD) δ: 8.23 (s, 1H), 8.06-7.93 (m, 1H), 7.48-7.39 (m, 1H), 7.35-7.28 (m, 1H), 7.20-7.12 (m, 1H), 4.45-4.39 (m, 1H), 4.36 (dd, J=7.8, 9.8 Hz, 1H), 4.18 (dd, J=7.3, 9.5 Hz, 1H), 2.68 (s, 6H), 2.63-2.52 (m, 1H), 2.40-2.29 (m, 1H), 2.21-2.09 (m, 1H), 1.99-1.90 (m, 1H), 1.89-1.80 (m, 1H) ppm. LC/MS: R$_t$=3.28 min, ES$^+$ 448 (FA Waters).

Example 105

((1S,2S,4R)-4-{[8-(2,3-dihydro-1,4-benzodioxin-5-yl)-9H-purin-6-yl]amino}-2-hydroxycyclopentyl)methyl sulfamate (Compound I-41)

The title compound was prepared following the procedure described in Example 89 (steps a-e) using 2,3-Dihydro-1,4-benzodioxine-5-carboxylic acid. $^1$H NMR (DMSO-d, 400 MHz) δ: 8.30-7.79 (m, 2H), 7.69-7.61 (m, 1H), 7.06-6.89 (m, 3H), 4.94-4.15 (m, 9H), 2.46-2.40 (m, 1H), 2.26-1.84 (m, 4H), 1.82-1.67 (m, 2H) ppm. LC/MS: R$_t$=3.93 min, ES$^+$ 463 (FA Waters).

Example 106

[(1S,2S,4R)-4-({8-[2-(benzyloxy)phenyl]-9H-purin-6-yl}amino)-2-hydroxycyclopentyl]methyl sulfamate (Compound I-68)

The title compound was prepared following the procedure described in Example 89 (steps a-e) using 2-Benzyloxybenzoic acid. $^1$H NMR (400 MHz, CD$_3$OD) δ: 8.38-8.02 (m, 2H), 7.49-7.07 (m, 8H), 5.63-5.29 (m, 2H), 4.44-4.39 (m, 1H), 4.35 (dd, J=7.8, 9.8 Hz, 1H), 4.17 (dd, J=7.3, 9.8 Hz, 1H), 2.65-2.48 (m, 11H), 2.41-2.28 (m, 1H), 2.22-2.10 (m, 1H), 2.02-1.78 (m, 2H) ppm. LC/MS: R$_t$=4.71 min, ES$^+$ 511 (FA Waters).

Example 107

{(1S,2S,4R)-4-[(8-cyclohexyl-9H-purin-6-yl)amino]-2-hydroxycyclopentyl}methyl sulfamate (Compound I-128)

The title compound was prepared following the procedure described in Example 89 (steps a-e) using Cyclohexanecarboxylic acid. $^1$H NMR (400 MHz, CD$_3$OD) δ: 8.16 (s, 1H), 4.82-4.77 (m, 1H), 4.42-4.39 (m, 1H), 4.34 (dd, J=7.6, 9.7 Hz, 1H), 4.16 (dd, J=7.3, 9.7 Hz, 1H), 2.89-2.83 (m, 1H), 2.59-2.52 (m, 1H), 2.35-2.29 (m, 1H), 2.17-2.07 (m, 3H), 1.95-1.75 (m, 5H), 1.67-1.27 (m, 5H) ppm. LC/MS: R$_t$=1.30 min, ES$^+$ 411.08 (AA standard).

Example 108

{(1S,2S,4R)-4-[(8-tert-butyl-9H-purin-6-yl)amino]-2-hydroxycyclopentyl}-methyl sulfamate (Compound I-131)

The title compound was prepared following the procedure described in Example 89 (steps a-e) using Trimethylacetic acid. $^1$H NMR (CD$_3$OD, 400 MHz) δ: 8.17 (s, 1H), 4.83-4.76 (m, 1H), 4.42-4.39 (m, 1H), 4.34 (dd, J=7.5, 9.5 Hz, 1H), 4.16 (dd, J=7.3, 9.8 Hz, 1H), 2.59-2.53 (m, 1H), 2.35-2.30 (m, 1H), 2.17-2.09 (m, 1H), 1.95-1.88 (m, 1H), 1.85-1.78 (m, 1H), 1.44 (s, 9H) ppm. LC/MS: R$_t$=1.08 min, ES$^+$ 385.24 (AA standard).

Example 109

((1S,2S,4R)-4-{[8-(4-chlorophenyl)-9H-purin-6-yl]amino}-2-hydroxycyclopentyl)methyl sulfamate (Compound I-111)

Step a: 6-chloro-8-(4-chlorophenyl)-9H-purine

To a solution of 6-Chloro-4,5-diaminopyrimidine (1 g, 0.007 mol) (Example 89, step a) in 1,4-Dioxane (60 mL, 0.8 mol) was added 4-Chlorobenzaldehyde (2.2 g, 0.016 mol) and Ferric chloride (2.5 g, 0.015 mol) mixed with 28.6 g silica gel, and the mixture was heated at 100° C. for 20 hours. The reaction was cooled to 23° C., filtered and washed with 10% ethanol/ethyl acetate and concentrated. The residue was dissolved in ethyl acetate and washed with water, brine, and concentrated. The residue was triturated in diethyl ether to obtain 272 mg (10%). LC/MS: R$_t$=1.54 min, ES$^+$ 265 (AA standard).

Step b: ((1S,2S,4R)-4-{[8-(4-chlorophenyl)-9H-purin-6-yl]amino}-2-hydroxycyclopentyl)methyl sulfamate (Compound I-111)

The title compound was prepared following the procedure described in Example 89 (steps c-d) and Example 1, step d. $^1$H NMR (CD$_3$OD, 400 MHz) δ: 8.22 (s, 1H), 8.03 (d, J=8.5 Hz, 2H), 7.55 (d, J=8.5 Hz, 2H), 4.90-4.85 (m, 1H), 4.43-4.41 (m, 1H), 4.35 (dd, J=7.6, 9.7 Hz, 1H), 4.17 (dd, J=7.3, 9.7 Hz, 1H), 2.62-2.56 (m, 1H), 2.37-2.31 (m, 1H), 2.20-2.12 (m, 1H), 2.00-1.93 (m, 1H), 1.89-1.82 (m, 1H) ppm. LC/MS: R$_t$=1.35 min, ES$^+$ 439.29 (AA standard).

Example 110

{(1S,2S,4R)-2-hydroxy-4-[(8-phenyl-9H-purin-6-yl)amino]cyclopentyl}methyl sulfamate (Compound I-69)

The title compound was prepared following the procedures described in Example 109 (step a) using benzaldehyde and Example 1 (step d) followed by TBAF deprotection of the TBS group. $^1$H NMR (CD$_3$OD, 400 MHz) δ: 8.22 (s, 1H), 8.06-8.04 (m, 2H), 7.56-7.51 (m, 3H), 4.90-4.84 (m, 1H), 4.43-4.41 (m, 1H), 4.38-4.33 (m, 1H), 4.20-4.15 (m, 1H), 2.62-2.56 (m, 1H), 2.37-2.31 (m, 1H), 2.20-2.11 (m, 1H), 2.00-1.92 (m, 1H), 1.89-1.81 (m, 1H) ppm. LC/MS: R$_t$=1.24 min, ES$^+$ 405 (AA standard).

Example 111

[(1S,2S,4R)-2-hydroxy-4-({8-[2-(trifluoromethoxy)phenyl]-9H-purin-6-yl}-amino)cyclopentyl]methyl sulfamate (Compound I-62)

The title compound was prepared following the procedures described in Example 109 (step a) and Example 89 (steps c-e) using 2-(Trifluoromethoxy) benzaldehyde. $^1$H NMR (400 MHz, CD$_3$OD) δ: 8.26 (bs, 1H), 8.05-7.95 (m, 1H), 7.69-7.61 (m, 1H), 7.60-7.50 (m, 2H), 4.45-4.39 (m, 1H), 4.35 (dd, J=7.5, 9.8 Hz, 1H), 4.17 (dd, J=7.3, 9.5 Hz, 1H), 2.67-2.51 (m, 1H), 2.40-2.29 (m, 1H), 2.22-2.10 (m, 1H), 2.07-1.91 (m, 1H), 1.90-1.81 (m, 1H) ppm. LC/MS: R$_t$=5.71 min, ES$^+$ 489 (AA Waters).

Example 112

((1S,2S,4R)-2-hydroxy-4-{[8-(2-methoxyphenyl)-9H-purin-6-yl]amino}cyclopentyl)methyl sulfamate (Compound I-133)

The title compound was prepared following the procedure described in Example 111 using 2-Methoxybenzaldehyde. $^1$H NMR (400 MHz, CD$_3$OD) δ: 8.41-8.00 (m, 2H), 7.53-7.44 (m, 1H), 7.24-7.16 (m, 1H), 7.15-7.06 (m, 1H), 4.85-4.76 (m, 1H), 4.45-4.40 (m, 1H), 4.36 (dd, J=7.8, 9.8 Hz, 1H), 4.18 (dd, J=7.3, 9.5 Hz, 1H), 4.05 (bs, 3H), 2.64-2.51 (m, 1H), 2.41-2.30 (m, 1H), 2.22-2.10 (m, 1H), 2.00-1.79 (m, 2H) ppm. LC/MS: R$_t$=3.93 min, ES$^+$ 435 (FA Waters).

Example 113

((1S,2S,4R)-2-hydroxy-4-{[6-(1-naphthyl)-7H-pyrrolo[2,3-d]pyrimidin-4-yl]-amino}cyclopentyl)methyl sulfamate (Compound I-74)

Step a: 4-chloro-6(1-naphthyl-7-(phenylsulfonyl-7H-pyrrolo[2,3-d]pyrimidine

To a stirred solution of N,N-diisopropylamine (265 µL, 1.89 mmol) in THF (3.00 mL) was added dropwise 1.60 M n-butyllithium in hexane (1.17 mL) at −78° C. under an atmosphere of Argon, and the mixture was stirred for 20 minutes at −78° C. To this mixture was added dropwise a solution of 4-chloro-7-(phenylsulfonyl)-7H-pyrrolo[2,3-d]pyrimidine (500 mg, 1.70 mmol) in THF (5.00 mL), and the mixture was stirred for 1 h at −78° C. A solution of zinc chloride (278 mg, 2.04 mmol) in THF (2.00 mL) was added dropwise, and the resulting mixture was taken out the cooling bath and allowed to stir for 1 h. To a suspension of tetrakis(triphenylphosphine)palladium(0) (100 mg, 0.08 mmol) in THF (2.00 mL) was added 1-iodonaphthalene (0.30 mL, 2.06 mmol), and the resulting yellow solution was immediately added to the reaction mixture. The resulting mixture was heated at 80° C. for 1 h. After cooling to 23° C., the reaction mixture was quenched by the addition of water (70.0 mL) and the water layer was acidified with 1.00 M hydrochloric acid. The mixture was extracted with DCM (3×100 mL), and the organic layers were combined. The organic layer was washed with brine, dried over MgSO$_4$, filtered, and evaporated under vacuum. The residue was purified via silica gel column chromatography eluting with 30% ethyl acetate in hexanes to afford the title compound (665 mg, 82%). LC/MS: R$_t$=11.11 min, ES$^+$ 420.0 (FA long).

Step b: 4-chloro-6-(1-naphthyl-7H-pyrrolo[2,3-d]pyrimidine

To a stirred solution of 4-chloro-6-(1-naphthyl)-7-(phenylsulfonyl)-7H-pyrrolo[2,3-d]pyrimidine (350 mg, 0.73 mmol) in THF (2.50 mL) was added a solution of NaOH (205 mg, 5.13 mmol) in methanol (1.19 mL), and the mixture was stirred for 15 minutes. After quenching by addition of saturated NH$_4$Cl solution (80.0 mL), the mixture was extracted with ethyl acetate (3×100 mL). The organic layers were combined, dried over MgSO$_4$, filtered, and evaporated under vacuum. The residue was dissolved in a small amount of methanol, and the suspension was filtered through a glass pad filter. The white solid was dried under high to afford the title compound (141 mg, 65%).

Step c: ((1S,2S,4R)-2-hydroxy-4-{[6-(1-naphthyl)-7H-pyrrolo[2,3-d]pyrimidin-4-yl]-amino}cyclopentyl)methyl sulfamate (Compound I-74)

The title compound was prepared following the procedure described in Example 89 (steps c-e). $^1$H-NMR (400 MHz, CD$_3$OD) δ: 8.31-8.25 (m, 1H), 8.16 (s, 1H), 7.96-7.89 (m, 2H), 7.65 (dd, 1H, J=7.0, 0.8 Hz), 7.58-7.49 (m, 3H), 6.91 (s, 1H), 4.92-4.80 (m, 1H), 4.45-4.39 (m, 1H), 4.35 (dd, 1H, J=9.6, 7.5 Hz), 4.18 (dd, 1H, J=9.6, 7.3 Hz), 2.65-2.53 (m, 1H), 2.34 (ddd, 1H, J=13.8, 7.5, 1.3 Hz), 2.21-2.11 (m, 1H), 2.00 (ddd, 1H, J=13.8, 7.0, 5.1 Hz), 1.87 (ddd, 1H, J=13.0, 8.6, 4.0 Hz). LC/MS: R$_t$=5.22 min, ES$^+$ 454.1 (FA long).

Example 114

{(1S,2S,4R)-2-hydroxy-4-[(6-phenyl-7H-pyrrolo[2,3-d]pyrimidin-4-yl)-amino]cyclopentyl}methyl sulfamate (Compound I-38)

The title compound was prepared following the procedure described in Example 113. $^1$H NMR (400 MHz, CD$_3$OD) δ: 8.10 (s, 1H), 7.78-7.71 (m, 2H), 7.45-7.38 (m, 2H), 7.33-7.26 (m, 1H), 6.93 (s, 1H), 4.86-4.79 (m, 1H), 4.44-4.39 (m, 1H), 4.35 (dd, J=7.5, 9.5 Hz, 1H), 4.17 (dd, J=7.3, 9.8 Hz, 1H), 2.64-2.52 (m, 1H), 2.36-2.27 (m, 1H), 2.19-2.08 (m, 1H), 2.02-1.93 (m, 1H), 1.88-1.79 (m, 1H) ppm. LC/MS: R$_t$=4.02 min, ES$^+$ 404 (FA Waters).

Example 115

((1S,2S,4R)-4-{[8-(7-chloroquinolin-4-yl)-7H-purin-6-yl]oxy}-2-hydroxycyclopentyl)methyl sulfamate (Compound I-73)

Step a: 6-{[(1R,3S,4S)-3-{[tert-butyl(dimethyl)silyl]oxy}-4-({[tert-butyl(dimethyl)silyl]-oxy}methyl)cyclopentyl]oxy}-9-(tetrahydro-2H-pyran-2-yl-9H-purine In DMF (4 mL, 0.05 mol) was suspended sodium hydride (47 mg, 0.0012 mol) at 0° C., to which was added a solution of (1R,3S,4S)-3-{[tert-butyl(dimethyl)silyl]oxy}-4-({[tert-butyl(dimethyl)silyl]oxy}methyl)cyclopentanol (0.200 g, 0.000554 mol) in 2.5 mL DMF. The mixture was stirred at 0° C. for 10 minutes and was added a solution of 6-Chloro-9-(tetrahydropyranyl)purine (0.265 g, 0.00111 mol) (Example 33, step b) in 4 mL DMF. The reaction was stirred at 0° C. for 1 h and warmed to 23° C. overnight. The reaction was quenched by addition of saturated aqueous NH$_4$Cl, and the mixture was extracted with ethyl acetate, washed with brine, dried (Na$_2$SO$_4$), filtered and concentrated. The residue was purified by flash chromatography (0 to 5% acetone/toluene) to obtain 271 mg (86.8%).

Step b: 6-{[(1R,3S,4S)-3-{[tert-butyl(dimethyl)silyl]oxy}-4-({[tert-butyl(dimethyl)silyl]-oxy}methyl)cyclopentyl]oxy}-8-iodo-9-(tetrahydro-2H-pyran-2-yl)-9H-purine To a solution of 6-{[(1R,3S,4S)-3-{[tert-butyl(dimethyl)silyl]oxy}-4-({[tert-butyl(dimethyl)silyl]oxy}methyl)cyclopentyl]oxy}-9-(tetrahydro-2H-pyran-2-yl)-9H-purine (288 mg, 0.000512 mol) in THF (10 mL, 0.1 mol) was added N-Iodosuccinimide (0.576 g, 0.00256 mol), and the mixture was heated at 70° C. overnight. The reaction was cooled, quenched by addition of saturated aqueous NaHSO$_3$ and the mixture was extracted with DCM (3×), washed with water, brine dried (Na$_2$SO$_4$), filtered and concentrated. The residue was purified by flash chromatography (0 to 10% EtOAc/hexanes) to obtain 271 mg (76.9%). Reference: Nolsoe, J. M. J.; Gundersen, L-L.; Rise, F. *Acta Chemica Scandinavica*, 1999, 53, 366-372.

Step c: 4-[6-{[(1R,3S,4S)-3-{[tert-butyl(dimethyl)silyl]oxy}-4-({[tert-butyl(dimethyl)silyl]-oxy}methyl)cyclopentyl]oxy}-9-(tetrahydro-2H-pyran-2-yl)-9H-purin-8-yl]-7-chloroquinoline To a solution of 6-{[(1R,3S,4S)-3-{[tert-butyl(dimethyl)silyl]oxy}-4-({[tert-butyl(dimethyl)silyl]oxy}methyl)cyclopentyl]oxy}-8-iodo-9-(tetrahydro-2H-pyran-2-yl)-9H-purine (258.4 mg, 0.0003752 mol) in 1,2-Dimethoxyethane (3.0 mL, 0.029 mol) was added 7-chloroquinoline-4-boronic acid pinacol ester (0.158 g, 0.000546 mol), barium hydroxide (0.228 g, 0.00133 mol), water (0.5 mL, 0.03 mol) and Tetrakis(triphenylphosphine)palladium(0) (0.02 g, 0.00002 mol), and the mixture was heated at 90° C. overnight. The reaction was cooled, quenched by addition of water and the mixture was extracted with DCM (3×), washed with water, brine, dried (Na$_2$SO$_4$), filtered and concentrated. The residue was purified by flash chromatography (0 to 30% EtOAc/hexanes) to obtain 180 mg (66.2%) mg. Reference: Cammidge, A. N.; Crepy, K. V. L. *Tetrahedron*, 2004, 60, 4377-4386.

Step d: ((1S,2S,4R)-4-{[8-(7-chloroquinolin-4-yl)-7H-purin-6-yl]oxy}-2-hydroxycyclopentyl)methyl sulfamate (Compound I-73)

The title compound was prepared following the procedure described in Example 89 (steps d-e). $^1$H NMR (CD$_3$OD, 400 MHz) δ: 9.05 (d, J=4.5 Hz, 1H), 8.91 (d, J=9.1 Hz, 1H), 8.57 (s, 1H), 8.15 (d, J=2.2 Hz, 1H), 7.92 (d, J=4.5 Hz, 1H), 7.72 (dd, J=2.1, 9.1 Hz, 1H), 6.00-5.95 (m, 1H), 4.48-4.45 (m, 1H), 4.37 (dd, J=7.6, 9.8 Hz, 1H), 4.21 (dd, J=7.3, 9.7 Hz, 1H), 2.70-2.63 (m, 1H), 2.49-2.43 (m, 1H), 2.31-2.25 (m, 1H), 2.21-2.17 (m, 2H) ppm. LC/MS: R$_t$=6.12 min, ES$^+$ 490.98 (AA long).

Example 116

((1S,2S,4R)-2-hydroxy-4-{[8-(1H-indol-3-yl)-7H-purin-6-yl]oxy}cyclopentyl)-methyl sulfamate (Compound I-140)

The title compound was prepared following the procedure described in Example 115 using 1-(Phenylsulfonyl)indole-3-boronic acid pinacol ester. $^1$H NMR (CD$_3$OD, 400 MHz) δ: 8.41-8.33 (m, 2H), 8.08-8.03 (m, 1H), 7.48-7.45 (m, 1H), 7.26-7.19 (m, 2H), 5.94-5.88 (m, 1H), 4.48-4.42 (m, 1H), 4.38 (dd, J=7.3, 9.8 Hz, 1H), 4.21 (dd, J=7.0, 9.8 Hz, 1H), 2.70-2.63 (m, 1H), 2.46-2.40 (m, 1H), 2.28-2.22 (m, 1H), 2.17-2.140 (m, 2H) ppm. LC/MS: R$_t$=5.78 min, ES$^+$ 445.04 (AA long).

Example 117

[(1S,2S,4R)-4-({8-[4-(dimethylamino)-1-naphthyl]-7H-purin-6-yl}oxy)-2-hydroxycyclopentyl]methyl sulfamate (Compound I-103)

The title compound was prepared following the procedure described in Example 115 using N,N-dimethyl-4-(4,4,5,5-tetramethyl-1,3,2-dioxaborolan-2-yl)naphthalen-1-amine. $^1$H NMR (CD$_3$OD, 400 MHz) δ: 8.55-8.52 (m, 1H), 8.50 (s, 1H), 8.30-8.28 (m, 1H), 7.80-7.77 (m, 1H), 7.55-7.53 (m, 2H), 7.20-7.17 (m, 1H), 5.94-5.92 (m, 1H), 4.46-4.43 (m, 1H), 4.36 (dd, J=7.5, 9.8 Hz, 1H), 4.20 (dd, J=7.3, 9.8 Hz, 1H), 2.95 (s, 6H), 2.66-2.60 (m, 1H), 2.46-2.39 (m, 1H), 2.28-2.22 (m, 1H), 2.17 (m, 2H) ppm. LC/MS: R$_t$=6.75 min, ES$^+$ 499.16 (AA long).

Example 118

((1S,2S,4R)-4-{[8-(1-benzyl-1H-pyrazol-4-yl)-7H-purin-6-yl]oxy}-2-hydroxycyclopentyl)methyl sulfamate (Compound I-129)

The title compound was prepared following the procedure described in Example 115 using 1-Benzylpyrazole-4-boronic acid pinacol ester. $^1$H NMR (CD$_3$OD, 400 MHz) δ: 8.41 (s, 1H), 8.34 (s, 1H), 8.17 (s, 1H), 7.39-7.30 (m, 5H), 5.90-5.85 (m, 1H), 5.43 (s, 2H), 4.46-4.43 (m, 1H), 4.36 (dd, J=7.6, 9.8 Hz, 1H), 4.19 (dd, J=7.2, 9.8 Hz, 1H), 2.66-2.60 (m, 1H), 2.40-2.37 (m, 1H), 2.26-2.19 (m, 1H), 2.15-2.11 (m, 2H) ppm. LC/MS: R$_t$=5.72 min, ES$^+$ 486.13 (AA long).

Example 119

{(1S,2S,4R)-2-hydroxy-4-[(8-isoquinolin-4-yl-7H-purin-6-yl)oxy]cyclopentyl}-methyl sulfamate (Compound I-112)

The title compound was prepared following the procedure described in Example 115 using 4-Isoquinolineboronic acid pinacol ester. $^1$H NMR (CD$_3$OD, 400 MHz) δ: 9.41 (s, 1H), 8.87 (s, 1H), 8.74 (d, J=8.6 Hz, 1H), 8.55 (s, 1H), 8.25 (d, J=8.4 Hz, 1H), 7.94 (m, 1H), 7.82 (m, 1H), 5.98-5.96 (m, 1H), 4.49-4.46 (m, 1H), 4.37 (dd, J=7.5, 9.8 Hz, 1H), 4.20 (dd, J=7.3, 9.7 Hz, 1H), 2.70-2.63 (m, 1H), 2.48-2.42 (m, 1H), 2.32-2.26 (m, 1H), 2.20-2.16 (m, 2H) ppm. LC/MS: R$_t$=5.15 min, ES$^+$ 457.08 (AA long).

Example 120

((1S,2S,4R)-2-hydroxy-4-{[8-(4-pyrrolidin-1-yl-1-naphthyl)-7H-purin-6-yl]-oxy}cyclopentyl)methyl sulfamate (Compound I-139)

Step a: 1-(4-bromo-1-naphthyl)pyrrolidine

To a solution of 1,4-dibromonaphthalene (500 mg, 0.002 mol), Pyrrolidine (0.18 mL, 0.0021 mol), (R)-(+)-2,2'-Bis(diphenylphosphino)-1,1'-binaphthyl (0.022 g, 0.000035 mol), Sodium tert-butoxide (0.24 g, 0.0024 mol) in Toluene (5.00 mL, 0.0469 mol) was added Tris(dibenzylideneacetone)dipalladium(0) (0.008 g, 0.000009 mol), and the mixture was heated at 70° C. overnight. The reaction was cooled, quenched by addition of water and the mixture was extracted with DCM (3×), washed with water, brine, dried (Na$_2$SO$_4$), filtered and concentrated. The residue was purified by flash chromatography (0 to 25% hexanes/DCM) to obtain 400 mg (80%). Reference: Jean, L.; Rouden, J.; Maddaluno, J.; Lasne, M-C. *J. Org. Chem.* 2004, 69, 8893-8902.

Step b: 1-[4-(4,4,5,5-tetramethyl-1,3,2-dioxaborolan-2-yl)-1-naphthyl]pyrrolidine To a solution of 1-(4-bromo-1-naphthyl)pyrrolidine (400 mg, 0.001 mol), bis(pinacolato)diboron (0.40 g, 0.0016 mol), potassium acetate (0.43 g, 0.0043 mol) in N,N-Dimethylformamide (8 mL, 0.1 mol) was added Tetrakis (triphenylphosphine)palladium(0) (0.050 g, 0.000043 mol), and the mixture was heated at 100° C. overnight. The reaction was cooled, quenched by addition of water and the mixture was extracted with diethyl ether, washed with water, brine, dried (Na$_2$SO$_4$), filtered and concentrated. The residue was purified by flash chromatography (0 to 25% DCM/hexanes) to obtain 221 mg (50%). Reference: Miyashita, K.; Sakai, T.; Imanishi, T. *Org. Lett.* 2003, 5, 2683-2686.

Step c: ((1S,2S,4R)-2-hydroxy-4-{[8-(4-pyrrolidin-1-yl-1-naphthyl-7H-purin-6-yl]oxy}cyclopentyl) methyl sulfamate (Compound I-139)

The title compound was prepared following the procedure described in Example 115 using 1-[4-(4,4,5,5-tetramethyl-1,3,2-dioxaborolan-2-yl)-1-naphthyl]pyrrolidine. $^1$H NMR (CD$_3$OD, 400 MHz) δ: 8.58 (d, J=8.1 Hz, 1H), 8.48 (s, 1H), 8.31 (d, J=8.0 Hz, 1H), 7.75 (d, J=8.4 Hz, 1H), 7.54-7.46 (m, 2H), 7.02 (d, J=8.2 Hz, 1H), 5.95-5.92 (m, 1H), 4.47-4.45 (m, 1H), 4.37 (dd, J=7.5, 9.8 Hz, 1H), 4.20 (dd, J=7.2, 9.8 Hz, 1H), 3.5 (m, 4H), 2.70-2.62 (m, 1H), 2.47-2.40 (m, 1H), 2.31-2.24 (m, 1H), 2.16 (dd, J=5.0, 9.0 Hz, 2H), 2.07-2.04 (m, 4H) ppm. LC/MS: R$_t$=7.35 min, ES$^+$ 525.26 (AA long).

Example 121

[(1S,2S,4R)-2-hydroxy-4-({8-[(3-methylphenyl) sulfanyl]-7H-purin-6-yl}-oxy)cyclopentyl]methyl sulfamate (Compound I-136)

Step a: 6-{[(1R,3S,4S)-3-{[tert-butyl(dimethyl)silyl] oxy}-4-({[tert-butyl(dimethyl)silyl]-oxy}methyl) cyclopentyl]oxy}-8-[(3-methylphenyl)sulfanyl]-9H-purine To a solution of 3-methylbenzenethiol (0.55 mL, 0.0046 mol) in DMF (10 mL, 0.2 mol) was added sodium hydride (0.093 g, 0.0023 mol). The mixture was stirred at room temperature for 10 minutes and then 6-{[(1R,3S,4S)-3-{ [tert-butyl(dimethyl)silyl]oxy}-4-({[tert-butyl(dimethyl)silyl]oxy}methyl)cyclopentyl]oxy}-8-iodo-9-(tetrahydro-2H-pyran-2-yl)-9H-purine (400 mg, 0.0006 mol) (Example 115, steps a-b) was added and the solution was heated at 150° C. for 8 hours. The reaction was cooled, quenched by addition of water and the mixture was extracted with ethyl acetate, washed with water, brine, dried (Na$_2$SO$_4$), filtered and concentrated. The residue was purified by flash chromatography (0 to 30% ethyl acetate/hexanes) to obtain 296 mg (80%) of the title compound.

Step b: [(1S,2S,4R)-2-hydroxy-4-({8-[(3-methylphenyl)sulfanyl]-7H-purin-6-yl}-oxy)cyclopentyl] methyl sulfamate (Compound I-136)

The title compound was prepared following the procedure described in Example 89 (steps d-e) $^1$H NMR (CD$_3$OD, 400 MHz) δ: 8.39 (s, 1H), 7.40-7.20 (m, 4H), 5.84-5.82 (m, 1H), 4.40-4.39 (m, 1H), 4.35-4.30 (m, 1H), 4.17-4.13 (m, 1H), 2.57-2.52 (m, 1H), 2.39-2.33 (m, 1H), 2.33 (s, 3H), 2.19-2.04 (m, 3H) ppm. LC/MS: R$_t$=6.35 min, ES$^+$ 452.04 (AA long).

Example 122

[(1S,2S,4R)-2-hydroxy-4-({8-[(3-methylphenyl) sulfonyl]-9H-purin-6-yl}-oxy)cyclopentyl]methyl sulfamate (Compound I-101)

To a solution of [(1S,2S,4R)-2-hydroxy-4-({8-[(3-methylphenyl)sulfanyl]-9H-purin-6-yl}oxy)cyclopentyl]methyl sulfamate (13 mg, 0.000029 mol) in methanol (1.0 mL, 0.025 mol) at 0° C. was added a solution of Oxone® (0.0354 g, 0.0000576 mol) in water (0.5 mL, 0.03 mol). The reaction was stirred for 4 hours at 0° C. and then warmed to 23° C. overnight. The reaction was partitioned with water and ethyl acetate:isopropanol. The layers were separated and the aqueous extracted with ethyl acetate:isopropanol. The combined organics were washed with water, brine, dried (Na$_2$SO$_4$), filtered, and collected in vacuo. The residue was purified by flash chromatography (20% MeOH/DCM) to obtain 9 mg (60%). Reference: Ref.: Ramani R. Ranatunge,* et Al., *J. Med. Chem.*, 2004, 47, 2180-2193. $^1$H NMR (CD$_3$OD, 400 MHz) δ: 8.54 (s, 1H), 7.94 (s, 1H), 7.91 (d, J=7.5 Hz, 1H), 7.56 (d, J=7.5 Hz, 1H), 7.52 (dd, J=7.6, 13.3 Hz, 1H), 5.91-5.86 (m, 1H), 4.45-4.42 (m, 1H), 4.34 (dd, J=7.5, 9.8 Hz, 1H), 4.18 (dd, J=7.3, 9.6 Hz, 1H), 2.65-2.59 (m, 1H), 2.44 (s, 3H), 2.41-2.35 (m, 1H), 2.24-2.18 (m, 1H), 2.13-2.09 (m, 2H) ppm. LC/MS: R$_t$=5.10 min, ES$^+$ 484.11 (AA standard).

Example 123

{(1S,2S,4R)-4-[(9-benzyl-9H-purin-6-yl)oxy]-2-hydroxycyclopentyl}methyl sulfamate (Compound I-80)

Step a: 5-Amino-4-benzylamino-6-chloropyrimidine

To a solution of 5-amino-4,6-dichloropyrimidine (8.4 g, 0.051 mol) in 1-butanol (50.0 mL, 0.547 mol) was added triethylamine (12 mL, 0.084 mol) and benzylamine (17 mL, 0.15 mol), and the mixture was heated at 100° C. for 3 hours. The reaction was cooled at 0 C, filtered and washed with ethanol. The residue was dissolved in CH$_2$Cl$_2$ and washed with saturated aqueous NaHCO$_3$, and concentrated. The residue was triturated in diethyl ether to obtain 11.5 g (96%) of a light brown solid.

Step b: 6-T Chloro-9-benzylpurine

To a solution of 4.0 M of hydrochloric acid in 1,4-dioxane (2.3 mL) in N,N-dimethylformamide (10.0 mL, 0.129 mol) was added ethyl orthoformate (2.00 mL, 0.0120 mol) and $N^4$-benzyl-6-chloropyrimidine-4,5-diamine (500 mg, 0.002 mol). The mixture was stirred for 3 days. The reaction was quenched by addition of triethylamine (1.5 mL, 0.011 mol), extracted with ethyl acetate, washed with saturated aqueous sodium bicarbonate, water, brine, dried ($Na_2SO_4$), filtered and concentrated. The residue was purified by flash chromatography (3 to 5% MeOH/DCM) to obtain 336 g (60%). LC/MS: $R_t$=1.49 min, $ES^+$ 245.08 (AA standard).

Step c: {(1S,2S,4R)-4-[(9-benzyl-9H-purin-6-yl) oxy]-2-hydroxycyclopentyl}methyl sulfamate (Compound I-80)

The title compound was prepared following the procedure described in Example 115 (steps a and d). $^1$H NMR ($CD_3OD$, 400 MHz) δ: 8.51 (s, 1H), 8.32 (s, 1H), 7.34-7.28 (m, 5H), 5.93-5.88 (m, 1H), 5.49 (s, 2H), 4.46-4.43 (m, 1H), 4.35 (dd, J=7.5, 9.9 Hz, 1H), 4.18 (dd, J=7.1, 9.6 Hz, 1H), 2.66-2.59 (m, 1H), 2.43-2.37 (m, 1H), 2.25-2.18 (m, 1H), 2.14-2.10 (m, 2H) ppm. LC/MS: $R_t$=6.04 min, $ES^+$ 420.11 (AA long).

Example 124

((1S,2S,4R)-4-{[8-(2,3-dihydro-1-benzofuran-7-yl)-7H-purin-6-yl]amino}-2-hydroxycyclopentyl)methyl sulfamate (Compound I-117)

The title compound was prepared following the procedure described in Example 89 using the appropriate carboxylic acid. $^1$H NMR ($CD_3OD$, 400 MHz) δ: 8.29-8.20 (m, 1H), 8.05-7.81 (m, 1H), 7.36 (dd, J=0.9, 7.3 Hz, 1H), 7.01 (t, J=7.7 Hz, 1H), 4.86-4.78 (m, 3H), 4.44-4.41 (m, 1H), 4.36 (dd, J=7.7, 9.6 Hz, 1H), 4.18 (dd, J=7.2, 9.8 Hz, 1H), 3.35-3.31 (m, 2H), 2.63-2.55 (m, 1H), 2.38-2.32 (m, 1H), 2.20-2.12 (m, 1H), 1.99-1.92 (m, 1H), 1.89-1.83 (m, 1H) ppm. LC/MS: $R_t$=5.75 min, $ES^+$ 447.14 (AA long).

Example 125

{(1S,2S,4R)-2-hydroxy-4-[(8-quinolin-8-yl-7H-purin-6-yl)amino]cyclopentyl}-methyl sulfamate (Compound I-84)

The title compound was prepared following the procedure described in Example 89 using the appropriate carboxylic acid. $^1$H NMR (DMSO-$d_6$, 300 MHz) δ: 9.22-9.12 (m, 1H), 8.93-8.76 (m, 1H), 8.62-8.54 (m, 1H), 8.30-8.09 (m, 2H), 7.86-7.69 (m, 2H), 7.40-7.39 (m, 1H), 4.81-4.70 (m, 1H), 4.30-4.19 (m, 2H), 4.08-3.98 (m, 1H), 2.48-2.42 (m, 1H), 2.28-2.20 (m, 1H), 2.13-1.74 (m, 3H) ppm. LC/MS: $R_t$=6.00 min, $ES^+$ 456.04 (AA long).

Example 126

[(1S,2S,4R)-4-({8-[4-(benzyloxy)phenyl]-7H-purin-6-yl}amino)-2-hydroxycyclopentyl]methyl sulfamate (Compound I-102)

The title compound was prepared following the procedure described in Example 89 using the appropriate carboxylic acid. $^1$H NMR (DMSO-$d_6$, 400 MHz) δ: 8.15 (s, 1H), 8.03 (d, J=8.2 Hz, 2H), 7.46-7.30 (m, 5H), 7.15 (d, J=8.8 Hz, 2H), 5.16 (s, 2H), 4.84-4.75 (m, 1H), 4.22-4.16 (m, 2H), 4.00-3.97 (m, 1H), 2.48-2.42 (m, 1H), 2.12-1.69 (m, 4H) ppm. LC/MS: $R_t$=7.22 min, $ES^+$ 511.06 (AA long).

Example 127

((1S,2S,4R)-4-{[8-(2,3-dimethoxyphenyl)-9H-purin-6-yl]amino}-2-hydroxycyclopentyl)methyl sulfamate (Compound I-67)

The title compound was prepared following the procedure described in Example 89 (steps a-d) using the appropriate carboxylic acid and Example 1 (step d, using HCl for TBS deprotection). $^1$H NMR ($CD_3OD$, 400 MHz) δ: 8.30-8.23 (m, 1H), 7.87-7.61 (m, 1H), 7.25-7.18 (m, 2H), 4.92-4.80 (m, 1H), 4.43-4.40 (m, 1H), 4.38-4.34 (m, 1H), 4.21-4.16 (m, 1H), 3.90 (d, 6H), 2.63-2.54 (m, 1H), 2.40-2.31 (m, 1H), 2.20-2.12 (m, 1H), 2.00-1.91 (m, 1H), 1.90-1.83 (m, 1H) ppm. LC/MS: $R_t$=5.92 min, $ES^+$ 465 (AA long).

Example 128

((1S,2S,4R)-2-hydroxy-4-{methyl[8-(1-naphthyl)-9H-purin-6-yl]amino}cyclopentyl)methyl sulfamate (Compound I-46)

Step a: (1S,3S,4S)-3-{[tert-butyl(dimethyl)silyl]oxy}-4-({[tert-butyl(dimethyl)silyl]oxy}-methyl) cyclopentyl methanesulfonate To a solution of (1S,3S,4S)-3-{[tert-butyl(dimethyl)silyl]oxy}-4-({[tert-butyl(dimethyl)silyl]oxy}methyl)cyclopentanol (2.02 g, 0.00560 mol) in $CH_2Cl_2$ (55.0 mL, 0.858 mol) at 0° C. was added triethylamine (1.8 mL, 0.013 mol) and methanesulfonyl chloride (0.650 mL, 0.00840 mol) under an atmosphere of nitrogen. The mixture was stirred at 0° C. for 30 minutes, and then warmed to 23° C. for 1 hour. The reaction was quenched by addition of saturated aqueous sodium bicarbonate, extracted with DCM, dried ($Na_2SO_4$), filtered and concentrated to give 2.66 g (100%).

Step b: [((1 S,2S,4R)-4-azido-2-{[tert-butyl(dimethyl)silyl]oxy}cyclopentyl)methoxyl](tert-butyl) dimethylsilane To a solution of (1S,3S,4S)-3-{[tert-butyl(dimethyl)silyl]oxy}-4-({[tert-butyl(dimethyl)silyl]oxy}methyl)cyclopentyl methanesulfonate (2.66 g, 0.00606 mol) in N,N-Dimethylformamide (20 mL, 0.2 mol) was added sodium azide (1.21 g, 0.0186 mol), and the mixture was heated at 55° C. for 3 hours. The reaction was cooled to 23° C., quenched by addition of water and extracted with $Et_2O$ (3×), washed with water, brine, dried ($Na_2SO_4$), filtered and concentrated. The residue was purified by flash chromatography (0 to 15% ethyl acetate/hexane) to obtain 2.13 g (91.1%).

Step c: (1R,3S,4S)-3-{[tert-butyl(dimethyl)silyl]oxy}-4-({[tert-butyl(dimethyl)silyl]oxy}methyl) cyclopentanamine A suspension of [((1S,2S,4R)-4-azido-2-{[tert-butyl(dimethyl)silyl]oxy}cyclopentyl)methoxy](tert-butyl)dimethylsilane (2.13 g, 0.00552 mol) and 10% Pd/C (0.27 g, 0.00026 mol) in EtOAc (45.0 mL, 0.461 mol) was stirred under an atmosphere of hydrogen overnight. The reaction was purged with nitrogen and filtered the mixture through celite with EtOAc. The filtrate was concentrated to obtain 1.83 g (92.1%) of the title compound.

Step d: Benzyl-[(1R,3S,4S)-3-{[tert-butyl(dimethyl)
silyl]oxy}-4-({[tert-butyl(dimethyl)-silyl]
oxy}methyl)cyclopentyl]carbamate To a solution of (1R,3S,4S)-3-{[tert-butyl(dimethyl)silyl]oxy}-4-({[tert-butyl(dimethyl)silyl]oxy}methyl)cyclopentanamine (0.098 g, 0.00027 mol) in Methylene chloride (2.0 mL, 0.031 mol) at 0° C. was added triethylamine (0.076 mL, 0.00054 mol) and benzyl chloroformate (0.044 mL, 0.00031 mol). The reaction was warmed to 23° C. overnight. The reaction was quenched by addition of water, and the mixture was extracted with methylene chloride (3×). The organic layers were washed with brine, dried ($Na_2SO_4$), filtered and concentrated. The residue was purified by flash chromatography (0 to 8% EtOAc/hexanes) to obtain 73 mg (54%).

Step e: Benzyl-[(1R,3S,4S)-3-{[tert-butyl(dimethyl)
silyl]oxy}-4-({[tert-butyl(dimethyl)-silyl]
oxy}methyl)cyclopentyl]methylcarbamate To a solution of benzyl-[(1R,3S,4S)-3-{[tert-butyl(dimethyl)silyl]oxy}-4-({[tert-butyl(dimethyl)silyl]oxy}methyl)cyclopentyl]carbamate (0.073 g, 0.00015 mol) in N,N-dimethylformamide (2 mL, 0.02 mol) was added sodium hydride (0.028 g, 0.0012 mol). The suspension was stirred for 10 minutes and was added methyl iodide (0.023 mL, 0.00037 mol) (purified on alumina) and the mixture was stirred overnight. The reaction was quenched by addition of saturated aqueous ammonium chloride and the mixture was extracted with ethyl acetate, washed with brine, dried ($Na_2SO_4$), filtered and concentrated.

Step f: (1R,3S,4S)-3-{[tert-butyl(dimethyl)silyl]
oxy}-4-({[tert-butyl(dimethyl)silyl]oxy}methyl)-N-
methylcyclopentanamine A suspension of benzyl-[(1R,3S,4S)-3-{[tert-butyl(dimethyl)silyl]oxy}-4-({[tert-butyl(dimethyl)silyl]oxy}methyl)cyclopentyl]methylcarbamate (0.394 g, 0.000776 mol) and 10% Pd/C (0.04 g, 0.00004 mol) in ethanol (5.0 mL) was stirred under an atmosphere of hydrogen overnight. The reaction was purged with nitrogen and filtered the mixture through celite with ethanol. The filtrate was concentrated to obtain 0.290 g (99%).

Step g: ((1S,2S,4R)-2-hydroxy-4-{methyl[8-(1-
naphthyl)-9H-purin-6-yl]amino}-cyclopentyl)methyl
sulfamate (Compound I-46)

The title compound was prepared following the procedures described in Example 89 (steps c-d) and Example 1 (step d, using HCl for TBS deprotection). $^1$H NMR ($CD_3OD$, 400 MHz) δ: 8.95 (d, J=7.5 Hz, 1H), 8.23 (s, 1H), 8.03 (d, J=8.3 Hz, 1H), 7.97-7.92 (m, 2H), 7.63-7.54 (m, 3H), 6.58-6.44 (m, 1H), 4.43-4.41 (m, 1H), 4.35 (dd, J=7.8, 9.7 Hz, 1H), 4.19 (dd, J=7.5, 9.5 Hz, 1H), 3.38 (s, 3H), 2.68-2.60 (m, 1H), 2.20-1.97 (m, 4H) ppm. LC/MS: $R_t$=1.49 min, ES$^-$ 467.16 (AA standard).

Example 129

((1S,2S,4R)-2-hydroxy-4-{[8-(2-methylphenyl)-9H-
purin-6-yl]amino}cyclopentyl)methyl sulfamate
(Compound I-107)

The title compound was prepared following the procedure described in Example 89 using the appropriate carboxylic acid. $^1$H NMR ($CD_3OD$, 400 MHz) δ: 8.23 (s, 1H), 7.60 (d, J=7.7 Hz, 1H), 7.44-7.32 (m, 3H), 4.43-4.40 (m, 1H), 4.34 (dd, J=7.5, 9.8 Hz, 1H), 4.17 (dd, J=7.3, 9.8 Hz, 1H), 2.61-2.53 (m, 1H), 2.53 (s, 3H), 2.37-2.31 (m, 1H), 2.20-2.12 (m, 1H), 1.99-1.92 (m, 1H), 1.89-1.82 (m, 1H) ppm. LC/MS: $R_t$=1.27 min, ES$^+$ 419.20 (AA standard).

Example 130

{(1S,2S,4R)-2-hydroxy-4-[methyl(9-methyl-8-phe-
nyl-9H-purin-6-yl)-amino]cyclopentyl}methyl sulfa-
mate (Compound I-123)

Step a: 6-Chloro-9-methyl-8-phenyl-9H-purine

To a solution of 6-chloro-8-phenyl-7H-purine (0.200 g, 0.000867 mol) (Example 109, step a) in DMF (8.0 mL, 0.10 mol) was added sodium hydride (0.025 g, 0.0010 mol). The mixture was stirred for 20 minutes and to this was added methyl iodide (0.065 mL, 0.0010 mol) and the mixture was stirred for 2 hours. The reaction was quenched by addition of saturated aqueous $NH_4Cl$, and the mixture was extracted with ethyl acetate, washed with water, brine, dried ($Na_2SO_4$), filtered and concentrated. The residue was purified by flash chromatography (3 to 10% acetone/toluene) to obtain 145 mg (68%).

Step b: N-[(1R,3S,4S)-3-{[tert-butyl(dimethyl)silyl]
oxy}-4-({[tert-butyl(dimethyl)silyl]oxy}-methyl)
cyclopentyl]-9-methyl-8-phenyl-9H-purin-6-amine The title compound was prepared following the procedure described in Example 89 (step c).

Step c: N-[(1R,3S,4S)-3-{[tert-butyl(dimethyl)silyl]
oxy}-4-{[tert-butyl(dimethyl)silyl]oxy}-methyl)
cyclopentyl]-9-dimethyl-8-phenyl-9H-purin-6-amine To a solution of N-[(1R,3S,4S)-3-{[tert-butyl(dimethyl)silyl]oxy}-4-({[tert-butyl(dimethyl)silyl]oxy}methyl)cyclopentyl]-9-methyl-8-phenyl-9H-purin-6-amine (200 mg, 0.0004 mol) in N,N-dimethylformamide (10 mL, 0.1 mol) was added sodium hydride (0.112 g, 0.00280 mol). The mixture was stirred for 30 minutes and to this was added methyl iodide (0.05 mL, 0.0008 mol) and the mixture was stirred overnight. The reaction was quenched by addition of saturated aqueous $NH_4Cl$, and the mixture was extracted with ethyl acetate, washed with water, brine, dried ($Na_2SO_4$), filtered and concentrated. The residue was purified by flash chromatography (0 to 10% MeOH/DCM) to obtain 200 mg (100%).

Step d: {(1S,2S,4R)-2-hydroxy-4-[methyl(9-methyl-
8-phenyl-9H-purin-6-yl)amino]-cyclopentyl}methyl
sulfamate (Compound I-123)

The title compound was prepared following the procedure described in Example 89 (steps d-e). $^1$H NMR ($CD_3OD$, 400 MHz) δ: 8.24 (s, 1H), 7.84-7.80 (m, 2H), 7.57-7.52 (m, 3H), 6.44-6.36 (m, 1H), 4.40-4.38 (m, 1H), 4.33 (dd, J=7.7, 9.8 Hz, 1H), 4.17 (dd, J=7.3, 9.8 Hz, 1H), 3.83 (s, 3H), 3.34 (s, 3H), 2.63-2.56 (m, 1H), 2.16-1.92 (m, 4H) ppm. LC/MS: $R_t$=1.41 min, ES$^+$ 433 (AA standard).

217

Example 131

{(1S,2S,4R)-2-hydroxy-4-[(9-methyl-8-phenyl-9H-purin-6-yl)-amino]cyclopentyl}methyl sulfamate (Compound I-130)

The title compound was prepared following the procedures described in Example 130 (step a) and Example 89 (steps c-e). $^1$H NMR (CD$_3$OD, 400 MHz) δ: 8.28 (s, 1H), 7.82-7.80 (m, 2H), 7.60-7.58 (m, 3H), 4.87-4.86 (m, 1R), 4.42-4.39 (m, 1H), 4.36-4.31 (m, 1H), 4.18-4.14 (m, 1H), 3.85 (s, 3H), 2.59-2.54 (m, 1H), 2.36-2.30 (m, 1H), 2.19-2.11 (m, 1H), 2.00-1.91 (m, 1H), 1.87-1.80 (m, 1H) ppm. LC/MS: R$_t$=1.30 min, ES$^-$ 417 (AA standard).

Example 132

{(1S,2S,4R)-2-hydroxy-4-[(7-methyl-8-phenyl-7H-purin-6-yl)-amino]cyclopentyl}methyl sulfamate (Compound I-36)

Step a: N-(4,6-dichloropyrimidin-5-yl)benzamide

A mixture of 5-amino-4,6-dichloropyrimidine (1.15 g, 0.00701 mol) and benzoyl chloride (1.0 mL, 0.0086 mol) was heated at 100° C. overnight. The reaction was cooled and the residue was triturated with diethyl ether, filtered and collected to obtain 1.6 g (85%).

Step b: N-(4,6-dichloropyrimidin-5-yl)-N-methylbenzamide

To a solution of N-(4,6-dichloropyrimidin-5-yl)benzamide (3.0 g, 0.011 mol) in tetrahydrofuran (70 mL, 0.9 mol) was added cesium carbonate (9.8 g, 0.030 mol). The suspension was stirred for 5 minutes and to this was added methyl iodide (1.4 mL, 0.022 mol) (purified on aluminum oxide). After stirring for 1 hour, cesium carbonate (5.0 g, 0.015 mol) and methyl iodide (0.70 mL, 0.011 mol) (purified on alumina) were added. The reaction was stirred for 2 hours, quenched by addition of saturated aqueous NH$_4$Cl, and the mixture was extracted with ethyl acetate, washed with water, brine, dried (Na$_2$SO$_4$), filtered, concentrated and trituration in diethyl ether to obtain 2.54 g (80%).

Step c: N-(4-amino-6-chloropyrimidin-5-yl)-N-methylbenzamide

To a solution of N-(4,6-dichloropyrimidin-5-yl)-N-methylbenzamide (0.455 g, 0.00161 mol) in 1-butanol (5 mL, 0.05 mol) was added ammonium hydroxide (0.50 mL, 0.013 mol) and the mixture was refluxed for 24 h. To the reaction was added ammonium hydroxide (1.0 mL, 0.026 mol) and the mixture was refluxed for 24 h, cooled, extracted with a mixture of ethyl acetate:isopropanol, washed with saturated aqueous sodium bicarbonate, brine, dried (Na$_2$SO$_4$), filtered, concentrated and triturated in diethyl ether to obtain 284 mg (67.1%).

Step d: 6-Chloro-7-methyl-8-phenyl-7H-purine

A suspension of N-(4-amino-6-chloropyrimidin-5-yl)-N-methylbenzamide (0.285 g, 0.00108 mol) in phosphoryl chloride (8 mL, 0.08 mol) was heated at 115° C. overnight. The mixture was cooled, concentrated and triturated in diethyl ether to obtain 224 mg (84.4%) yellow solid. LC/MS: R$_t$=1.30 min, ES$^+$ 245.08 (AA standard).

Step e: {(1S,2S,4R)-2-hydroxy-4-[(7-methyl-8-phenyl-7H-purin-6-yl)amino]cyclopentyl}methyl sulfamate (Compound I-36)

The title compound was prepared following the procedure described in Example 89 (steps c-e). $^1$H NMR (CD$_3$OD, 400 MHz) δ: 8.32 (s, 1H), 7.77-7.73 (m, 2H), 7.61-7.57 (m, 3H), 4.98-4.91 (m, 1H), 4.42-4.39 (m, 1H), 4.34 (dd, J=7.8, 9.5 Hz, 1H), 4.16 (dd, J=7.3, 9.9 Hz, 1H), 4.06 (s, 3H), 2.66-2.59 (m, 1H), 2.37-2.31 (m, 1H), 2.21-2.12 (m, 1H), 2.03-1.96 (m, 1H), 1.92-1.85 (m, 1H) ppm. LC/MS: R$_t$=1.12 min, ES$^+$ 419.13 (AA standard).

Example 133

((1S,2S,4R)-4-{[8-(2-chlorophenyl)-9H-purin-6-yl]amino}-2-hydroxycyclopentyl)methyl sulfamate (Compound I-34)

The title compound was prepared following the procedures described in Example 89 (steps a, c-d), Example 109 (step a), and Example 1 (step d, using TBAF for TBS group deprotection). $^1$H NMR (CD$_3$OD, 400 MHz) δ: 8.25 (s, 1H), 7.82-7.88 (m, 1H), 7.61 (d, J=8.0 Hz, 1H), 7.55-7.47 (m, 2H), 4.42-4.41 (m, 1H), 4.35 (dd, J=7.7, 9.6 Hz, 1H), 4.17 (dd, J=7.5, 9.6 Hz, 1H), 2.61-2.55 (m, 1H), 2.37-2.32 (m, 1H), 2.20-2.12 (m, 1H), 1.99-1.92 (m, 1H), 1.89-1.82 (m, 1H) ppm. LC/MS: R$_t$=4.35 min, ES$^+$ 439 (FA long).

Example 134

{(1S,2S,4R)-2-hydroxy-4-[(8-phenyl-9H-purin-6-yl)oxy]cyclopentyl}methyl sulfamate (Compound I-63)

Step a: 9-benzyl-6-{[(1R,3S,4S)-3-{[tert-butyl(dimethyl)silyl]oxy}-4-({[tert-butyl(dimethyl)-silyl]oxy}methyl)cyclopentyl]oxy}-8-phenyl-9H-purine The title compound was prepared following the procedures described in Example 123 (step a), Example 109 (step a), and Example 115 (step a).

Step b: {(1S,2S,4R)-2-{[tert-butyl(dimethyl)silyl]oxy}-4-[(8-phenyl-9H-purin-6-yl)-oxy]cyclopentyl}methanol A suspension of 9-benzyl-6-{[(1R,3S,4S)-3-{[tert-butyl(dimethyl)silyl]oxy}-4-({[tert-butyl(dimethyl)silyl]oxy}methyl)cyclopentyl]oxy}-8-phenyl-9H-purine (0.161 g, 0.000249 mol), 10% Pd/C (0.04 g, 0.00004 mol) and formic acid (0.1 mL, 0.003 mol) in methanol (11.0 mL, 0.272 mol) was stirred under an atmosphere of nitrogen overnight. Added formic acid (0.2 mL, 0.005 mol) and 10% Pd/C (0.04 g, 0.00004 mol) to the reaction and stirred 24 h. Added 10% Pd/C (0.060 g, 0.000056 mol) and formic acid (0.2 mL, 0.005 mol) to the reaction and stirred an additional 24 h. The reaction was purged with nitrogen and filtered the mixture through celite with DCM. The filtrate was concentrated, purified by flash chromatography (30 to 50% ethyl acetate/hexane) to obtain 30 mg (27%). LC/MS: R$_t$=2.08 min, ES$^+$ 441.18 (AA standard).

Step c: {(1S,2S,4R)-2-hydroxy-4-[(8-phenyl-9H-purin-6-yl)oxy]cyclopentyl}methyl sulfamate (Compound I-63)

The title compound was prepared following the procedure described in Example 89 (step e). $^1$H NMR (CD$_3$OD, 400 MHz) δ: 8.47 (s, 1H), 8.16-8.11 (m, 2H), 7.57-7.54 (m, 3H), 5.94-5.90 (m, 1H), 4.49-4.45 (m, 1H), 4.37 (dd, J=7.5, 9.5 Hz, 1H), 4.20 (dd, J=7.5, 9.6 Hz, 1H), 2.70-2.64 (m, 1H), 2.46-2.40 (m, 1H), 2.30-2.24 (m, 1H), 2.18-2.14 (m, 2H) ppm. LC/MS: R$_t$=1.15 min, ES$^+$ 406.11 (AA standard).

Example 135

{(1S,2S,4R)-2-hydroxy-4-[(2-phenyl[1,3]oxazolo[5,4-d]pyrimidin-7-yl)-amino]cyclopentyl}methyl sulfamate (Compound I-90)

Step a: 7-Chloro-2-phenyl[1,3]oxazolo[5,4-d]pyrimidine

A mixture of 5-amino-4,6-dichloropyrimidine (1.05 g, 0.00640 mol) and benzoyl chloride (0.89 mL, 0.0077 mol) was subjected to microwave irradiation (100° C.) for 2 hours. The reaction was cooled and the residue was triturated with diethyl ether, filtered and collected to obtain 1.15 g (77.5%) of a yellow solid. LC/MS: R$_t$=1.84 min, ES$^+$ 232.19 (AA standard).

Step c: {(1 S,2S,4R)-2-hydroxy-4-[(2-phenyl[1,3]oxazolo[5,4-d]pyrimidin-7-yl)-amino]cyclopentyl}methyl sulfamate (Compound I-90)

The title compound was prepared following the procedures described in Example 89 (steps c-d) and Example 1 (step d, using TBAF for the TBS group deprotection). $^1$H NMR (CD$_3$OD, 400 MHz) δ: 8.28 (s, 1H), 8.19-8.16 (m, 2H), 7.58-7.53 (m, 3H), 4.89-4.86 (m, 1H), 4.43-4.40 (m, 1H), 4.34 (dd, J=7.8, 9.5 Hz, 1H), 4.17 (dd, J=7.3, 9.6 Hz, 1H), 2.64-2.55 (m, 1H), 2.35-2.27 (m, 1H), 2.18-2.09 (m, 1H), 2.01-1.95 (m, 1H), 1.89-1.83 (m, 1H) ppm. LC/MS: R$_t$=1.44 min, ES$^+$ 406.31 (AA standard).

Example 136

Enzyme Preparation

All protein accession numbers provided herein refer to the Entrez Protein database maintained by the National Center for Biotechnology Information (NCBI), Bethesda, Md.

Generation of E1 Enzymes

Following manufacturer instructions, baculoviruses were generated with the Bac-to-Bac Expression System (Invitrogen) for the following proteins: untagged NAEα (APPBP1; NP_003896.1), N-terminally His-tagged NAEβ (UBE1C; NP_003959.3), untagged SAEα (SAE1; NP_005491.1), N-terminally His-tagged SAE3 (UBA2; NP_005490.1), N-terminally His-tagged murine UAE (UBE1X; NP_033483). NAEα/His-NAEβ and SAEα/His-SAEβ complexes were generated by co-infection of Sf9 cells, which were harvested after 48 hours. His-mUAE was generated by single infection of Sf9 cells and harvested after 72 hours. Expressed proteins were purified by affinity chromatography (Ni-NTA agarose, Qiagen) using standard buffers.

Generation of E2 Enzymes

Ubc12 (UBE2M; NP_003960.1), Ubc9 (UBE2I; NP_003336.1), Ubc2 (UBE2A; NP_003327.2) were subcloned into pGEX (Pharmacia) and expressed as N-terminally GST tagged fusion proteins in *E. coli*. Expressed proteins were purified by conventional affinity chromatography using standard buffers.

Generation of Ubl Proteins

Nedd8 (NP_006147), Sumo-1 (NP_003343) and Ubiquitin (with optimized codons) were subcloned into pFLAG-2 (Sigma) and expressed as N-terminally Flag tagged fusion proteins in *E. coli*. Expressed proteins were purified by conventional chromatography using standard buffers.

Example 137

E1 Enzyme Assays

Nedd8-Activating Enzyme (NAE) HTRF Assay.

The NAE enzymatic reaction totaled 50 µL and contained 50 mM HEPES (pH 7.5), 0.05% BSA, 5 mM MgCl$_2$, 20 µM ATP, 250 µM GSH, 0.01 µM Ubc12-GST, 0.075 µM Nedd8-Flag and 0.20 nM recombinant human NAE enzyme. The enzymatic reaction mixture, with and without compound inhibitor, was incubated at room temperature 24° C. for 105 minutes in a 384-well plate before termination with 25 µL of Stop/Detection buffer (0.1M HEPES pH 7.5, 0.05% Tween20, 20 mM EDTA, 410 mM KF, 0.53 nM Europium-Cryptate labeled monoclonal anti-FLAG M2 antibody (Cis-Bio International) and 8.125 µg/mL PHYCOLINK goat anti-GST allophycocyanin (XL-APC) antibody (Prozyme)). After incubation for 1 hour at 24° C., quantification of the FRET was performed on the Analyst™ HT 96.384 (Molecular Devices).

Compounds I-1 to I-153 were tested in this assay. Compounds I-1, I-2, I-3, I-5, I-6, I-8 to I-12, I-14, I-15, I-17, I-18, I-19, I-21, I-24 to I-27, I-29, I-32, I-34, I-37 to I-43, I-45, I-46, I-47, I-49, I-55, I-56, I-60, I-62 to I-65, I-67, I-68, I-69, I-71, I-73, I-74, I-82, I-83, I-84, I-87, I-88, I-90, I-93, I-99, I-100, I-101, I-102, I-103m, 1-105 to I-109, I-111, I-112, I-115, I-117, I-118, I-121, I-122, I-124, I-125, I-126, I-128 to I-131, I-133, I-134, I-136, I-137, I-139, I-140, I-142, I-143, I-146, I-147, I-150, I-151, and 1-153 exhibited IC$_{50}$ values less than or equal to 500 nM in this assay. Compounds I-4, I-7, I-16, I-28, I-33, I-35, I-36, I-48, I-53, I-54, I-59, I-66, I-77, I-79, I-80, I-81, I-86, I-92, I-94, I-96, I-98, I-110, I-113, I-114, I-119, I-120, I-123, I-127, I-132, I-138, I-141, I-148, I-149, and 1-152 exhibited IC$_{50}$ values greater than 500 nM and less than 10 µM in this assay. Compounds I-13, I-20, I-22, I-23, I-30, I-31, I-58, I-61, I-76, I-85, I-89, I-97, I-144, and I-145 exhibited 1050 values greater than 10 µM in this assay.

Sumo-Activating Enzyme (SAE) HTRF Assay.

The SAE enzymatic reaction was conducted as outlined above for NAE except that Ubc12-GST and Nedd8-Flag were replaced by 0.01 µM Ubc9-GST and 0.125 µM Sumo-Flag respectively and the concentration of ATP was 0.5 µM. Recombinant human SAE (0.11 nM) was the source of enzyme.

Ubiquitin-Activating Enzyme (UAE) HTRF Assay.

The UAE enzymatic reaction was conducted as outlined above for NAE except that Ubc12-GST and Nedd8-Flag were replaced by 0.005 µM Ubc2-GST and 0.125 µM Ubiquitin-Flag respectively and the concentration of ATP was 0.1 µM. Recombinant mouse UAE (0.3 nM) was the source of enzyme.

Example 138

Cellular Assays

Anti-Proliferation Assay (WST)

Calu-6 (2400/well) or other tumor cells in 80 µL of appropriate cell culture medium (MEM for Calu6, Invitrogen) supplemented with 10% fetal bovine serum (Invitrogen) was seeded in wells of a 96-well cell culture plate and incubated for 24 hours in a tissue culture incubator. Compound inhibitors were added in 20 µL culture media to the wells and the plates was incubated for 72 hours at 37° C. 10% final concentration of WST-1 reagent (Roche) was added to each well and incubated for 3.5 hours (for Calu6) at 37° C. The optical density for each well was read at 450 nm using a spectrophotometer (Molecular Devices). Percent inhibition was calculated using the values from a DMSO control set to 100% viability.

Anti-Proliferation Assay (ATPLite)

Calu-6 (1500 cells/well) or other tumor cells were seeded in 72 µL of appropriate cell culture medium (MEM for Calu6, Invitrogen) supplemented with 10% fetal bovine serum (Invitrogen) in wells of a 384-well Poly-D-Lysine coated cell culture plate. Compound inhibitors were added in 8 µL 10% DMSO/PBS to the wells and the plates were incubated for 72 hours at 37° C. Cell culture medium was aspirated, leaving 25 µL in each well. 25 µL of ATPlite 1Step™ reagent (Perkin Elmer) was added to each well. The luminescence for each well was read using the LeadSeeker Microplate Reader (Molecular Devices). Percent inhibition was calculated using the values from a DMSO control set to 100% viability.

Example 139

In Vivo Assays

In Vivo Tumor Efficacy Model

Calu6 ($5 \times 10^6$ cells), HCT116 ($2 \times 10^6$ cells) or other tumor cells in 100 phosphate buffered saline were aseptically injected into the subcutaneous space in the right dorsal flank of female Ncr nude mice (age 5-8 weeks, Charles River) using a 26-gauge needle. Beginning on day 7 after inoculation, tumors were measured twice weekly using a vernier caliper. Tumor volumes were calculated using standard procedures ($0.5 \times (\text{length} \Delta \text{width}^2)$). When the tumors reached a volume of approximately 200 mm$^3$ mice were randomized into groups and injected intravenously in the tail vein with compound inhibitor (100 µL) at various doses and schedules. Alternatively, compound inhibitor may be delivered to mice by intraperitoneal or subcutaneous injection or oral administration. All control groups received vehicle alone. Tumor size and body weight was measured twice a week and the study terminated when the control tumors reached approximately 2000 mm$^3$.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

While a number of embodiments of this invention have been described, it is apparent that the provided basic examples may be altered to convey other embodiments, which utilize the compounds and methods of this invention. It will thus be appreciated that the scope of this invention has been represented herein by way of example and is not intended to be limited to the specific embodiments, rather is defined by the appended claims.

What is claimed is:

1. A compound chosen from:

I-16 {(1R,2R,3S,4R)-2,3-dihydroxy-4-[(pyridin-3-ylcarbonyl)amino]cyclopentyl}methyl sulfamate I-23 {(1R,2R,3S,4R)-2,3-dihydroxy-4-[(pyridin-2-ylcarbonyl)amino]cyclopentyl}methyl sulfamate I-42 [(1S,2S,4R)-2-hydroxy-4-({6-[(1-naphthylmethyl)amino]pyrimidin-4-yl}oxy)cyclopentyl]methyl sulfamate I-53 ((1S,2S,4R)-4-{[6-({(1S,2R)-2-[(dimethylamino)methyl]-2,3-dihydro-1H-inden-1-yl}amino)pyrimidin-4-yl]oxy}-2-hydroxycyclopentyl)methyl sulfamate I-54 [(1S,2S,4R)-4-({6-[(1S)-2,3-dihydro-1H-inden-1-ylamino]-2-oxo-2,3-dihydropyrimidin-4-yl}amino)-2-hydroxycyclopentyl]methyl sulfamate I-85 {(1R,2R,3S,4R)-4-[(6-{[(1R,2R)-2-(benzyloxy)cyclopentyl]amino}pyrimidin-4-yl)amino]-2,3-dihydroxycyclopentyl}methyl sulfamate I-92 {(1R,2R,3S,4R)-4-[(6-{[(1S,2S)-2-(benzyloxy)cyclopentyl]amino}pyrimidin-4-yl)amino]-2,3-dihydroxycyclopentyl}methyl sulfamate I-108 ((1R,2R,3S,4R)-2,3-dihydroxy-4-{[6-(phenylethynyl)pyrimidin-4-yl]amino}-cyclopentyl)methyl sulfamate I-119 ((1S,2S,4R)-2-hydroxy-4-{[6-(1-naphthylmethoxy)pyrimidin-4-yl]oxy}-cyclopentyl)methyl sulfamate I-141 ((1S,2S,4R)-2-hydroxy-4-{[6-(2-naphthylmethoxy)pyrimidin-4-yl]oxy}-cyclopentyl)methyl sulfamate; or I-146 ((1S,2S,4R)-4-{4-[(1S)-2,3-dihydro-1H-inden-1-ylamino]-5,6-dihydro-7H-pyrrolo[2,3-d]pyrimidin-7-yl}-2-hydroxycyclopentyl)methyl sulfamate.

* * * * *

UNITED STATES PATENT AND TRADEMARK OFFICE
CERTIFICATE OF CORRECTION

PATENT NO. : 9,718,788 B2
APPLICATION NO. : 15/249851
DATED : August 1, 2017
INVENTOR(S) : Claiborne et al.

Page 1 of 3

It is certified that error appears in the above-identified patent and that said Letters Patent is hereby corrected as shown below:

Column 15, Lines 1-10, replace:

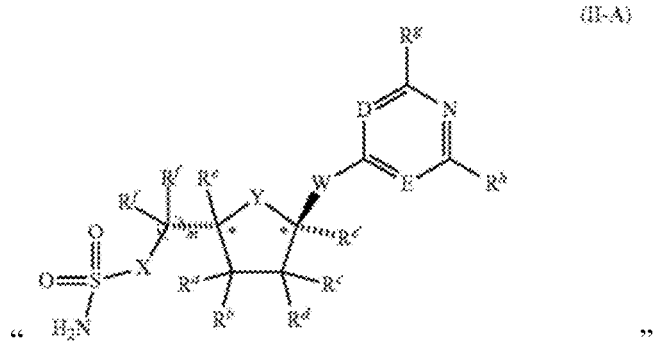

"

With:

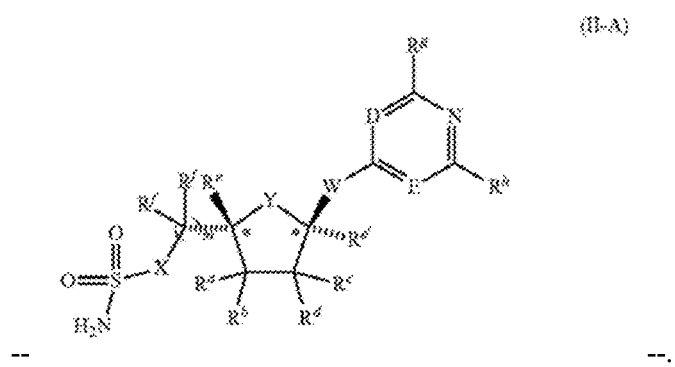

--  --.

Signed and Sealed this
Twenty-ninth Day of May, 2018

Andrei Iancu
*Director of the United States Patent and Trademark Office*

Column 23, Lines 1-10, replace:
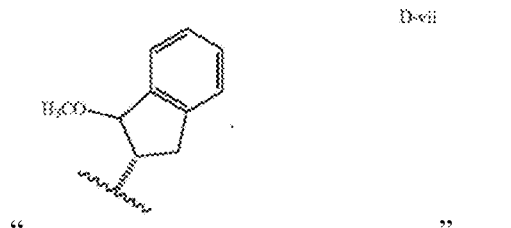
"
With:
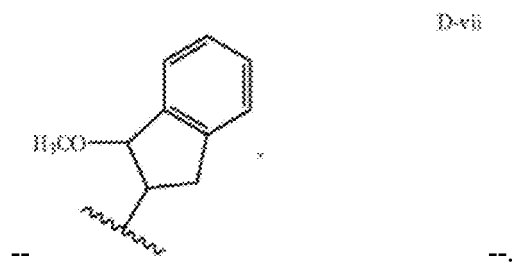
--.
Column 67, replace:
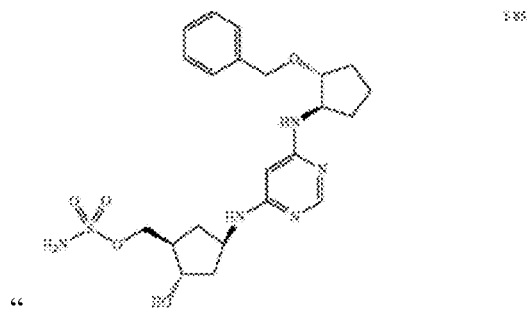
"
With:
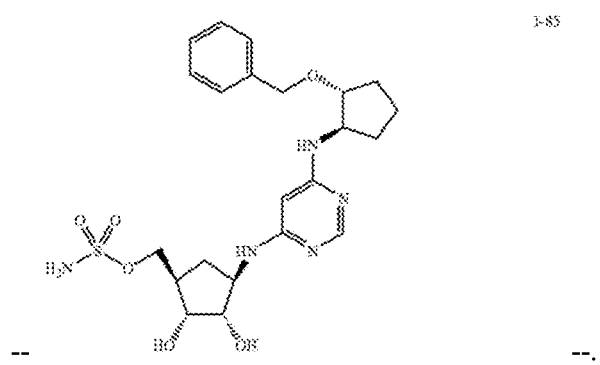
--.

CERTIFICATE OF CORRECTION (continued)
U.S. Pat. No. 9,718,788 B2

Column 93, replace:

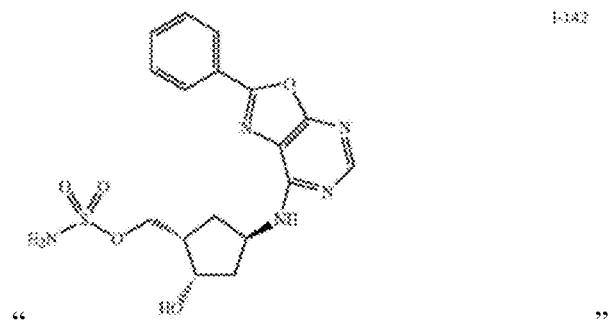

"          "

With:

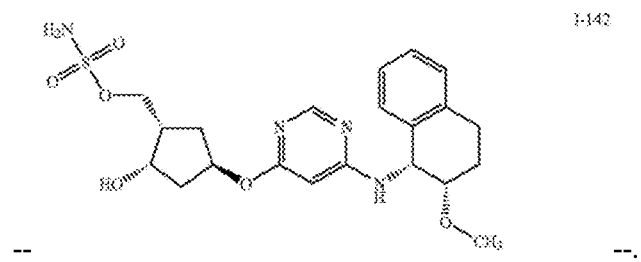

--          --.